US012509472B2

(12) United States Patent
Jung et al.

(10) Patent No.: US 12,509,472 B2
(45) Date of Patent: Dec. 30, 2025

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: So-Young Jung, Gyeonggi-do (KR); Ji-Song Jun, Gyeonggi-do (KR); Su-Hyun Lee, Gyeonggi-do (KR); Sang-Hee Cho, Gyeonggi-do (KR); Jin-Ri Hong, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 0 days.

(21) Appl. No.: 18/406,700

(22) Filed: Jan. 8, 2024

(65) Prior Publication Data

US 2024/0174694 A1 May 30, 2024

Related U.S. Application Data

(63) Continuation of application No. 17/214,253, filed on Mar. 26, 2021, now abandoned.

(30) Foreign Application Priority Data

Mar. 26, 2020 (KR) ........................ 10-2020-0036924

(51) Int. Cl.

| | |
|---|---|
| ***C07D 519/00*** | (2006.01) |
| ***H10K 85/60*** | (2023.01) |
| *H10K 101/00* | (2023.01) |

(52) U.S. Cl.

CPC ......... *C07D 519/00* (2013.01); *H10K 85/622* (2023.02); *H10K 85/654* (2023.02); *H10K 85/6572* (2023.02); *H10K 85/6574* (2023.02); *H10K 85/6576* (2023.02); *H10K 2101/90* (2023.02)

(58) Field of Classification Search

CPC .. C07D 519/00; C07D 487/16; C07D 209/56; C07D 403/04; C07D 403/10; C07D 403/14; C07D 405/04; C07D 409/04; C07D 409/14; C07D 413/14; C07D 417/14; H10K 85/622; H10K 85/654; H10K 85/6572; H10K 85/6574

USPC ........................................................... 257/40

See application file for complete search history.

(56) References Cited

U.S. PATENT DOCUMENTS

| | | | |
|---|---|---|---|
| 2019/0036059 | A1 | 1/2019 | Ji et al. |
| 2021/0265569 | A1 | 8/2021 | Kim et al. |

FOREIGN PATENT DOCUMENTS

| | | | | |
|---|---|---|---|---|
| CN | 111548354 | A | | 8/2020 |
| JP | 2000077186 | A | * | 3/2000 |
| KR | 20150086069 | A | | 7/2015 |
| KR | 20200000329 | A | | 1/2020 |
| WO | 2019245164 | A1 | | 12/2019 |

OTHER PUBLICATIONS

Search Report from CNIPA for Chinese application No. 202110256020.5; Application Date: Mar. 9, 2021.

KR20150086069 Translation.

Search Report from China National Intellectual Property Administration for China patent application No. 202110256020.5; Application Date: Mar. 9, 2021.

KR20200000329 Translation.

* cited by examiner

*Primary Examiner* — Ruiyun Zhang

(74) *Attorney, Agent, or Firm* — G. Creston Campbell

(57) ABSTRACT

The present disclosure relates to a plurality of host materials comprising at least one first host compound and at least one second host compound, and an organic electroluminescent device comprising the same. By comprising a specific combination of the compounds wherein the first host compound is represented by formula 1 and the second host compound is represented by formula 2, it is possible to provide an organic electroluminescent device having improved driving voltage, luminous efficiency, power efficiency and/or lifetime property.

11 Claims, No Drawings

PLURALITY OF HOST MATERIALS AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 17/214,253, filed Mar. 26, 2021, which is the National Stage Entry of KR 10-2020-0036924, filed Mar. 26, 2020, all of which are incorporated by reference herein in their entirety.

TECHNICAL FIELD

The present disclosure relates to a plurality of host materials and an organic electroluminescent device comprising the same.

BACKGROUND ART

A small molecular green organic electroluminescent device (OLED) was first developed by Tang, et al., of Eastman Kodak in 1987 by using TPD/ALq3 bi-layer consisting of a light-emitting layer and a charge transport layer. Thereafter, the development of OLEDs was rapidly effected and OLEDs have been commercialized. At present, OLEDs primarily use phosphorescent materials having excellent luminous efficiency in panel implementation. An OLED having high luminous efficiency and/or long lifetime characteristics is required for long time use and high resolution of a display.

In order to enhance luminous efficiency, driving voltage and/or lifetime, various materials or concepts for an organic layer of an organic electroluminescent device have been proposed. However, they were not satisfactory in practical use.

Korean Patent Application Laying-Open No. 2020-0000329 discloses a plurality of host materials comprising a compound having a heteroaryl bonded to a phenanthrene moiety and a compound having a heteroaryl bonded to a carbazole moiety. However, said reference does not specifically disclose a specific combination of host materials claimed in the present disclosure. In addition, development of a light-emitting material having improved performances, for example, improved driving voltage, luminous efficiency, power efficiency and/or lifetime property as compared with combinations of specific compounds conventionally disclosed is still required.

DISCLOSURE OF INVENTION

Technical Problem

The objective of the present disclosure is to provide an organic electroluminescent device having low driving voltage, high luminous efficiency, high power efficiency and/or excellent lifetime property by comprising a plurality of host materials including a specific combination of compounds.

Solution to Problem

The present inventors found that the above objective can be achieved by a plurality of host materials comprising at least one first host compound and at least second host compound, wherein the first host compound is represented by the following formula 1, and the second host compound is represented by the following formula 2:

(1)

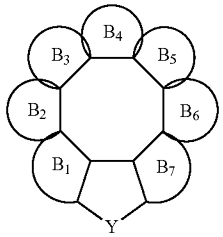

wherein $B_1$ to $B_7$, each independently, are not present, or represent a substituted or unsubstituted (C5-C20) ring, in which carbon atoms of the ring may be replaced with at least one heteroatom selected from nitrogen, oxygen, and sulfur, with the proviso that at least five of $B_1$ to $B_7$ are present, and adjacent rings of $B_1$ to $B_7$ are fused with each other;

Y represents —$N(L_1-(Ar_1)_n)$—, —O—, —S—, or —$C(R_1)(R_2)$—;

$L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ represents a substituted or unsubstituted (C6-C30) aryl, a substituted or unsubstituted (3- to 30-membered) heteroaryl, or —$N(R_3)(R_4)$;

$R_1$ to $R_4$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, or a substituted or unsubstituted (C3-C30) cycloalkyl; or may be linked to an adjacent substituent to form a ring(s); and n represents an integer of 1 or 2, where if n is 2, each of $Ar_1$ may be the same or different;

(2)

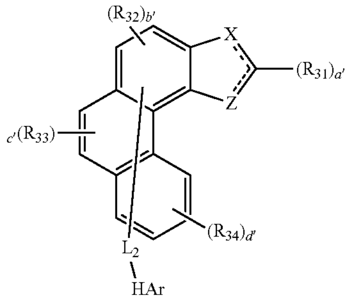

wherein

X represents —N═, —$NR_{35}$—, —O— or —S—;

Z represents —N═, —$NR_{36}$—, —O— or —S—, where if X represents —N═, Z represents —$NR_{36}$—, —O— or —S—, and if X represents —$NR_{35}$—, Z represents —N═, —O— or —S—;

HAr represents a substituted or unsubstituted (3- to 30-membered)heteroaryl;

$R_{31}$ represents a substituted or unsubstituted (C6-C30) aryl, or a substituted or unsubstituted (3- to 30-membered)heteroaryl;

$R_{32}$ to $R_{34}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or $-L_3-N(Ar_2)(Ar_3)$; or may be linked to an adjacent substituent to form a ring(s);

$R_{35}$ and $R_{36}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or $-L_3-N(Ar_2)(Ar_3)$;

$L_2$ and $L_3$, each independently, represent a single bond, a substituted or unsubstituted (C6-C30)arylene, or a substituted or unsubstituted (3- to 30-membered)heteroarylene;

$Ar_2$ and $Ar_3$, each independently, represent hydrogen, a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl; and a' represents 1, b' and c', each independently, represent an integer of 1 or 2, and d' represents an integer of 1 to 4, where if each of b', c' and d' is an integer of 2 or more, each of $R_{32}$ to each of $R_{34}$ may be the same or different.

Advantageous Effects of Invention

By comprising a plurality of host materials according to the present disclosure, an organic electroluminescent device having lower driving voltage, higher luminous efficiency, higher power efficiency and/or better lifetime property compared to conventional organic electroluminescent devices can be provided, and it is possible to produce a display system or a lighting system using the same.

MODE FOR THE INVENTION

Hereinafter, the present disclosure will be described in detail. However, the following description is intended to explain the invention and is not meant in any way to restrict the scope of the present disclosure.

The term "organic electroluminescent material" in the present disclosure means a material that may be used in an organic electroluminescent device, and may comprise at least one compound. The organic electroluminescent material may be comprised in any layer constituting an organic electroluminescent device as necessary. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials of the present disclosure may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. The at least two compounds may be comprised in the same layer or different layers, and may be mixture-evaporated or co-evaporated, or may be individually evaporated.

The term "a plurality of host materials" in the present disclosure means an organic electroluminescent material comprising a combination of at least two host materials. It may mean both a material before being comprised in an organic electroluminescent device (for example, before vapor deposition) and a material after being comprised in an organic electroluminescent device (for example, after vapor deposition). The plurality of host materials of the present disclosure may be comprised in any light-emitting layer constituting an organic electroluminescent device. At least two compounds comprised in the plurality of host materials of the present disclosure may be comprised together in one light-emitting layer or may respectively be comprised in different light-emitting layers. When at least two host materials are comprised in one layer, for example, they may be mixture-evaporated to form a layer or may be separately co-evaporated at the same time to form a layer.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, and more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the above aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenylyl, 4"-t-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a] fluorenyl, 11,11-dimethyl-2-benzo[a] fluorenyl, 11,11-dimethyl-3-benzo[a] fluorenyl, 11,11-dimethyl-4-benzo[a] fluorenyl, 11,11-dimethyl-5-benzo[a] fluorenyl, 11,11-dimethyl-6-benzo[a] fluorenyl, 11,11-dimethyl-7-benzo[a] fluorenyl, 11,11-dimethyl-8-benzo[a] fluorenyl, 11,11-dimethyl-9-benzo[a] fluorenyl, 11,11-dimethyl-10-benzo[a] fluorenyl, 11,11-dimethyl-1-benzo[b] fluorenyl, 11,11-dimethyl-2-benzo[b] fluorenyl, 11,11-dimethyl-3-benzo[b] fluorenyl, 11,11-dimethyl-4-benzo[b] fluorenyl, 11,11-dimethyl-5-benzo[b] fluorenyl, 11,11-dimethyl-6-benzo[b] fluorenyl, 11,11-dimethyl-7-benzo[b] fluorenyl, 11,11-dimethyl-8-benzo[b] fluorenyl, 11,11-dimethyl-9-benzo[b] fluorenyl, 11,11-dimethyl-10-benzo[b] fluorenyl, 11,11-dimethyl-1-benzo[c] fluorenyl, 11,11-dimethyl-2-benzo[c] fluorenyl, 11,11-dimethyl-3-benzo[c] fluorenyl, 11,11-dimethyl-4-benzo[c] fluorenyl, 11,11-dimethyl-5-benzo[c] fluorenyl, 11,11-dimethyl-6-benzo[c] fluorenyl, 11,11-dimethyl-7-benzo[c] fluorenyl, 11,11-dimethyl-8-benzo[c] fluorenyl, 11,11-dimethyl-9-benzo[c] fluorenyl, 11,11-dimethyl-10-benzo[c] fluorenyl, 11,11-diphenyl-1-benzo[a] fluorenyl, 11,11-diphenyl-2-benzo[a] fluorenyl, 11,11-diphenyl-3-benzo[a] fluorenyl, 11,11-diphenyl-4-benzo[a] fluorenyl, 11,11-diphenyl-5-benzo[a] fluorenyl, 11,11-diphenyl-6-benzo[a] fluorenyl, 11,11-diphenyl-7-benzo[a] fluorenyl, 11,11-diphenyl-8-benzo[a] fluorenyl, 11,11-diphenyl-9-benzo[a] fluorenyl, 11,11-diphenyl-10-benzo[a] fluorenyl, 11,11-diphenyl-1-benzo[b] fluorenyl, 11,11-diphenyl-2-benzo[b] fluorenyl, 11,11-diphenyl-3-benzo[b] fluorenyl, 11,11-diphenyl-4-benzo[b] fluorenyl, 11,11-diphenyl-5-benzo[b] fluorenyl, 11,11-diphenyl-6-benzo[b] fluorenyl, 11,11-diphenyl-7-benzo[b] fluorenyl, 11,11-diphenyl-8-benzo[b] fluorenyl, 11,11-diphenyl-9-benzo[b] fluorenyl, 11,11-diphenyl-10-benzo[b] fluorenyl, 11,11-diphenyl-1-benzo[c] fluorenyl, 11,11-diphenyl-2-benzo[c] fluorenyl, 11,11-diphenyl-3-benzo[c] fluorenyl, 11,11-diphenyl-4-benzo[c] fluorenyl, 11,11-diphenyl-5-benzo[c] fluorenyl, 11,11-diphenyl-6-benzo[c] fluorenyl, 11,11-diphenyl-7-benzo[c] fluorenyl, 11,11-diphenyl-8-benzo[c] fluorenyl, 11,11-diphenyl-9-benzo[c] fluorenyl, 11,11-diphenyl-10-benzo[c] fluorenyl, etc.

The term "(3- to 30-membered)heteroaryl" or "(3- to 50-membered)heteroaryl" is meant to be an aryl having 3 to 30 ring backbone atoms or 3 to 50 ring backbone atoms, and including at least one, preferably 1 to 4 heteroatoms selected from the group consisting of B, N, O, S, Si, and P. The above heteroaryl may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, naphthobenzofuranyl, naphthobenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. More specifically, the above heteroaryl may include 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. Furthermore, "halogen" includes F, Cl, Br, and I.

In addition, "ortho (o-)," "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent. The substituents of the substituted alkyl, the substituted alkylene, the substituted alkenyl, the substituted aryl, the substituted arylene, the substituted heteroaryl, the substituted heteroarylene, the substituted cycloalkyl, the substituted cycloalkylene, the substituted alkoxy, the substituted trialkylsilyl, the substituted dialkylarylsilyl, the substituted alkyldiarylsilyl, the substituted triarylsilyl, the substituted fused ring of an aliphatic ring(s) and an aromatic ring(s), and the substituted ring in the formulas of the present disclosure, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 50-membered)heteroaryl unsubstituted or substituted with at least one of a (C1-C30)alkyl(s), a (C6-C30)aryl(s), and a di(C6-C30)arylamino(s); a (C6-C30)aryl unsubstituted or substituted with at least one of deuterium, a cyano(s), a (C1-C30)alkyl(s), a (3- to 50-membered)heteroaryl(s), a mono- or di-(C6-C30)arylamino(s), and a tri(C6-C30)arylsilyl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino; a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents, each independently, are at least one selected from the group consisting of deuterium; a (C1-C20)alkyl; a (3- to 30-membered)heteroaryl unsubstituted or substituted with at least one of a (C1-C20)alkyl(s) and a (C6-C25)aryl(s); a (C6-C25)aryl unsubstituted or substituted with at least one of deuterium, a (C1-C20)alkyl(s), a (3- to 30-membered)heteroaryl(s), and a di(C6-C25)arylamino(s); and a mono- or di-(C6-C25)arylamino. According to another embodiment of the present disclosure, the substituents, each independently, are at least one selected from the group consisting of deuterium; a (C1-C10)alkyl; a (5- to 26-membered)heteroaryl unsubstituted or substituted with a (C6-C18)aryl(s); a (C6-C20)aryl unsubstituted or substituted with at least one of deuterium, a (C1-C10)alkyl(s), a (5- to 26-membered)heteroaryl(s), and a di(C6-C18)arylamino(s); and a di(C6-C18)arylamino. Specifically, the substituents, each independently, may be at least one selected from the group consisting of deuterium; a methyl; a phenyl unsubstituted or substituted with at least one of deuterium, a 26-membered heteroaryl(s), and a diphenylamino(s); a naphthyl; a biphenyl; a naphthylphenyl; a phenylnaphthyl; a phenanthrenyl; a dimethylfluorenyl; a dimethylbenzofluorenyl; a terphenyl; a triphenylenyl; a pyridyl unsubstituted or substituted with a phenyl(s); a triazinyl substituted with a phenyl(s); a dibenzofuranyl; a dibenzothiophenyl; a benzonaphthothiophenyl; a carbazolyl unsubstituted or substituted with a phenyl(s); a benzocarbazolyl unsubstituted or substituted with a phenyl(s); a dibenzocarbazolyl; a 26-membered heteroaryl; and a diphenylamino.

In the formulas of the present disclosure, if a substituent is linked to an adjacent substituent to form a ring, the ring may be a substituted or unsubstituted, mono- or polycyclic, (3- to 30-membered) alicyclic or aromatic ring, or the combination thereof, which two or more adjacent substituents are linked to form. In addition, the formed ring may contain at least one heteroatom selected from B, N, O, S, Si, and P, preferably at least one heteroatom selected from N, O, and S. According to one embodiment of the present disclosure, the number of the ring backbone atoms is 5 to 20. According to another embodiment of the present disclosure, the number of the ring backbone atoms is 5 to 15.

In the formulas of the present disclosure, heteroaryl and heteroarylene may, each independently, contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The plurality of host materials according to one embodiment of the present disclosure comprises a first host material comprising the compound represented by formula 1 and a second host material comprising the compound represented by formula 2, and may be comprised in a light-emitting layer of an organic electroluminescent device according to one embodiment of the present disclosure.

Hereinafter, the compound represented by formula 1 will be described in more detail.

In formula 1, $B_1$ to $B_7$, each independently, are not present, or represent a substituted or unsubstituted (C5-C20) ring, preferably a substituted or unsubstituted (C5-C13) ring, in which carbon atoms of the ring may be replaced with at least one heteroatom selected from nitrogen, oxygen, and sulfur, with the proviso that at least five of $B_1$ to $B_7$ are present, and adjacent rings of $B_1$ to $B_7$ are fused with each other. Herein, "adjacent rings of $B_1$ to $B_7$ are fused with each other" means that ring $B_1$ and ring $B_2$, ring $B_2$ and ring $B_3$, ring $B_3$ and ring $B_4$, ring $B_4$ and ring $B_5$, ring $B_5$ and ring $B_6$, or ring $B_6$ and ring $B_7$ are fused with each other. According to one embodiment of the present disclosure, if any one of $B_1$ to $B_7$ represents a (C6-C20)aryl, an adjacent ring may not be present, or may be a C5 ring, carbon atoms of which may be replaced with at least one heteroatom selected from nitrogen, oxygen, and sulfur. According to another embodiment of the present disclosure, $B_1$ to $B_7$, each independently, are not present, or represent a substituted or unsubstituted benzene ring, a substituted or unsubstituted naphthalene ring, a substituted or unsubstituted pyrrole ring, a substituted or unsubstituted furan ring, a substituted or unsubstituted thiophene ring, a substituted or unsubstituted cyclopentadiene ring, a substituted or unsubstituted fluorene ring, a substituted or unsubstituted pyridine ring, or a substituted or unsubstituted dibenzofuran ring. For example, $B_1$ to $B_7$, each independently, may not be present, or may represent a benzene ring unsubstituted or substituted with a phenyl(s), a naphthyl(s) and/or a diphenyltriazinyl(s); a naphthalene ring; a cyclopentadiene ring unsubstituted or substituted with a methyl(s); a fluorene ring substituted with a methyl(s); a pyrrole ring substituted with an unsubstituted phenyl(s), a phenyl(s) substituted with at least one deuterium, a biphenyl(s) and/or a pyridiyl(s); a furan ring; a thiophene ring; a pyridine ring; or a dibenzofuran ring unsubstituted or substituted with a diphenyltriazinyl(s).

In formula 1, Y represents —$N(L_1\text{-}(Ar_1)_n)$—, —O—, —S—, or —$C(R_1)(R_2)$—. According to one embodiment of the present disclosure, Y represents —$N(L_1\text{-}(Ar_1)_n)$—.

$L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene. According to one embodiment of the present disclosure, $L_1$ represents a single bond, a substituted or unsubstituted (C6-C25) arylene, or a substituted or unsubstituted (3- to 30-membered)heteroarylene. According to another embodiment of the present disclosure, $L_1$ represents a single bond, an unsubstituted (C6-C18)arylene, or an unsubstituted (5- to 25-membered)heteroarylene. For example, $L_1$ may be a single bond, a phenylene, a naphthylene, a biphenylene, a pyridylene, a pyrimidinylene, a triazinylene, a quinoxalinylene, a quinazolinylene, a dibenzofuranylene, a benzofuropyrimidinylene, a benzothienopyrimidinylene, an indolopyrimidinylene, or a benzoquinoxalinylene.

$Ar_1$ represents a substituted or unsubstituted (C6-C30) aryl, a substituted or unsubstituted (3- to 30-membered) heteroaryl, or —$N(R_3)(R_4)$. According to one embodiment of the present disclosure, $Ar_1$ represents a substituted or unsubstituted (C6-C25)aryl, a substituted or unsubstituted (5- to 25-membered)heteroaryl, or —$N(R_3)(R_4)$. According to another embodiment of the present disclosure, $Ar_1$ represents a (C6-C25)aryl unsubstituted or substituted with at least one of deuterium, a (C1-C6)alkyl(s), and a (3- to 30-membered) heteroaryl(s); a (5- to 25-membered)heteroaryl unsubstituted or substituted with at least one of deuterium, a (C6-C18)aryl(s), and a (3- to 30-membered)heteroaryl (s); or —$N(R_3)(R_4)$. For example, $Ar_1$ may be an unsubstituted phenyl, a phenyl substituted with at least one deuterium, a phenyl substituted with a 26-membered heteroaryl(s), a naphthyl, a biphenyl, a fluorenyl substituted with a methyl(s), a spirobifluorenyl, a terphenyl, a triphenylenyl, a pyridyl unsubstituted and substituted with a phenyl(s), a pyrimidinyl substituted with a phenyl(s), a substituted triazinyl, a substituted quinoxalinyl, a substituted quinazolinyl, a benzoquinoxalinyl substituted with a phenyl(s), a carbazolyl, a dibenzofuranyl, a dibenzothiophenyl, a benzofuropyrimidinyl substituted with a phenyl(s), a benzothienopyrimidinyl substituted with a phenyl(s), an indolopyrimidinyl substituted with a phenyl(s), or —$N(R_3)(R_4)$. The substituents of the substituted triazinyl, the substituted quinoxalinyl, and the substituted quinazolinyl, each independently, may be at least one selected from the group consisting of a phenyl unsubstituted or substituted with at least one of deuterium and a 26-membered heteroaryl(s), a naphthyl, a biphenyl, a terphenyl, a dibenzofuranyl, a pyridyl substituted with a phenyl (s), a dimethylfluorenyl, and a dibenzothiophenyl.

$R_1$ to $R_4$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, or a substituted or unsubstituted (C3-C30) cycloalkyl; or may be linked to an adjacent substituent to form a ring(s). According to one embodiment of the present disclosure, $R_1$ to $R_4$, each independently, represent hydrogen, deuterium, a substituted or unsubstituted (C1-C20)alkyl, or a substituted or unsubstituted (C6-C25)aryl. According to another embodiment of the present disclosure, $R_1$ and $R_2$, each independently, represent an unsubstituted (C1-C10)alkyl, and $R_3$ and $R_4$, each independently, represent an unsubstituted (C6-

C18)aryl. For example, $R_1$ and $R_2$ may be a methyl, and $R_3$ and $R_4$ may be a phenyl.

n represents an integer of 1 or 2, where if n is 2, each of $Ar_1$ may be the same or different Formula 1 may be represented by at least one of the following formulas 1-1 to 1-4.

(1-1)

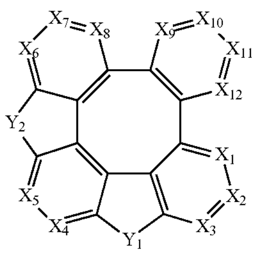

(1-2)

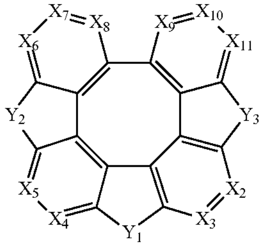

(1-3)

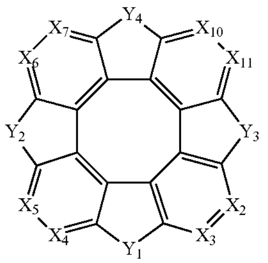

(1-4)

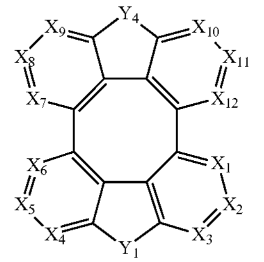

In formulas 1-1 to 1-4, $Y_1$, $Y_2$, $Y_3$, and $Y_4$, each independently, are the same as the definition of Y in formula 1, where if a plurality of $Ar_1$'s are present, each of $Ar_1$ may be the same or different; $X_1$ to $X_{12}$, each independently, represent —N═ or —C($R_a$)═; $R_a$, each independently, represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl; or adjacent $R_a$'s may be linked to each other to form a ring(s), where if a plurality of $R_a$'s are present, each of $R_a$ may be the same or different.

According to one embodiment of the present disclosure, $R_a$ represents hydrogen, deuterium, a substituted or unsubstituted (C6-C25)aryl, or a substituted or unsubstituted (5- to 25-membered)heteroaryl; or adjacent $R_a$'s may be linked to each other to form a ring(s). According to another embodiment of the present disclosure, $R_a$ represents hydrogen, an unsubstituted (C6-C18)aryl, or a (5- to 25-membered)heteroaryl substituted with a (C6-C18)aryl(s); or adjacent $R_a$'s may be linked to each other to form a benzene ring(s), an indene ring(s) substituted with a methyl(s), or a benzofuran ring(s) unsubstituted or substituted with a diphenyltriazinyl(s).

In any one of formulas 1-1 to 1-4, at least one of $Ar_1$(s) and $R_a$(s), each independently, may be at least one selected from those listed in the following group 1.

[Group 1]

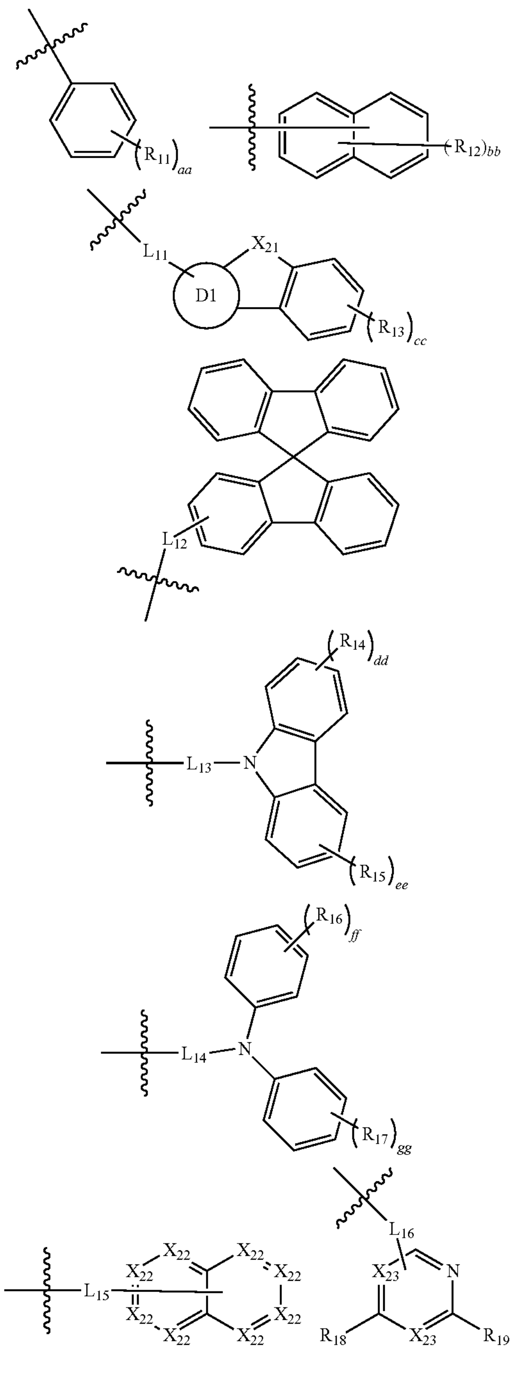

-continued

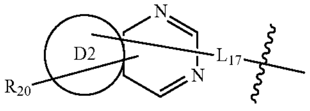

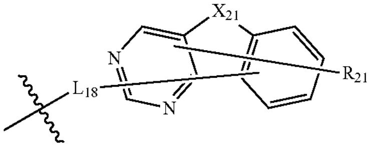

In group 1, D1 and D2, each independently, represent a benzene ring or a naphthalene ring; $X_{21}$ represents O, S, $NR_5$, or $C(R_6)(R_7)$; $X_{22}$, each independently, represents $CR_8$ or N, with the proviso that at least one of $X_{22}$ represents N; $X_{23}$, each independently, represents $CR_9$ or N; $L_{11}$ to $L_{18}$, each independently, represent a single bond, a substituted or unsubstituted (C6-C30)arylene, or a substituted or unsubstituted (3- to 30-membered)heteroarylene; $R_{11}$ to $R_{21}$ and $R_5$ to $R_9$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl, or may be linked to an adjacent substituent to form a ring(s); and aa, ff, and gg, each independently, represent an integer of 1 to 5, bb represents an integer of 1 to 7, and cc, dd, and ee, each independently, represent an integer of 1 to 4.

According to one embodiment of the present disclosure, D1 may be a benzene ring; $X_{21}$ may be O, S, or $C(R_6)(R_7)$; $L_{11}$ to $L_{18}$, each independently, may be a single bond; $R_{11}$ to $R_{21}$ and $R_5$ to $R_9$, each independently, may be hydrogen, deuterium, a substituted or unsubstituted (C1-C20)alkyl, a substituted or unsubstituted (C6-C25)aryl, or a substituted or unsubstituted (5- to 25-membered)heteroaryl, or may be linked to an adjacent substituent to form a ring(s); and aa, bb, ff, and gg, each independently, may be an integer of 1 to 5, and cc, dd, and ee, each independently, may be an integer of 1 to 4. For example, $R_{11}$ may be hydrogen, deuterium, a phenyl, a biphenyl, or a 26-membered heteroaryl; $R_{12}$ may be hydrogen, or adjacent $R_{12}$'s may be linked to each other to form a benzene ring(s); $R_{13}$, $R_{16}$, and $R_{17}$ may be hydrogen; $R_{18}$ and $R_{19}$ may be hydrogen or a phenyl; $R_{21}$ may be phenyl; $R_6$ and $R_7$ may be a methyl; $R_8$ may be hydrogen, a phenyl, a biphenyl, a dibenzofuranyl, or a dibenzothiophenyl, or adjacent $R_8$'s may be linked to each other to form a benzene ring(s); $R_9$ may be hydrogen, an unsubstituted phenyl, a phenyl substituted with at least one deuterium, a phenyl substituted with a 26-membered heteroaryl(s), a naphthyl, a biphenyl, a dimethylfluorenyl, a terphenyl, a pyridyl substituted with a phenyl(s), a dibenzofuranyl, or a dibenzothiophenyl; and aa may be an integer of 1 or 5, bb may be an integer of 1 or 4, and cc may be 1.

In any one of formulas 1-1 to 1-4, at least one of $Ar_1$(s) and $R_a$(s), each independently, may be at least one selected from those listed in the following group 2.

[Group 2]

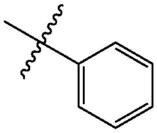
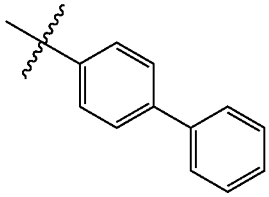
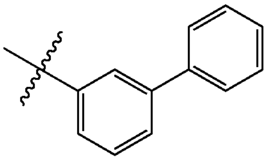
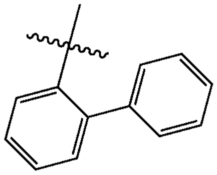
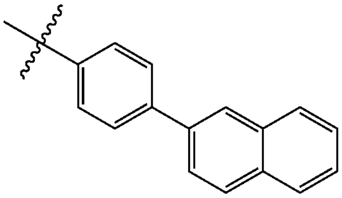
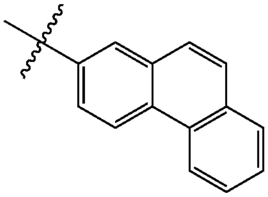
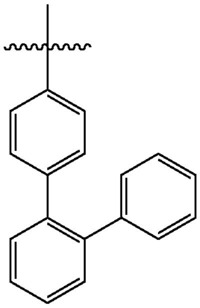
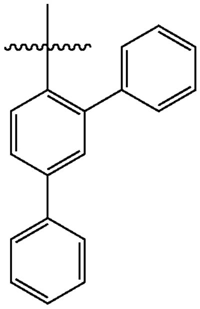
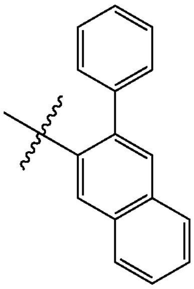
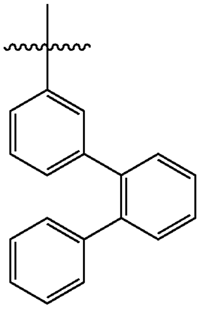
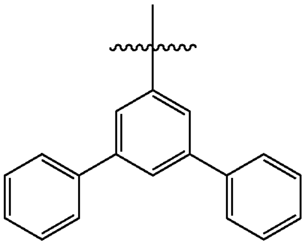
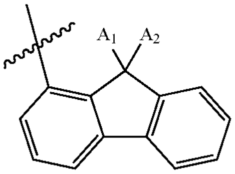
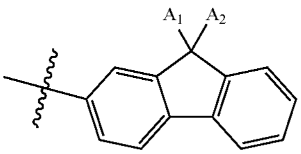

-continued
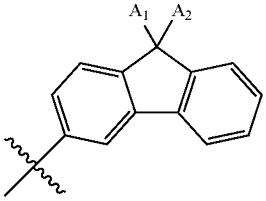
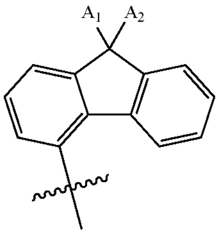
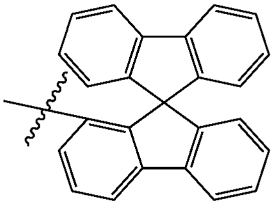
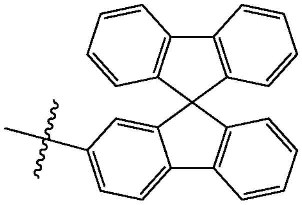
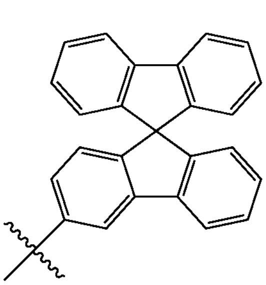
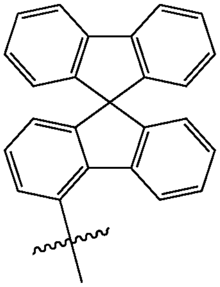
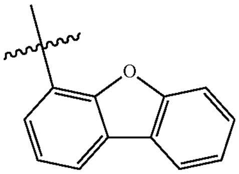
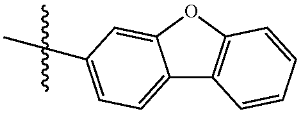
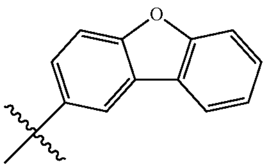
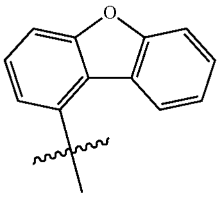
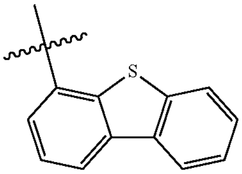
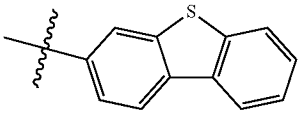
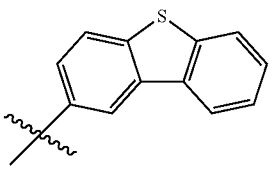
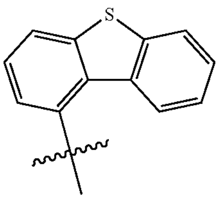
-continued
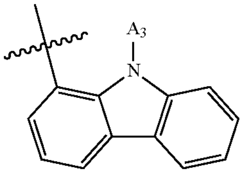
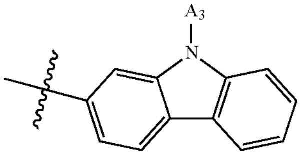
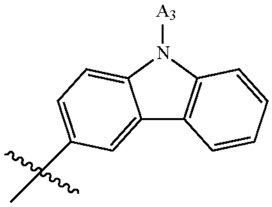
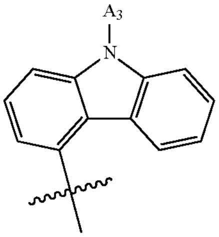
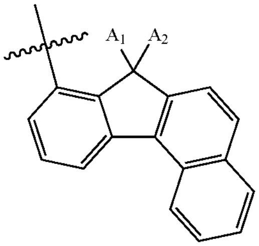
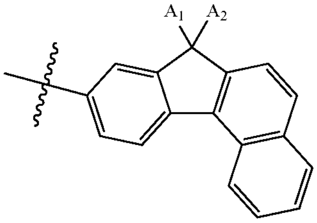
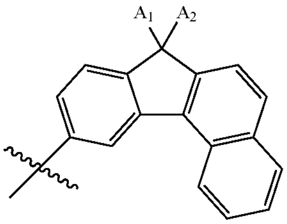
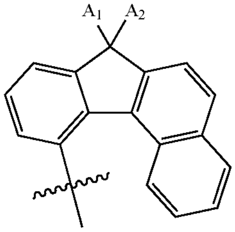
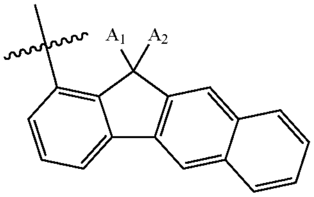
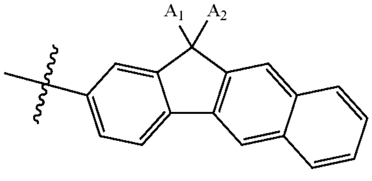
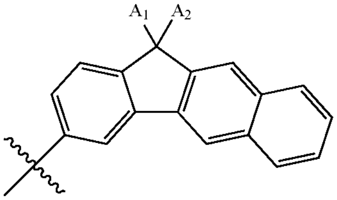

-continued
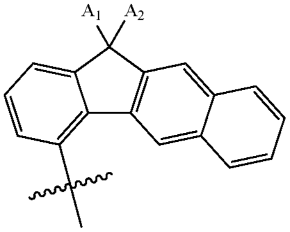
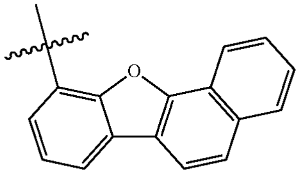
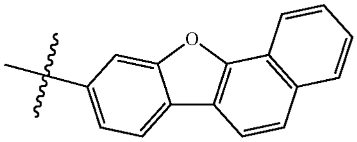
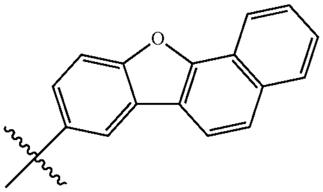
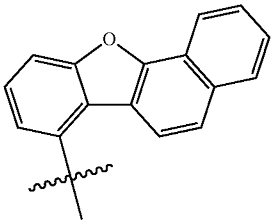
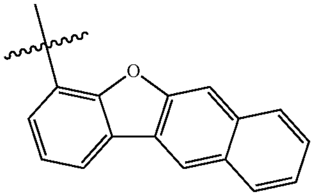
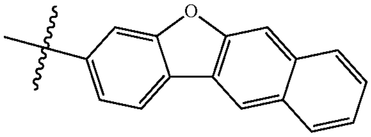
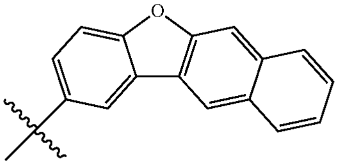
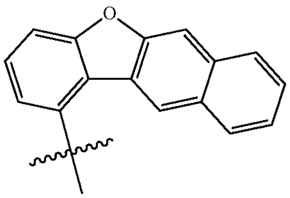
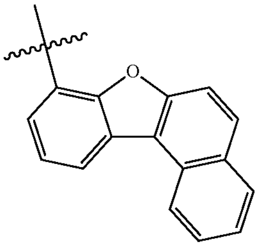
-continued
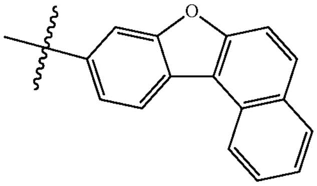
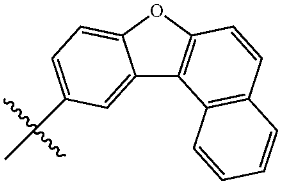
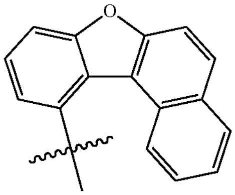
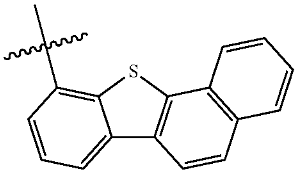
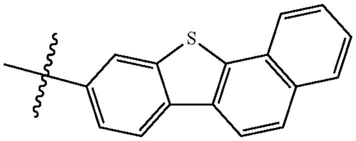
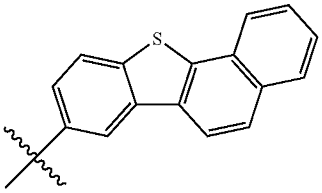
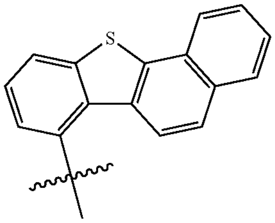
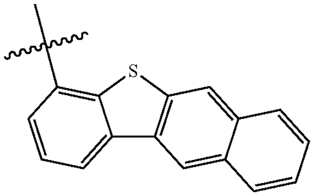
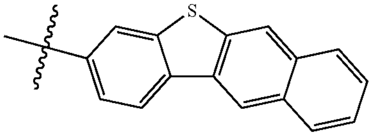
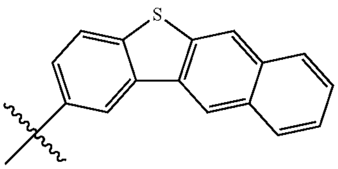

-continued
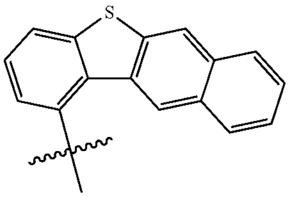
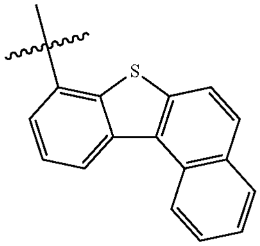
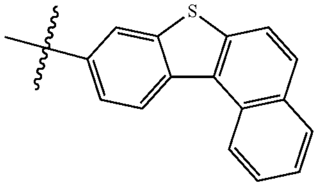
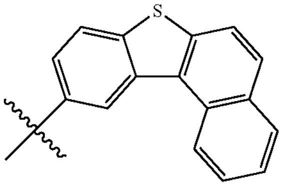
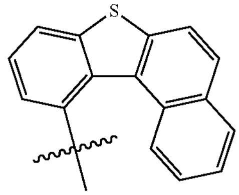
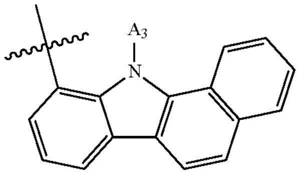
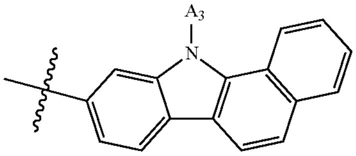
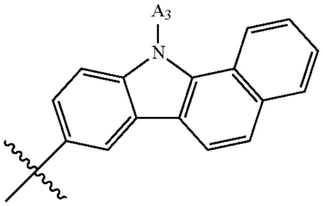
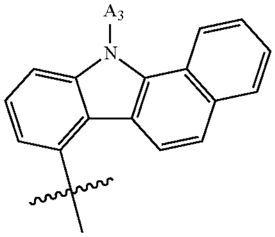
-continued
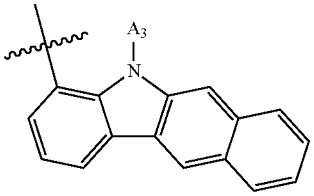
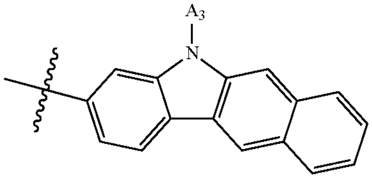
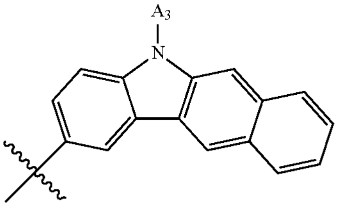
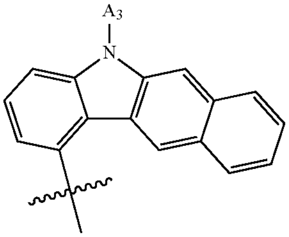
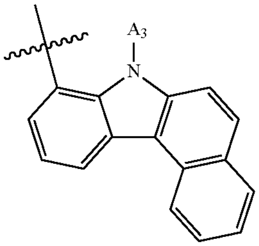
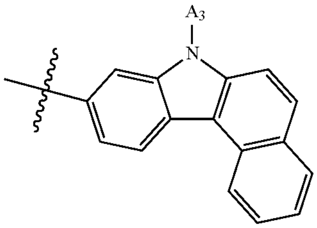
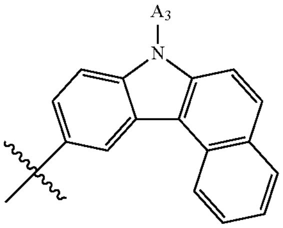
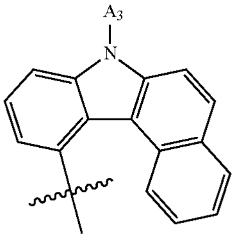
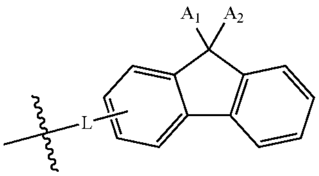
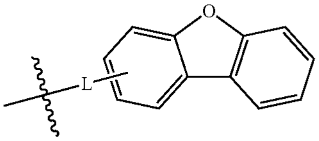

-continued
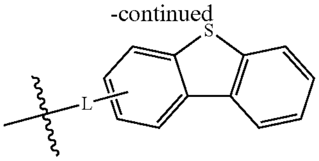
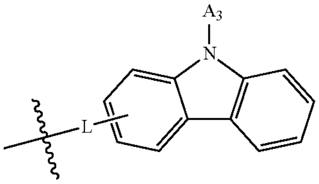
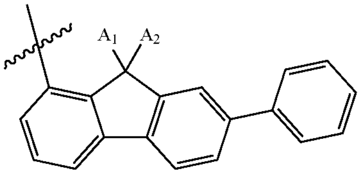
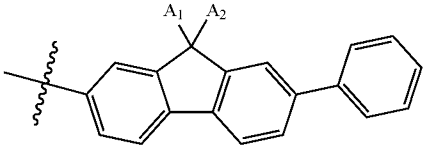
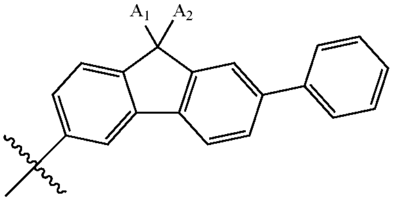
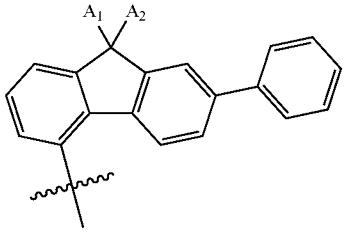
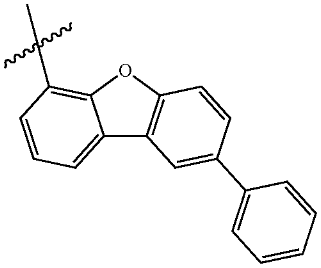
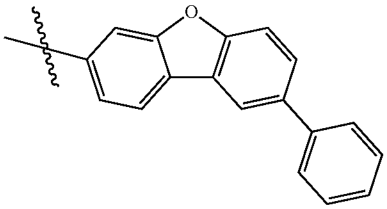
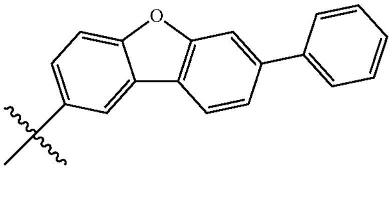
-continued
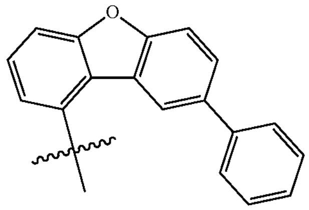
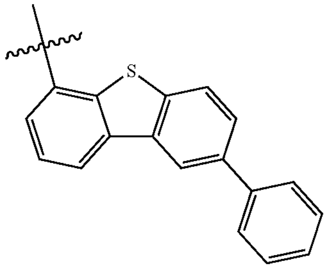
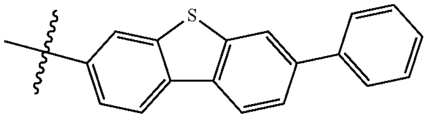
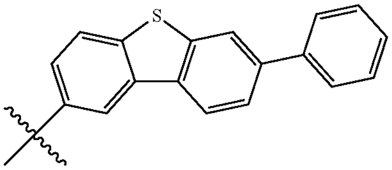
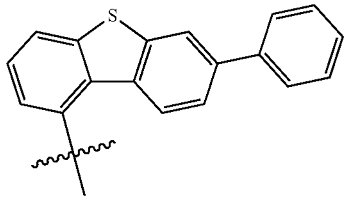
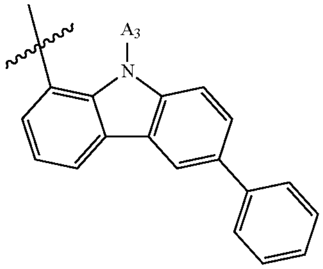
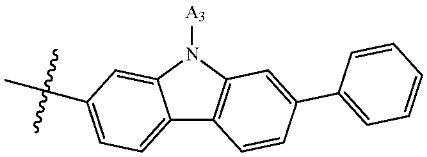
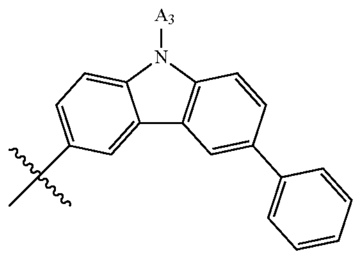

-continued
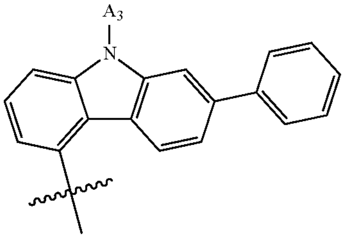
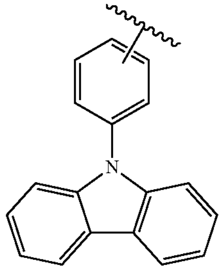
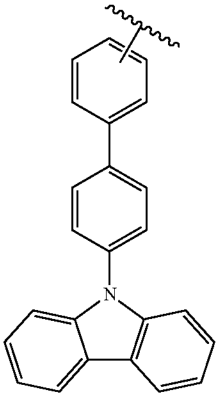
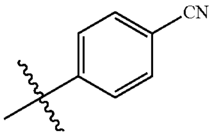
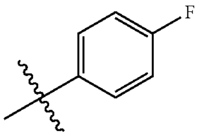
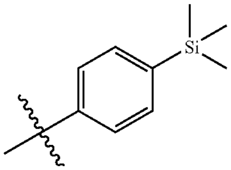
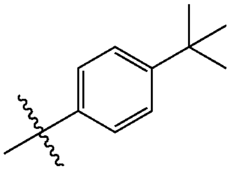
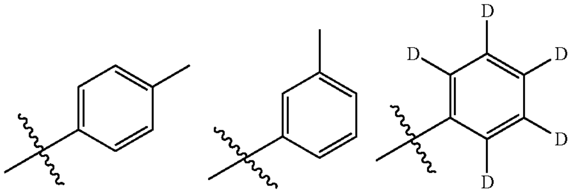
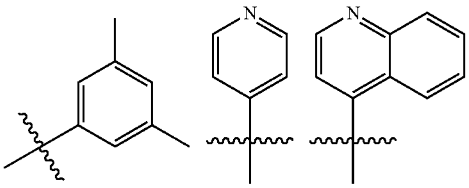
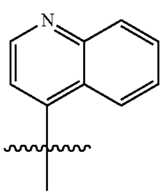
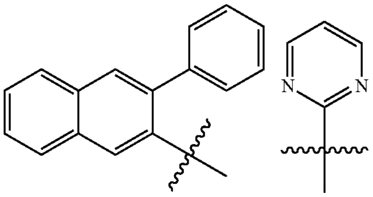
-continued
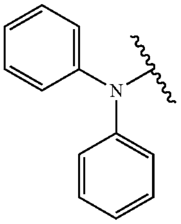
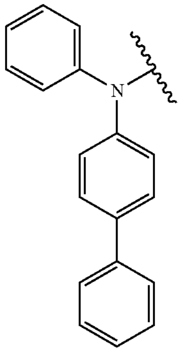
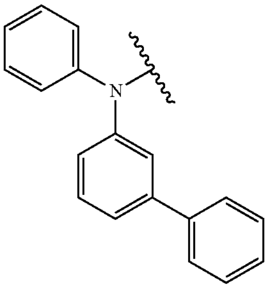
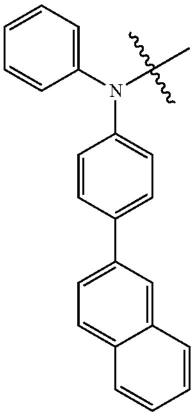
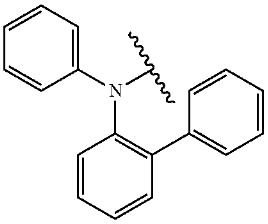
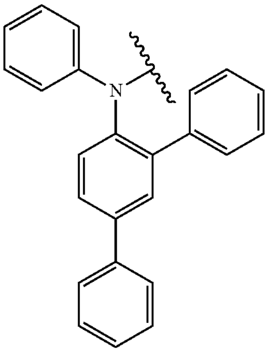
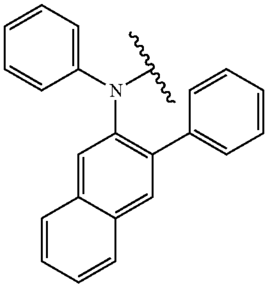
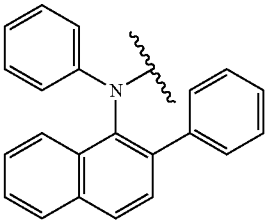

-continued

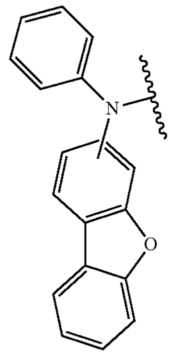

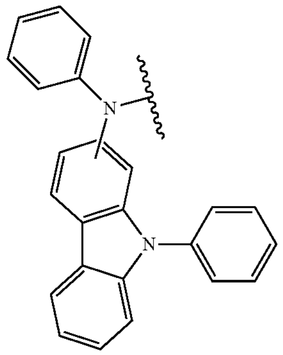

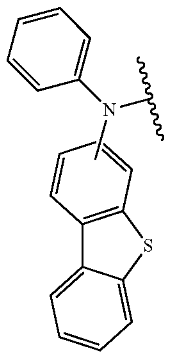

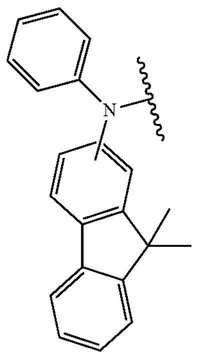

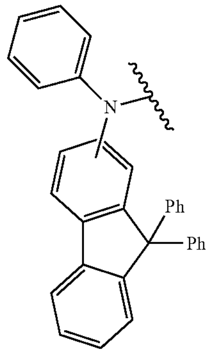

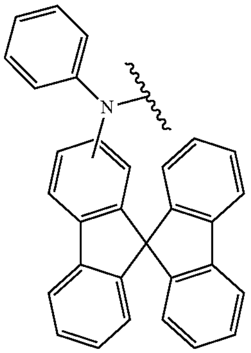

In group 2, L represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene; and $A_1$ to $A_3$, each independently, represent a substituted or unsubstituted (C1-C30) alkyl, or a substituted or unsubstituted (C6-C30)aryl. According to one embodiment of the present disclosure, L represents a single bond, a substituted or unsubstituted (C6-C25)arylene, or a substituted or unsubstituted (3- to 25-membered)heteroarylene; and $A_1$ to $A_3$, each independently, represent a substituted or unsubstituted (C1-C20) alkyl, or a substituted or unsubstituted (C6-C25)aryl. $A_1$ and $A_2$ may be the same or different. For example, $A_1$ and $A_2$, each independently, may be a methyl or a phenyl.

In any one of formulas 1-1 to 1-4, at least one of $Ar_1$(s) and $R_a$(s), each independently, may be at least one selected from those listed in the following group 3.

[Group 3]

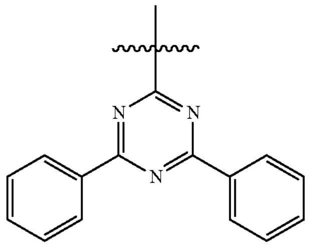

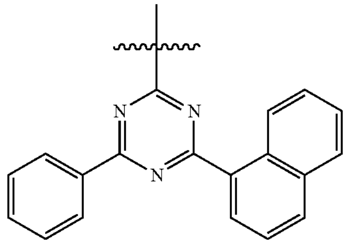

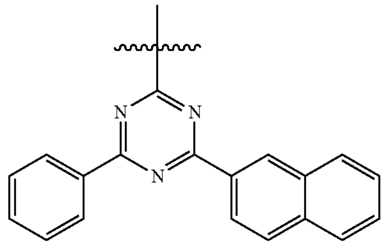

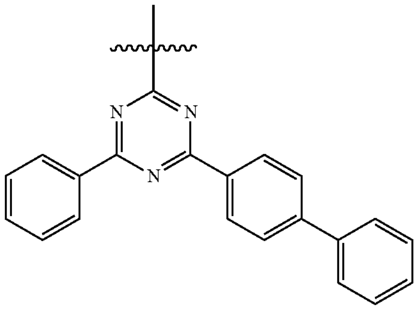

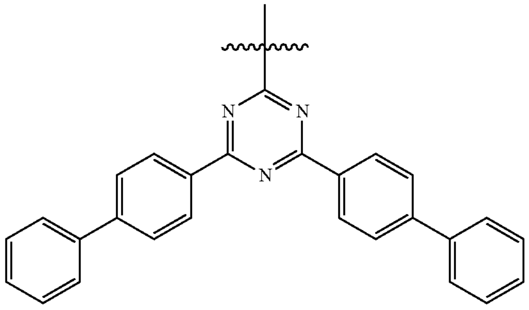

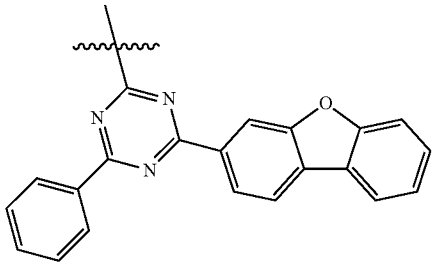

-continued
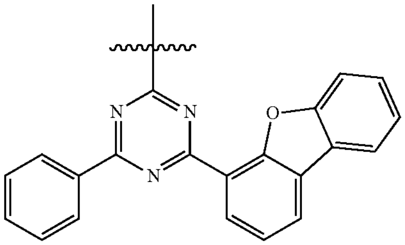
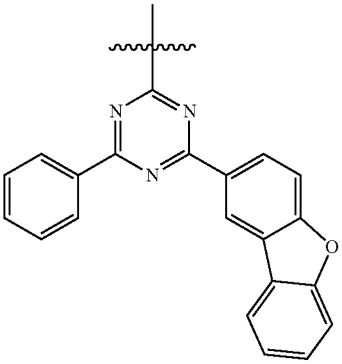
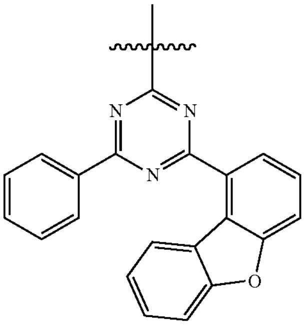
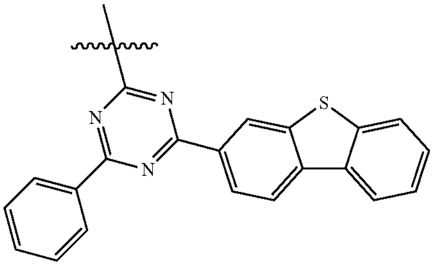
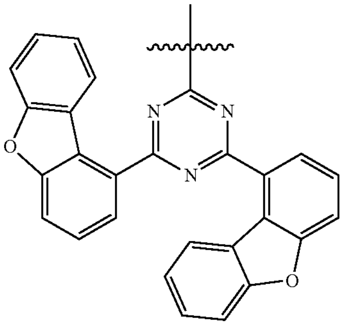
-continued
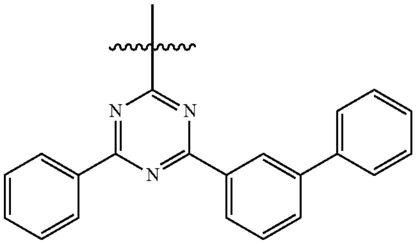
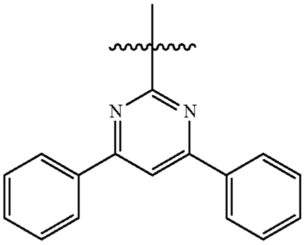
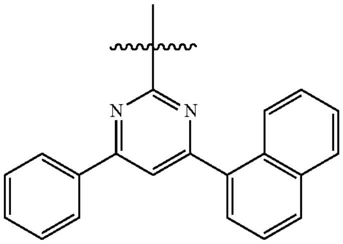
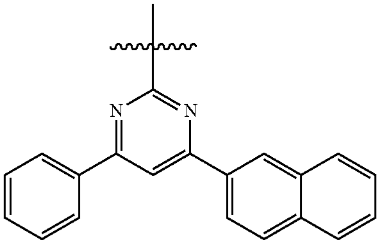
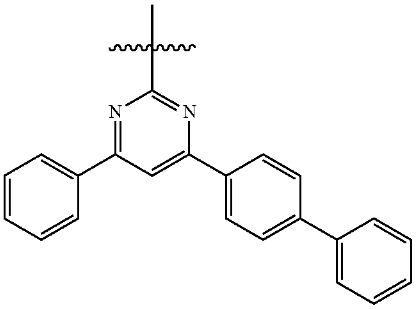
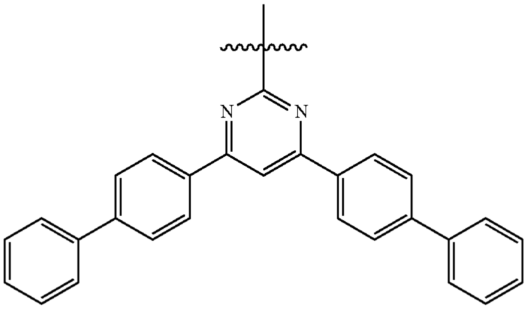

-continued
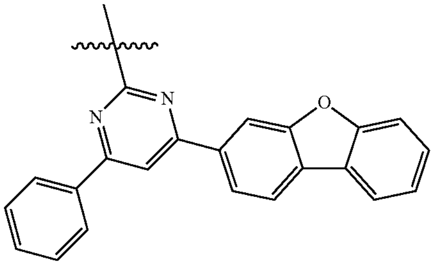
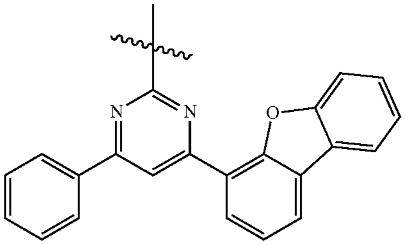
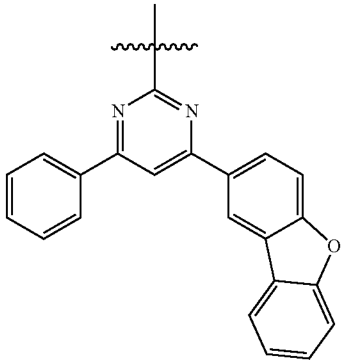
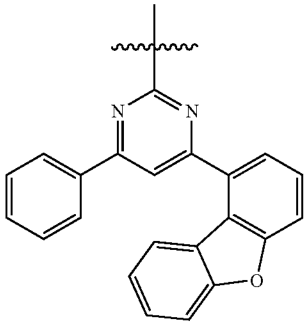
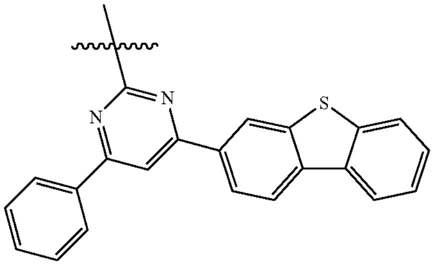
-continued
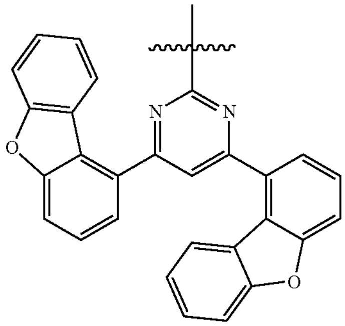
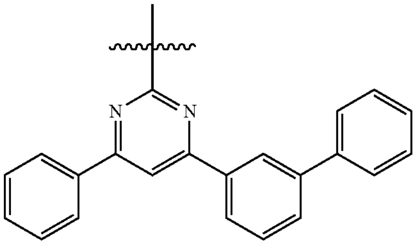
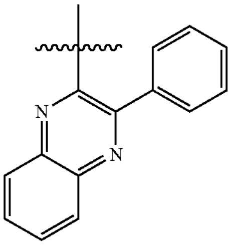
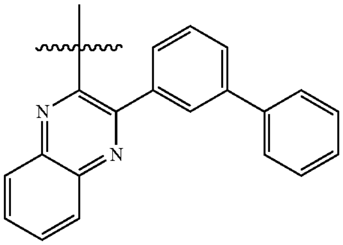
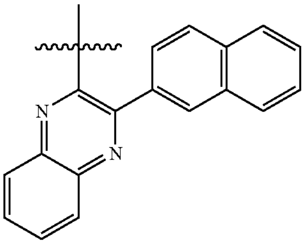
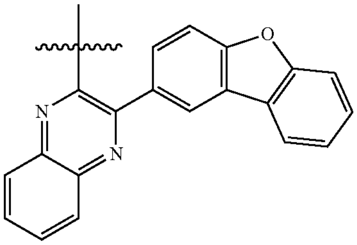

-continued
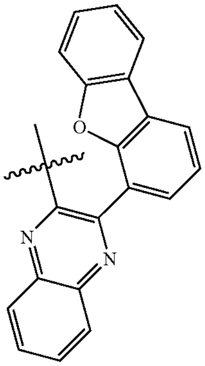
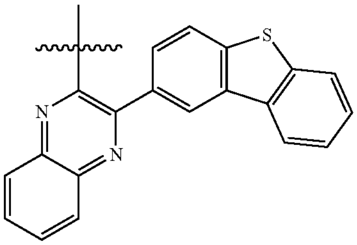
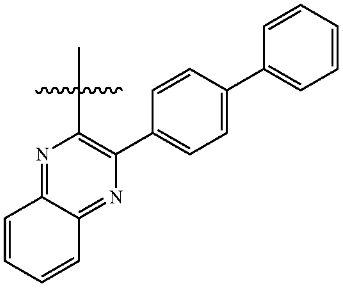
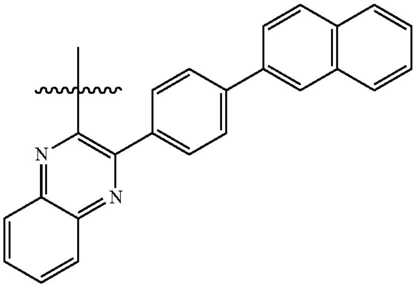
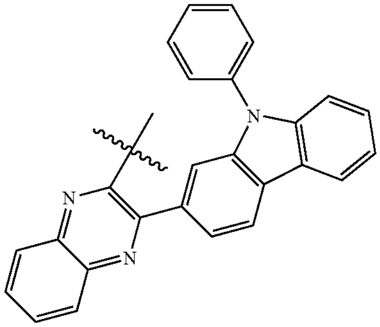
-continued
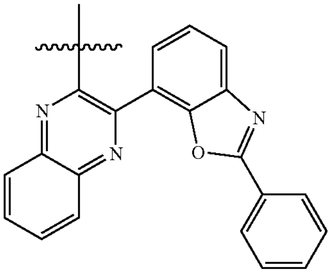
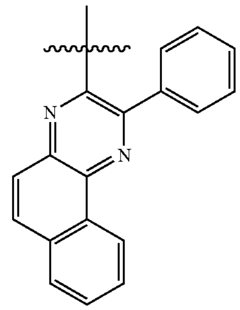
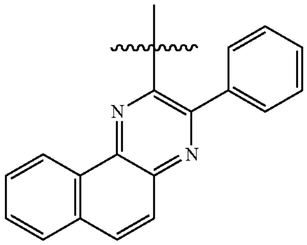
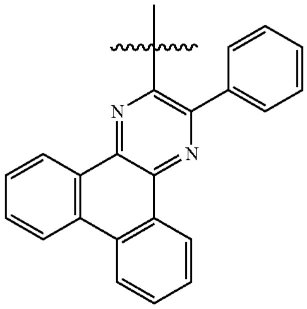
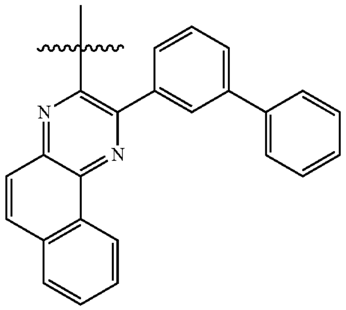
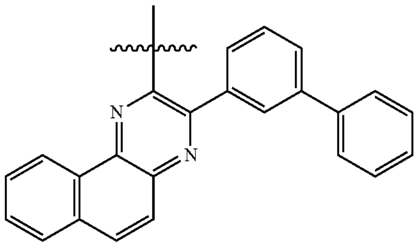

-continued
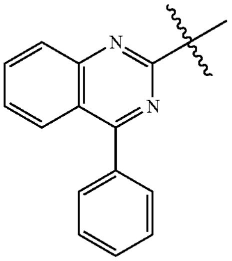
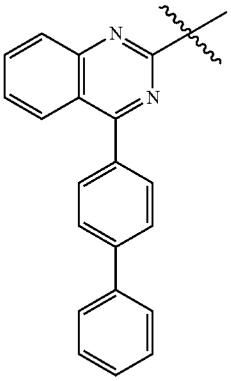
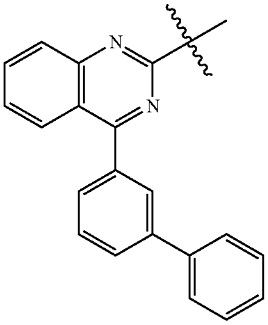
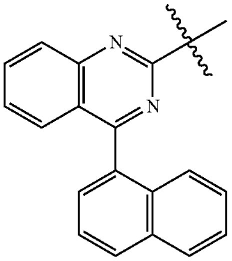
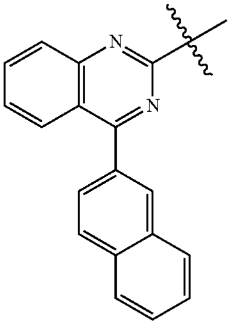
-continued
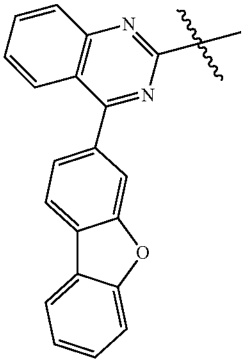
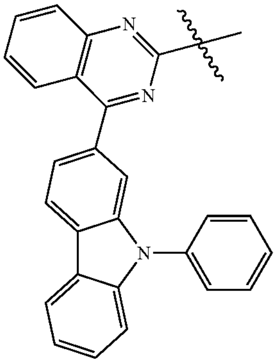
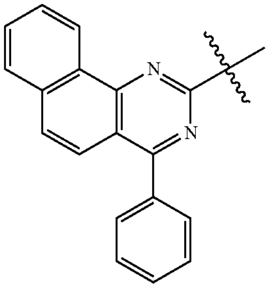
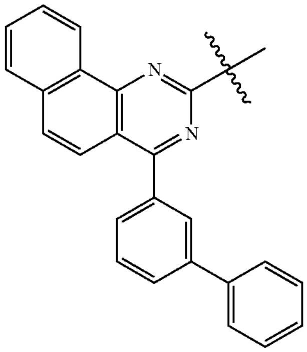
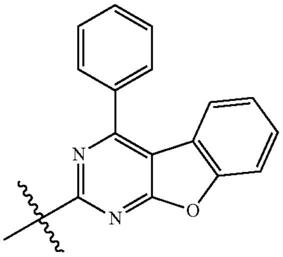

-continued
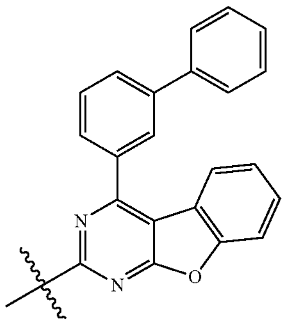
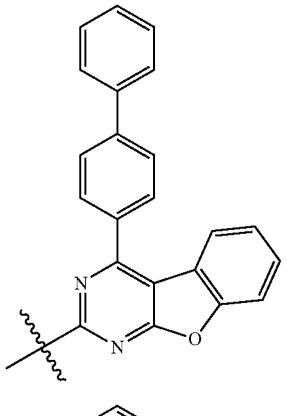
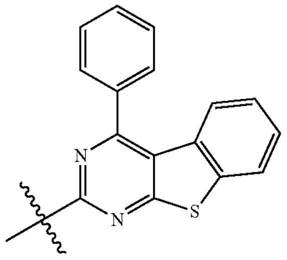
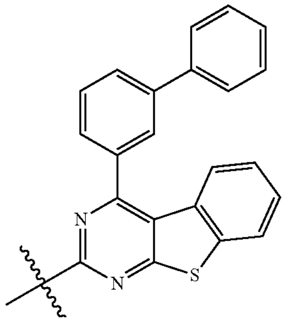
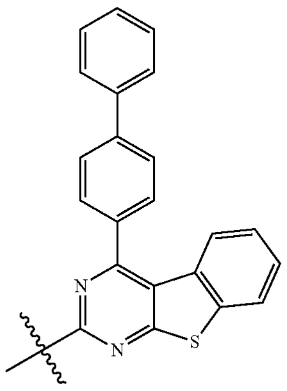
-continued
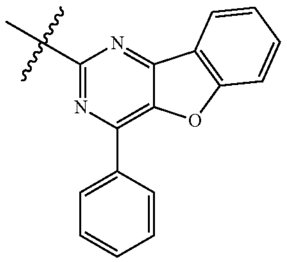
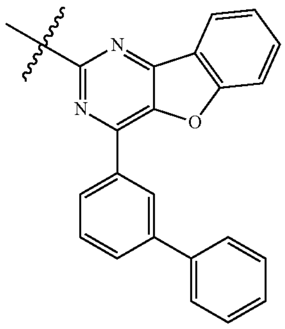
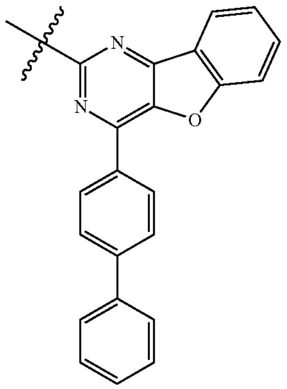
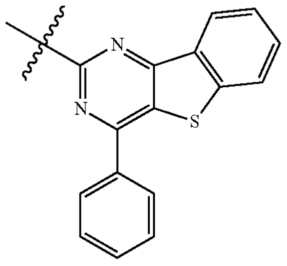
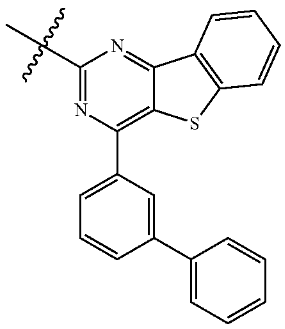

-continued
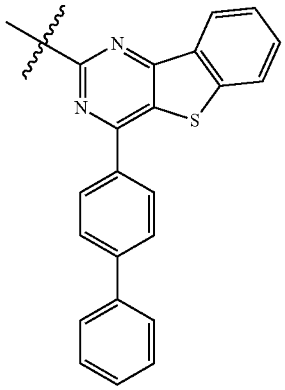
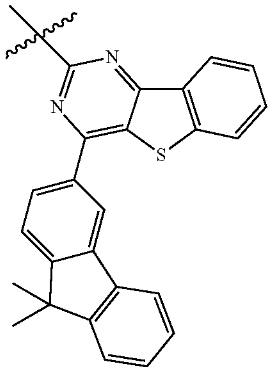
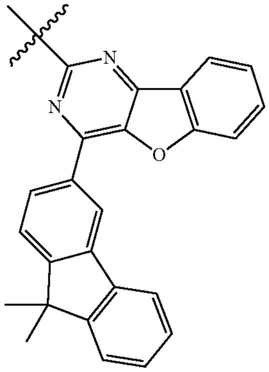
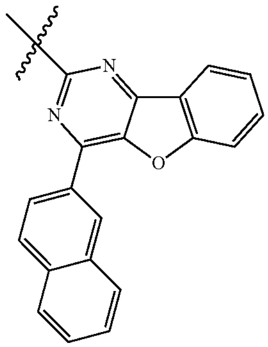
Hereinafter, the compound represented by formula 2 will be described in more detail.
According to one embodiment of the present disclosure, formula 2 may be represented by at least one selected from the following formulas 2-1 to 2-8.
(2-1)
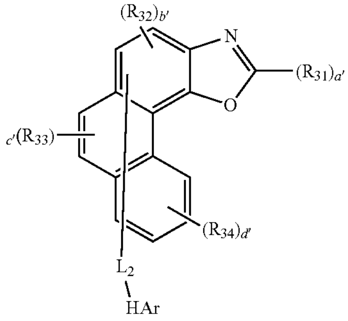
(2-2)
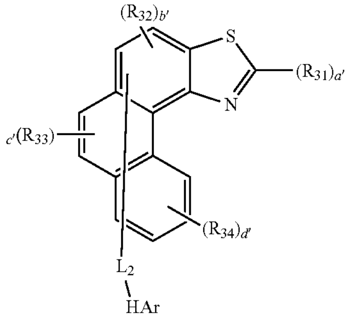
(2-3)
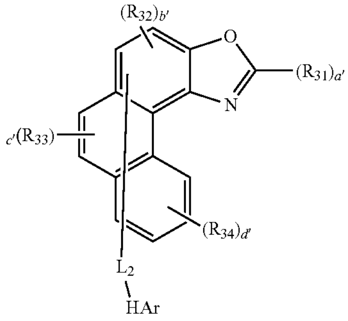
(2-4)
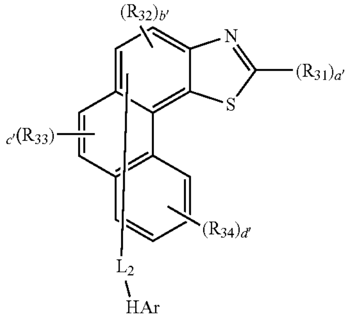
(2-5)
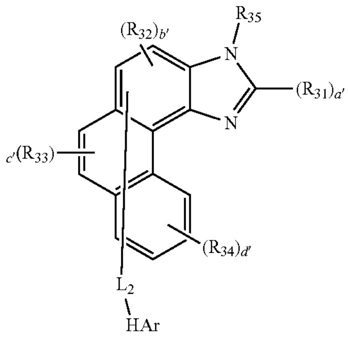

-continued (2-6)

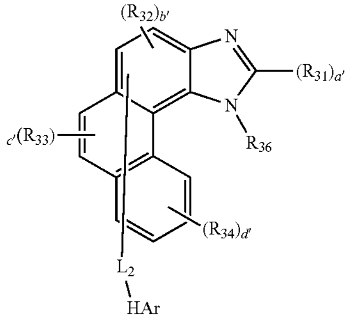

(2-7)

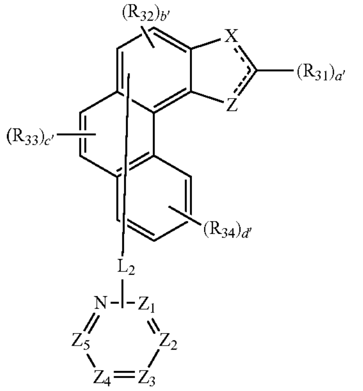

(2-8)

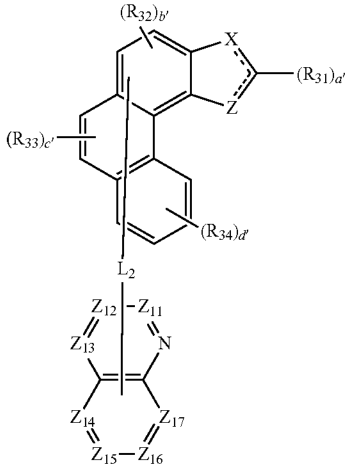

In formulas 2-1 to 2-8, X, Z, HAr, $R_{31}$ to $R_{36}$, $L_2$ and a' to d' are as defined in formula 2; $Z_1$ to $Z_5$ and $Z_{11}$ to $Z_{17}$, each independently, represent N or $CR_{37}$; and $R_{37}$, each independently, is the same as the definition of $R_{32}$ of formula 2.

According to one embodiment of the present disclosure, $R_{37}$, each independently, represents hydrogen, deuterium, a substituted or unsubstituted (C1-C30)alkyl, a substituted or unsubstituted (C6-C25)aryl, or a substituted or unsubstituted (5- to 25-membered)heteroaryl. According to another embodiment of the present disclosure, $R_{37}$, each independently, represents hydrogen; deuterium; a (C6-C18)aryl unsubstituted or substituted with at least one of a (C1-C10) alkyl(s) and a di(C6-C18)arylamino(s); or a (5- to 20-membered)heteroaryl unsubstituted or substituted with a (C6-C18)aryl(s). For example, $R_{37}$, each independently, may be hydrogen, a phenyl unsubstituted or substituted with a diphenylamino(s), a naphthyl, a biphenyl, a dimethylfluorenyl, a dimethylbenzofluorenyl, a dibenzothiophenyl, a dibenzofuranyl, a benzonaphthothiophenyl, a phenylcarbazolyl, or a phenylbenzocarbazolyl.

In formula 2, X represents —N═, —$NR_{35}$—, —O— or —S—, and Z represents —N═, —$NR_{36}$—, —O— or —S—, where if X represents —N═, Z represents —$NR_{36}$—, —O— or —S—, and if X represents —$NR_{35}$—, Z represents —N═, —O— or —S—. According to an embodiment of the present disclosure, X represents —N═, —$NR_{35}$—, —O— or —S—, and Z represents —N═, —$NR_{36}$—, —O— or —S—, with the proviso that at least one of X and Z represents —N═.

$R_{35}$ and $R_{36}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or -$L_3$-N($Ar_2$)($Ar_3$). According to one embodiment of the present disclosure, $R_{35}$ and $R_{36}$, each independently, represent a substituted or unsubstituted (C1-C20)alkyl, a substituted or unsubstituted (C6-C25)aryl, or a substituted or unsubstituted (5- to 25-membered)heteroaryl. According to another embodiment of the present disclosure, $R_{35}$ and $R_{36}$, each independently, represent an unsubstituted (C6-C18)aryl. For example, $R_{35}$ and $R_{36}$ may be a phenyl.

In formula 2, HAr represents a substituted or unsubstituted (3- to 30-membered)heteroaryl. According to one embodiment of the present disclosure, HAr represents a substituted or unsubstituted (3- to 30-membered)heteroaryl containing a nitrogen atom(s). According to another embodiment of the present disclosure, HAr represents a substituted or unsubstituted (5- to 25-membered)heteroaryl containing a nitrogen atom(s). According to further embodiment of the present disclosure, HAr represents a (5- to 20-membered) heteroaryl containing a nitrogen atom(s), substituted with a (5- to 25-membered)heteroaryl(s) and/or a (C6-C25)aryl(s). Specifically, HAr may be a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzothienopyrimidinyl. For example, HAr may be a substituted triazinyl, a substituted pyrimidinyl, a substituted quinoxalinyl, a substituted quinazolinyl, or a substituted naphthyridinyl. The substituents of the substituted triazinyl, the substituted pyrimidinyl, the substituted quinoxalinyl, the substituted quinazolinyl, and the substituted naphthyridinyl may be at least one of a phenyl unsubstituted or substituted with a diphenylamino(s), a naphthyl, a biphenyl, a dimethylfluorenyl, a dimethylbenzofluorenyl, a dibenzothiophenyl, a dibenzofuranyl, a benzonaphthothiophenyl, a phenylcarbazolyl, and a phenylbenzocarbazolyl.

In formula 2, $R_{31}$ represents a substituted or unsubstituted (C6-C30)aryl, or a substituted or unsubstituted (3- to 30-membered)heteroaryl. According to one embodiment of the present disclosure, $R_{31}$ represents a substituted or unsubstituted (C6-C30)aryl, or a substituted or unsubstituted (5- to 25-membered)heteroaryl. According to another embodiment of the present disclosure, $R_{31}$ represents a (C6-C29)aryl unsubstituted or substituted with at least one of a (C1-C10)

alkyl(s) and a (C6-C18)aryl(s); or a (5- to 25-membered) heteroaryl unsubstituted or substituted with a (C6-C18) aryl(s). For example, $R_{31}$ may be a phenyl, a naphthyl, a phenylnaphthyl, a biphenyl, a dimethylfluorenyl, a dimethylbenzofluorenyl, a spirobifluorenyl, a spiro[fluoren-benzofluoren]yl, a phenylcarbazolyl, a phenylbenzocarbazolyl, a dibenzofuranyl, or a dibenzothiophenyl.

In formula 2, $R_{32}$ to $R_{34}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or $-L_3-N(Ar_2)(Ar_3)$; or may be linked to an adjacent substituent to form a ring(s). For example, $R_{32}$ to $R_{34}$ may represent hydrogen.

In formula 2, $L_2$ and $L_3$, each independently, represent a single bond, a substituted or unsubstituted (C6-C30)arylene, or a substituted or unsubstituted (3- to 30-membered)heteroarylene. According to one embodiment of the present disclosure, $L_2$ and $L_3$, each independently, represent a single bond, a substituted or unsubstituted (C6-C25)arylene, or a substituted or unsubstituted (5- to 25-membered)heteroarylene. According to another embodiment of the present disclosure, $L_2$ and $L_3$, each independently, represent a single bond, an unsubstituted (C6-C18)arylene, or an unsubstituted (5- to 20-membered)heteroarylene. For example, $L_2$ and $L_3$, each independently, may be a single bond, a phenylene, or a pyridylene.

In formula 2, $Ar_2$ and $Ar_3$, each independently, represent hydrogen, a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl.

In formula 2, a' represents 1, b' and c', each independently, represent an integer of 1 or 2, and d' represents an integer of 1 to 4, where if each of b', c' and d' is an integer of 2 or more, each of $R_{32}$ to each of $R_{34}$ may be the same or different.

The compound represented by formula 1 may be at least one selected from the following compounds, but is not limited thereto.

C-1

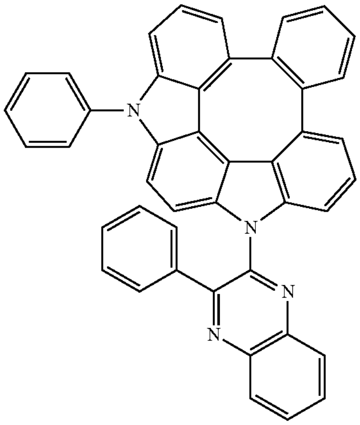

-continued

C-2

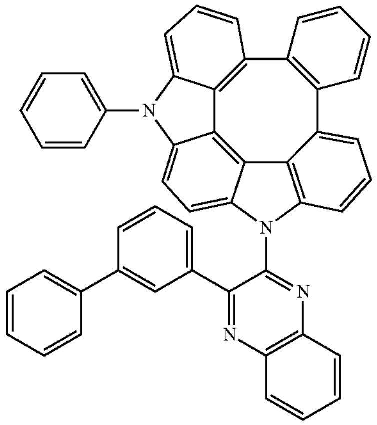

C-3

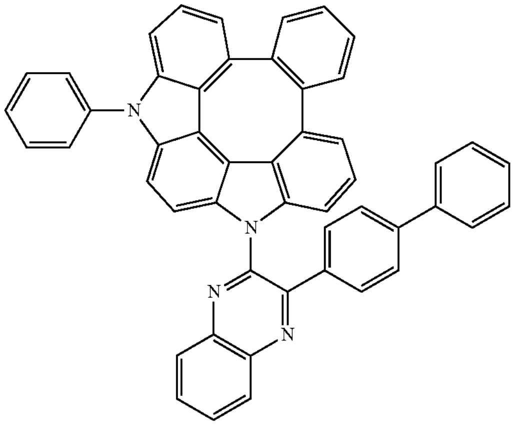

C-4

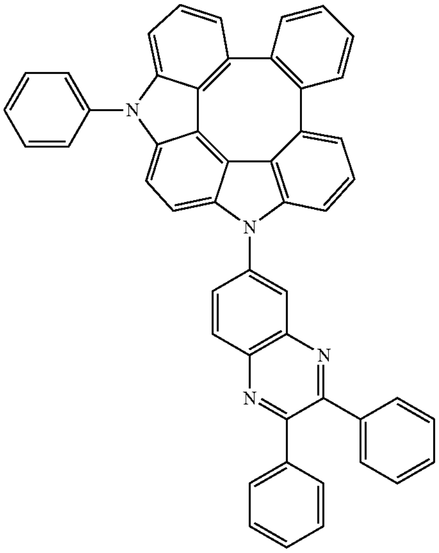

-continued
C-5
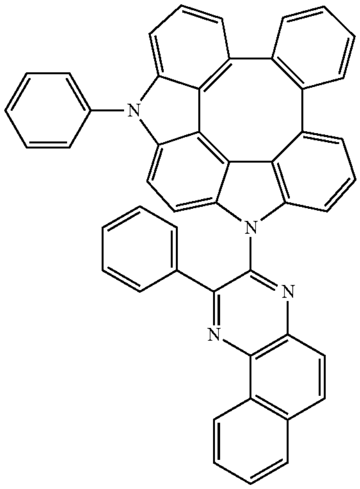
C-6
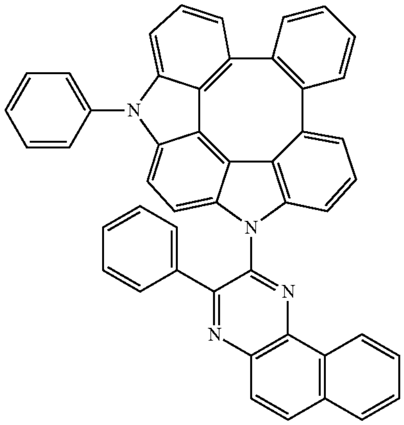
C-7
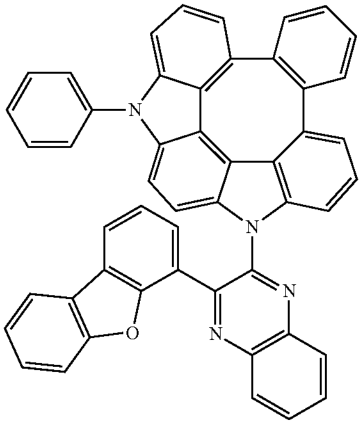
-continued
C-8
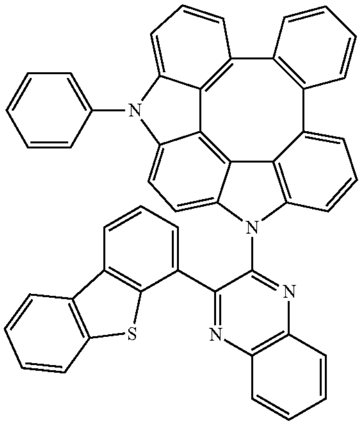
C-9
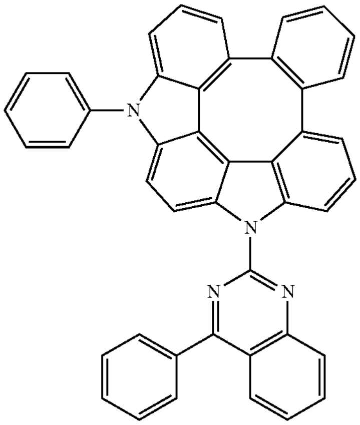
C-10
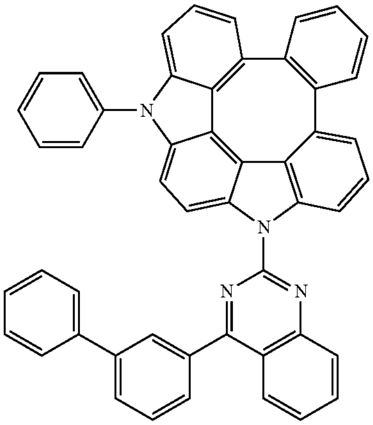

-continued
C-11
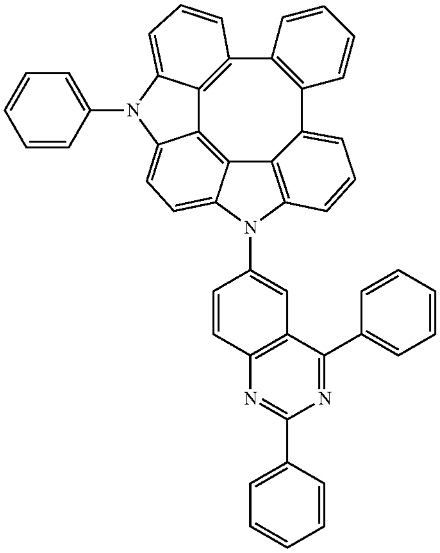
C-12
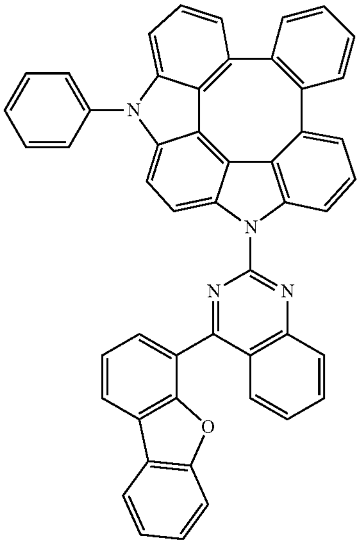
C-13
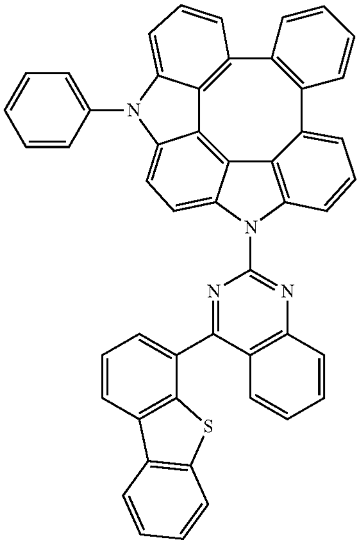
-continued
C-14
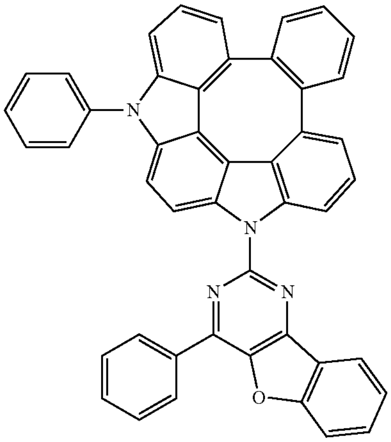
C-15
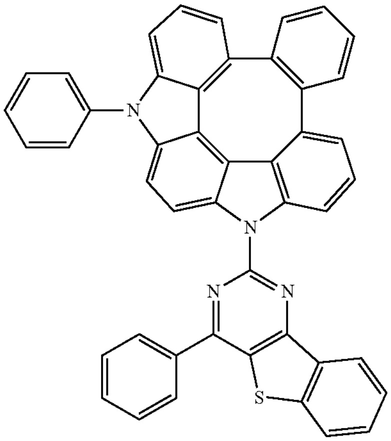
C-16
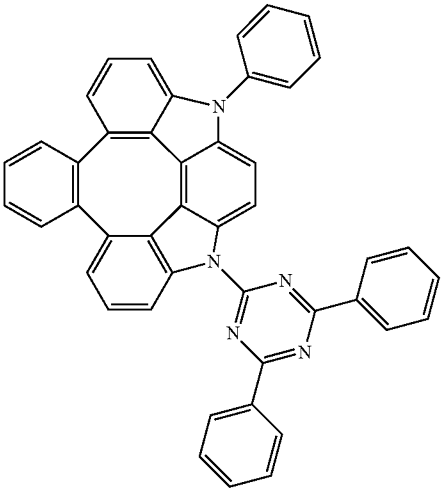

-continued
C-17
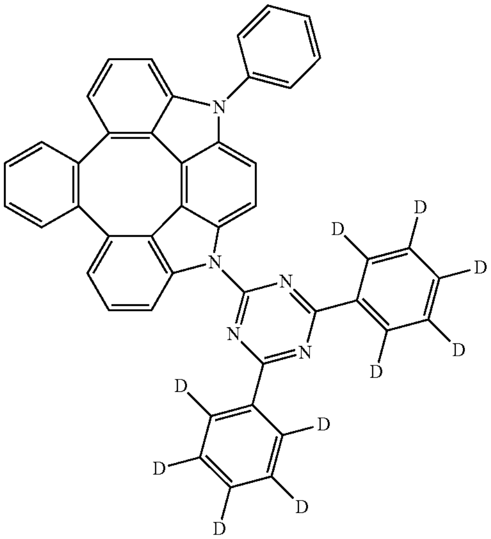
C-18
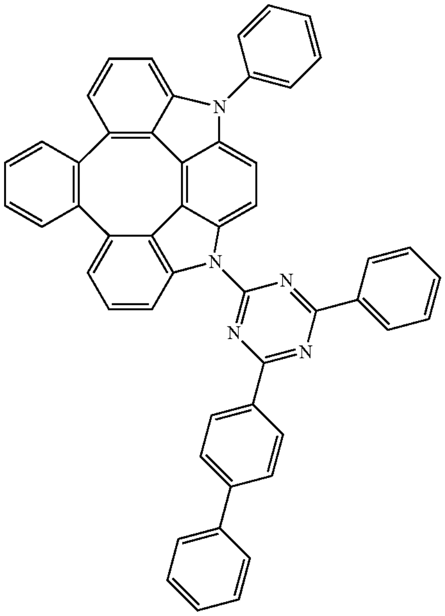
-continued
C-19
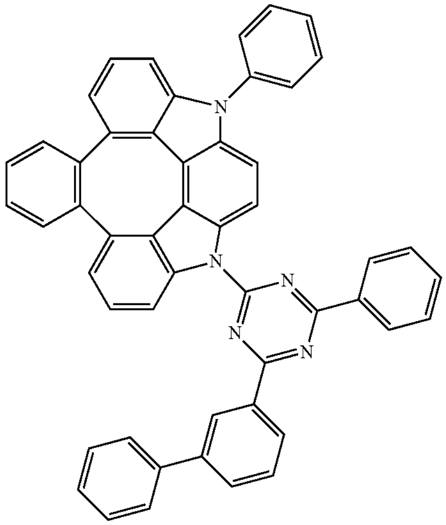
C-20
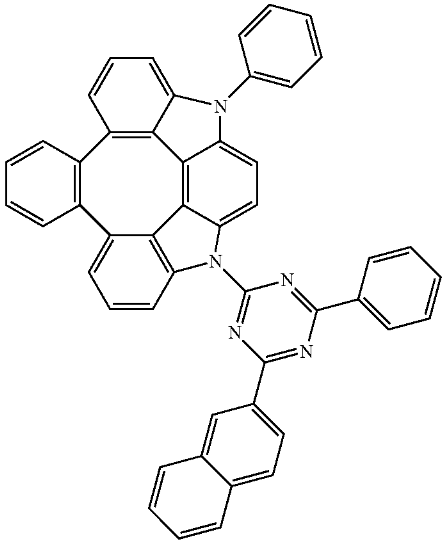

-continued
C-21
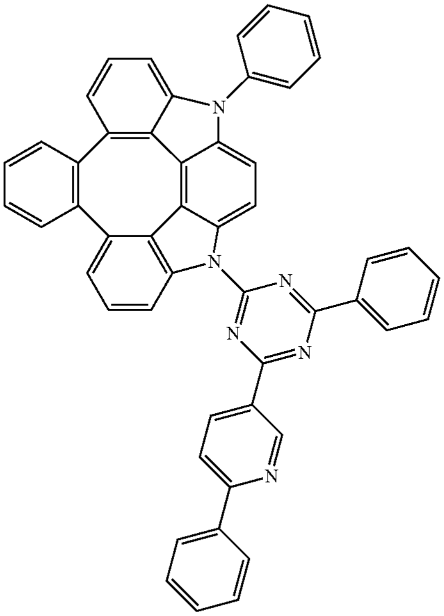
C-22
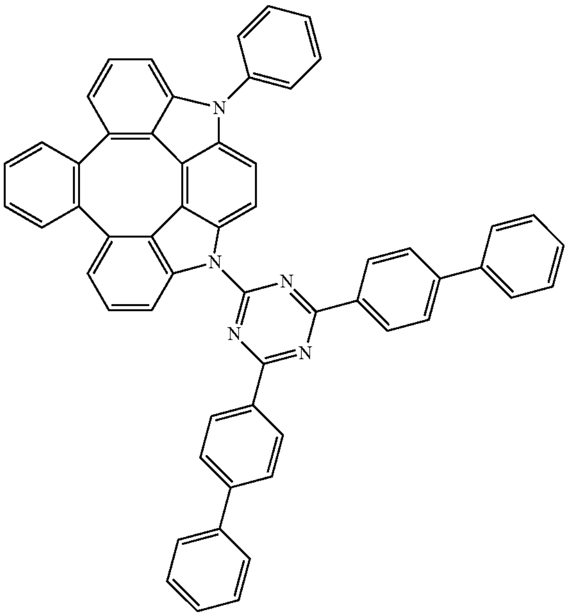
-continued
C-23
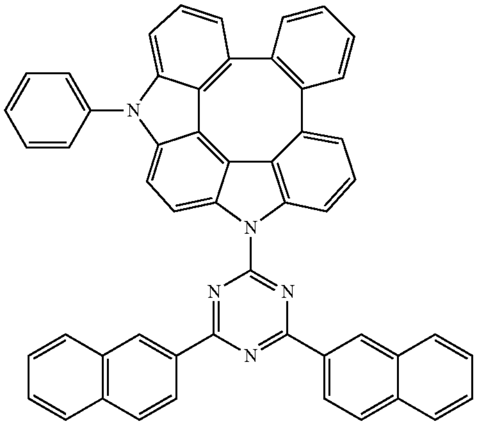
C-24
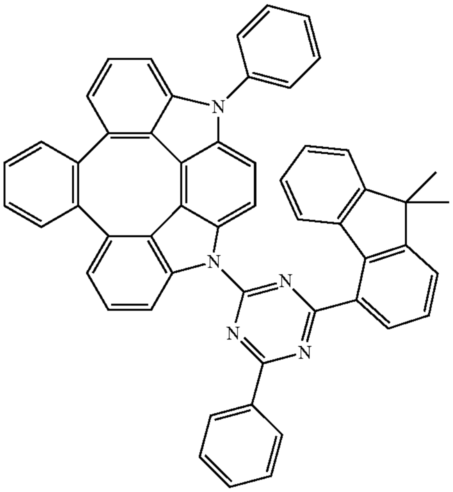
C-25
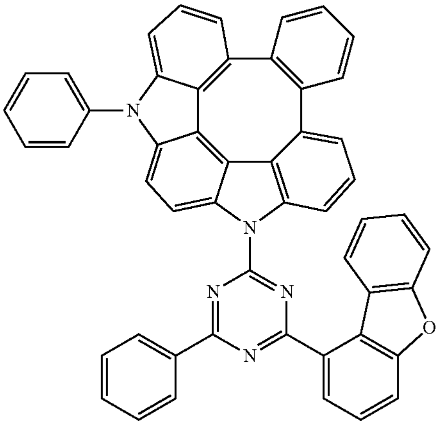

-continued
C-26
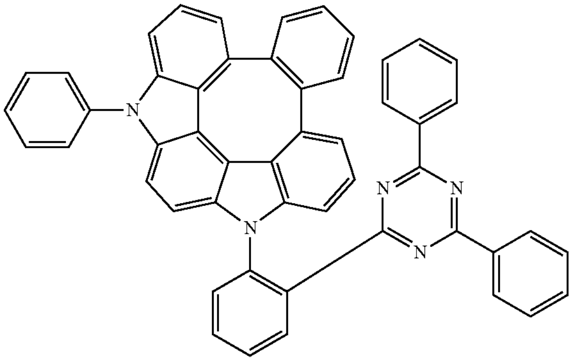
C-27
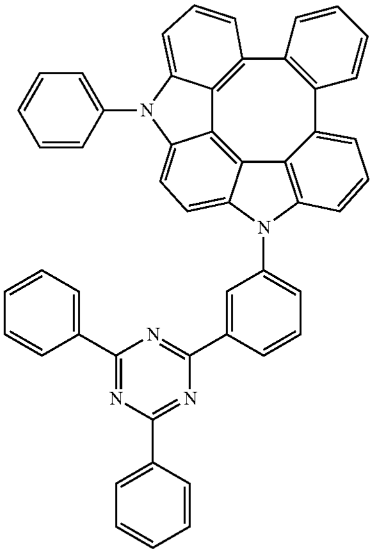
C-28
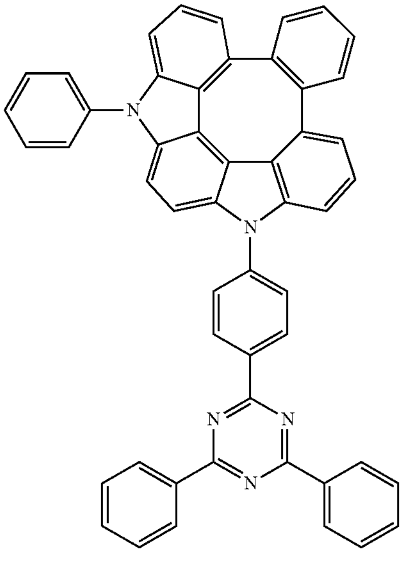
-continued
C-29
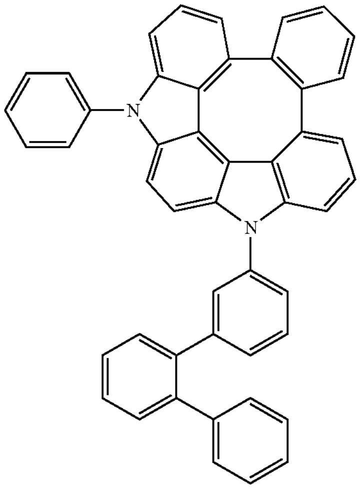
C-30
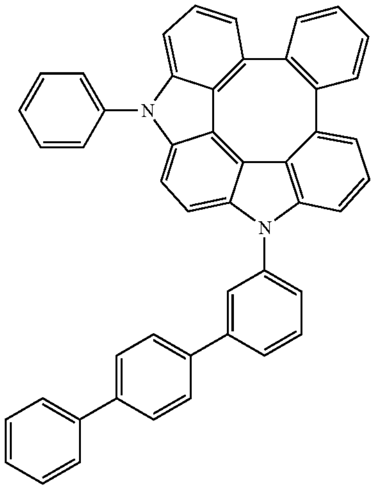
C-31
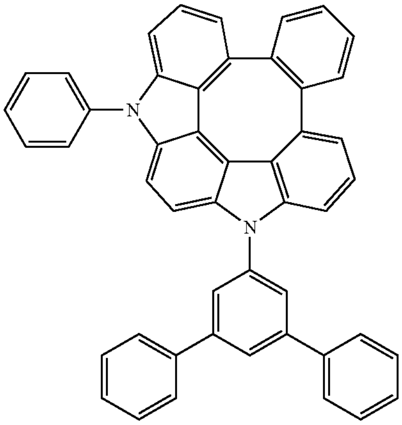

-continued
C-32
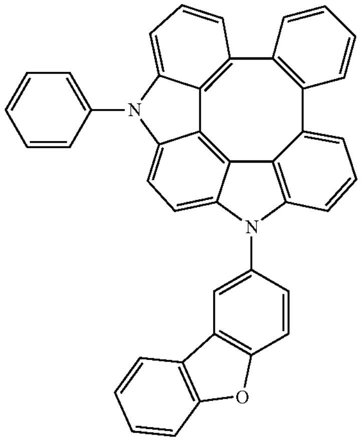
C-33
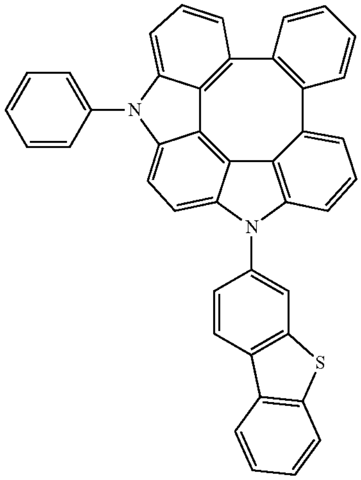
C-34
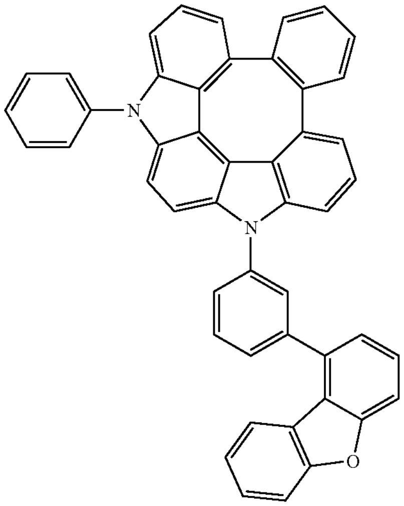
-continued
C-35
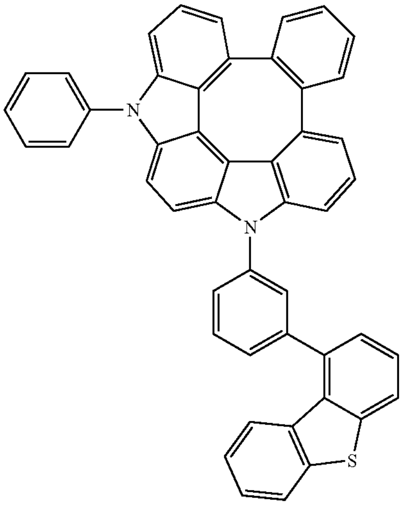
C-36
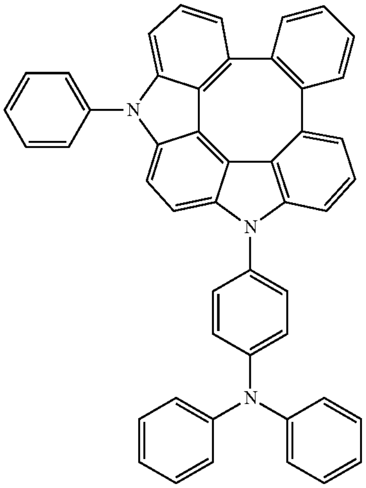
C-37
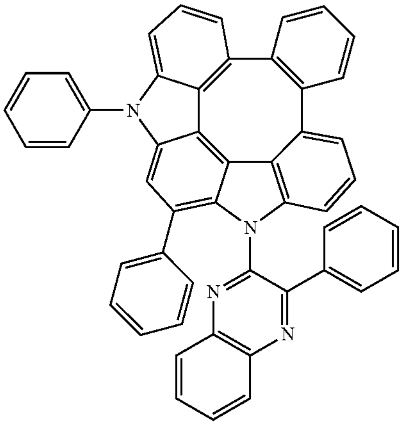

-continued
C-38
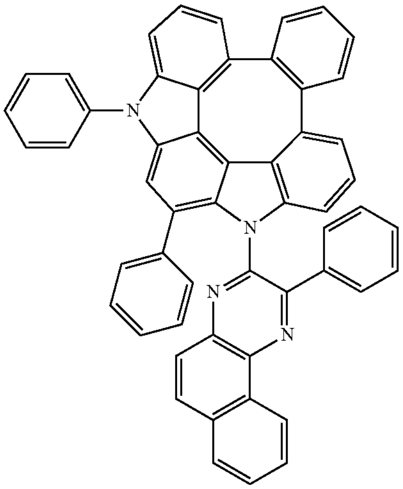
C-39
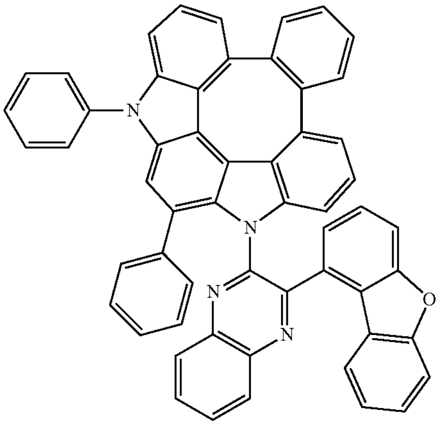
C-40
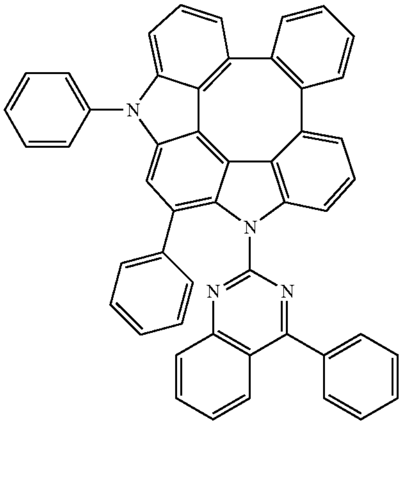
-continued
C-41
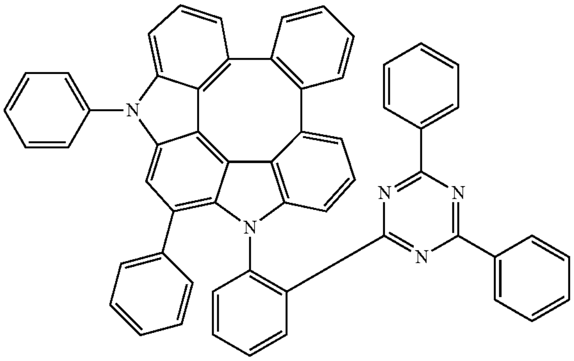
C-42
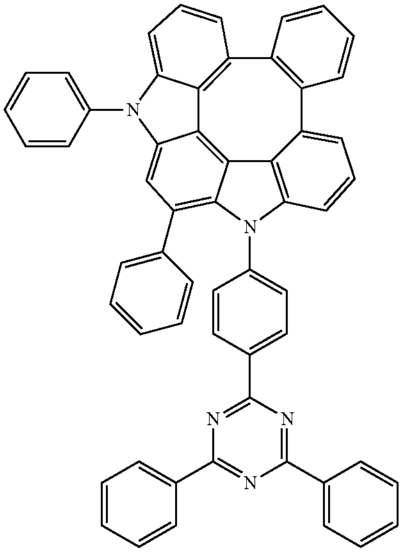
C-43
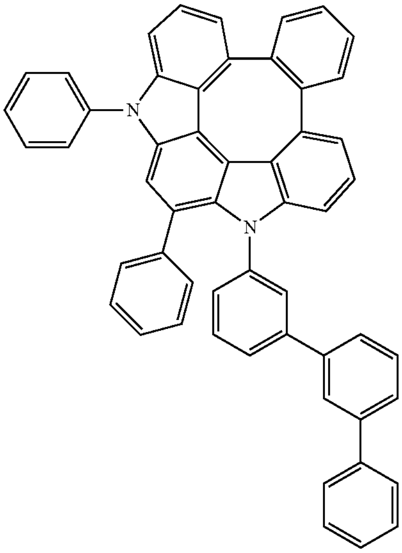

-continued
C-44
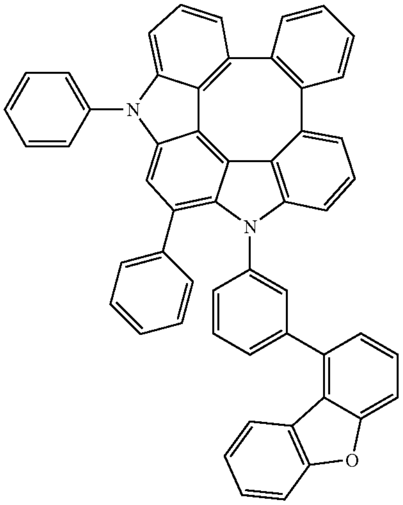
C-45
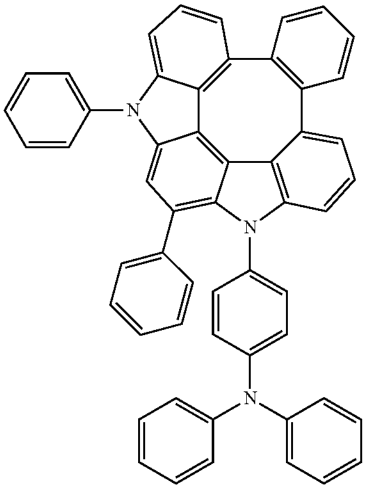
C-46
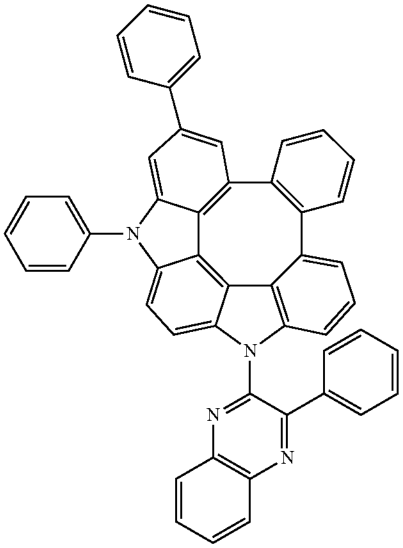
-continued
C-47
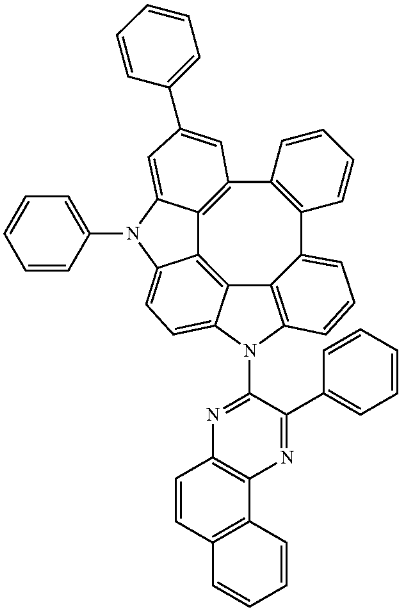
C-48
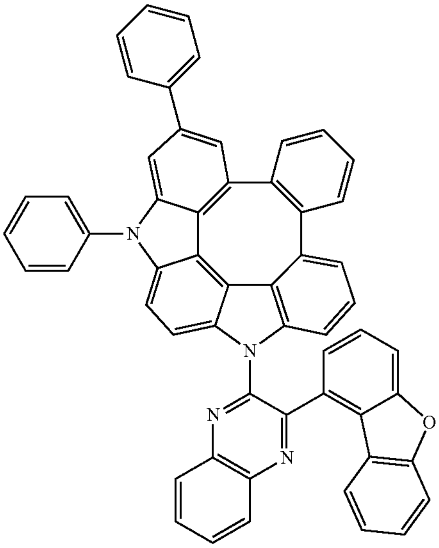

-continued
C-49
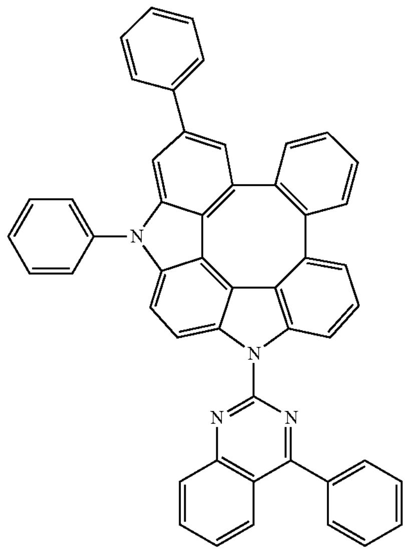
C-50
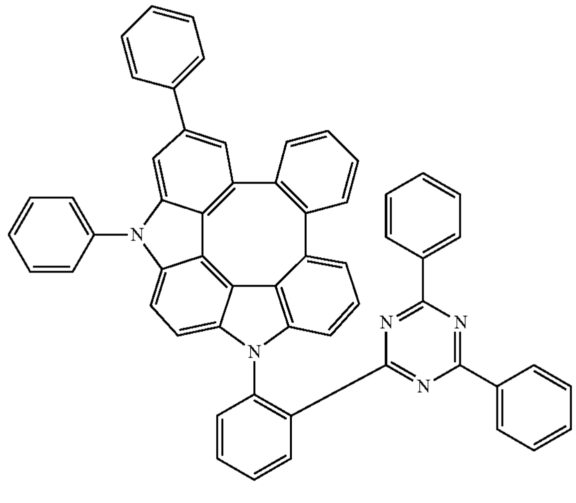
-continued
C-51
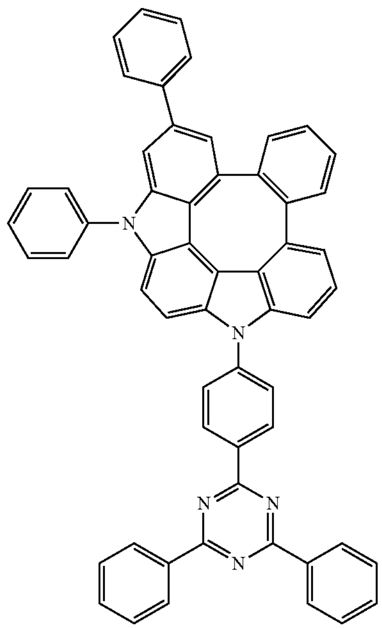
C-52
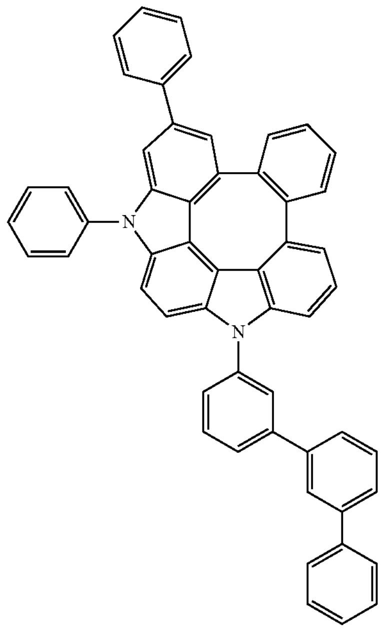

-continued
C-53
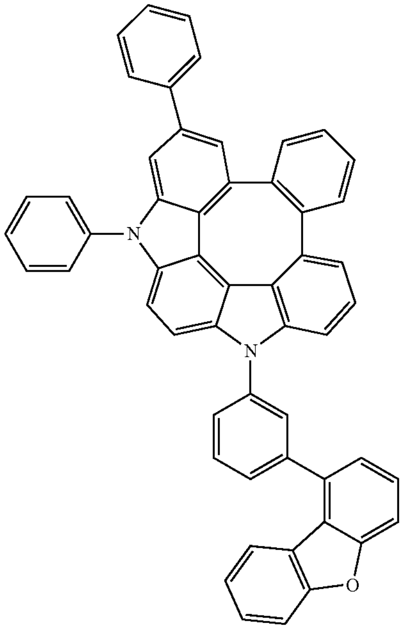
C-54
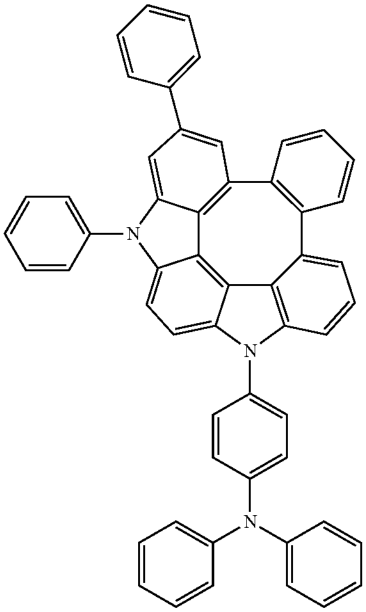
C-55
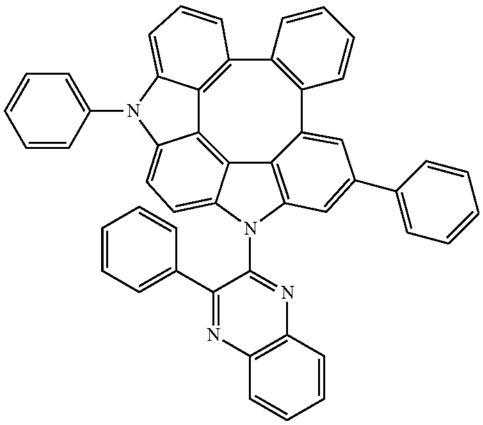
-continued
C-56
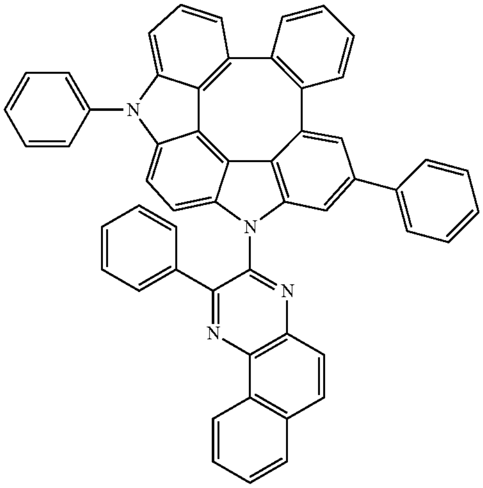
C-57
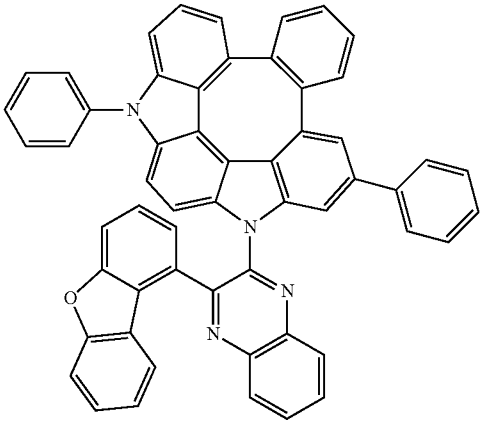
C-58
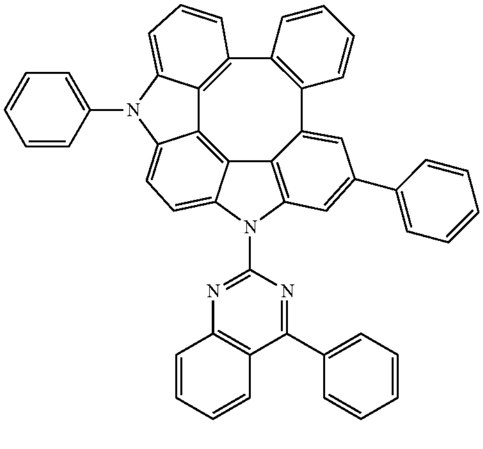

C-59
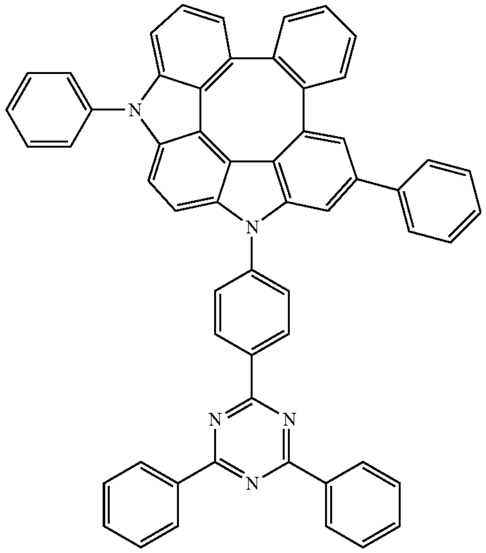
C-60
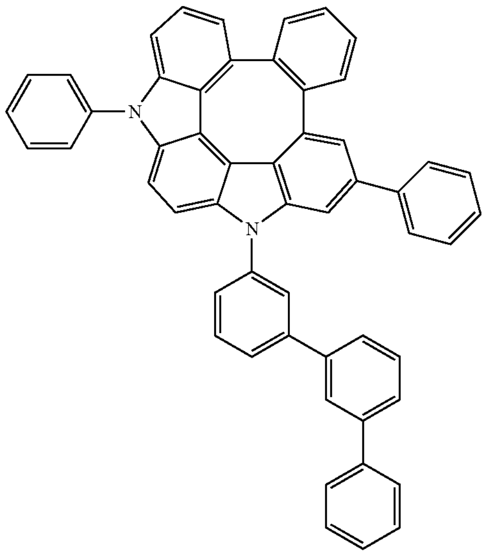
C-61
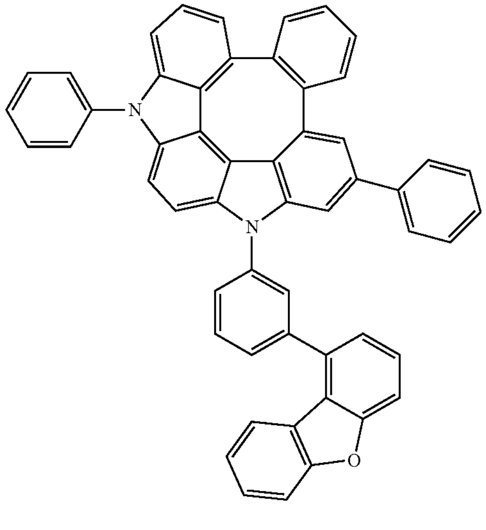
C-62
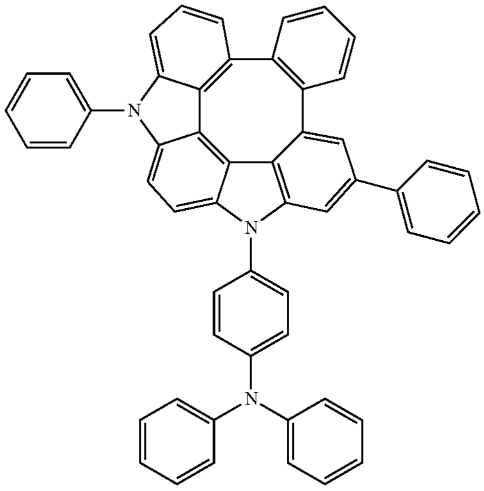
C-63
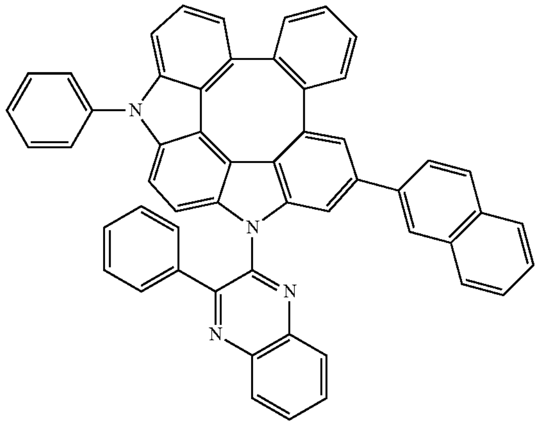
C-64
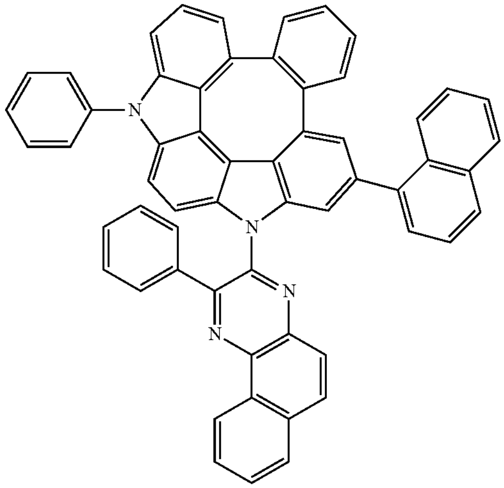

-continued
C-65
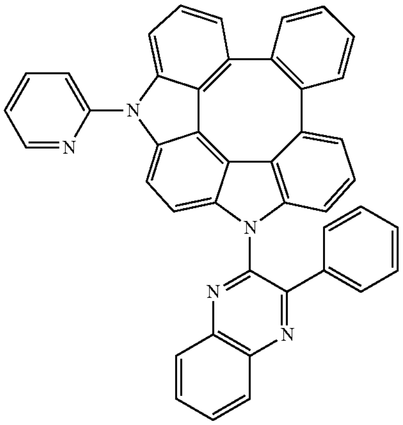
C-66
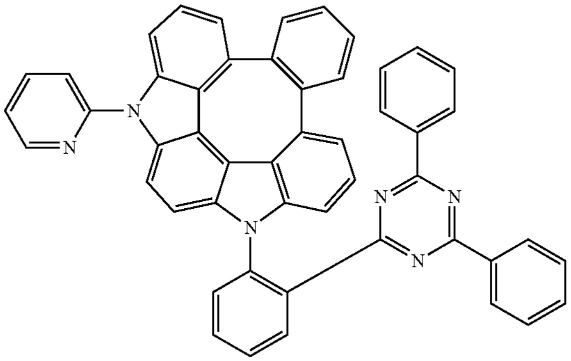
C-67
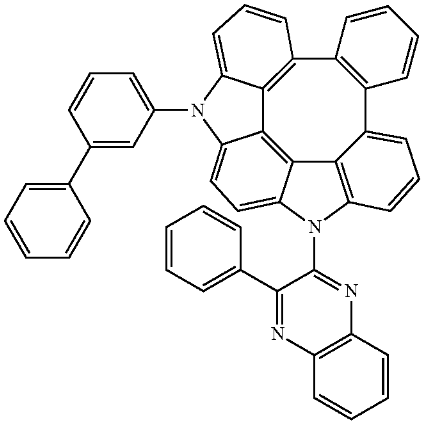
-continued
C-68
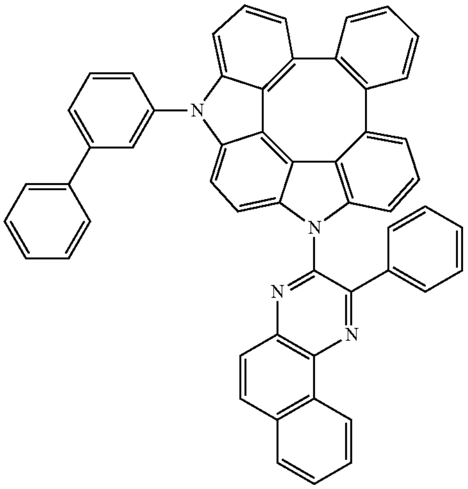
C-69
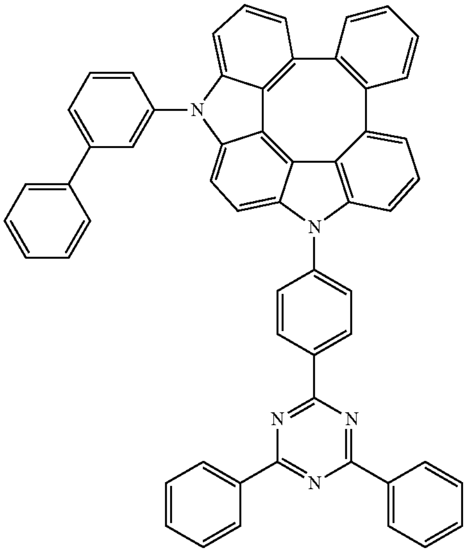
C-70
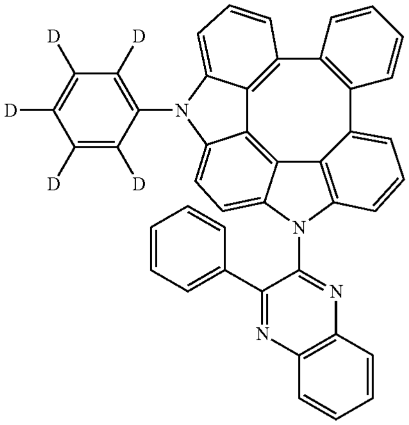

-continued
C-71
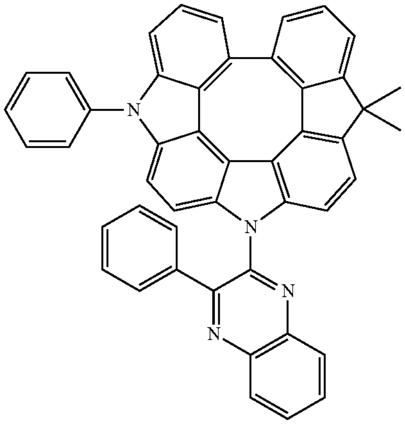
C-72
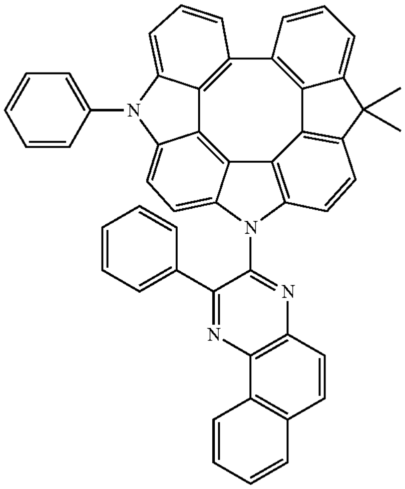
C-73
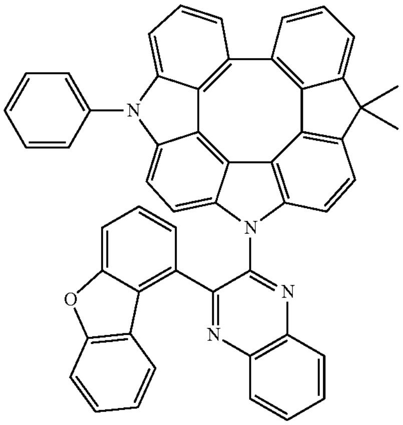
-continued
C-74
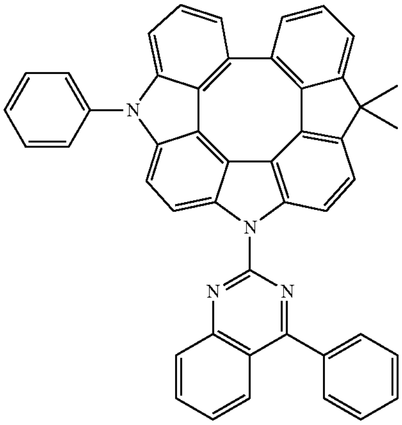
C-75
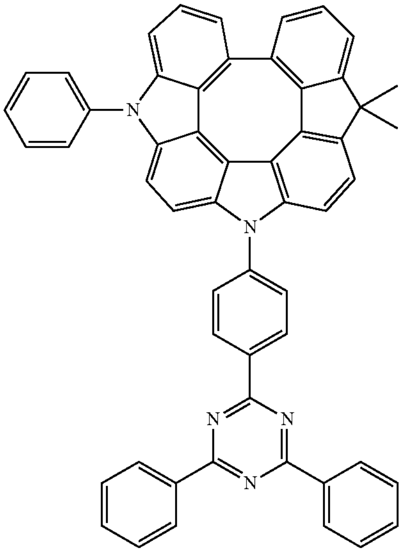
C-76
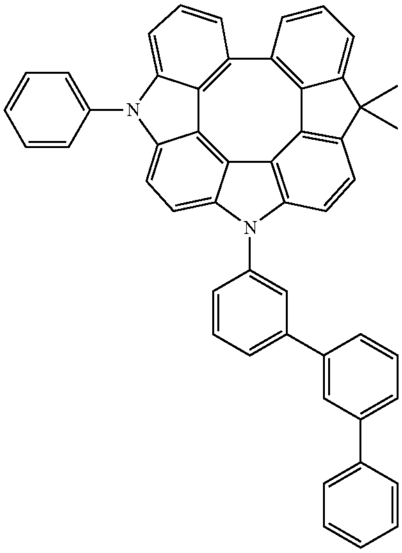

-continued
C-77
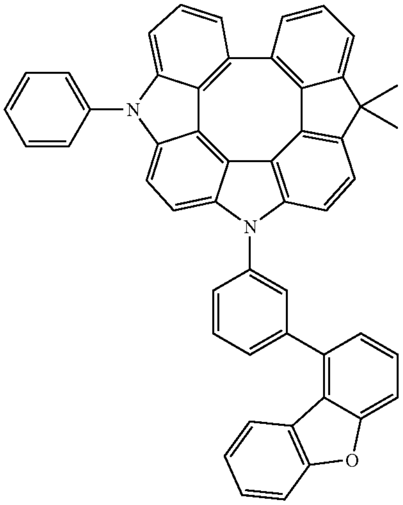
C-78
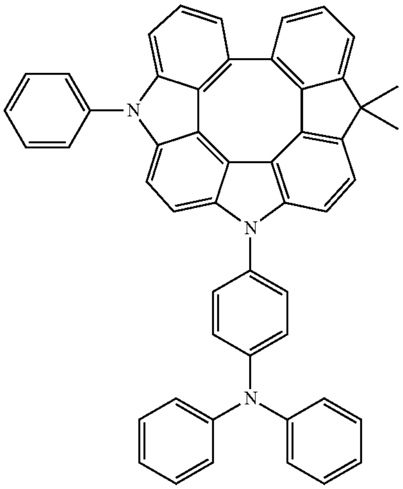
C-79
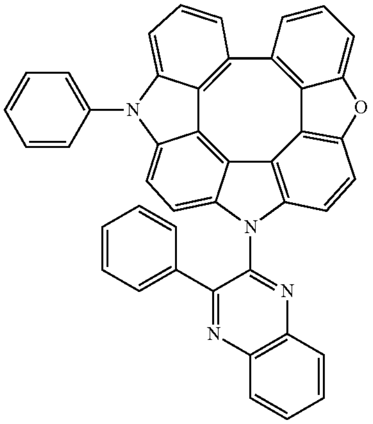
-continued
C-80
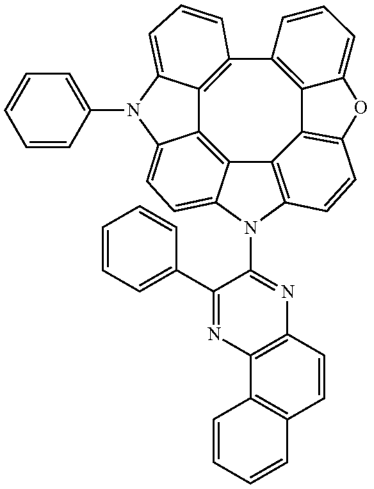
C-81
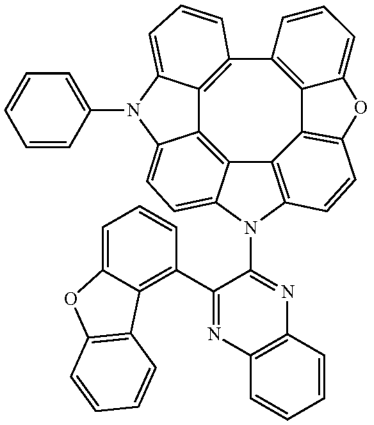
C-82
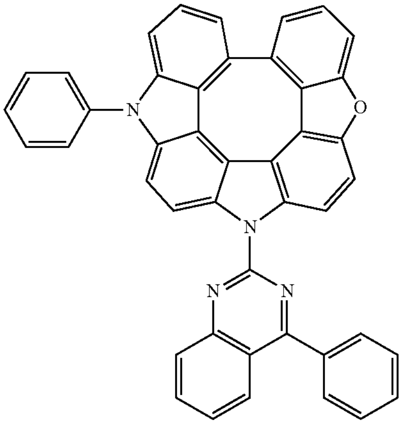

-continued
C-83
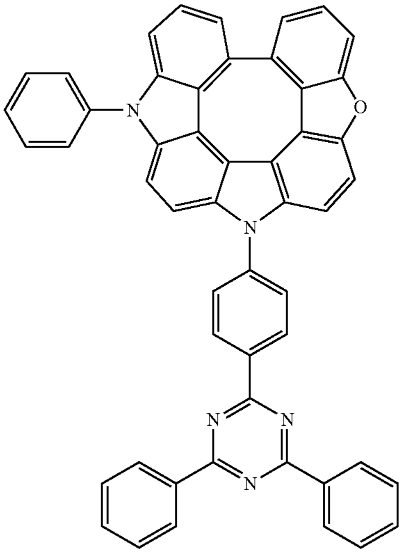
C-84
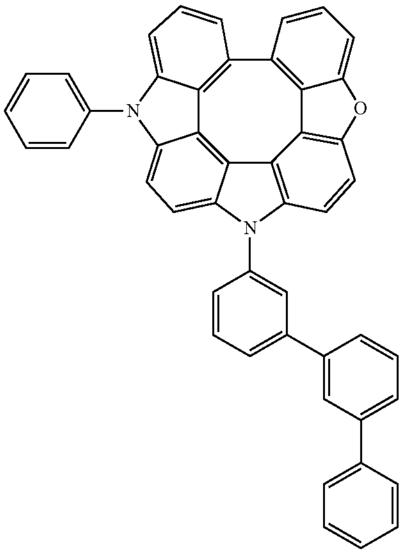
C-85
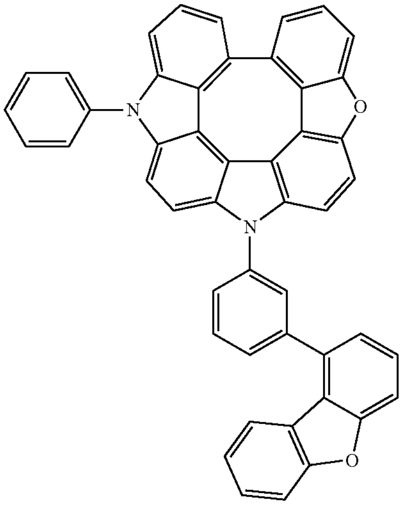
-continued
C-86
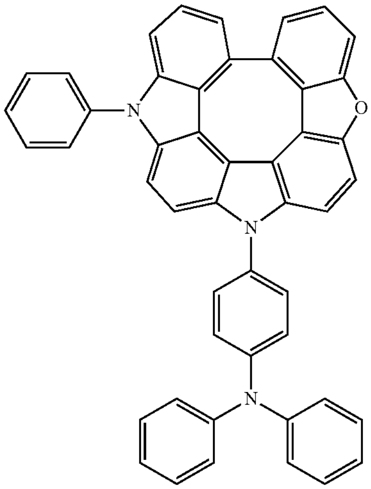
C-87
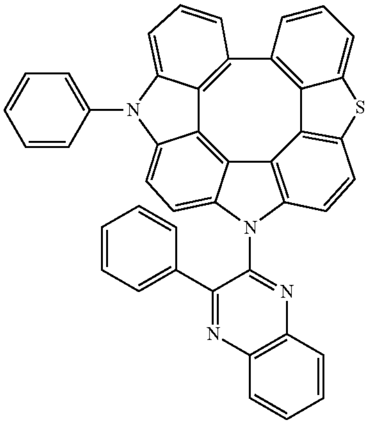
C-88
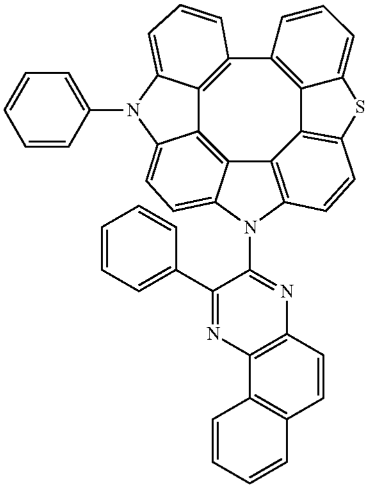

-continued
C-89
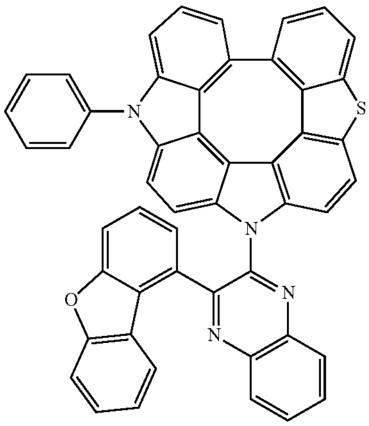
C-90
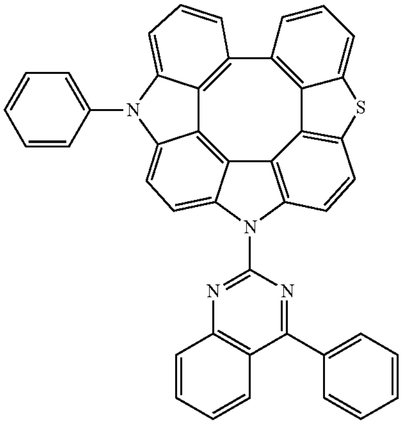
C-91
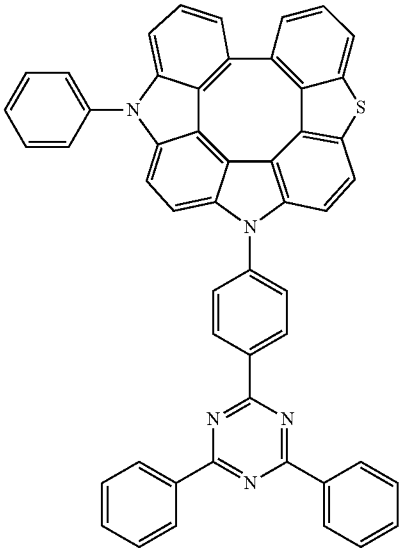
-continued
C-92
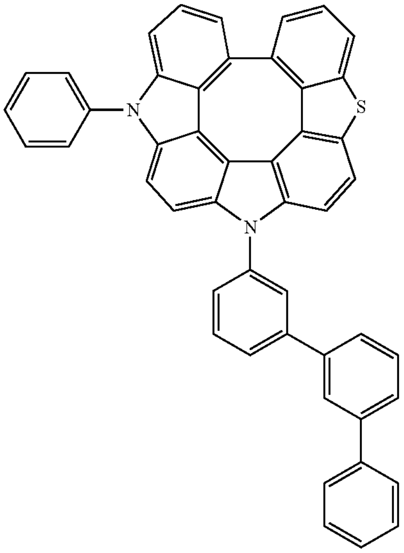
C-93
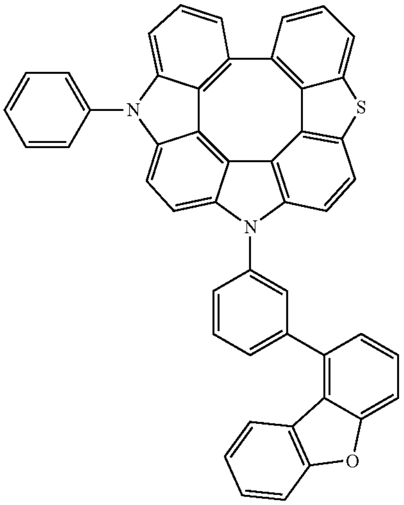
C-94
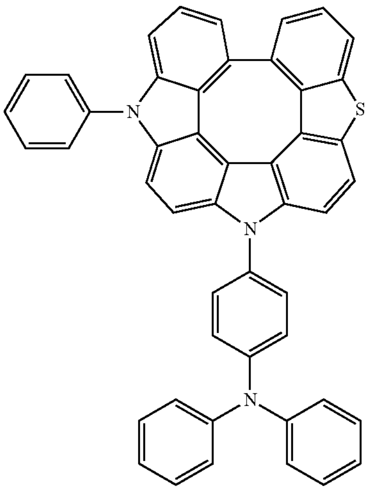

-continued
C-95
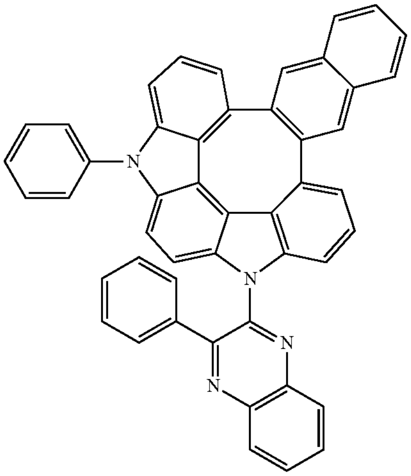
C-96
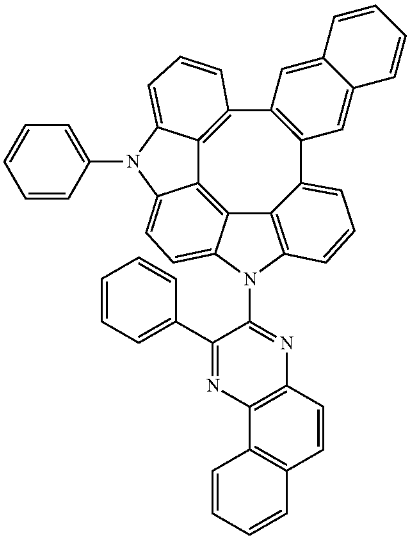
C-97
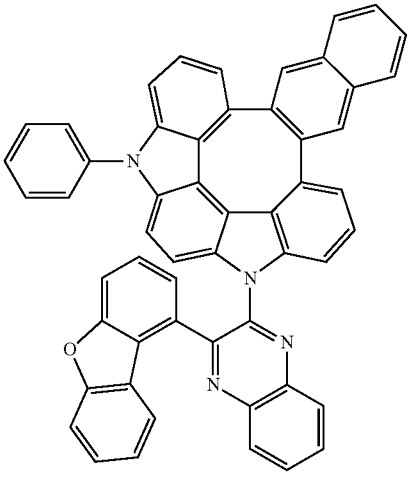
-continued
C-98
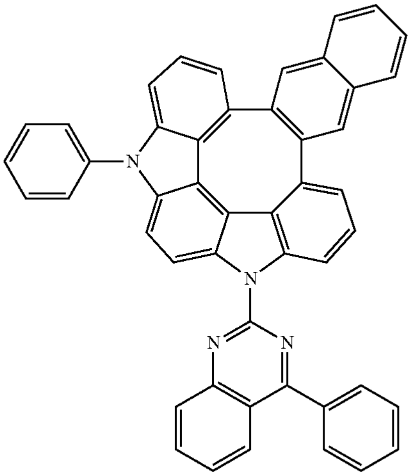
C-99
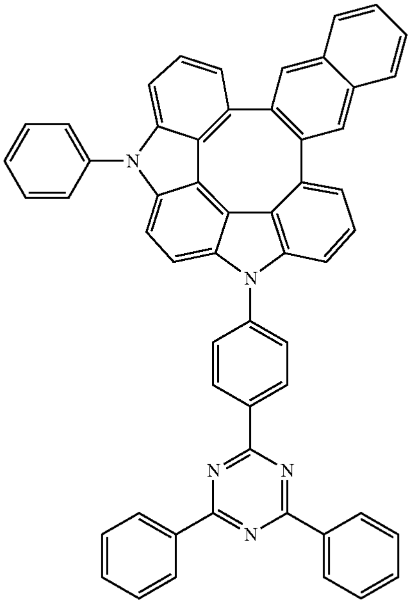

-continued
C-100
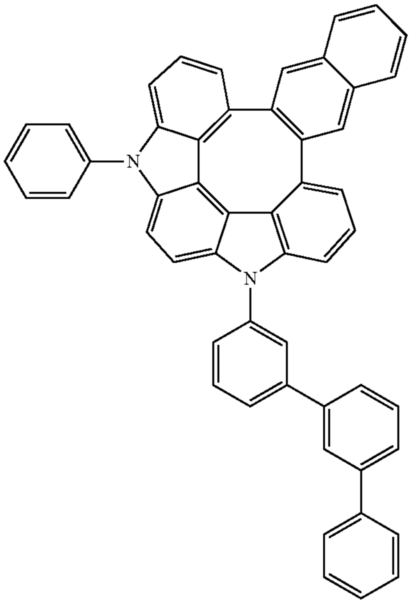
C-101
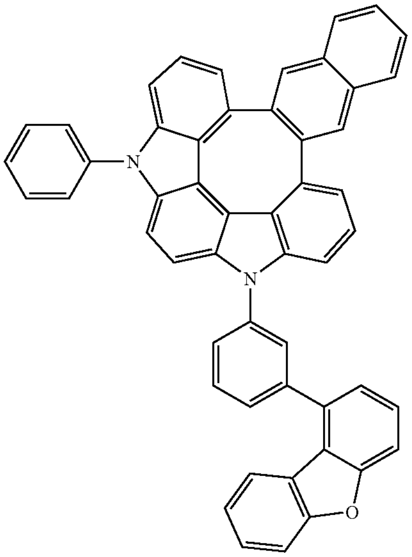
-continued
C-102
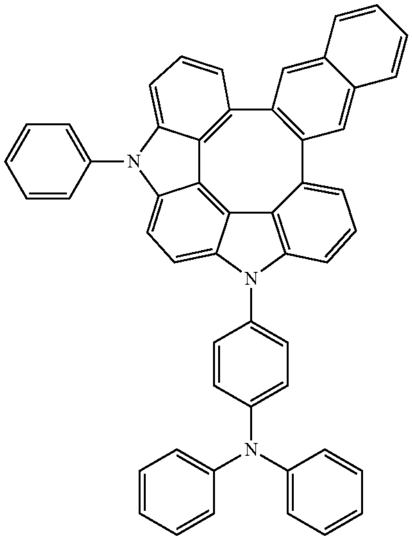
C-103
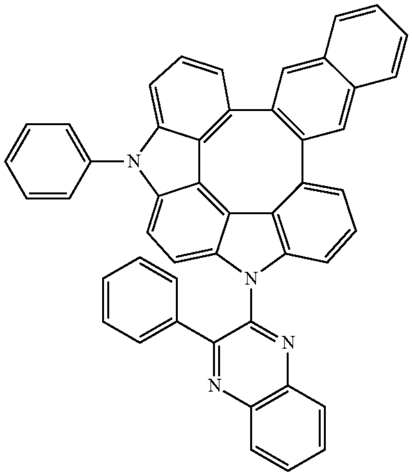
C-104
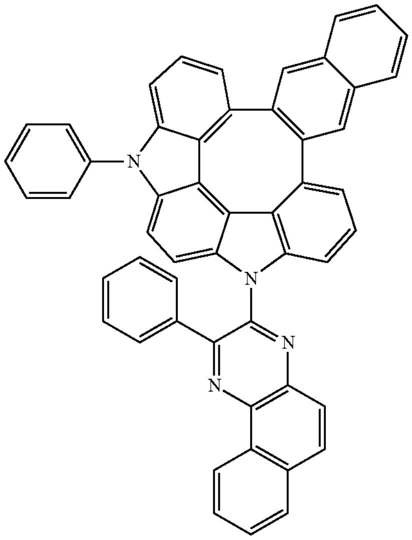

-continued
C-105
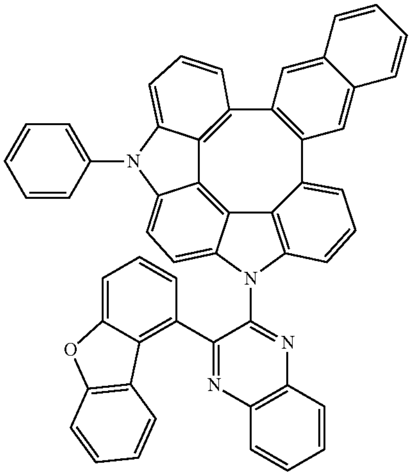
C-106
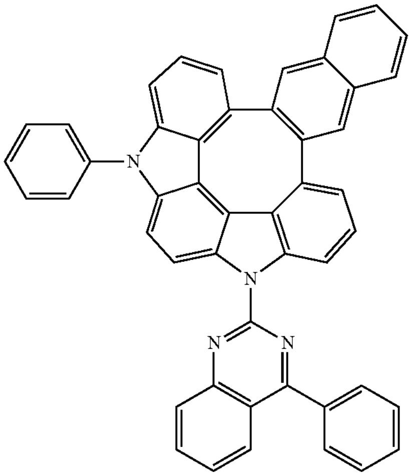
C-107
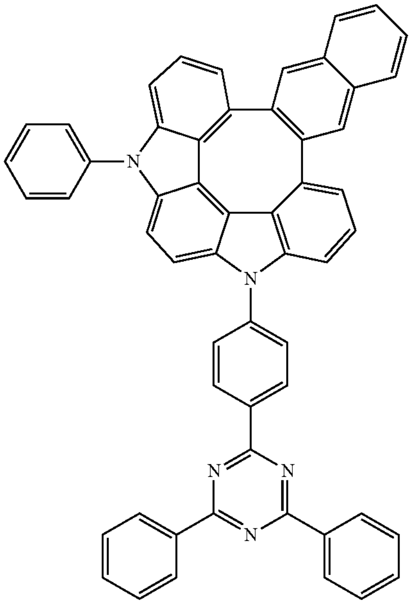
-continued
C-108
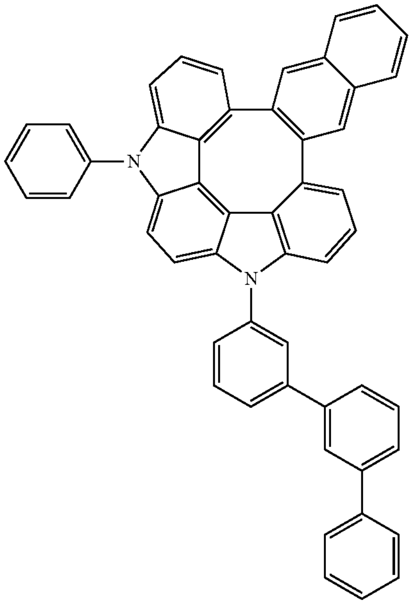
C-109
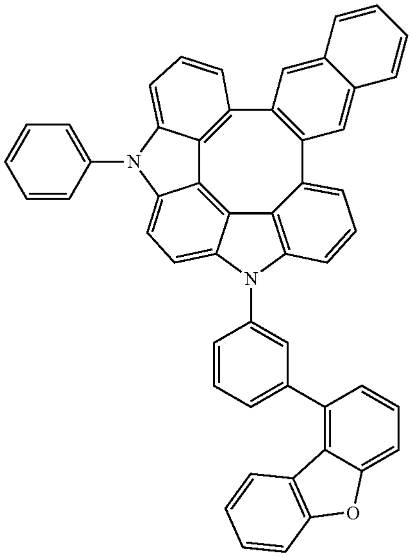

-continued
C-110
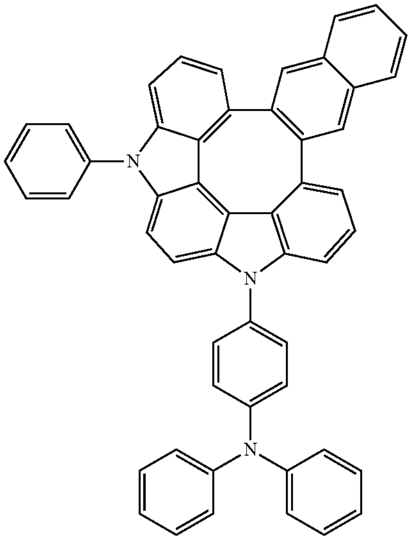
C-111
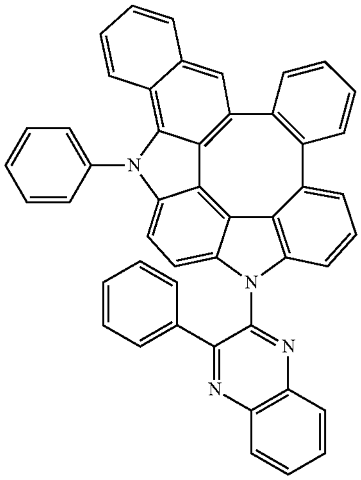
C-112
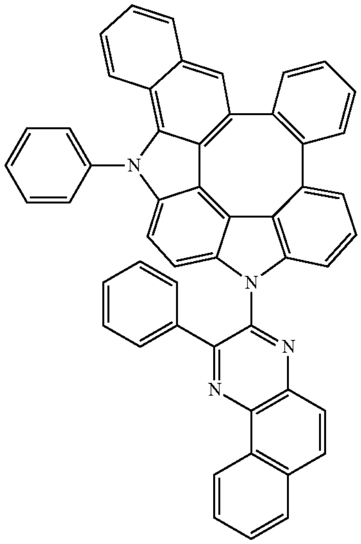
-continued
C-113
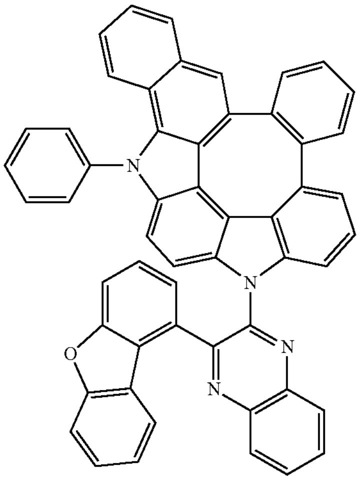
C-114
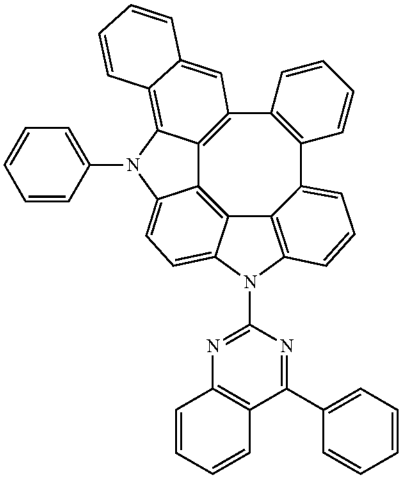
C-115
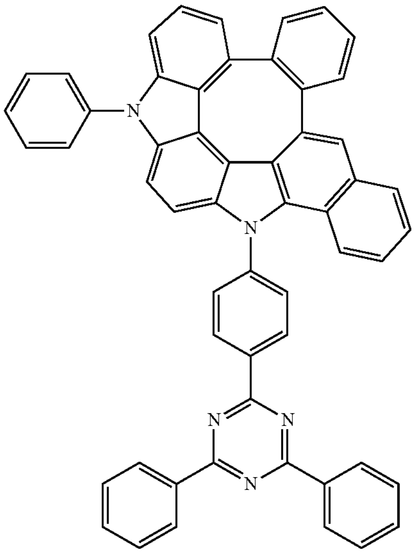

-continued
C-116
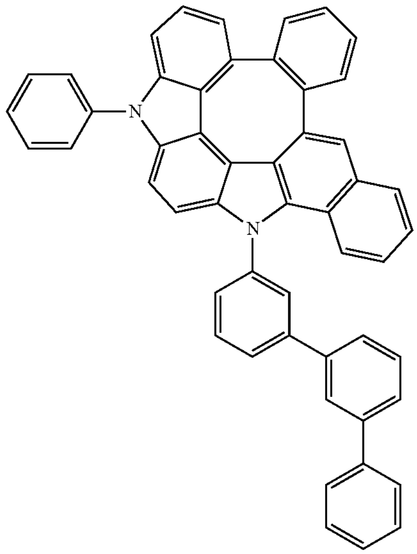
C-117
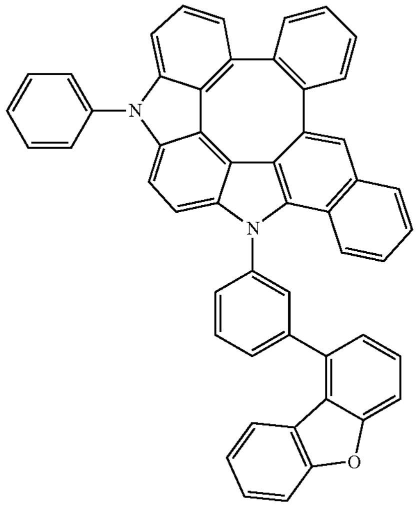
C-118
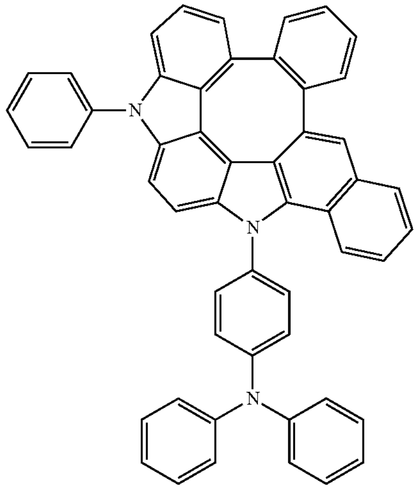
-continued
C-119
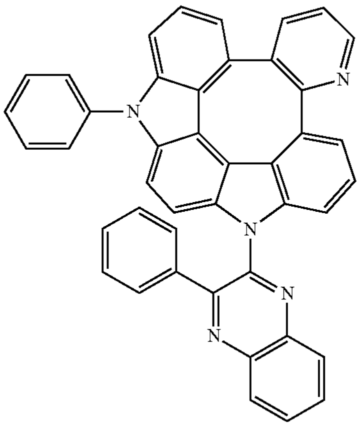
C-120
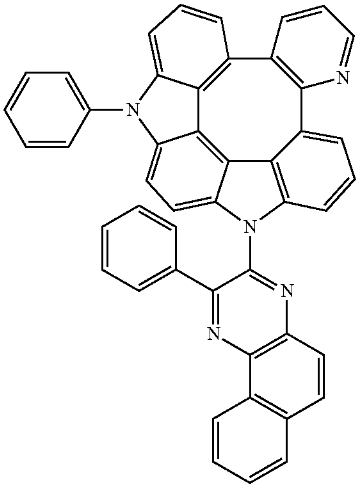
C-121
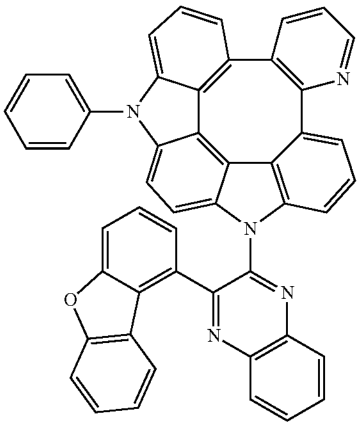

-continued
C-122
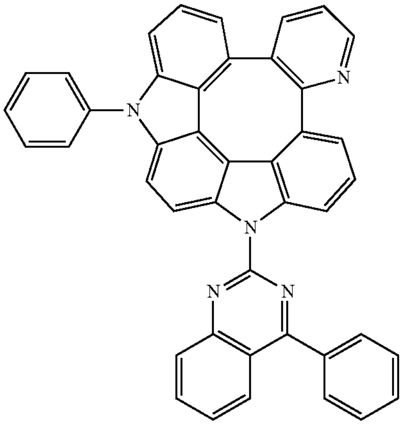
C-123
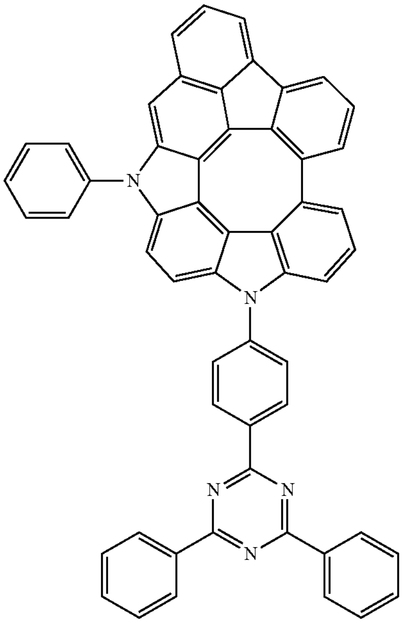
-continued
C-124
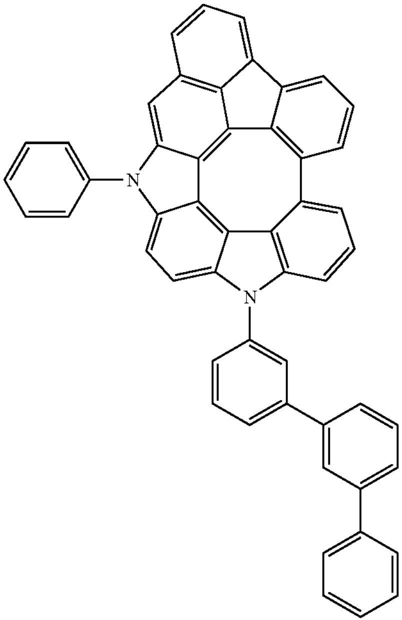
C-125
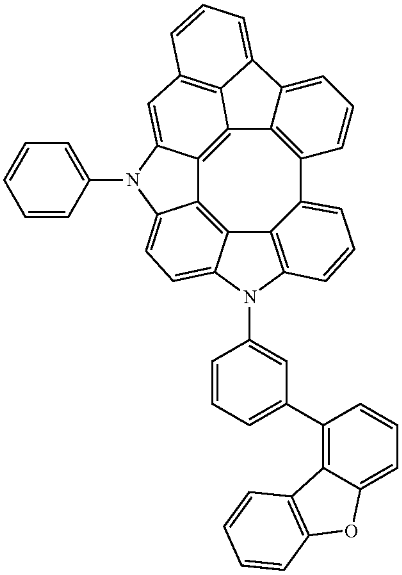

-continued
C-126
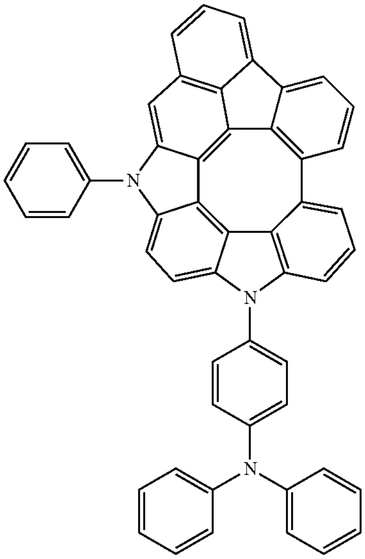
C-127
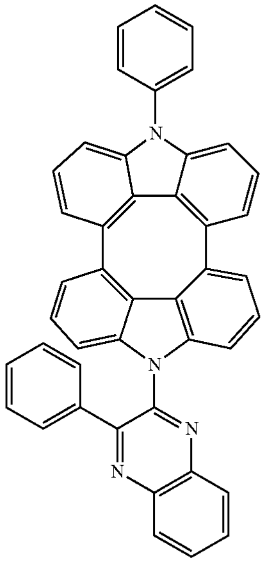
-continued
C-128
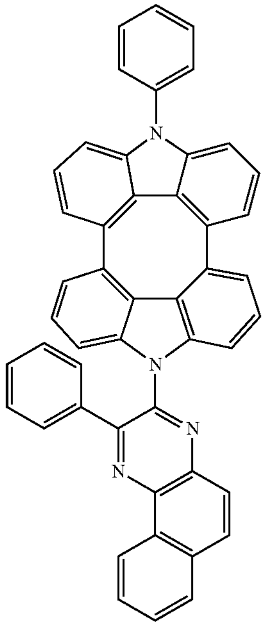
C-129
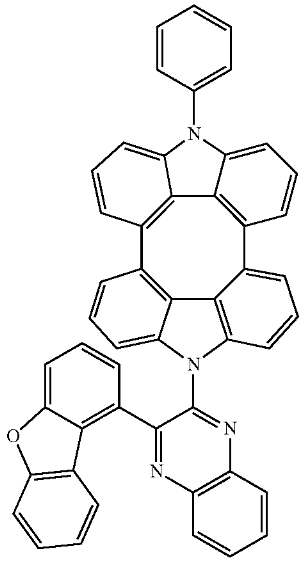

-continued
C-130
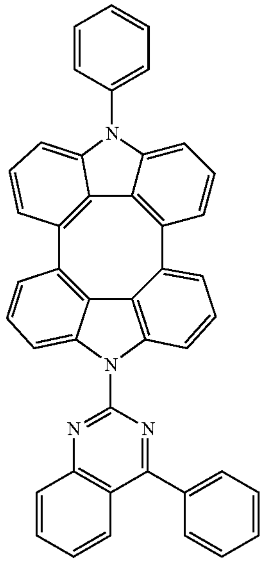
C-131
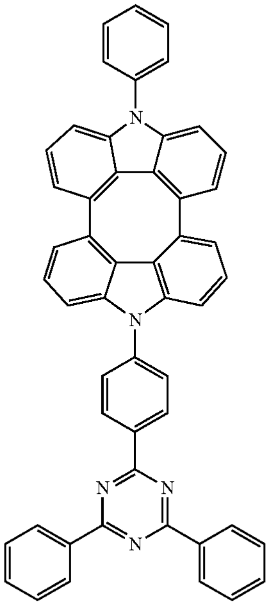
-continued
C-132
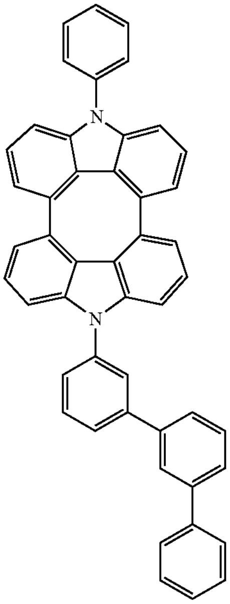
C-133
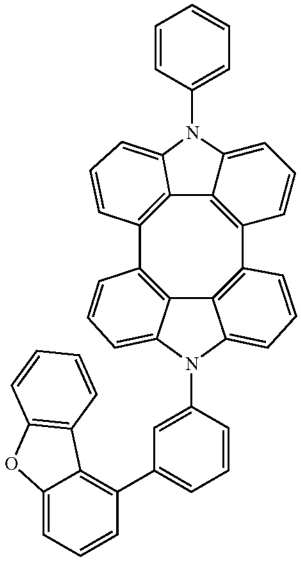

-continued
C-134
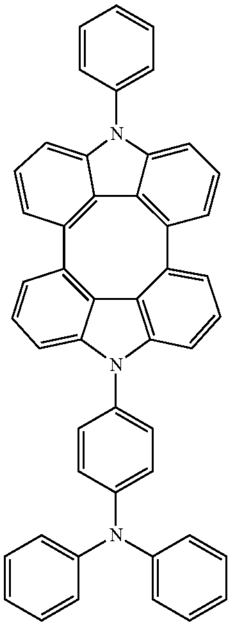
C-135
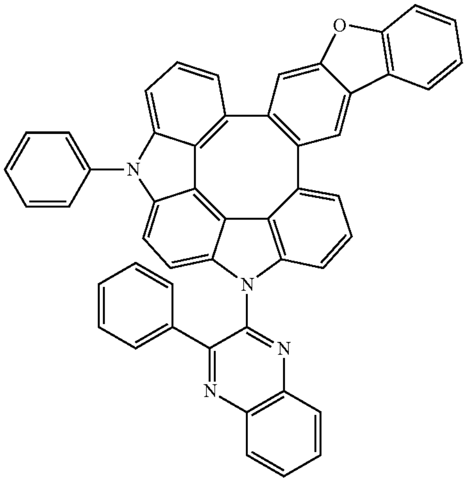
C-136
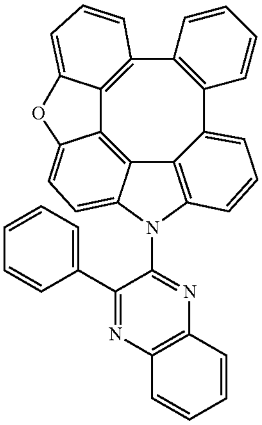
-continued
C-137
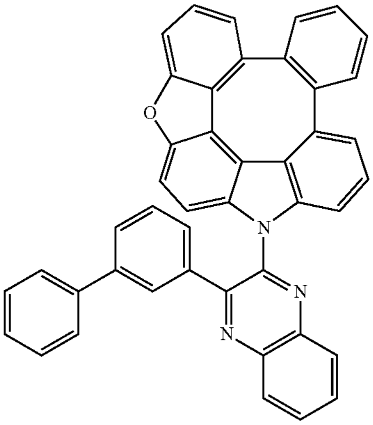
C-138
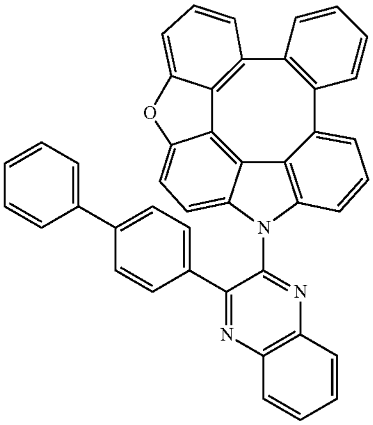
C-139
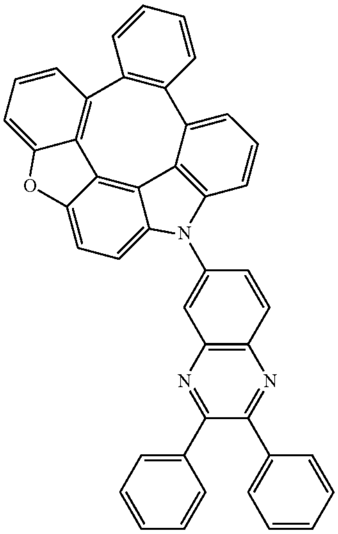

-continued
C-140
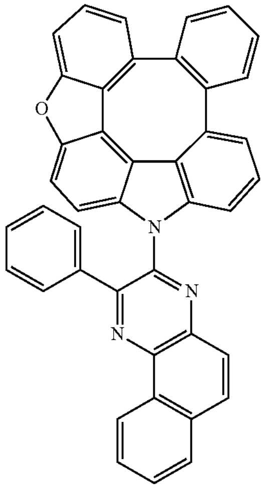
C-141
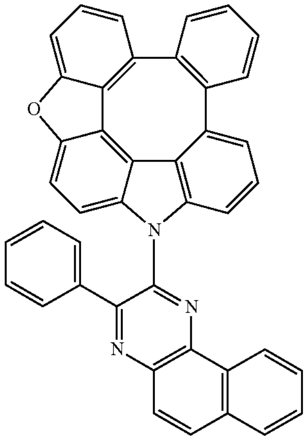
C-142
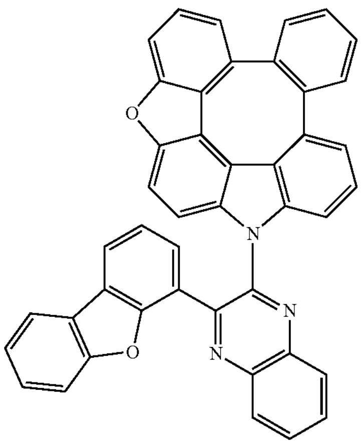
-continued
C-143
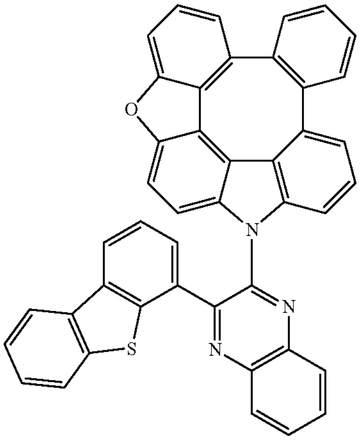
C-144
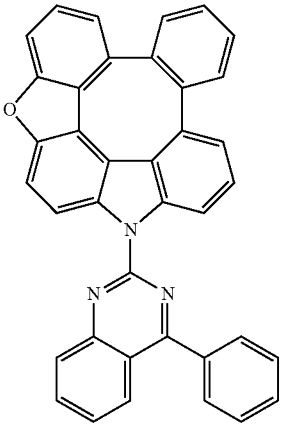
C-145
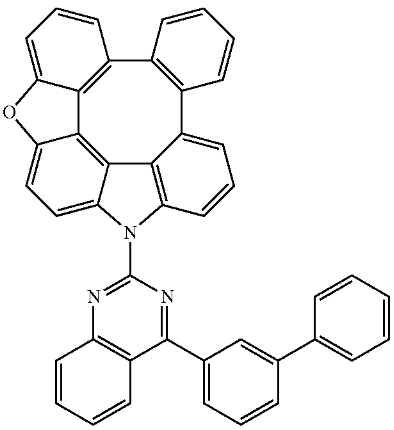

-continued
C-146
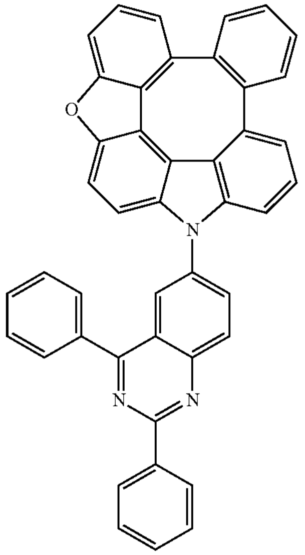
C-147
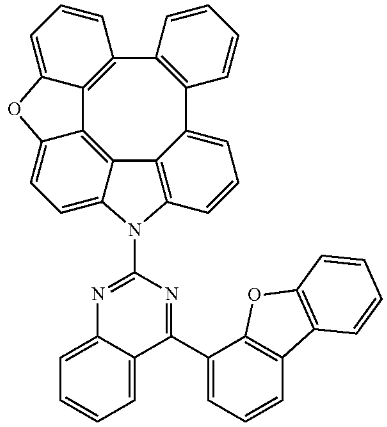
C-148
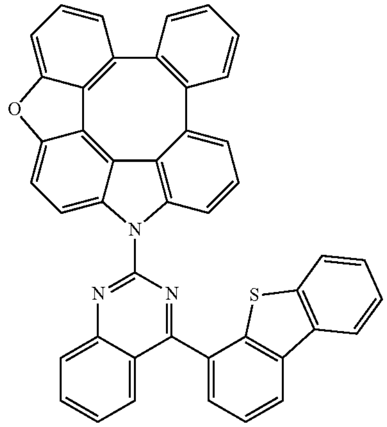
-continued
C-149
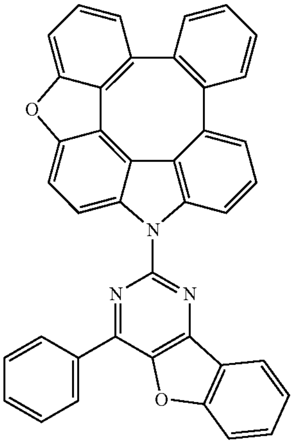
C-150
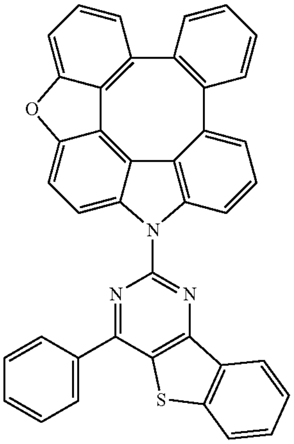
C-151
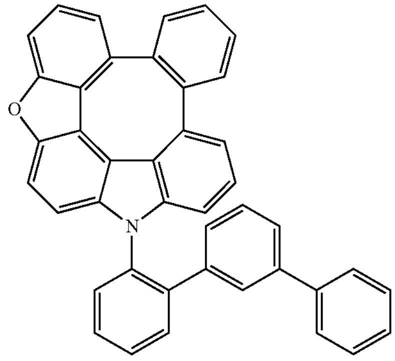

-continued
C-152
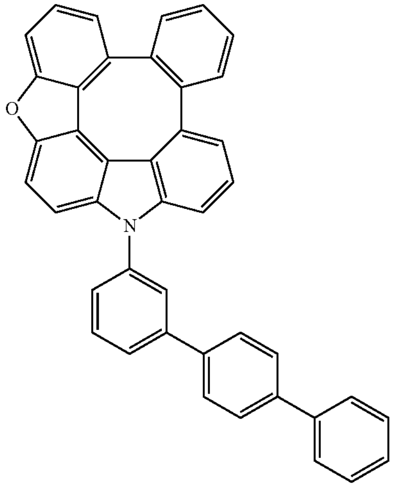
C-153
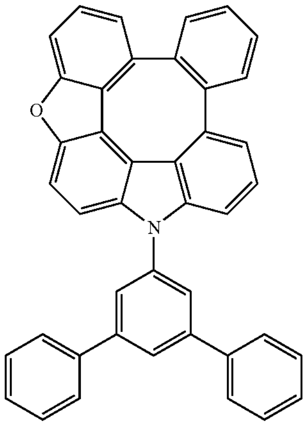
C-154
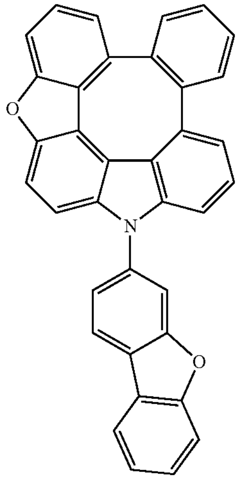
-continued
C-155
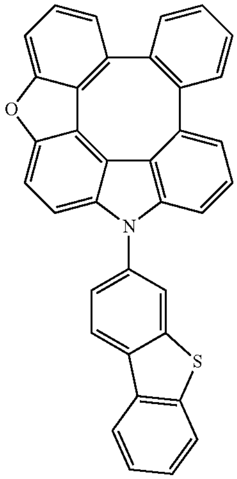
C-156
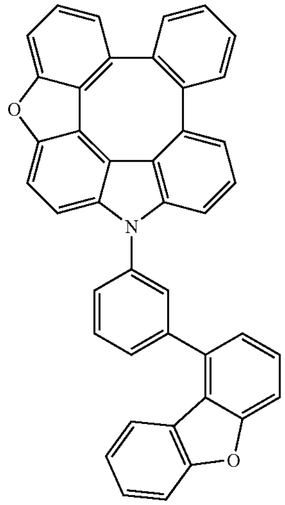
C-157
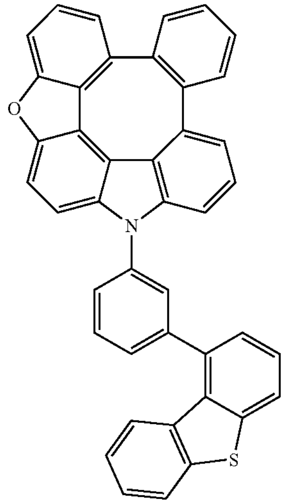

-continued
C-158
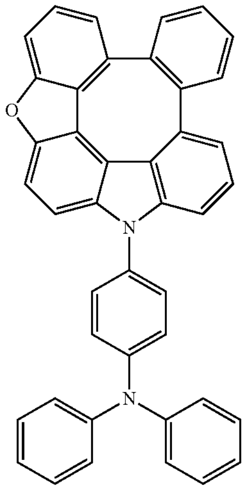
C-159
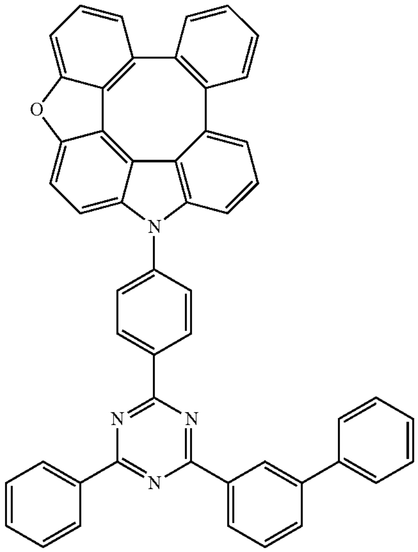
C-160
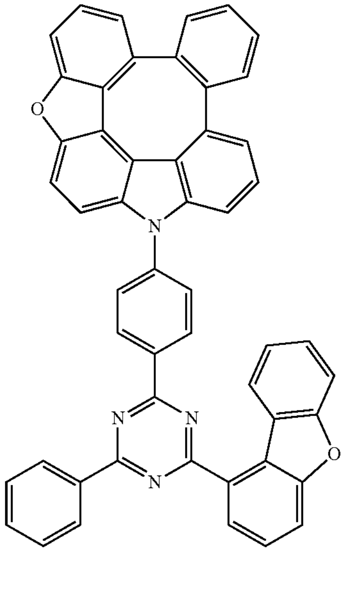
-continued
C-161
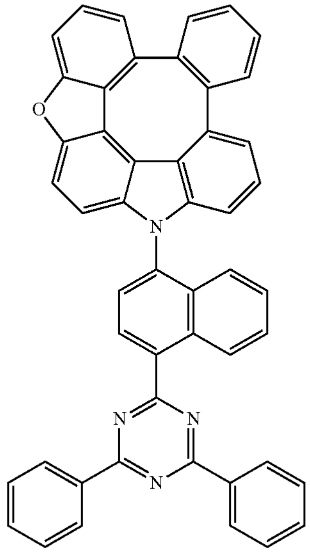
C-162
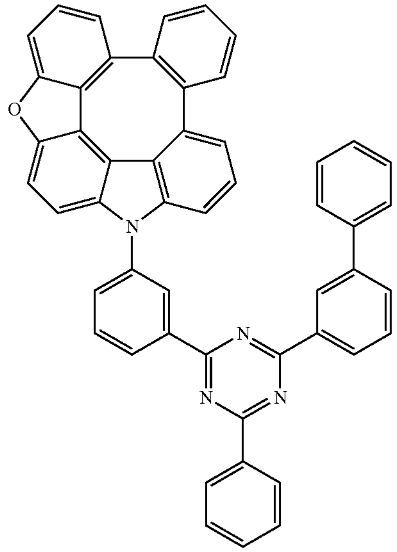
C-163
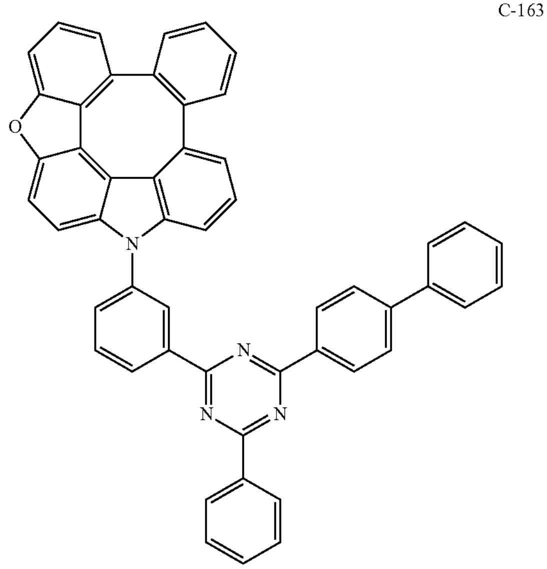

-continued
C-164
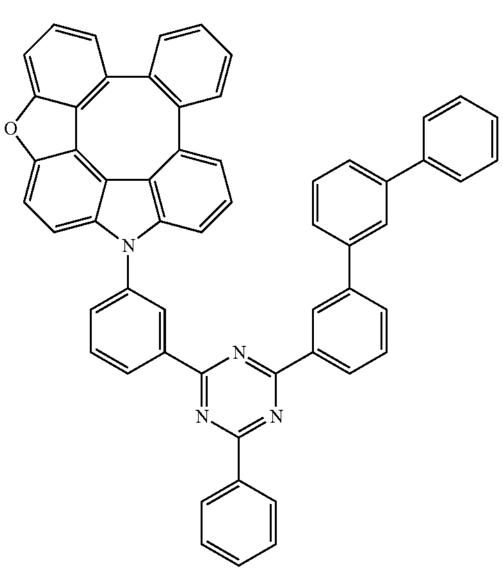
C-165
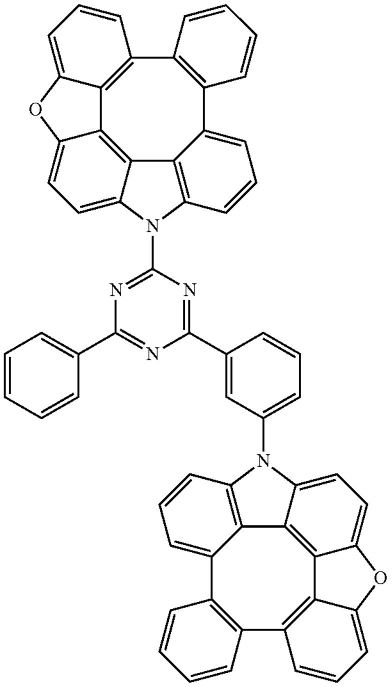
-continued
C-166
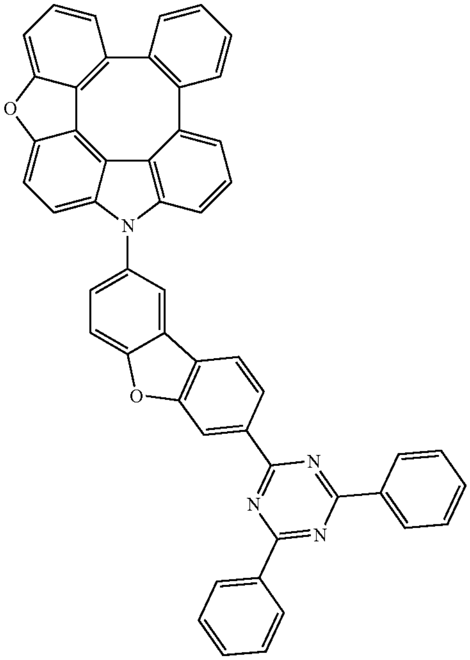
C-167
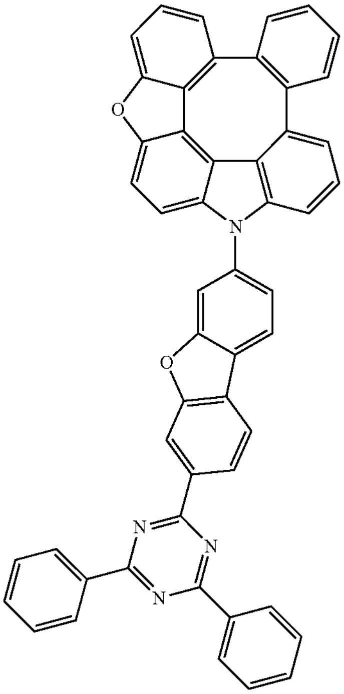

C-168
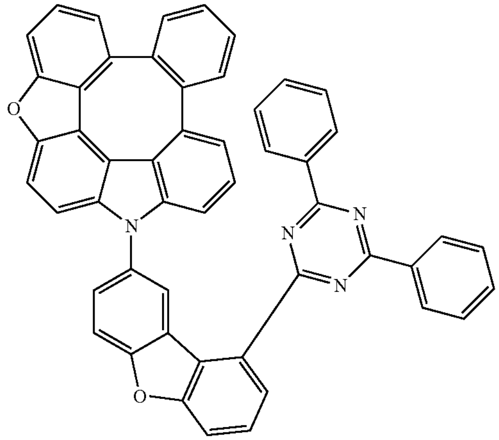
C-169
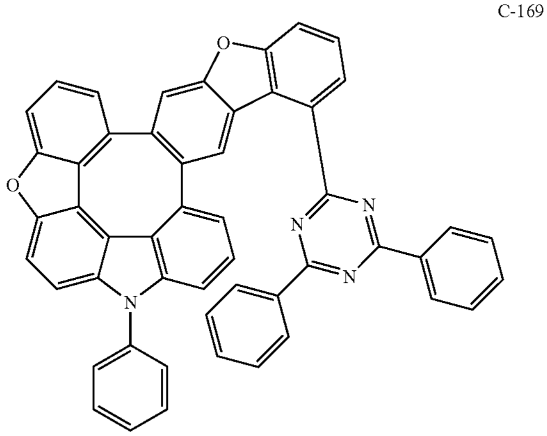
C-170
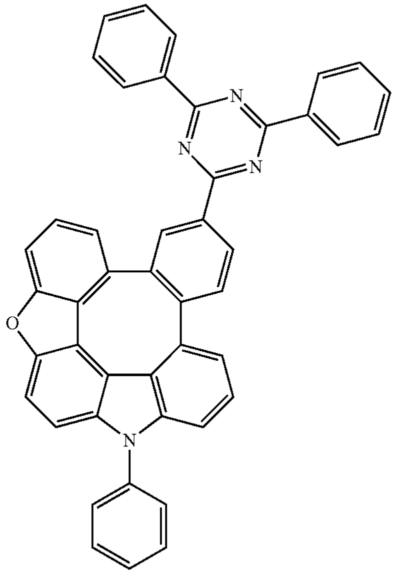
C-171
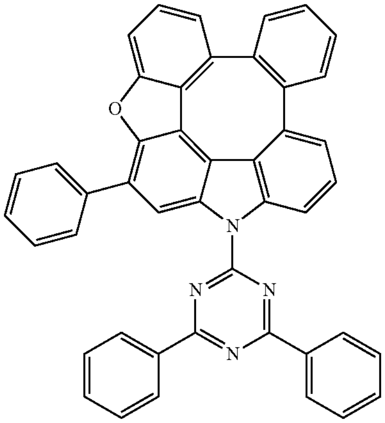
C-172
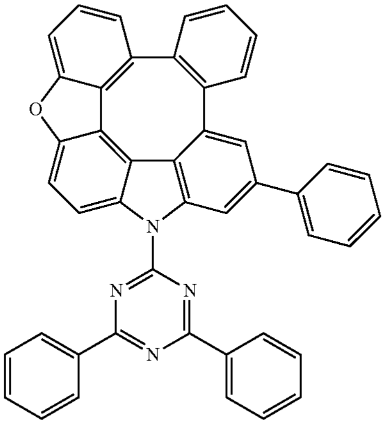
C-173
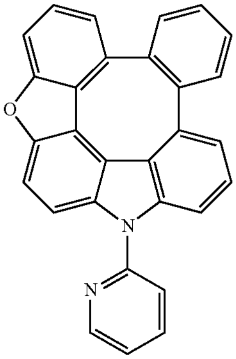

-continued
C-174
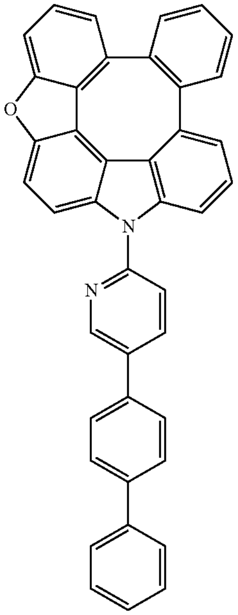
C-175
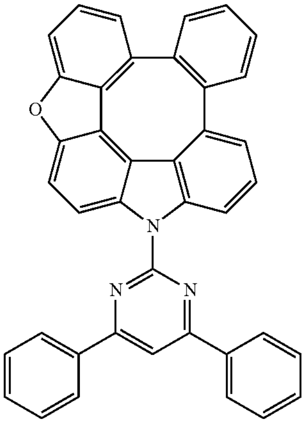
C-176
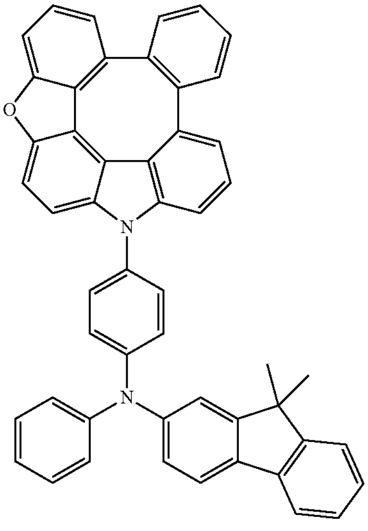
-continued
C-177
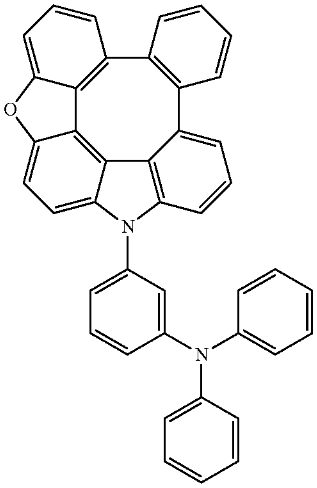
C-178
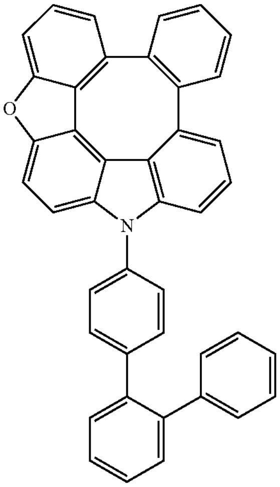
C-179
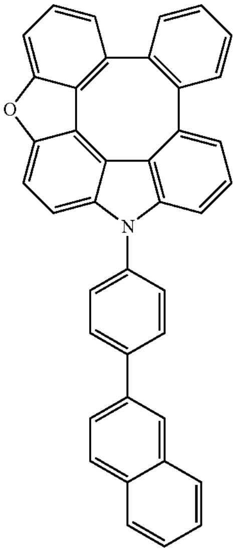

-continued
C-180
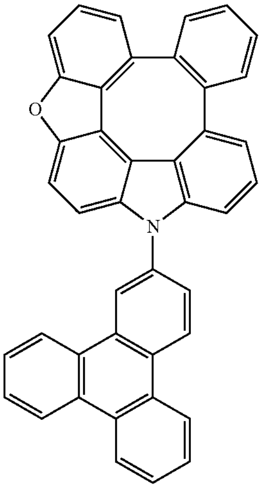
C-181
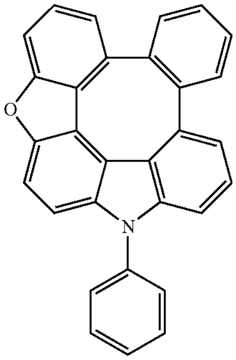
C-182
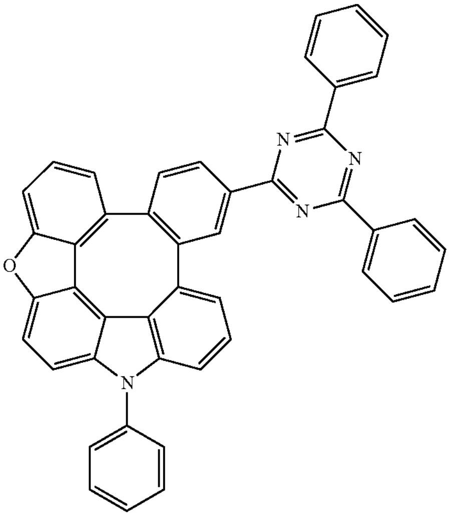
-continued
C-183
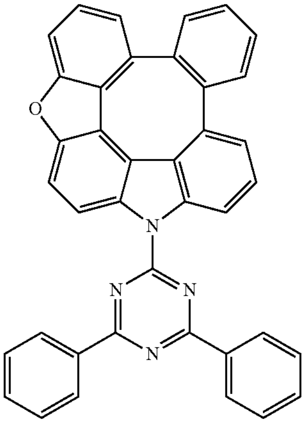
C-184
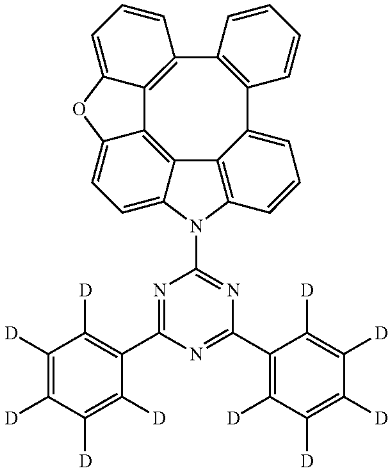
C-185
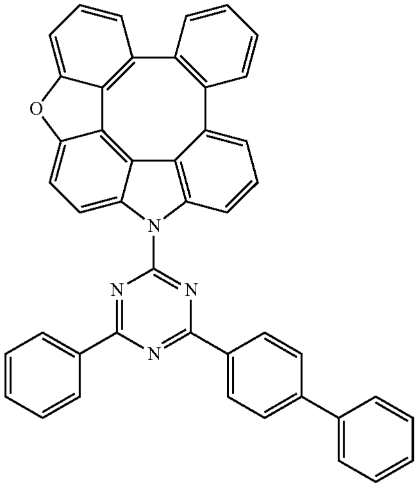

-continued
C-186
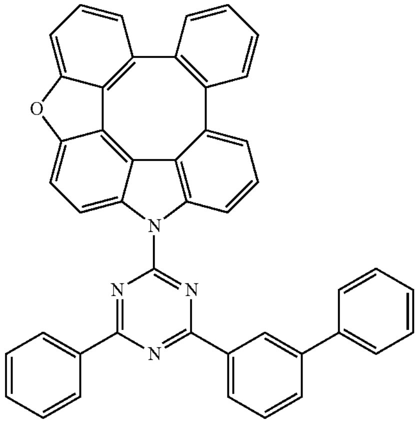
C-187
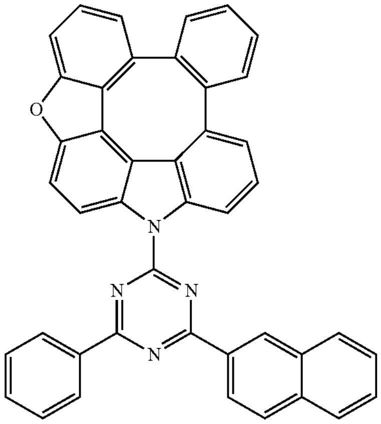
C-188
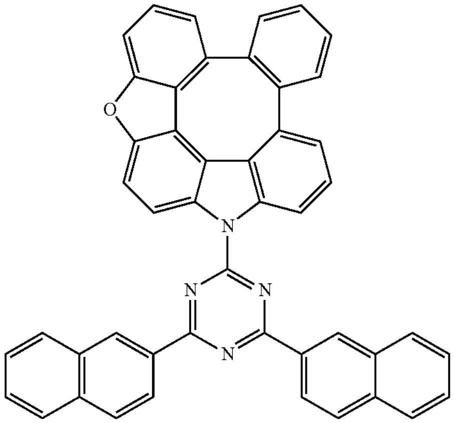
-continued
C-189
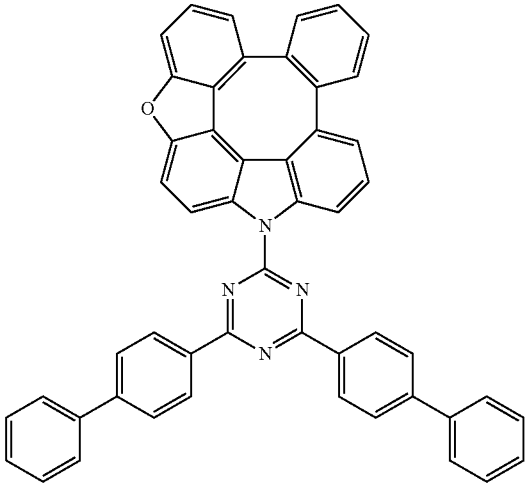
C-190
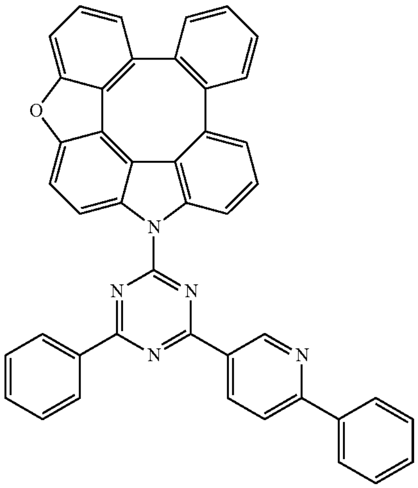
C-191
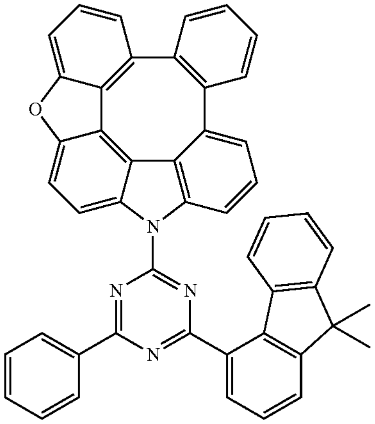

C-192
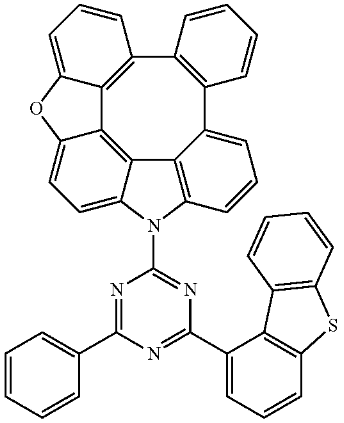
C-193
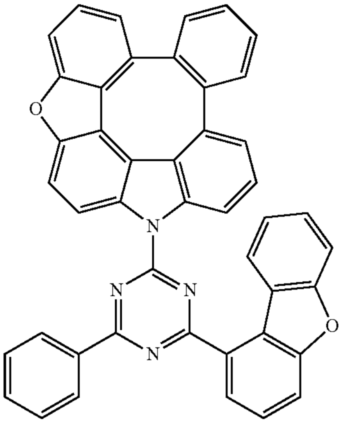
C-194
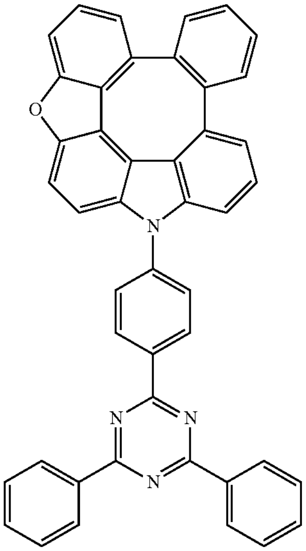
C-195
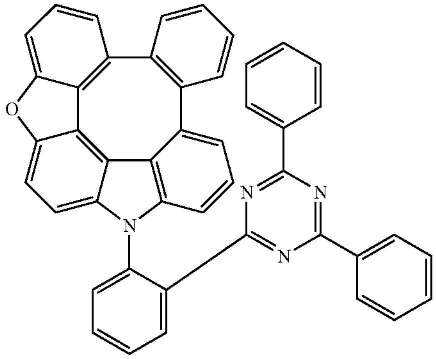
C-196
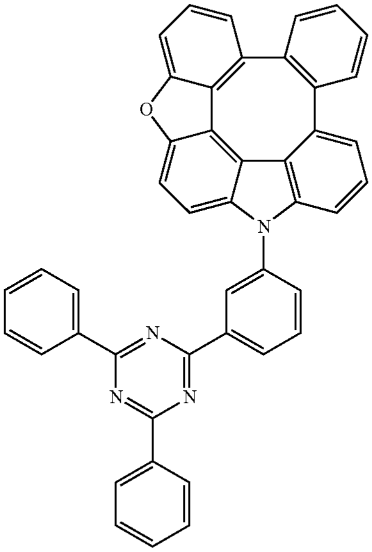
C-197
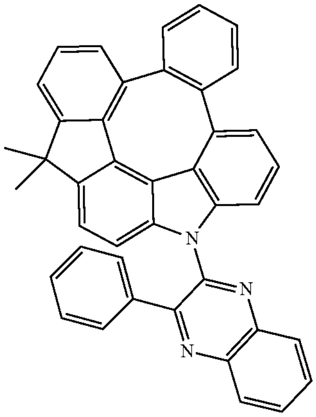

-continued
C-198
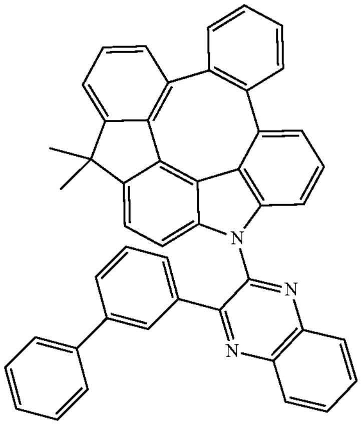
C-199
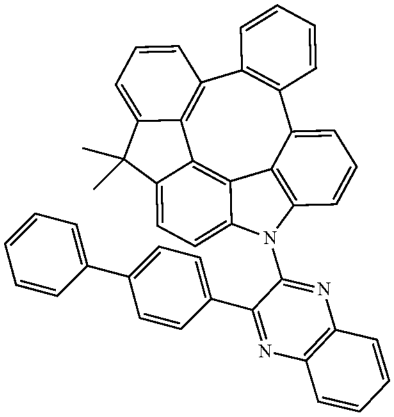
C-200
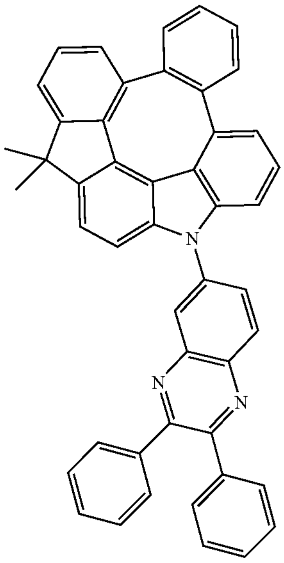
-continued
C-201
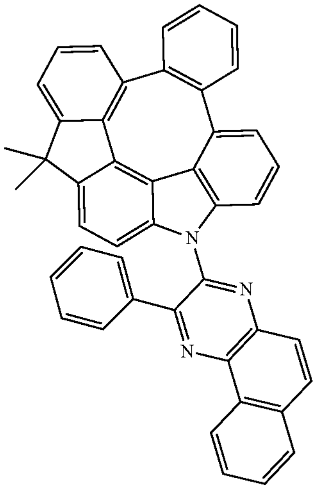
C-202
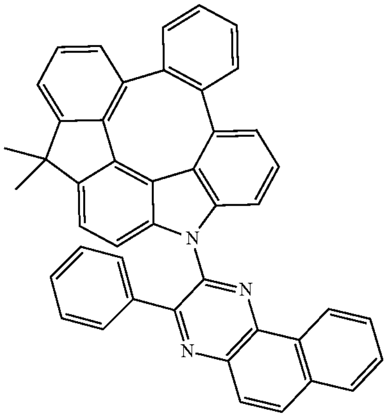
C-203
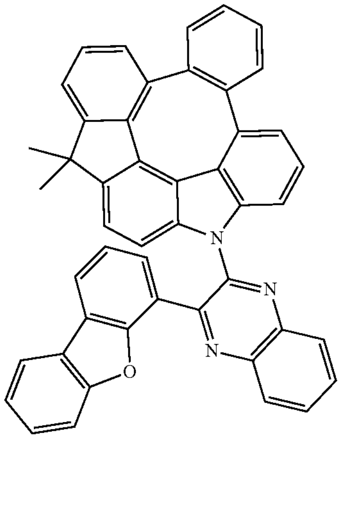

-continued
C-204
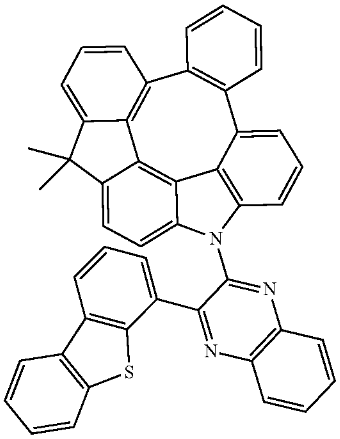
C-205
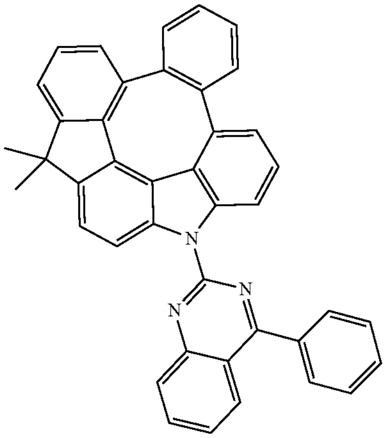
C-206
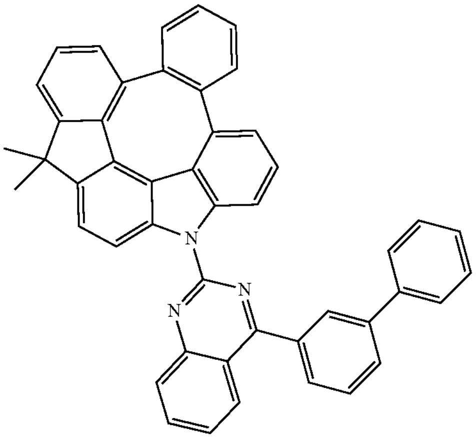
-continued
C-207
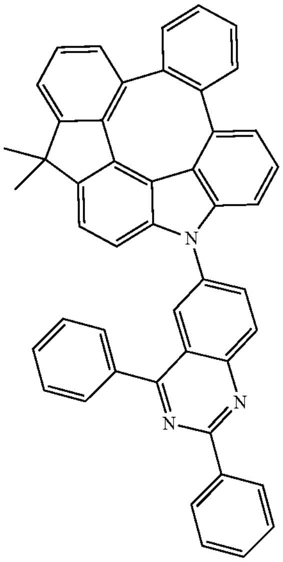
C-208
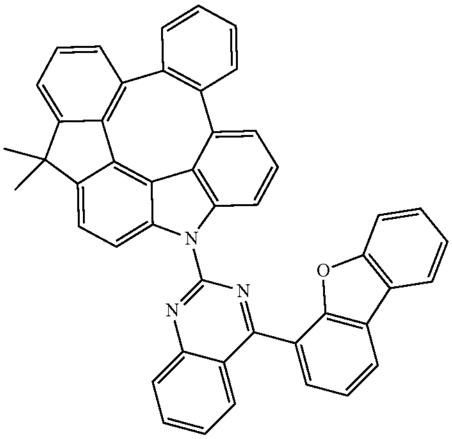
C-209
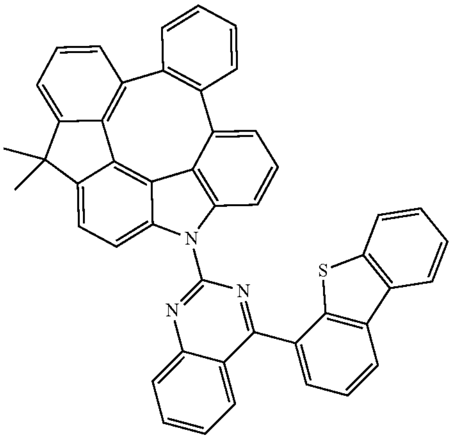

-continued
C-210
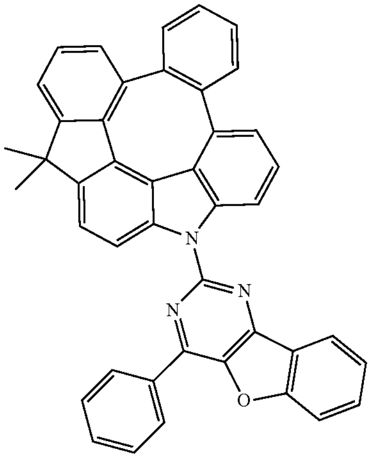
C-211
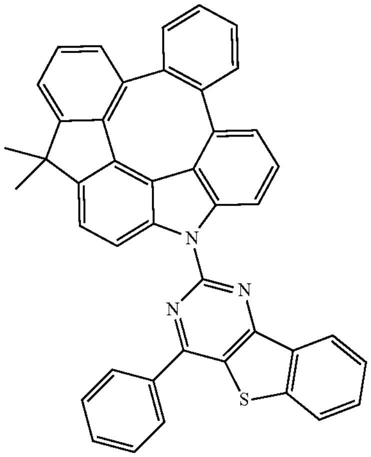
C-212
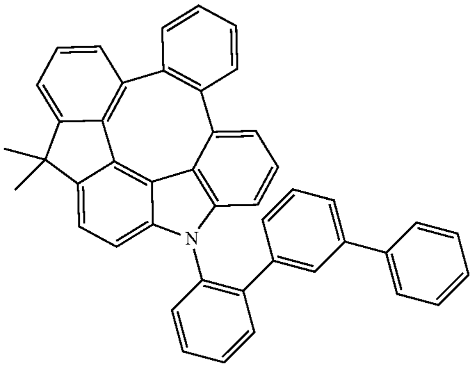
-continued
C-213
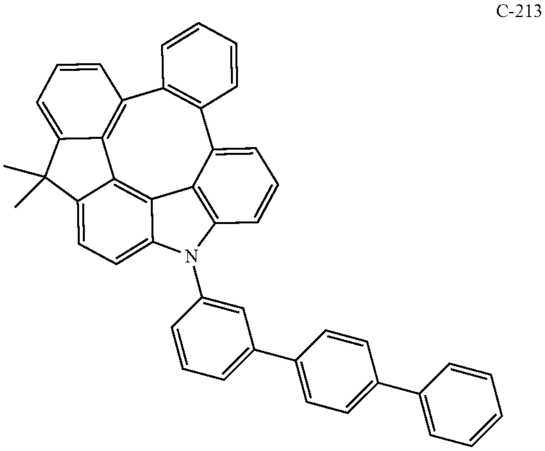
C-214
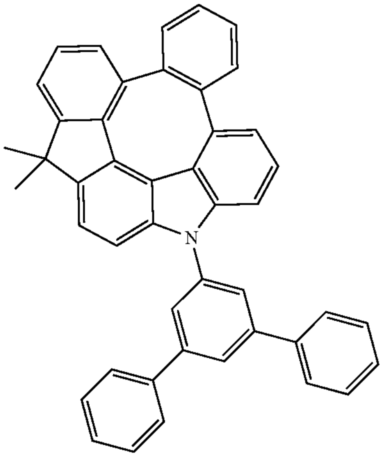
C-215
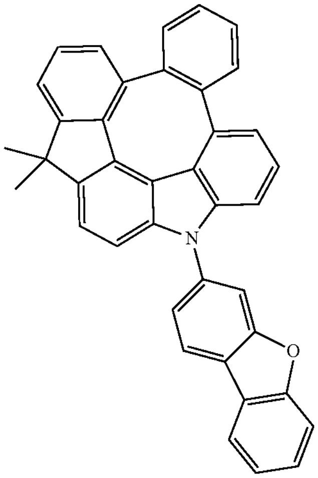

-continued
C-216
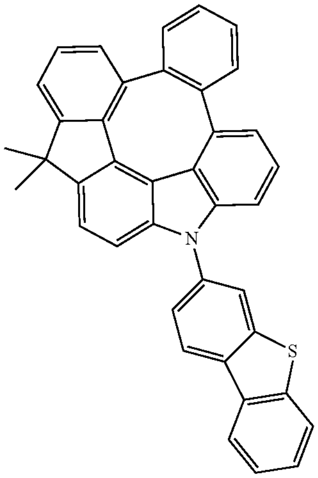
C-217
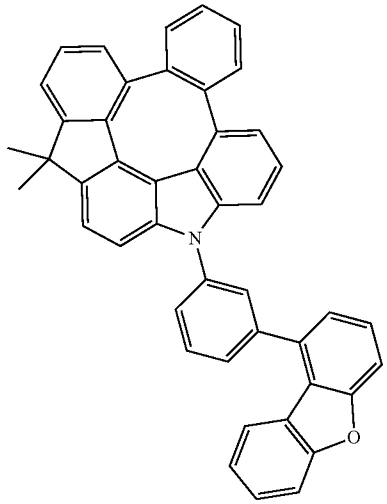
C-218
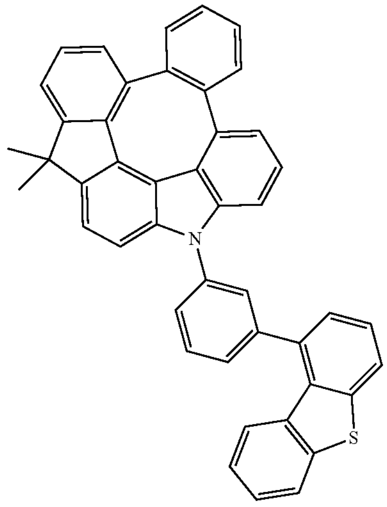
-continued
C-219
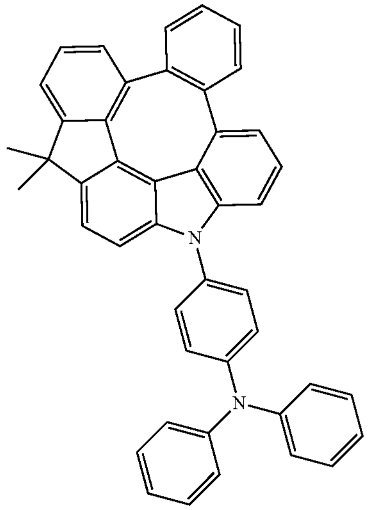
C-220
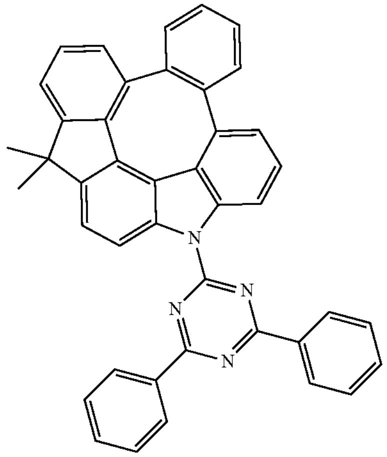
C-221
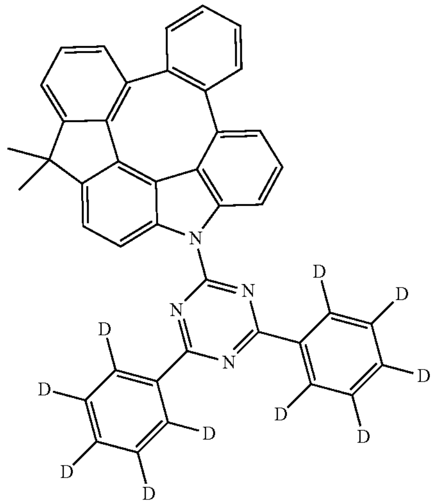

-continued
C-222
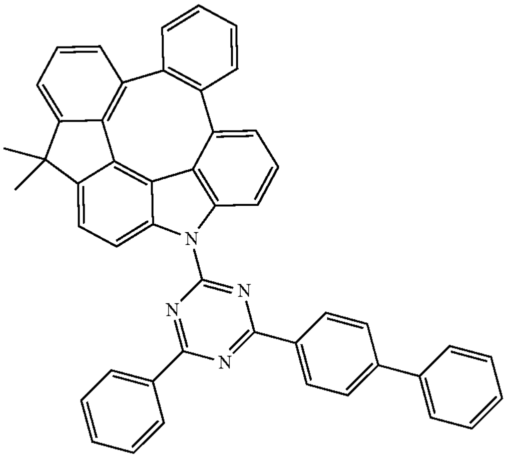
C-223
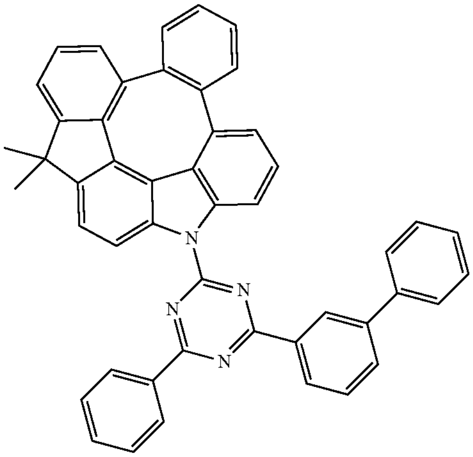
C-224
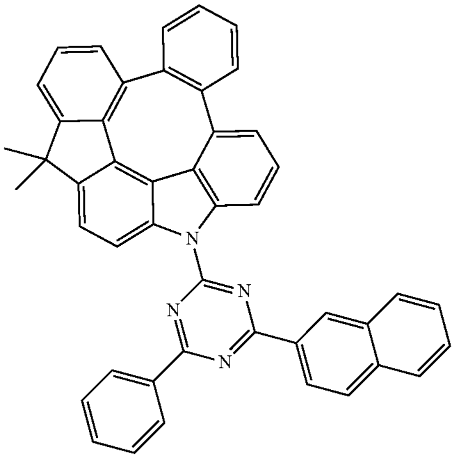
-continued
C-225
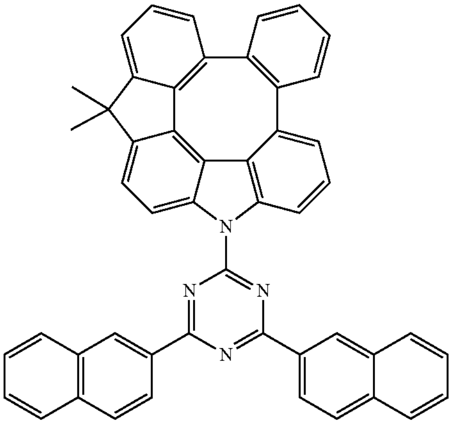
C-226
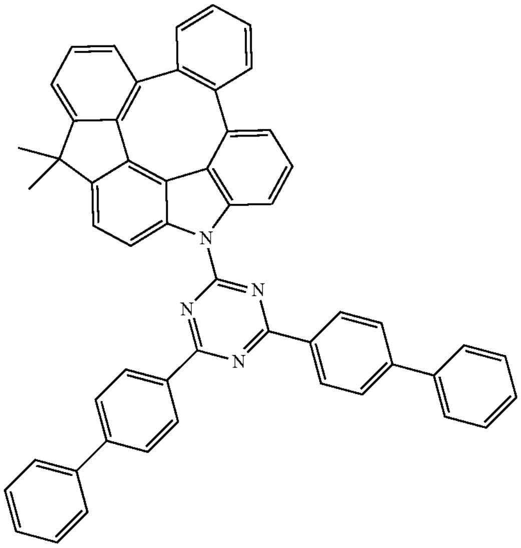
C-227
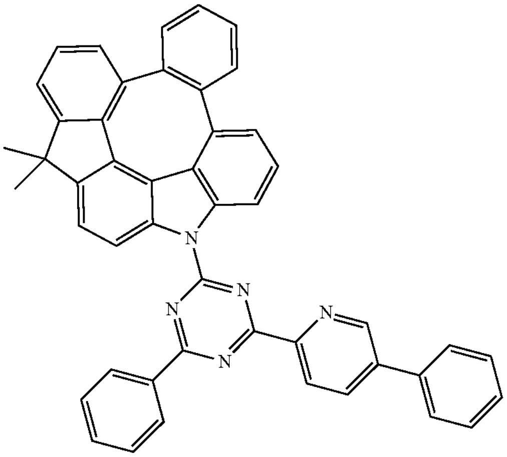

C-228
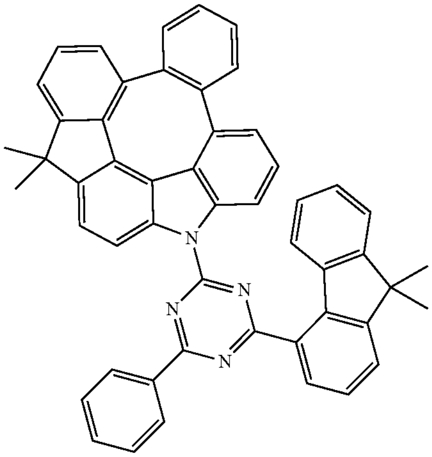
C-229
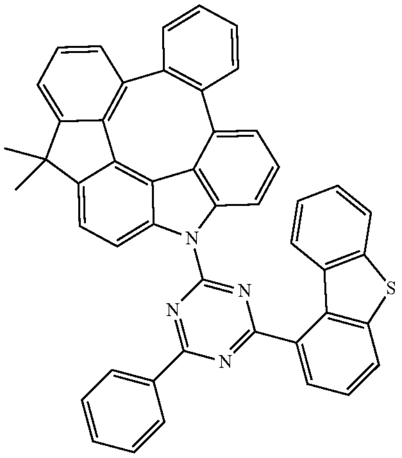
C-230
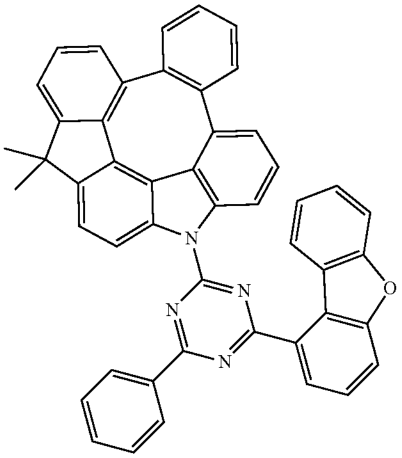
C-231
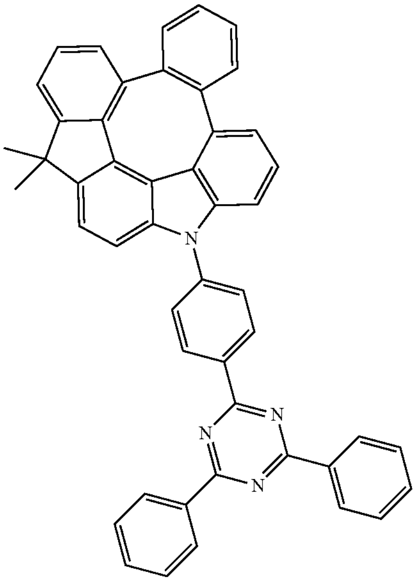
C-232
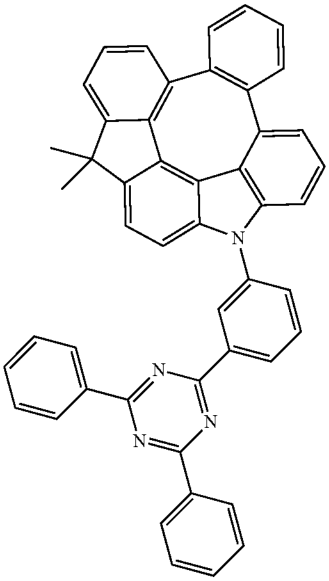
C-233
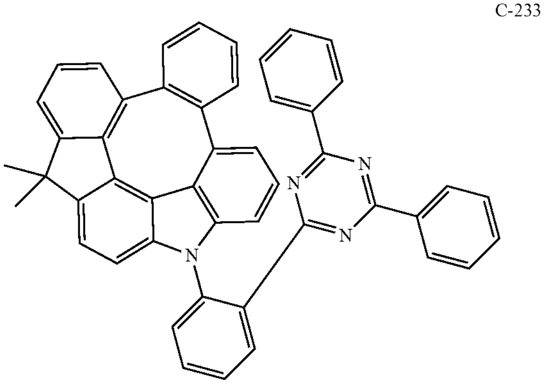

-continued
C-234
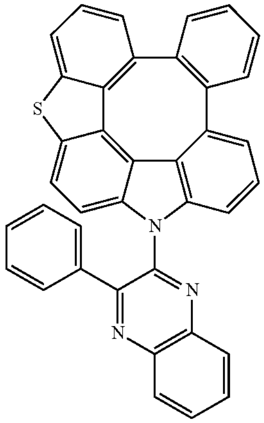
C-235
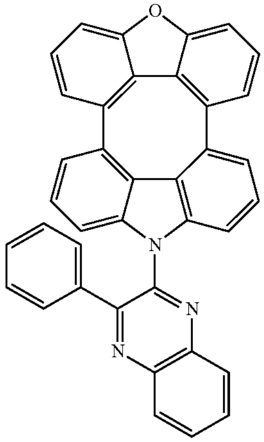
C-236
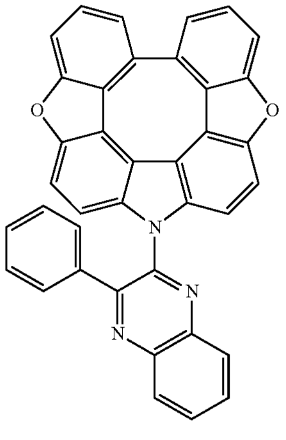
-continued
C-237
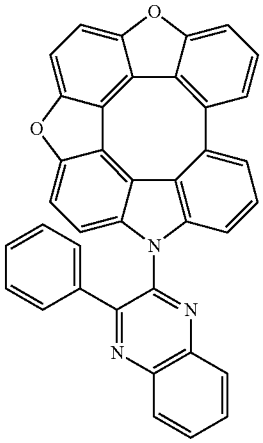
C-238
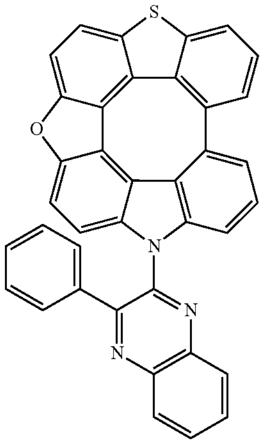
C-239
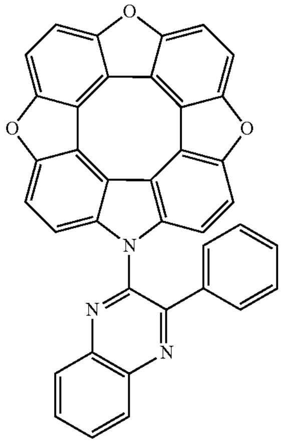

-continued
C-240
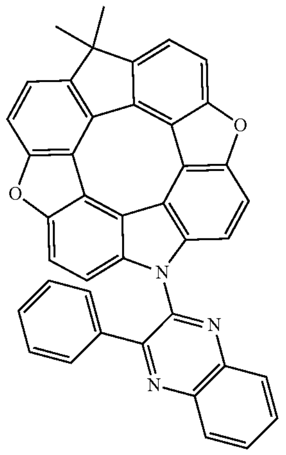
C-241
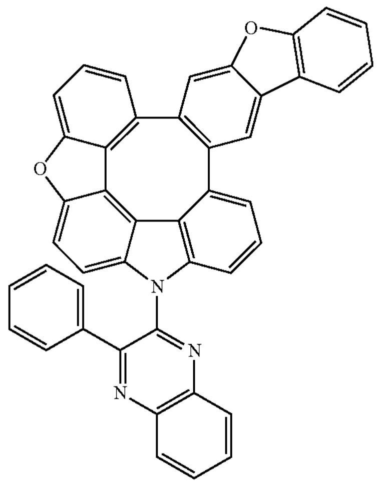
C-242
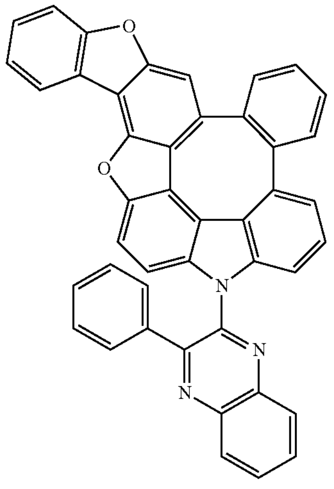
-continued
C-243
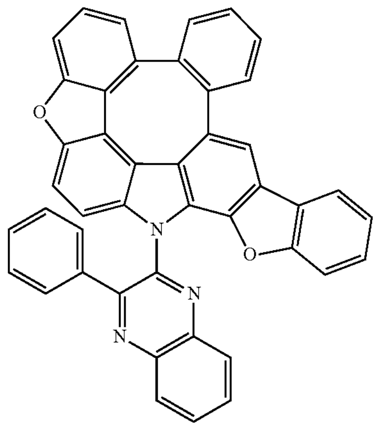
C-244
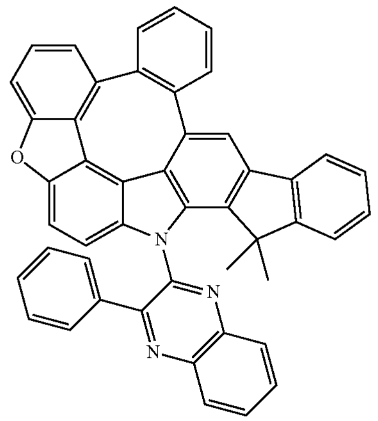
C-245
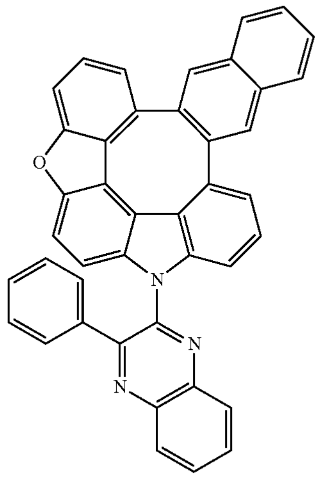

-continued
C-246
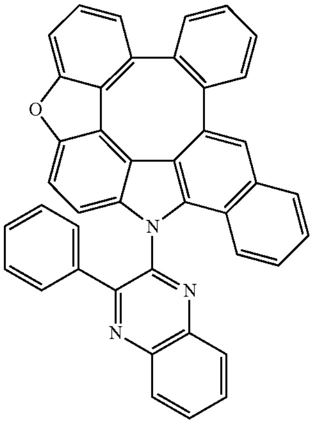
C-247
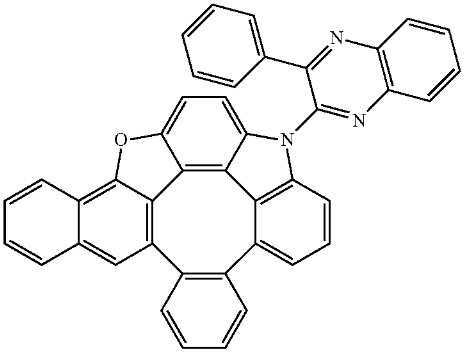
C-248
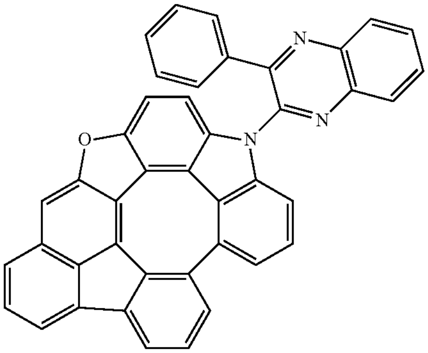
C-249
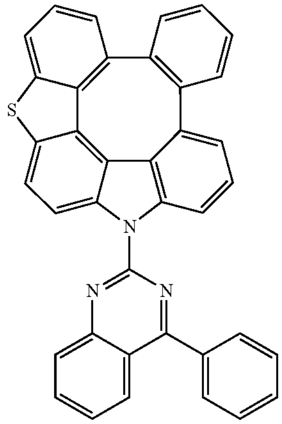
-continued
C-250
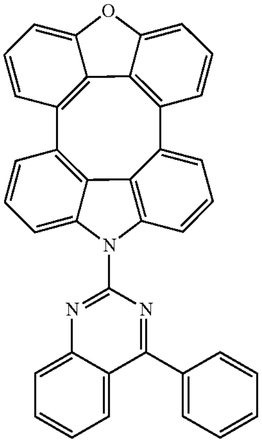
C-251
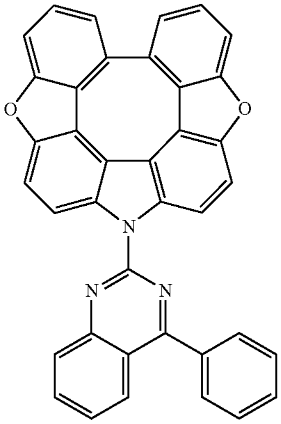
C-252
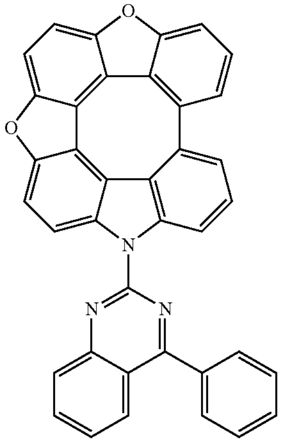

-continued
C-253
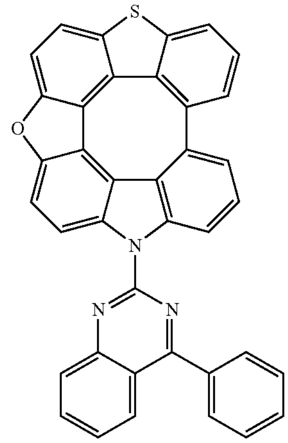
C-254
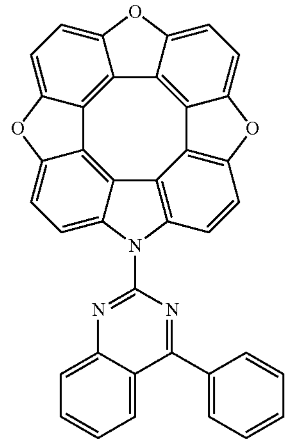
C-255
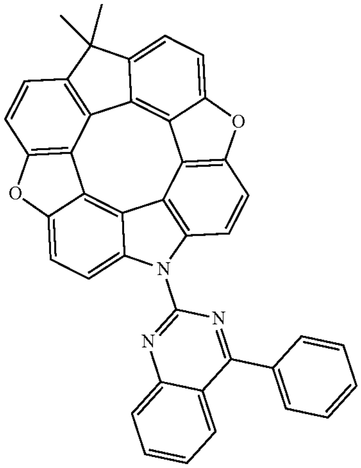
-continued
C-256
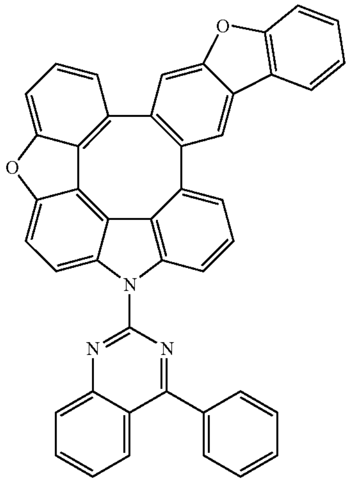
C-257
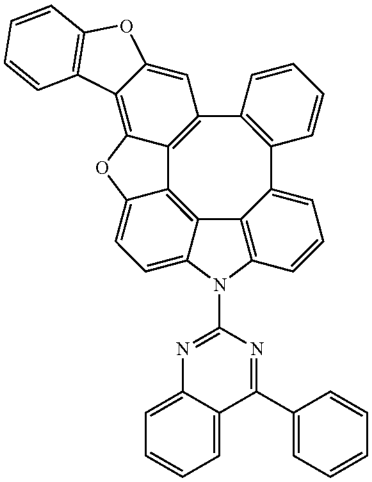
C-258
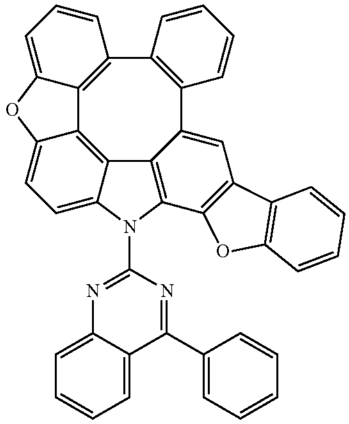

-continued
C-259
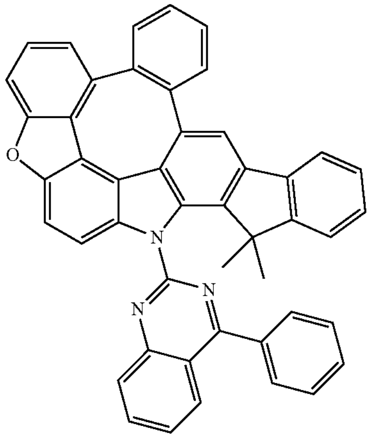
C-260
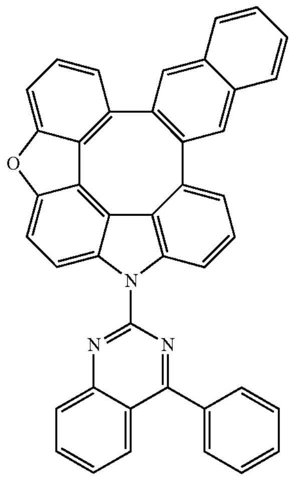
C-261
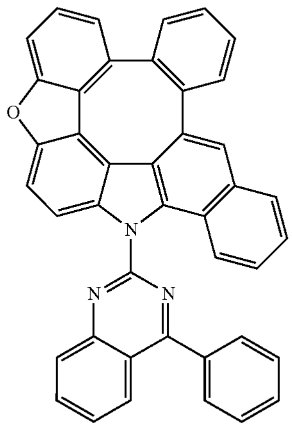
-continued
C-262
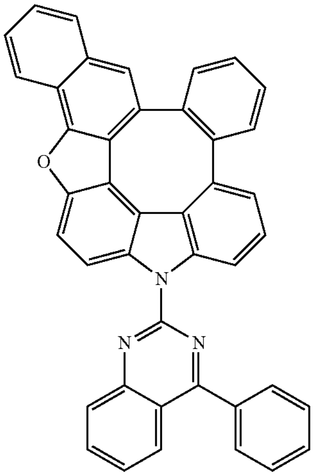
C-263
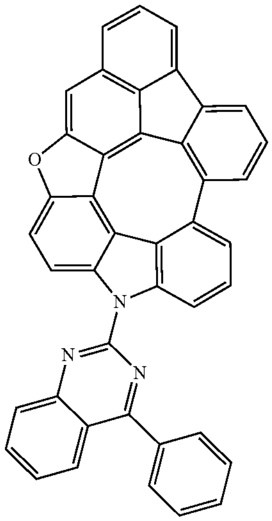
C-264
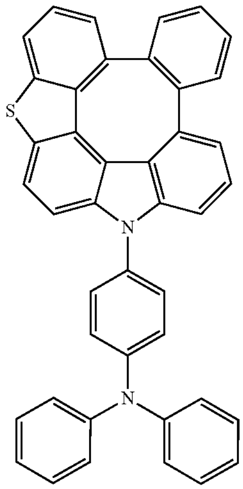

-continued
C-265
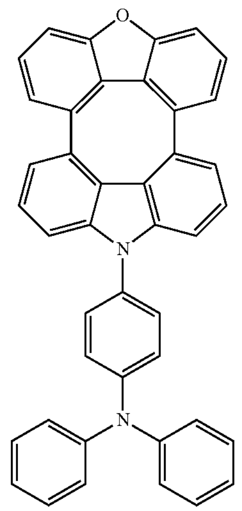
C-266
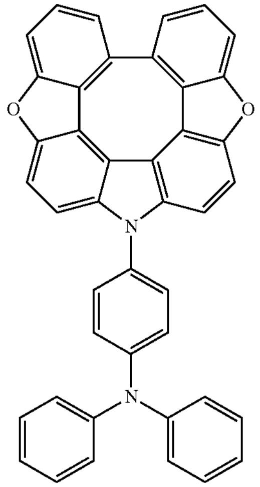
C-267
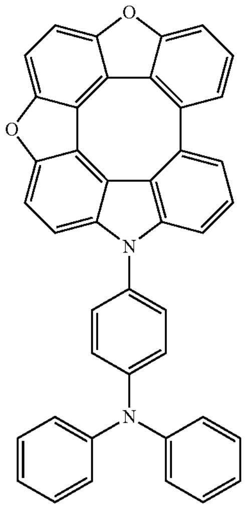
-continued
C-268
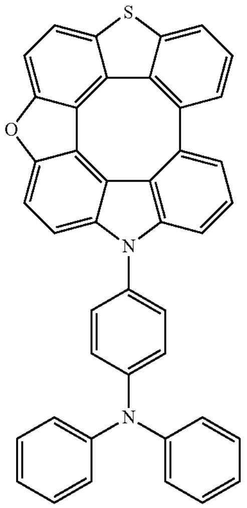
C-269
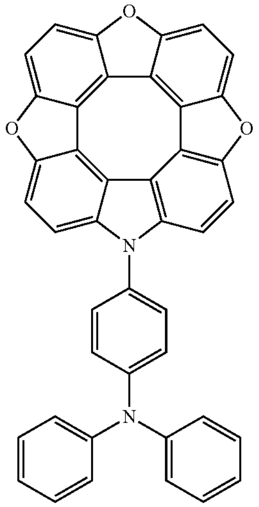
C-270
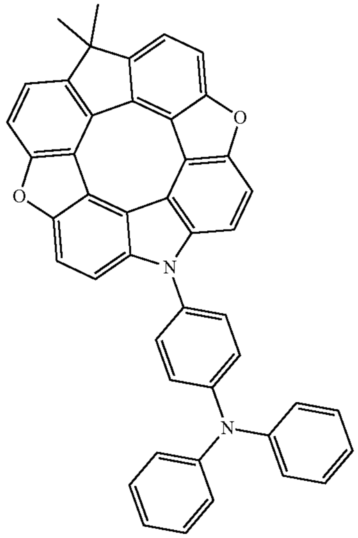

-continued
C-271
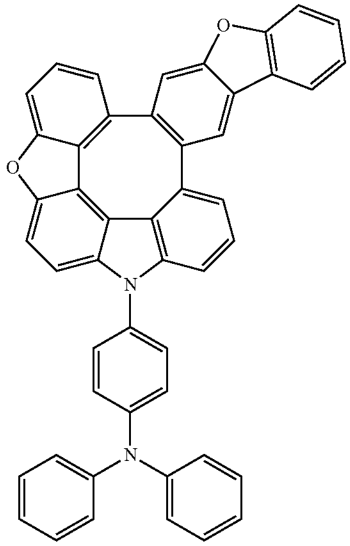
C-272
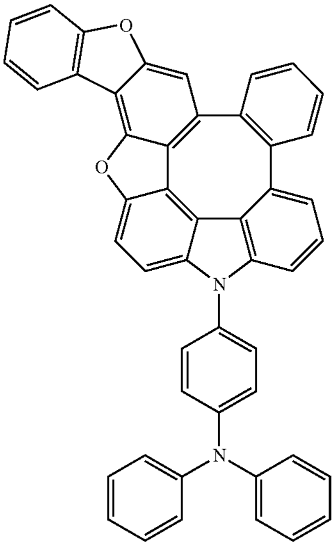
C-273
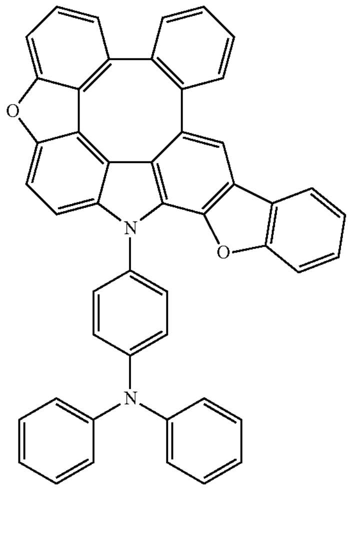
-continued
C-274
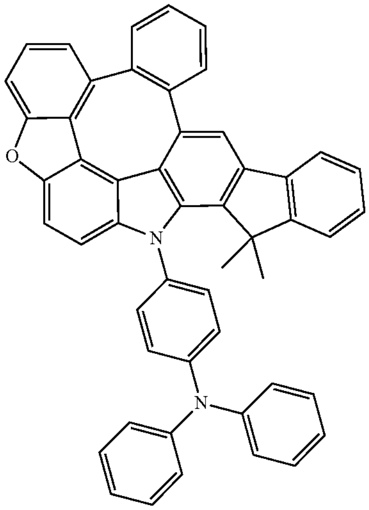
C-275
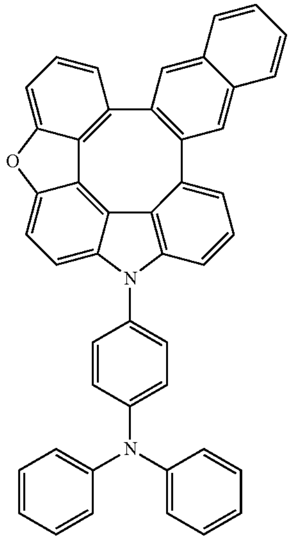
C-276
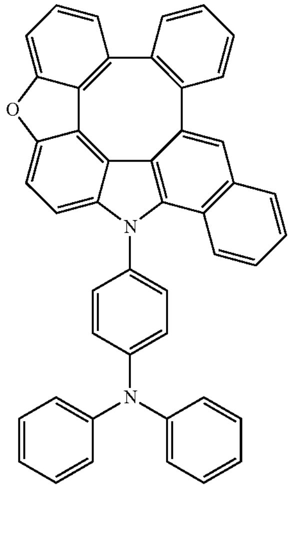

-continued
C-277
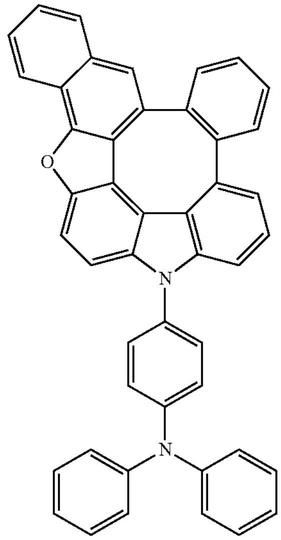
C-278
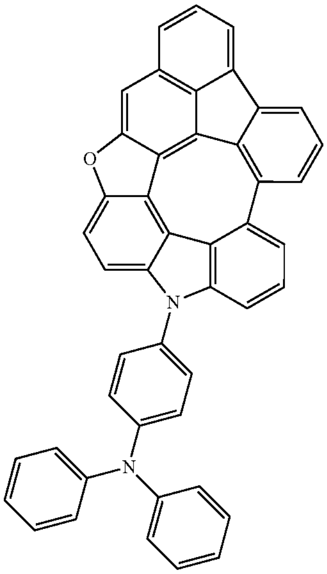
C-279
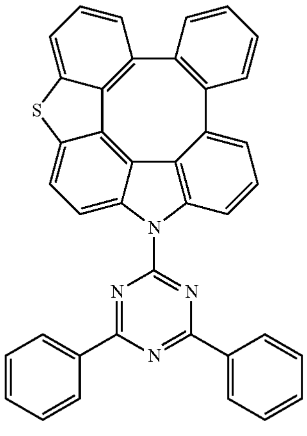
-continued
C-280
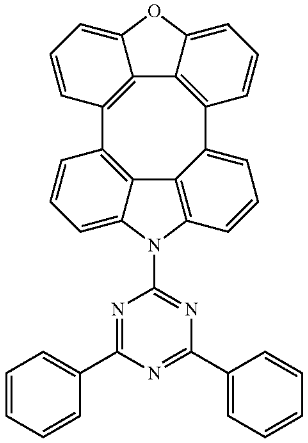
C-281
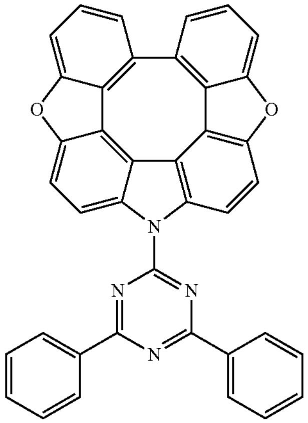
C-282
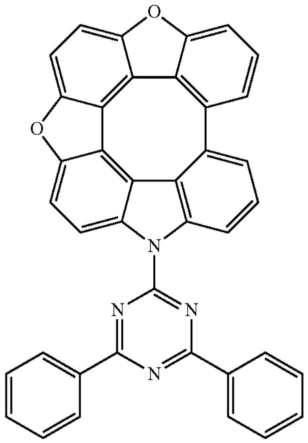

-continued
C-283
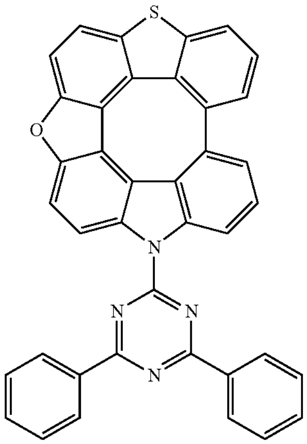
C-284
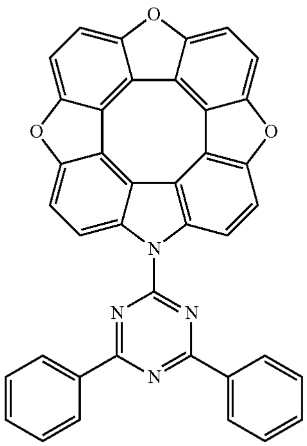
C-285
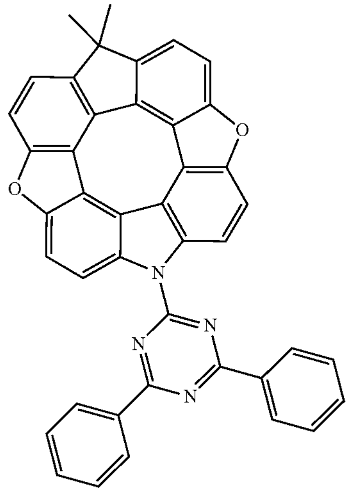
-continued
C-286
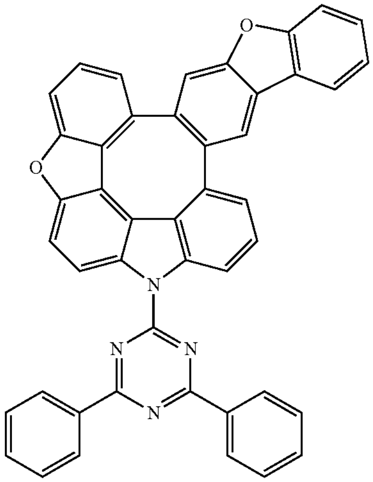
C-287
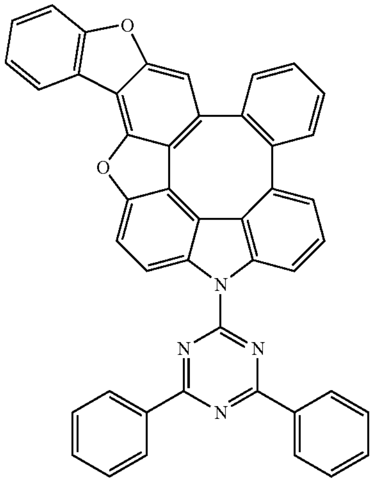
C-288
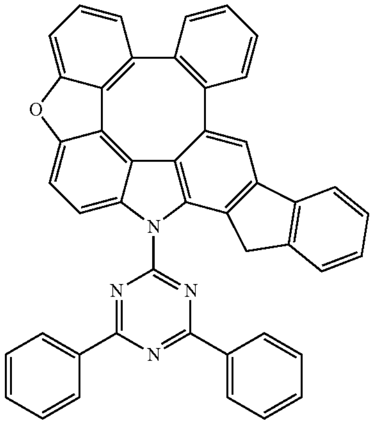

-continued
C-289
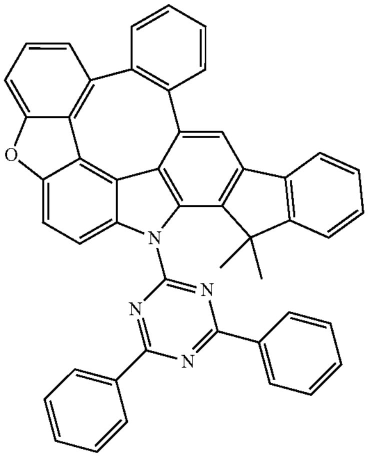
C-290
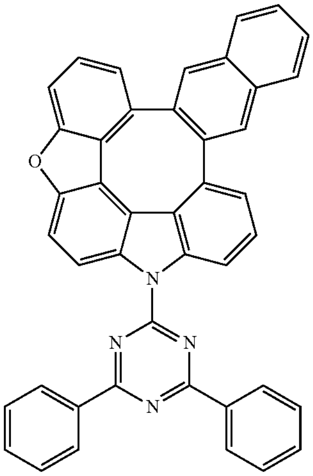
C-291
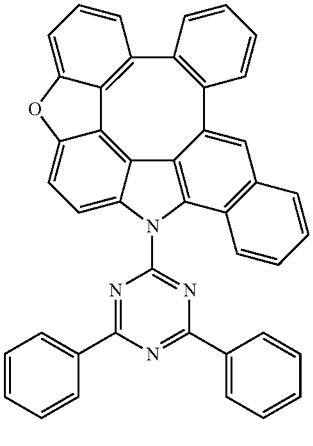
-continued
C-292
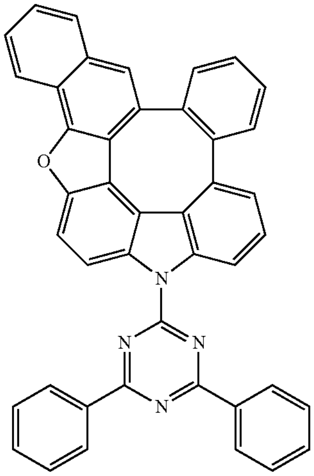
C-293
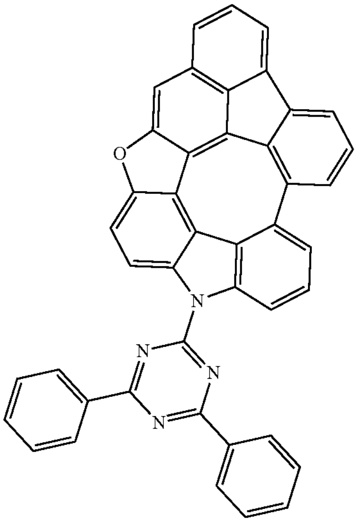
C-294
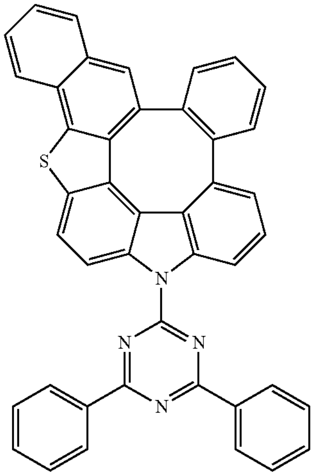

-continued
C-295
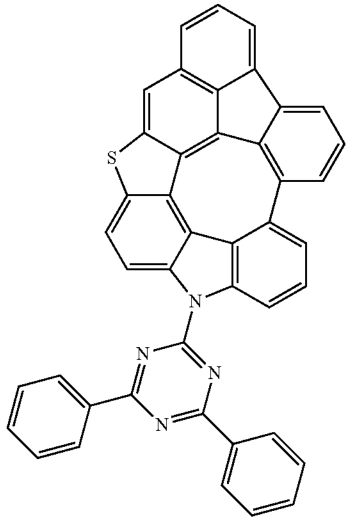
C-296
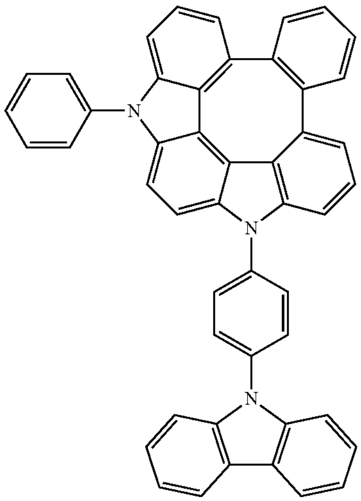
C-297
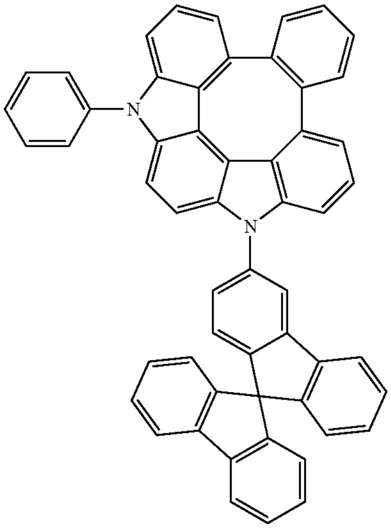
-continued
C-298
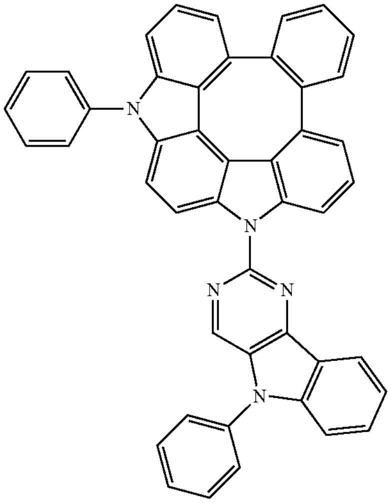
C-299
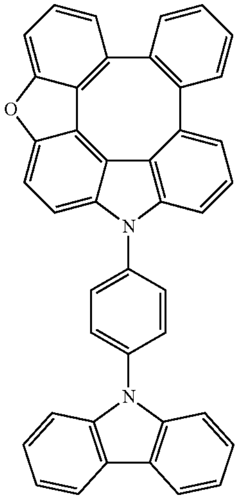
C-300
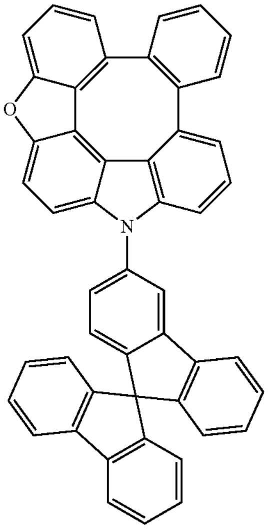
The compound represented by formula 2 may be at least one selected from the following compounds, but is not limited thereto.

-continued
C2-1
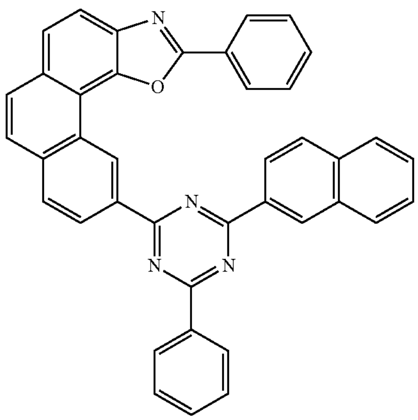
C2-2
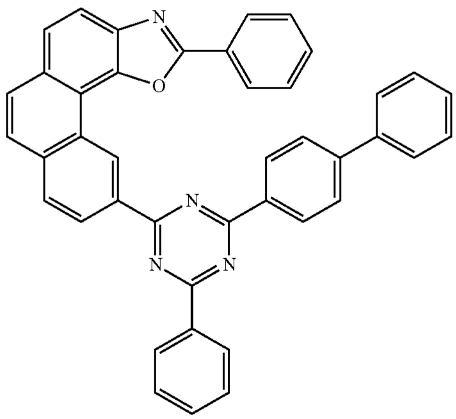
C2-3
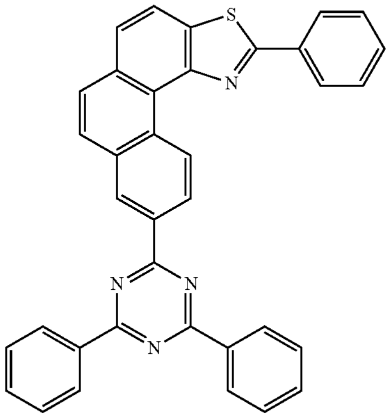
C2-4
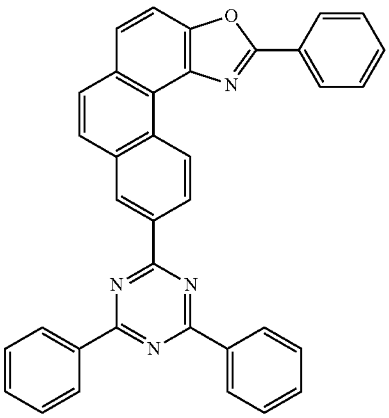
C2-5
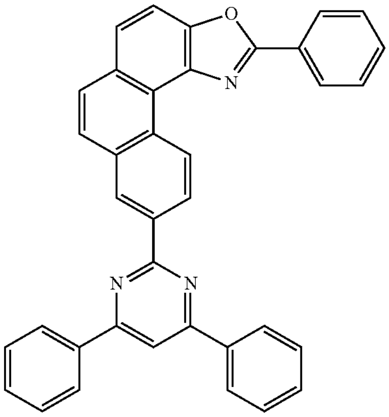
C2-6
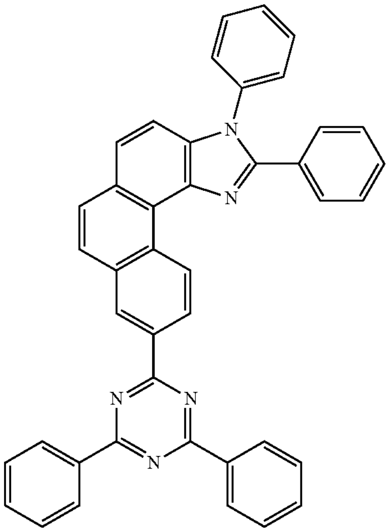

-continued
C2-7
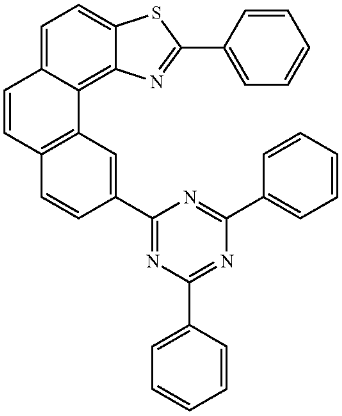
C2-8
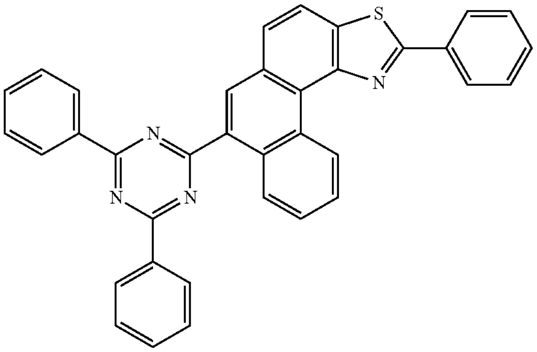
C2-9
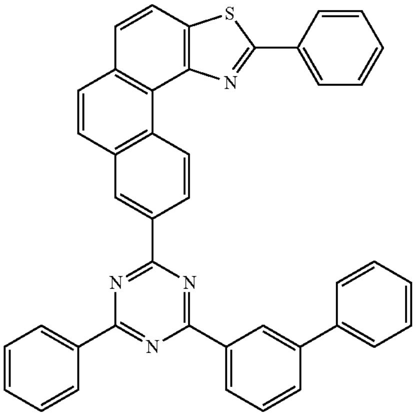
-continued
C2-10
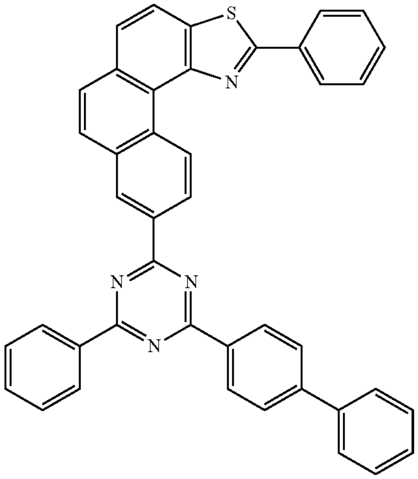
C2-11
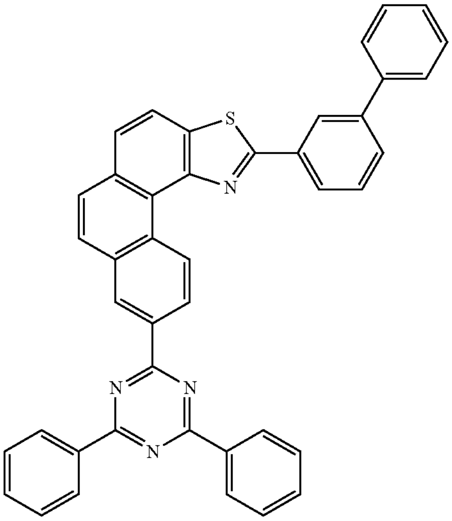
C2-12
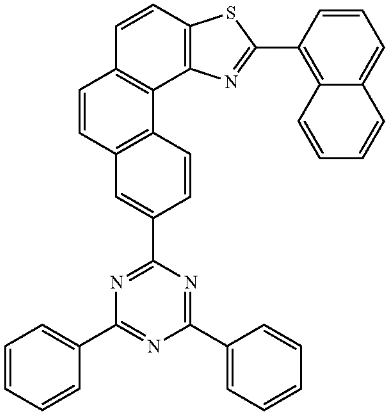

-continued
C2-13
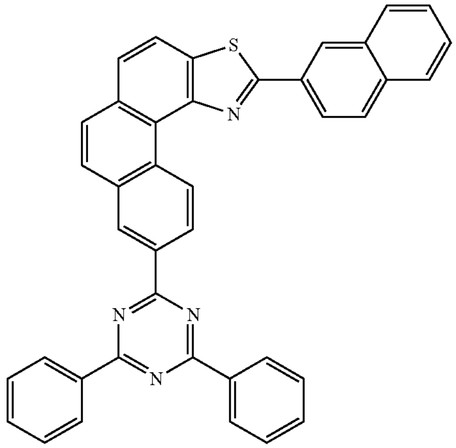
C2-14
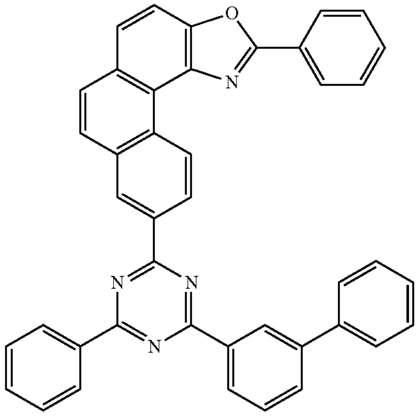
C2-15
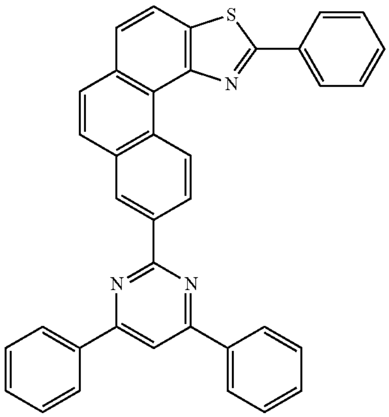
-continued
C2-16
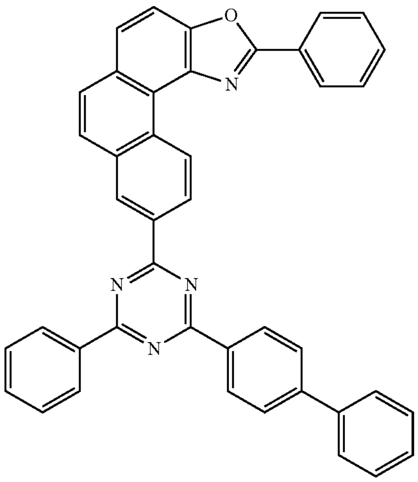
C2-17
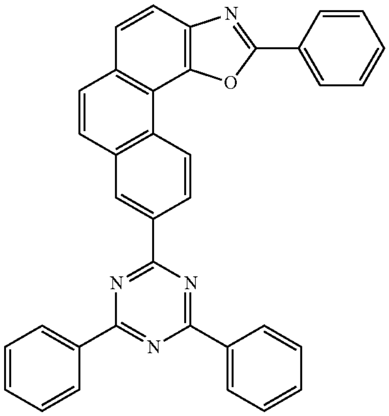
C2-18
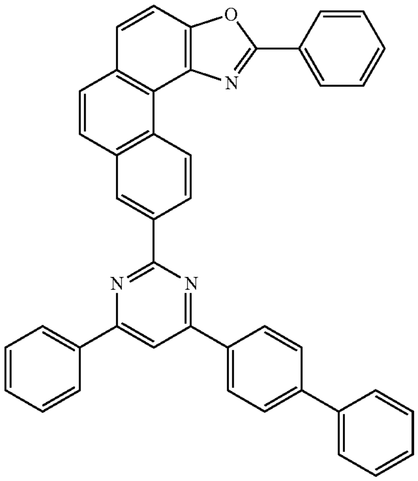

-continued
C2-19
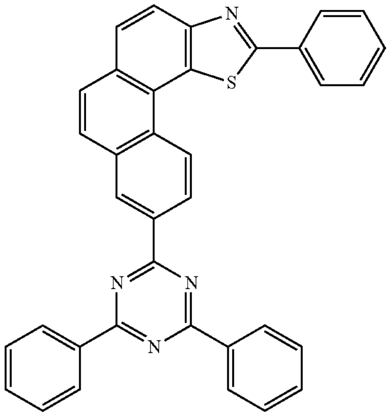
C2-20
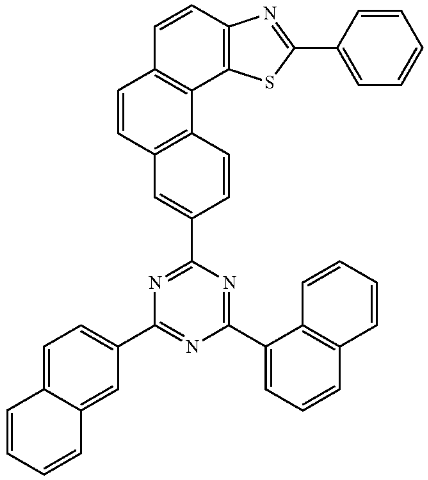
C2-21
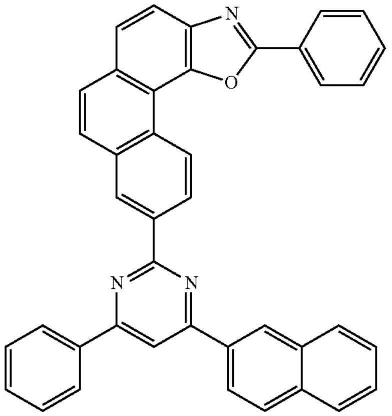
-continued
C2-22
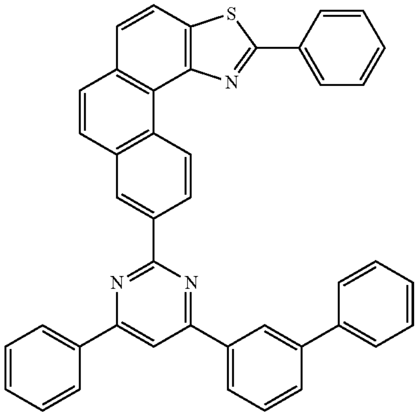
C2-23
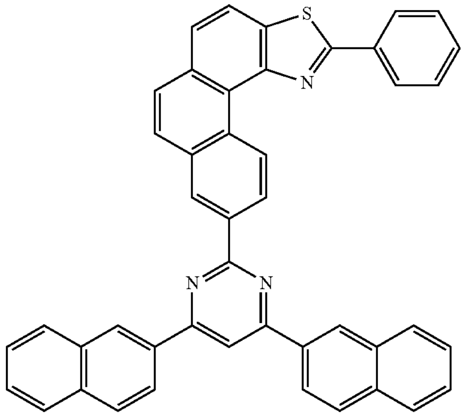
C2-24
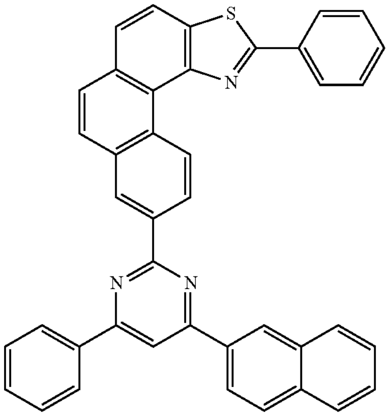

-continued
C2-25
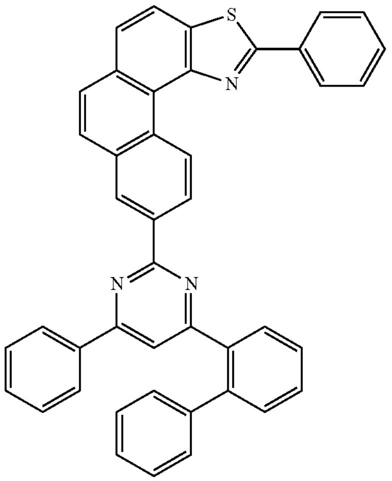
C2-26
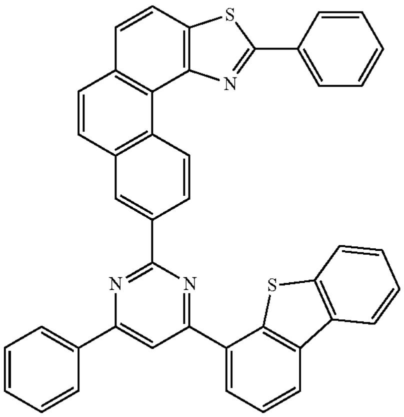
C2-27
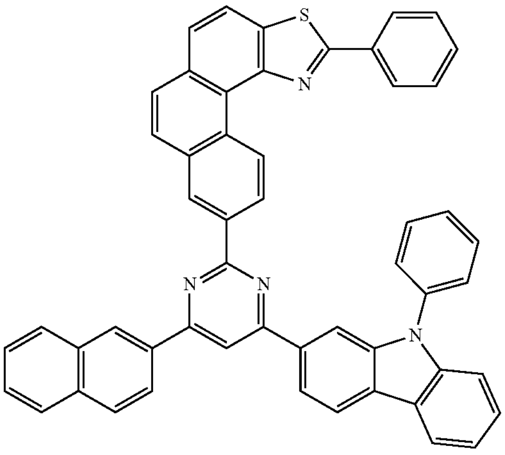
-continued
C2-28
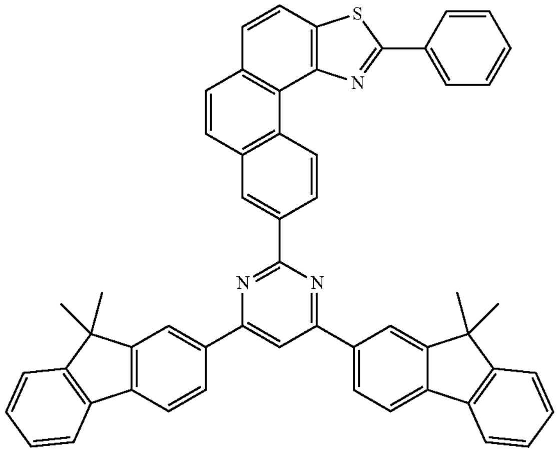
C2-29
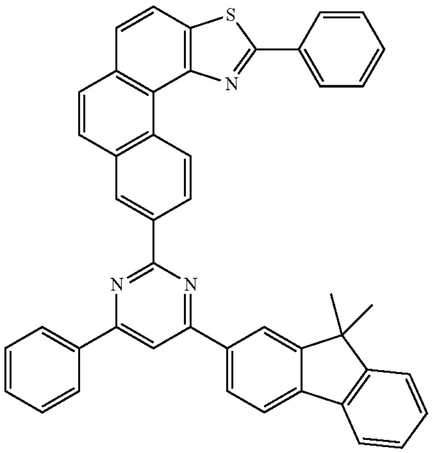
C2-30
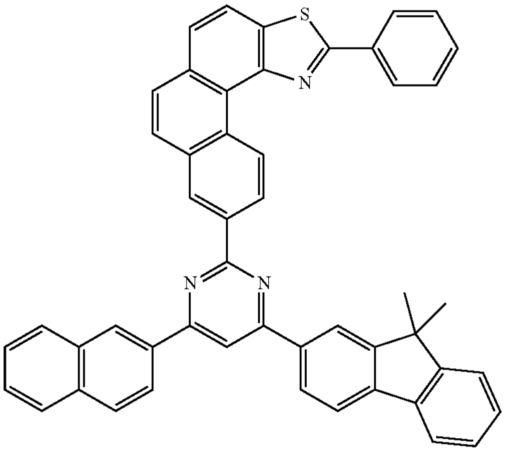

C2-31
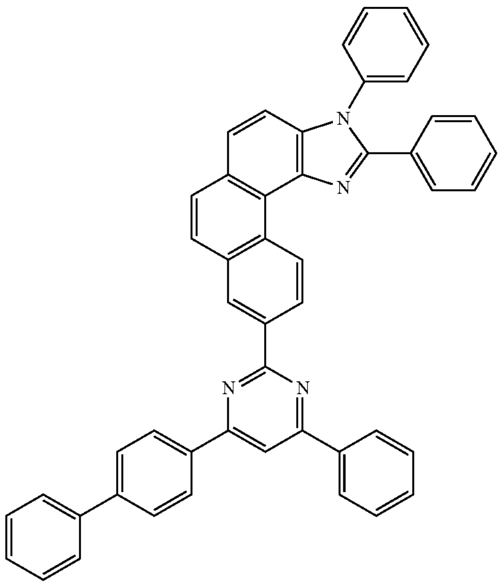
C2-32
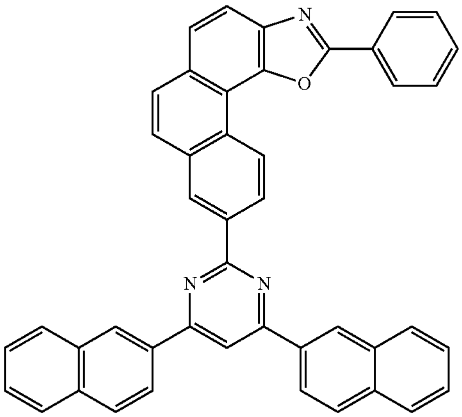
C2-33
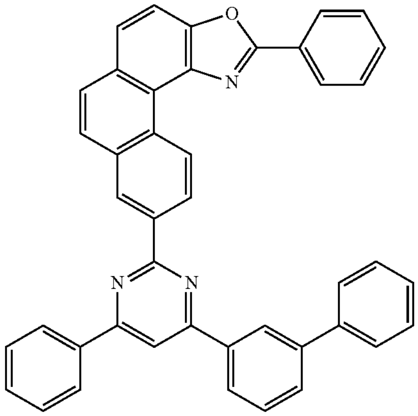
C2-34
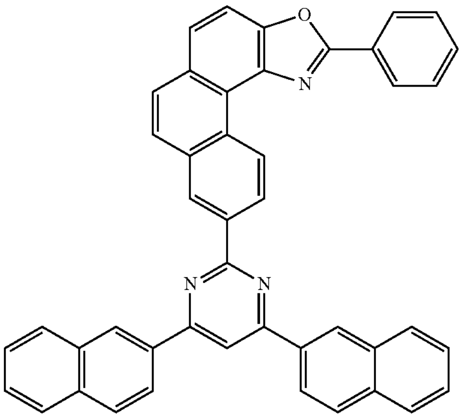
C2-35
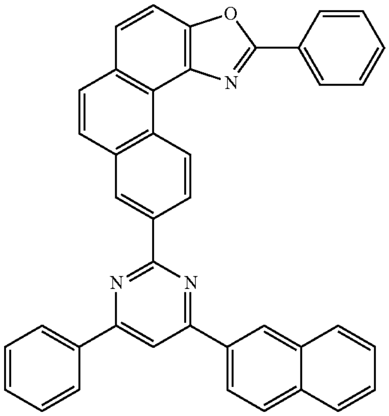
C2-36
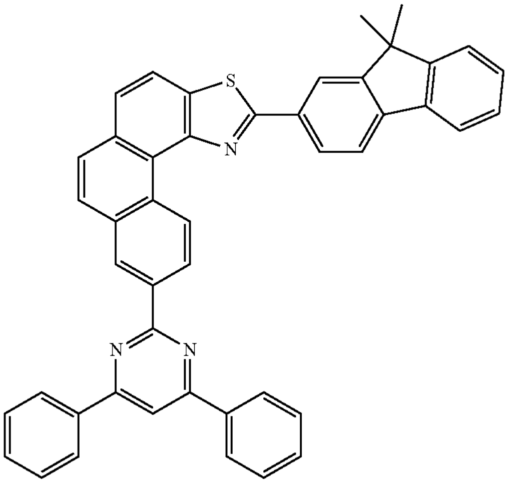

-continued
C2-37
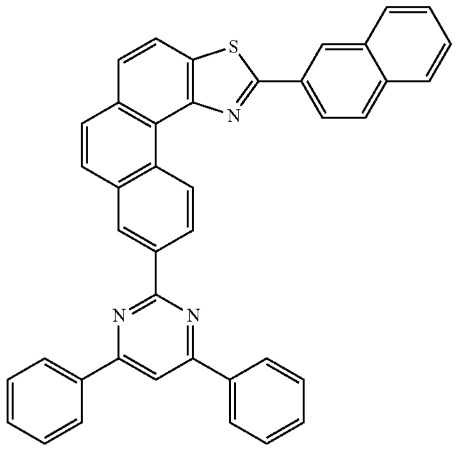
C2-38
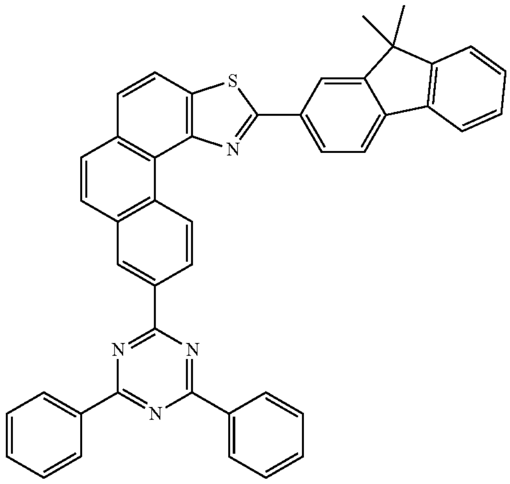
C2-39
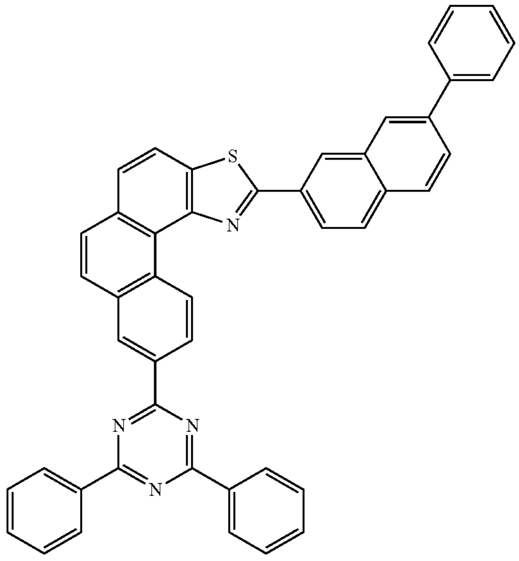
-continued
C2-40
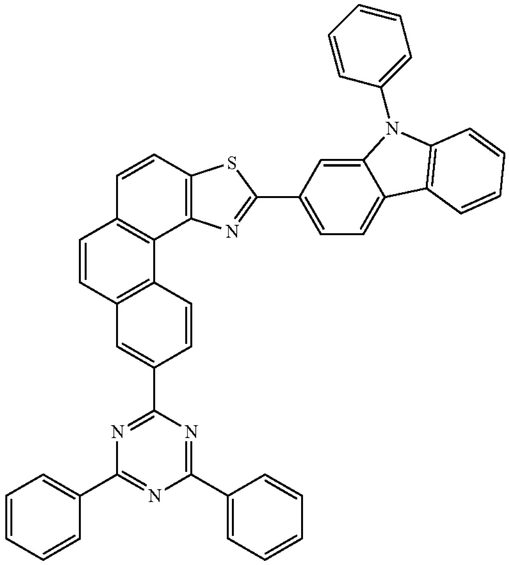
C2-41
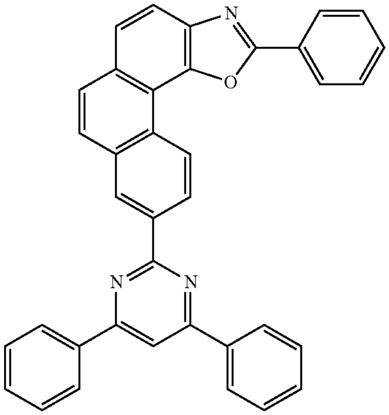
C2-42
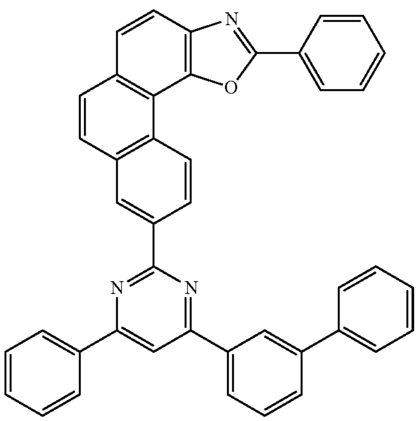

-continued
C2-43
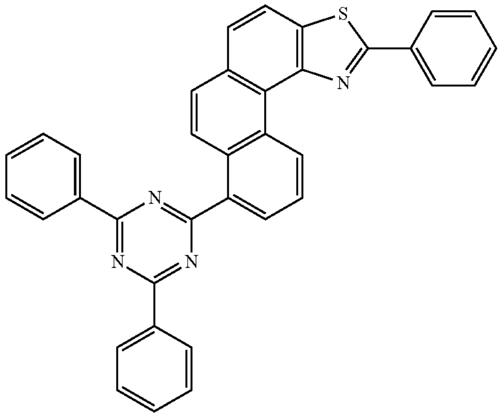
C2-44
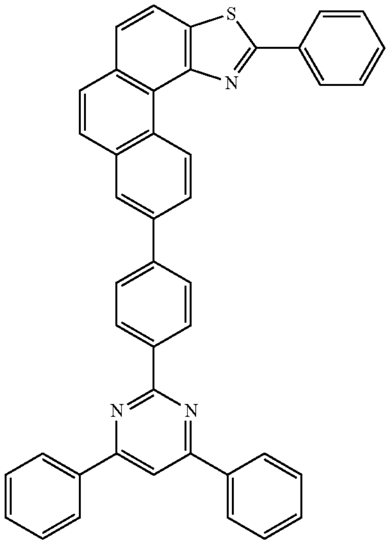
C2-45
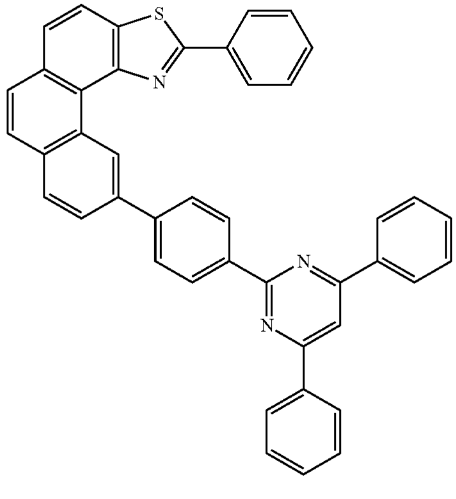
-continued
C2-46
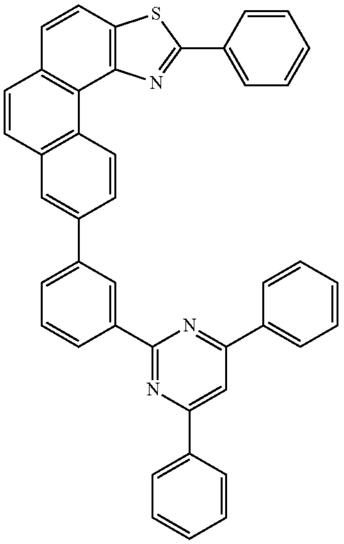
C2-47
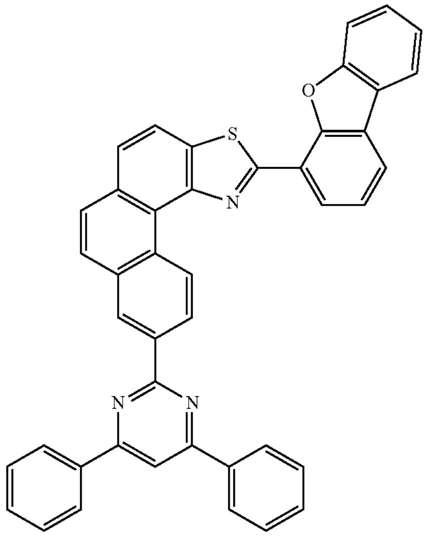
C2-48
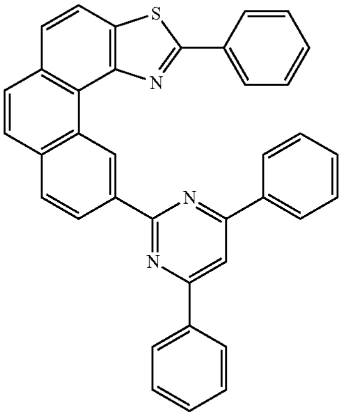

C2-49
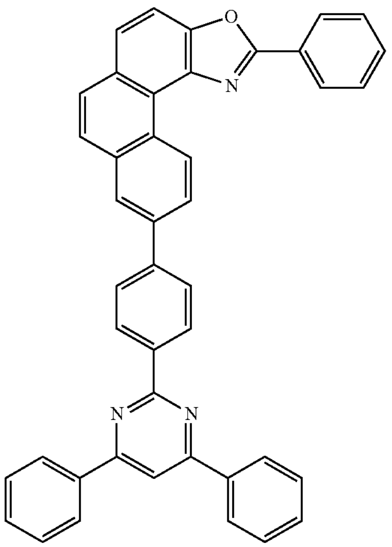
C2-50
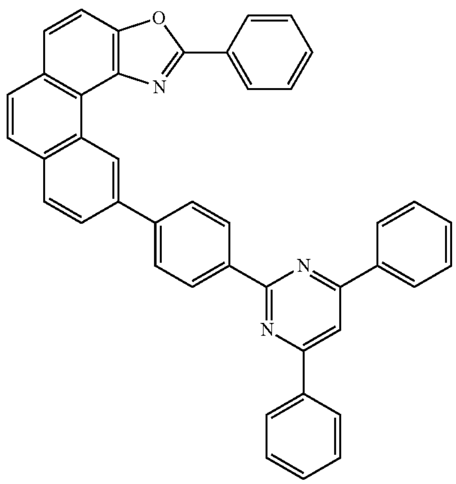
C2-51
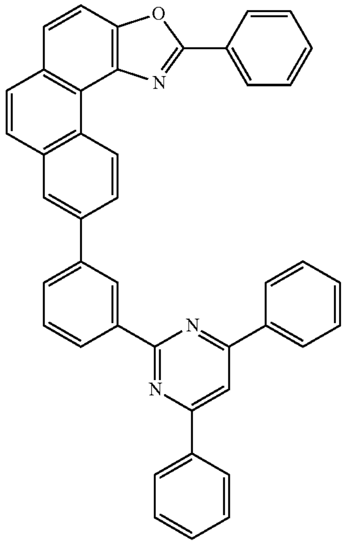
C2-52
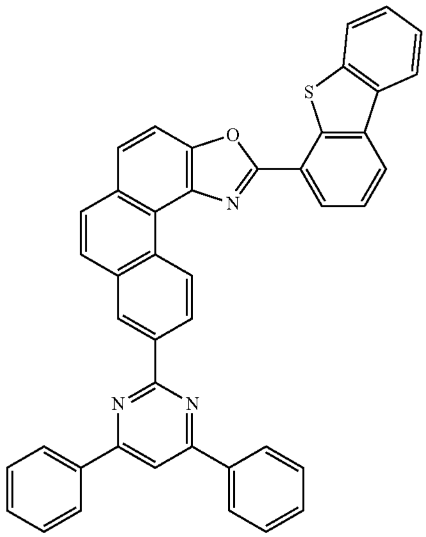
C2-53
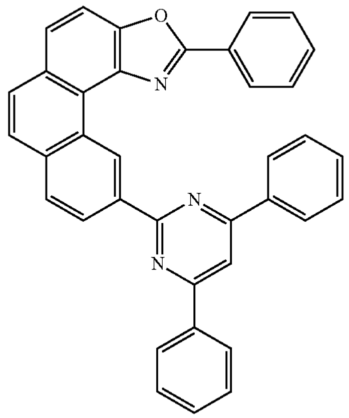
C2-54
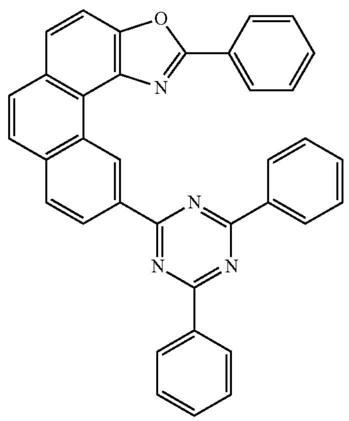

-continued
C2-55
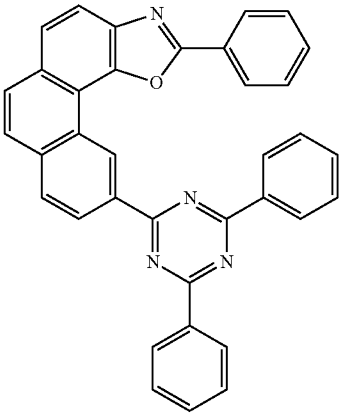
C2-56
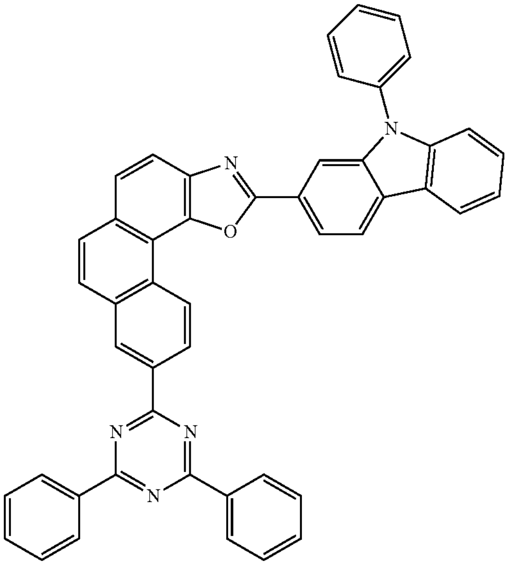
C2-57
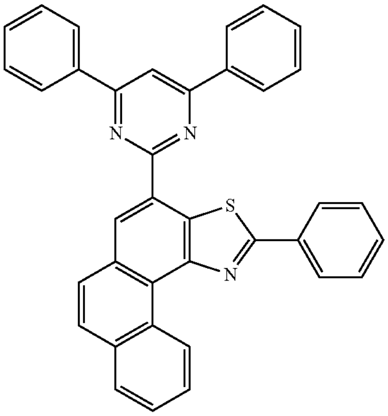
-continued
C2-58
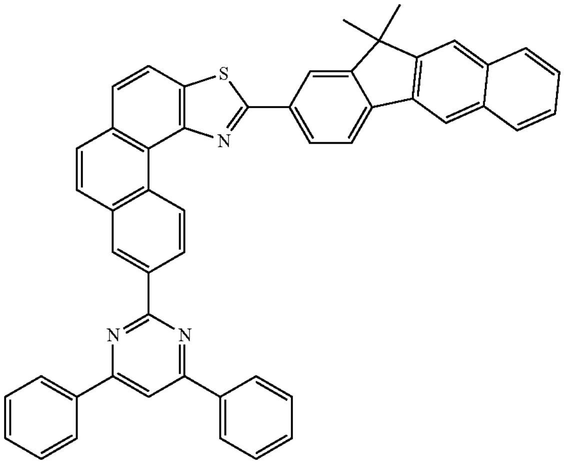
C2-59
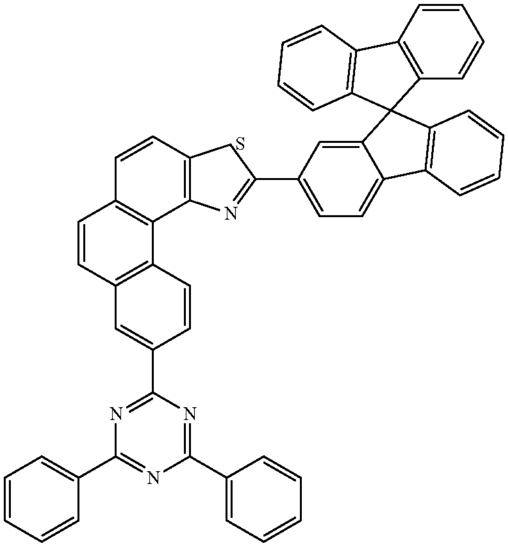
C2-60
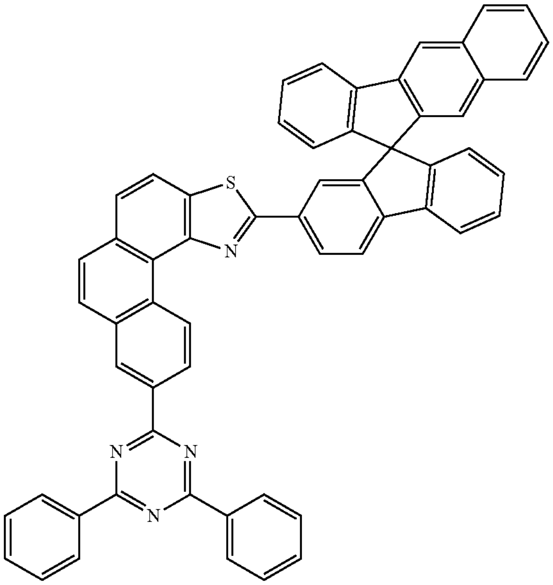

-continued
C2-61
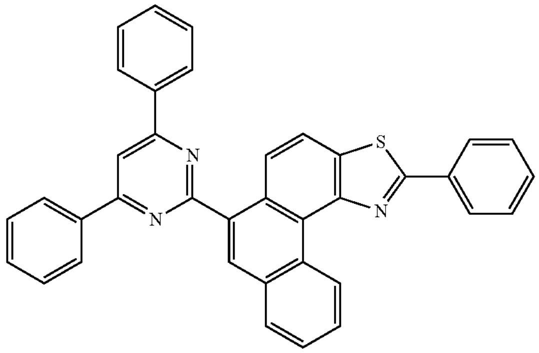
C2-62
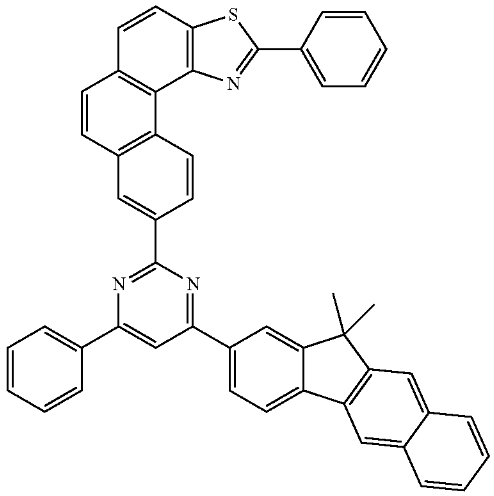
C2-63
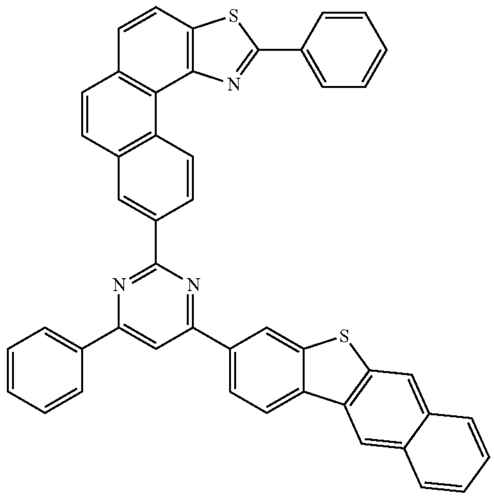
-continued
C2-64
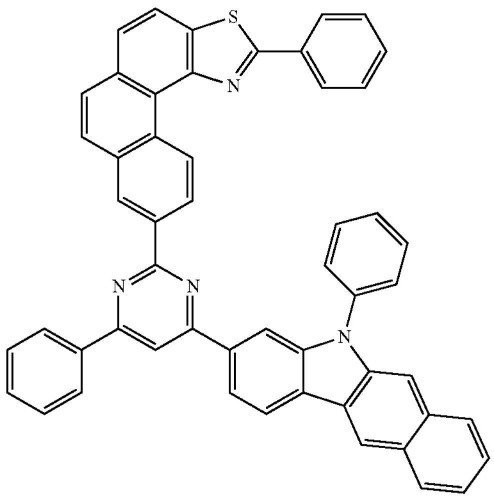
C2-65
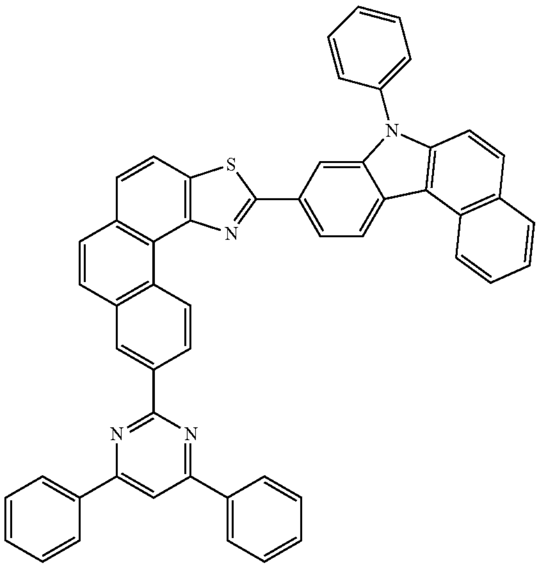
C2-66
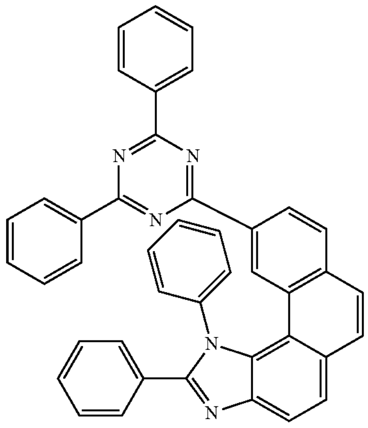

C2-67
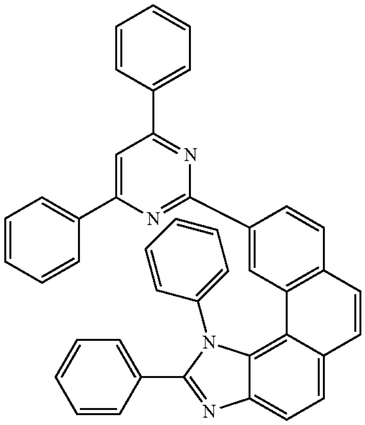
C2-68
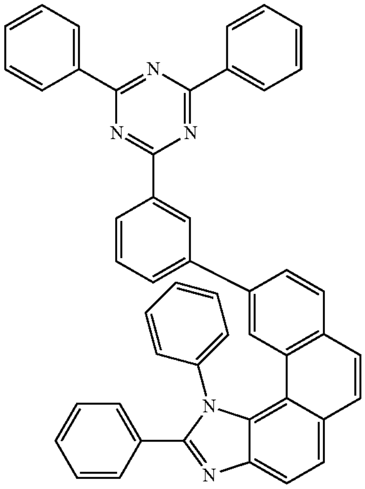
C2-69
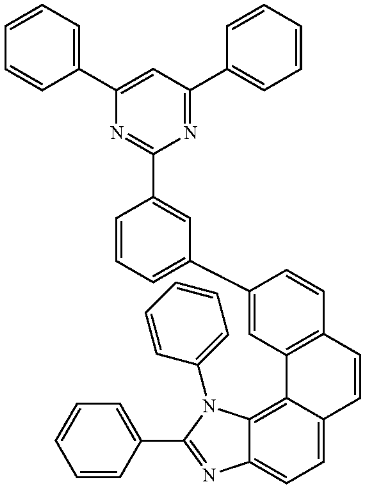
C2-70
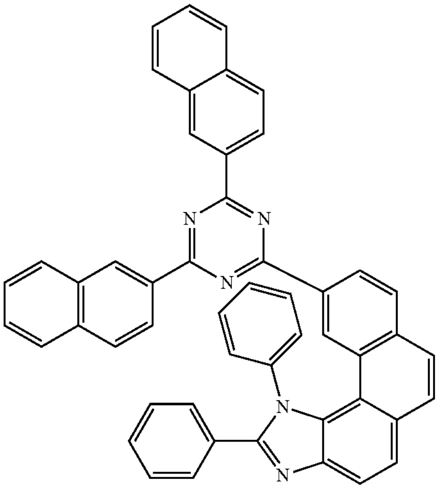
C2-71
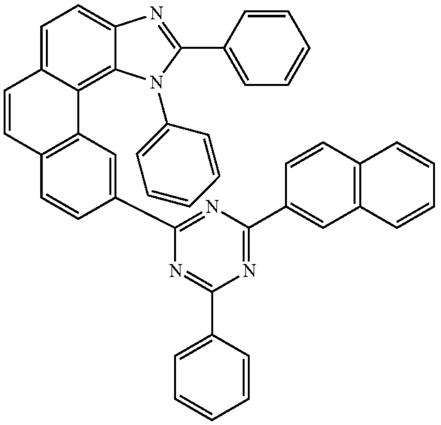
C2-72
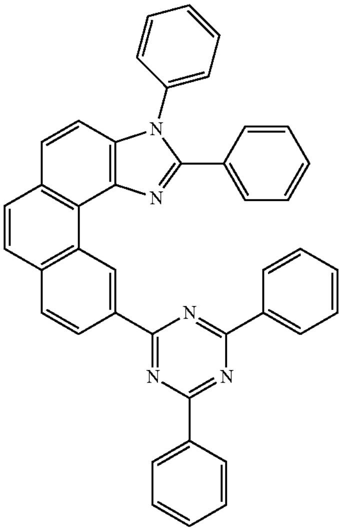

-continued
C2-73
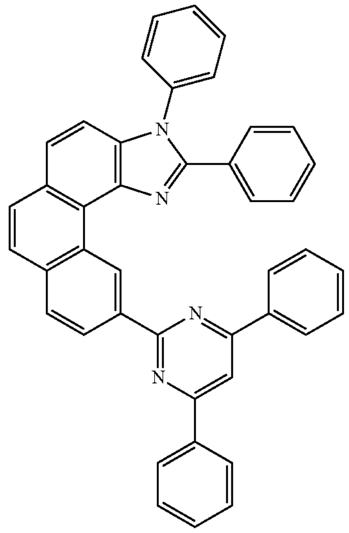
C2-74
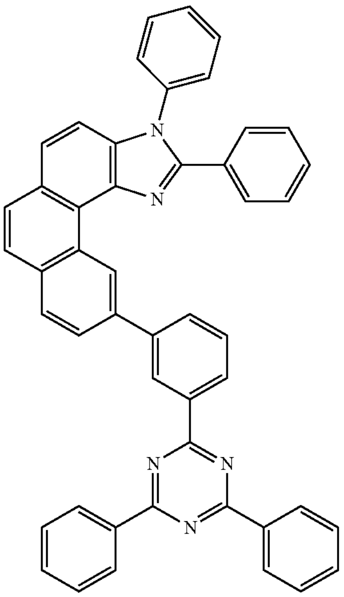
-continued
C2-75
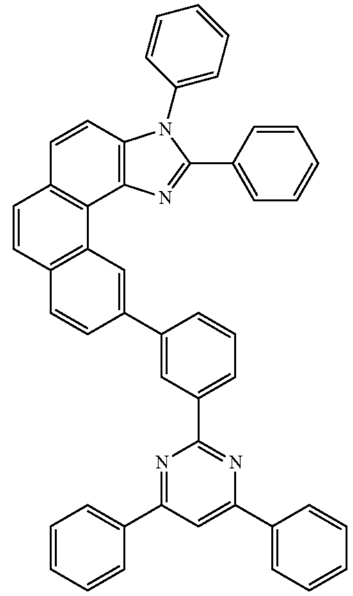
C2-76
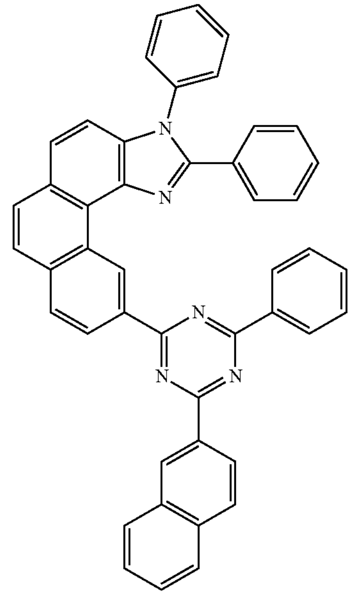

-continued
C2-77
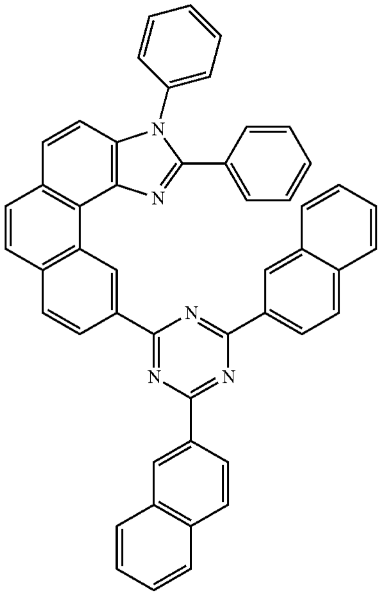
C2-78
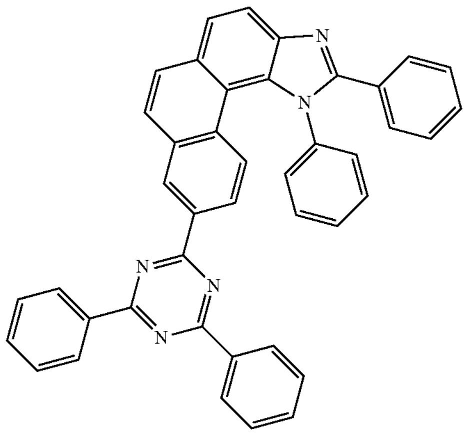
C2-79
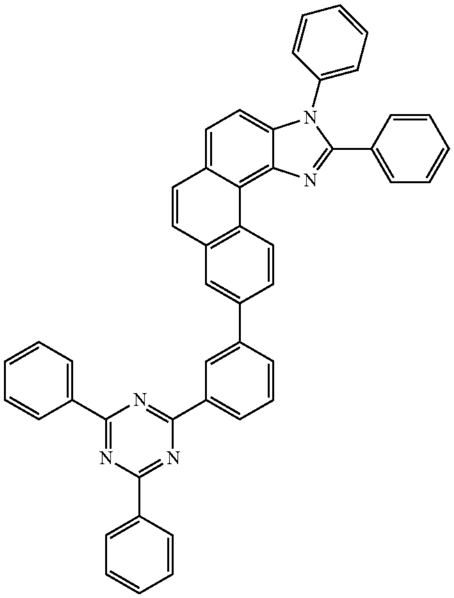
-continued
C2-80
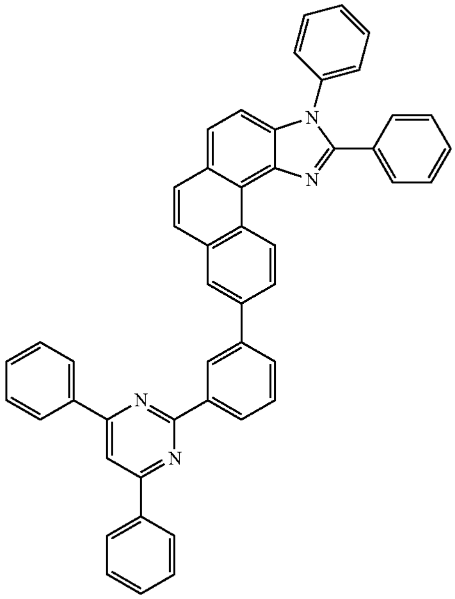
C2-81
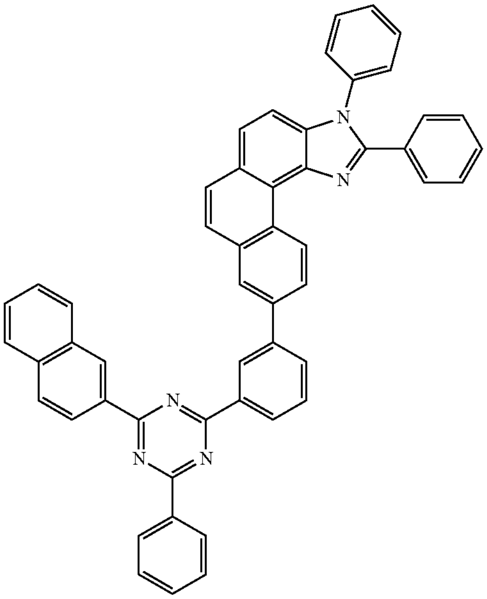

-continued
C2-82
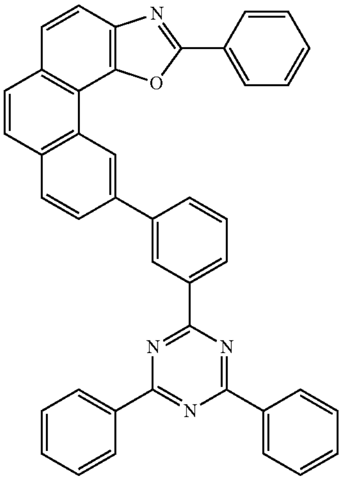
C2-83
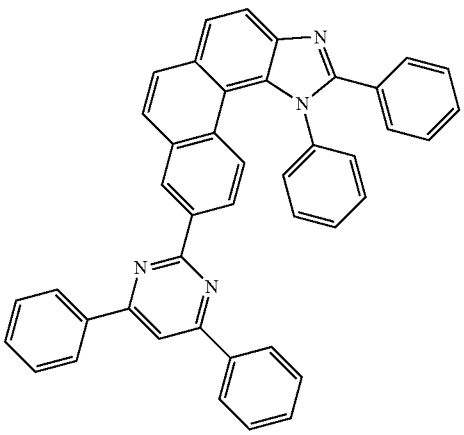
C2-84
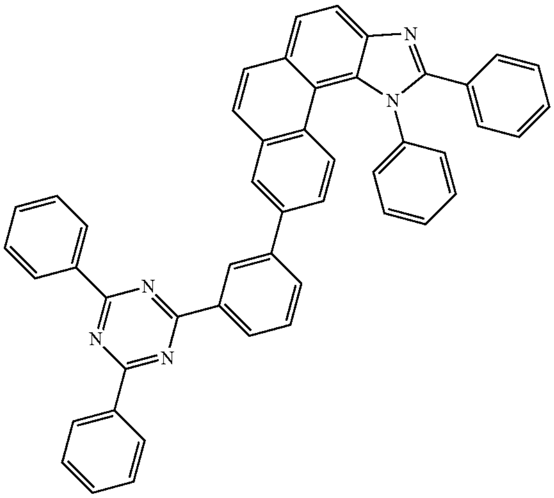
-continued
C2-85
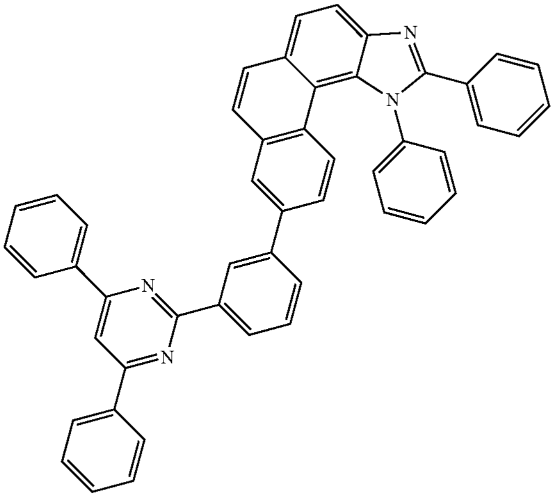
C2-86
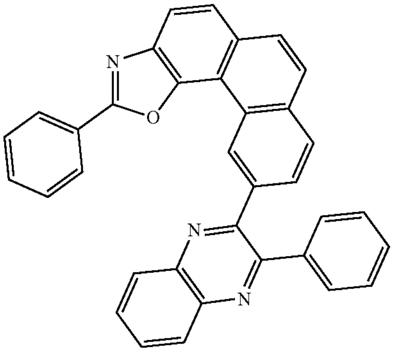
C2-87
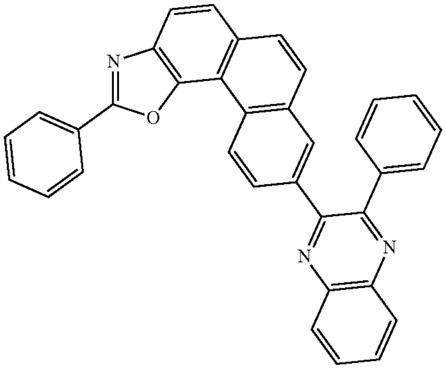

-continued
C2-88
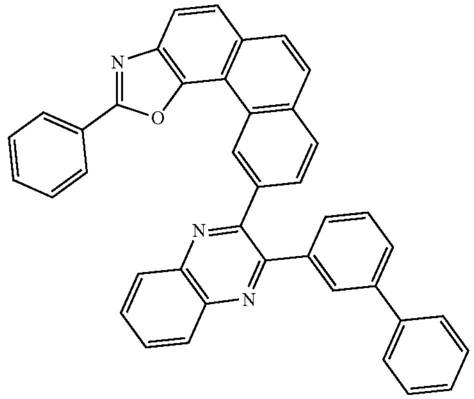
C2-89
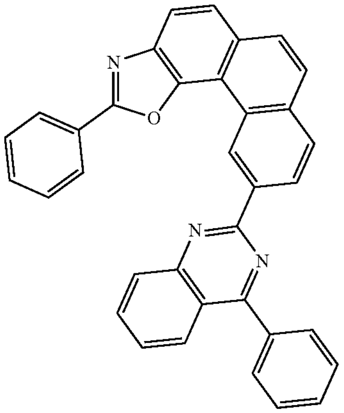
C2-90
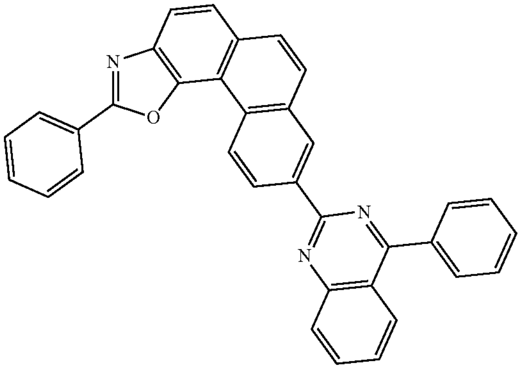
-continued
C2-91
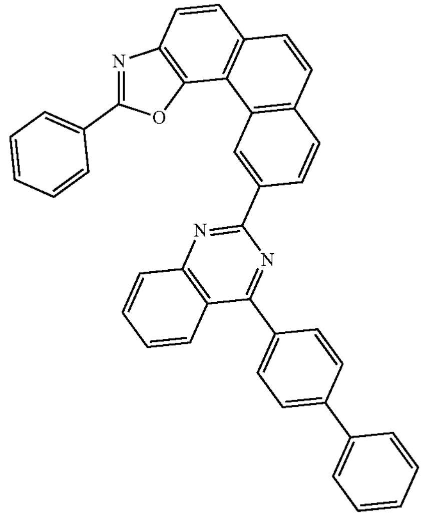
C2-92
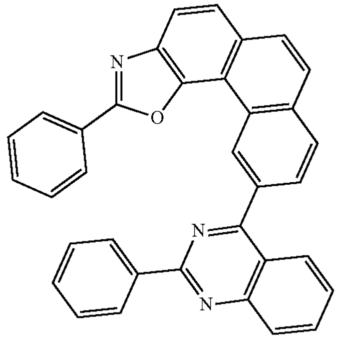
C2-93
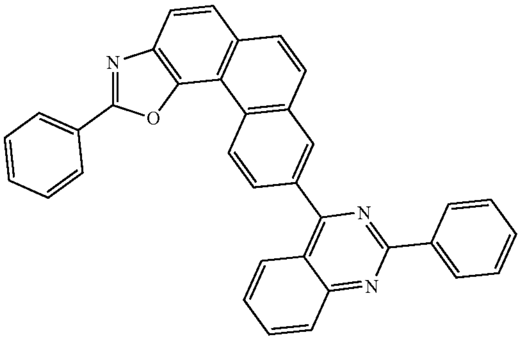
C2-94
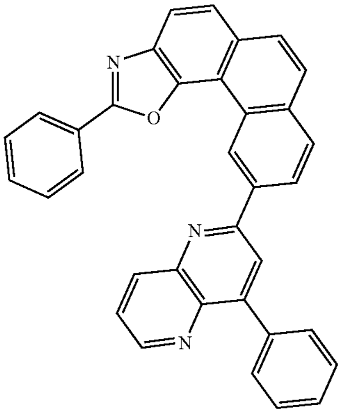

-continued
C2-95
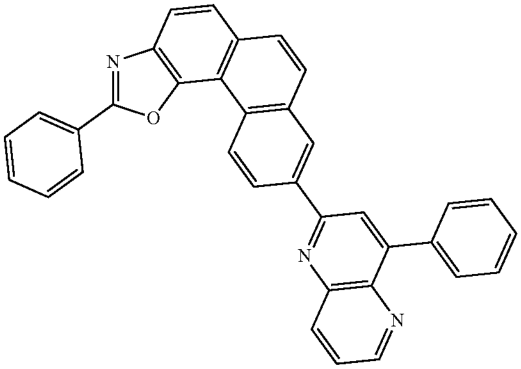
C2-96
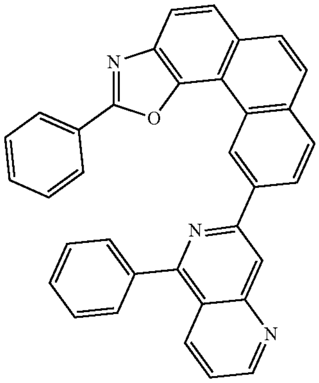
C2-97
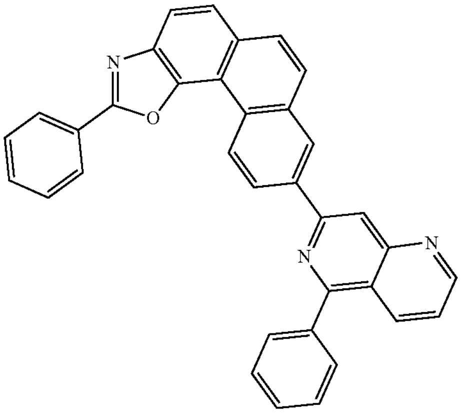
-continued
C2-98
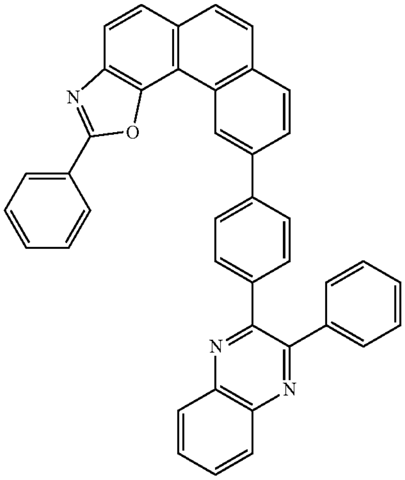
C2-99
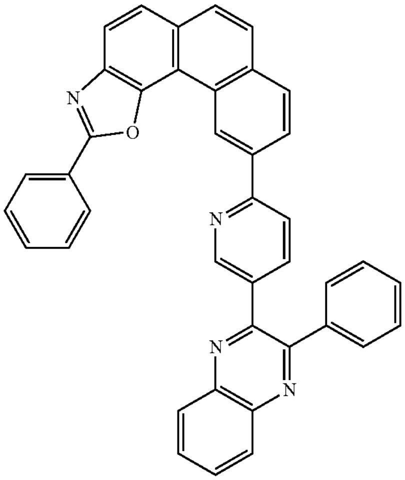
C2-100
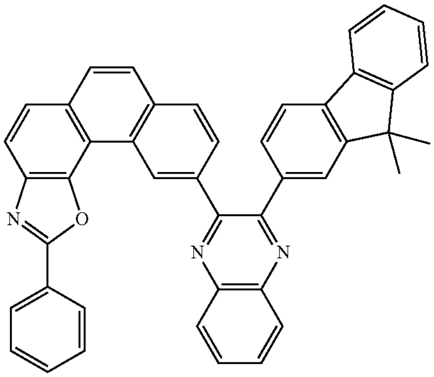

C2-101
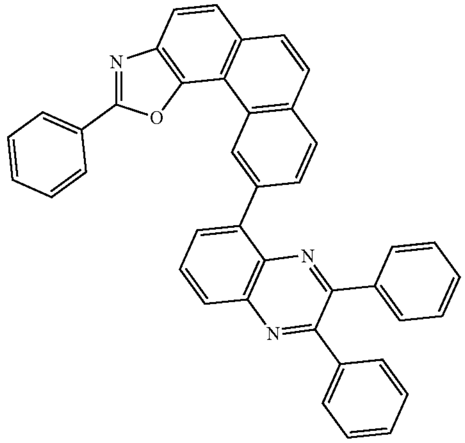
C2-102
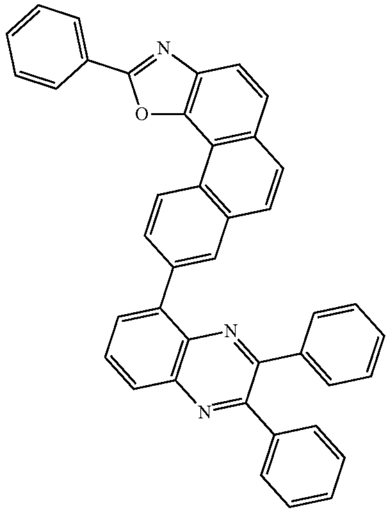
C2-103
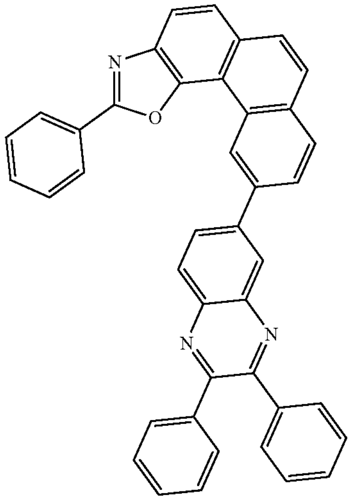
C2-104
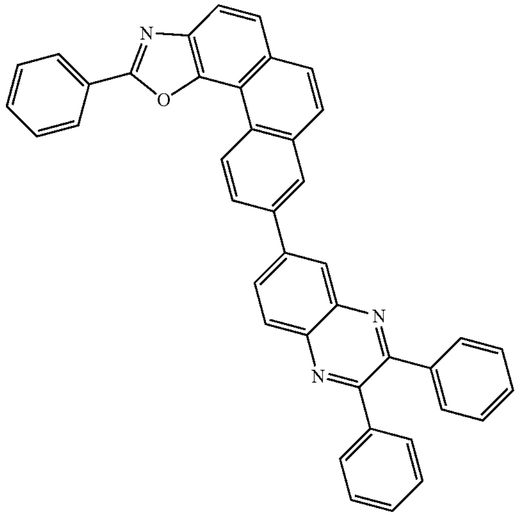
C2-105
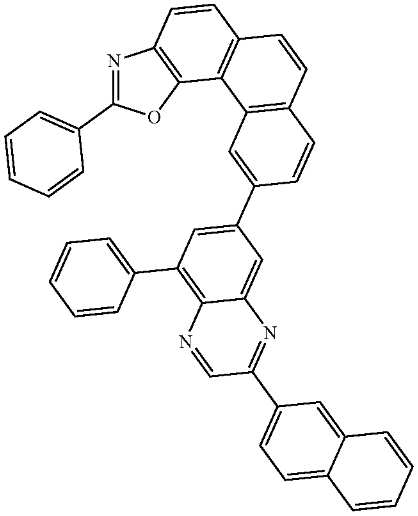
C2-106
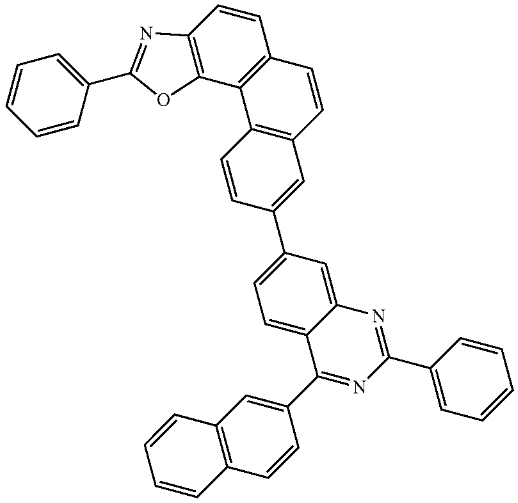

-continued
C2-107
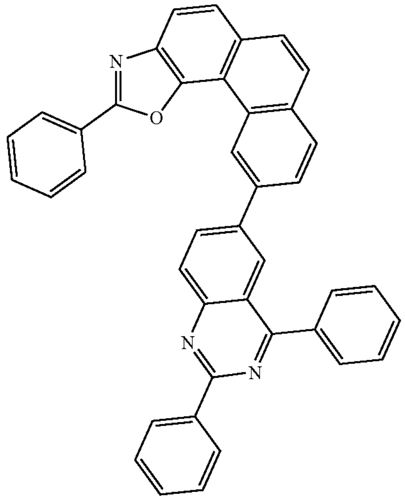
C2-108
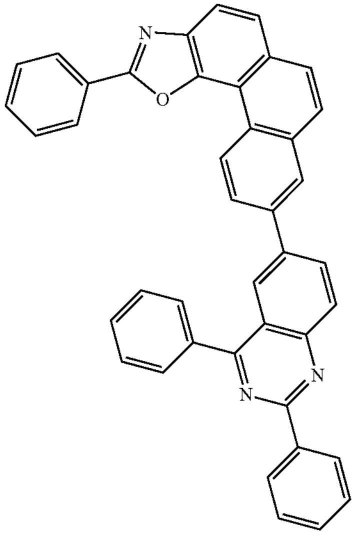
C2-109
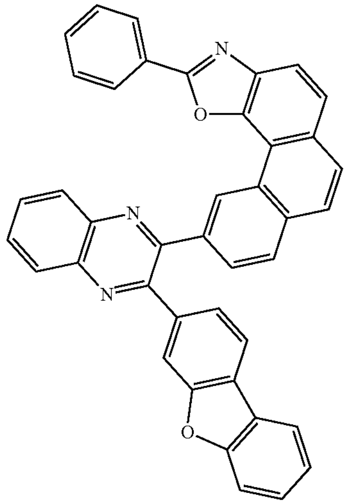
-continued
C2-110
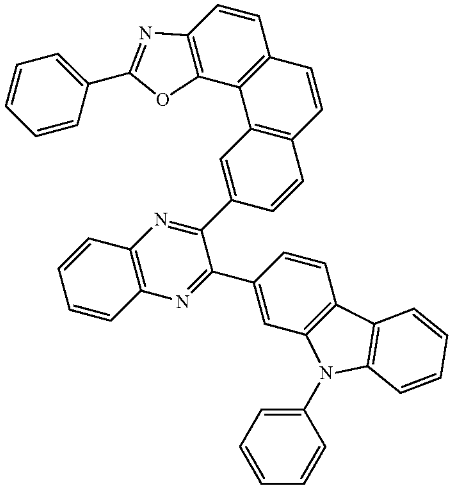
C2-111
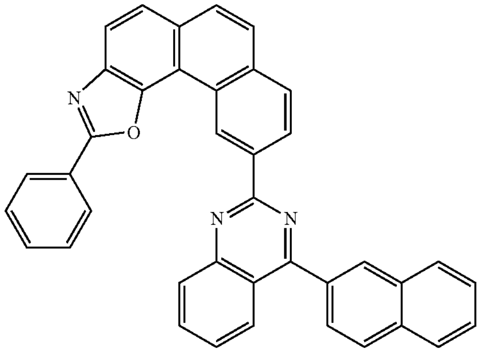
C2-112
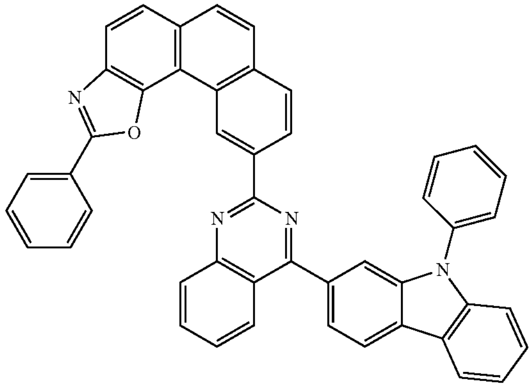
C2-113
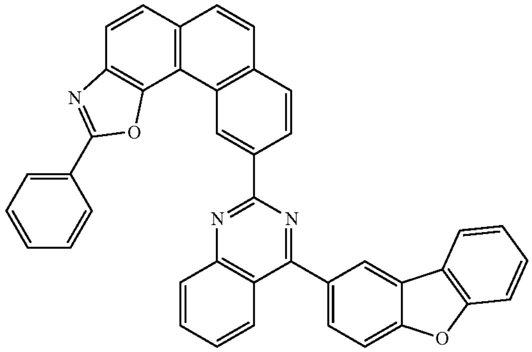

-continued
C2-114
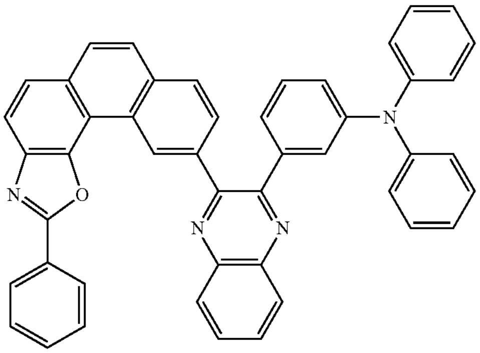
C2-115
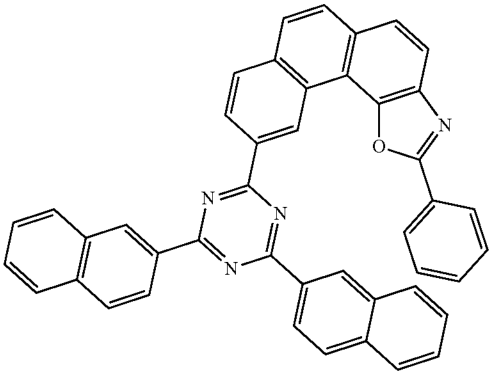
C2-116
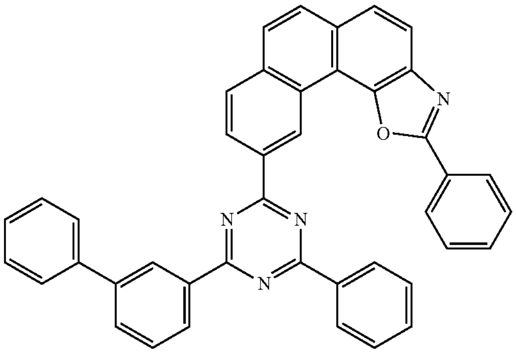
C2-117
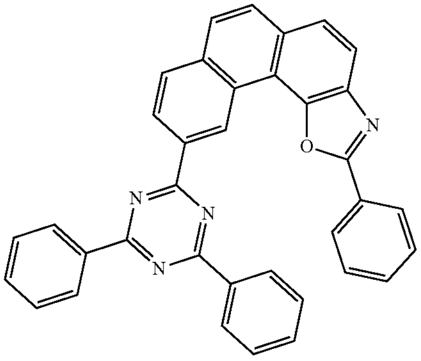
-continued
C2-118
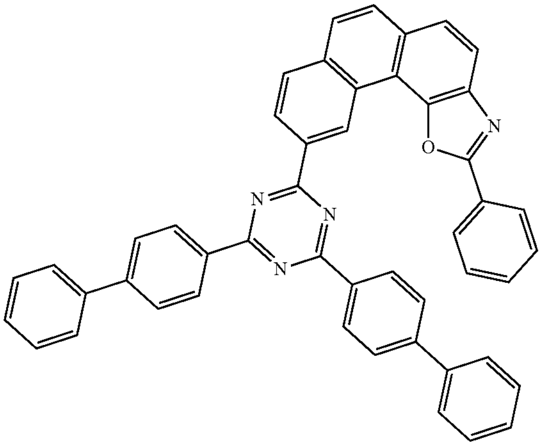
C2-119
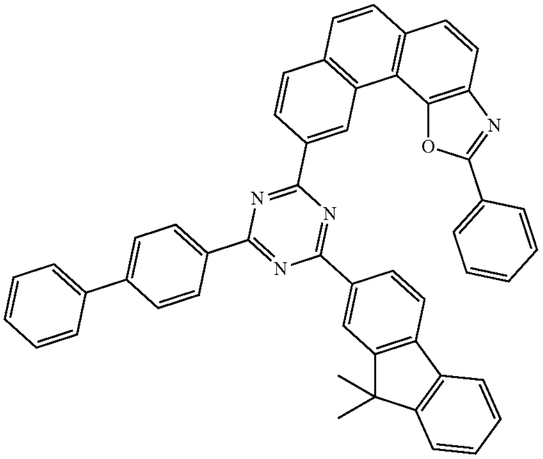
C2-120
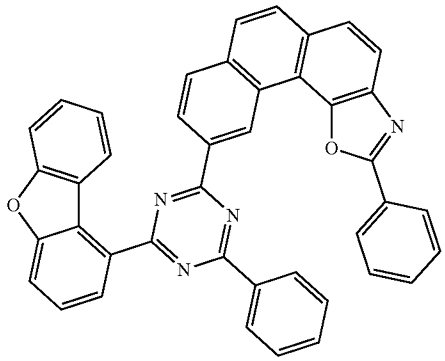

-continued

C2-121

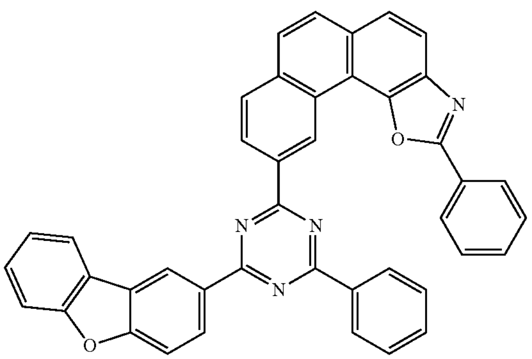

C2-122

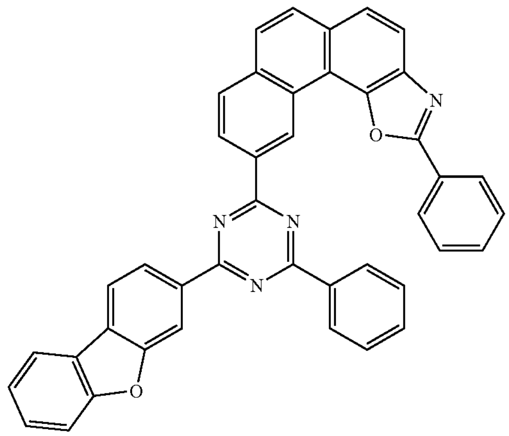

C2-123

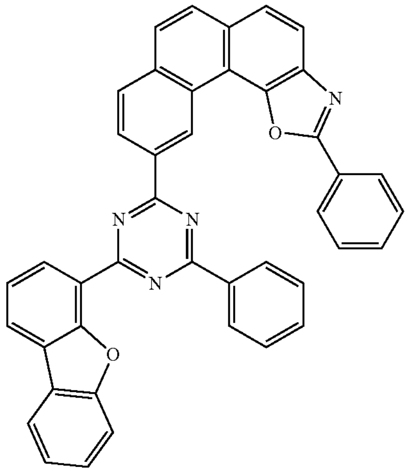

-continued

C2-124

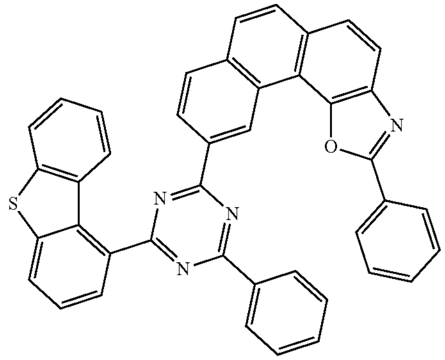

C2-125

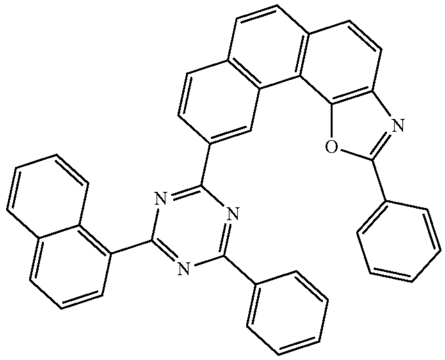

The combination of at least one of compounds C-1 to C-300 and at least one of compounds C2-1 to C2-125 may be used in an organic electroluminescent device.

The compound represented by formula 1 of the present disclosure may be produced by a synthetic method known to one skilled in the art, and for example, according to the following reaction schemes 1 to 4, but is not limited thereto:

[Reaction Scheme 1]

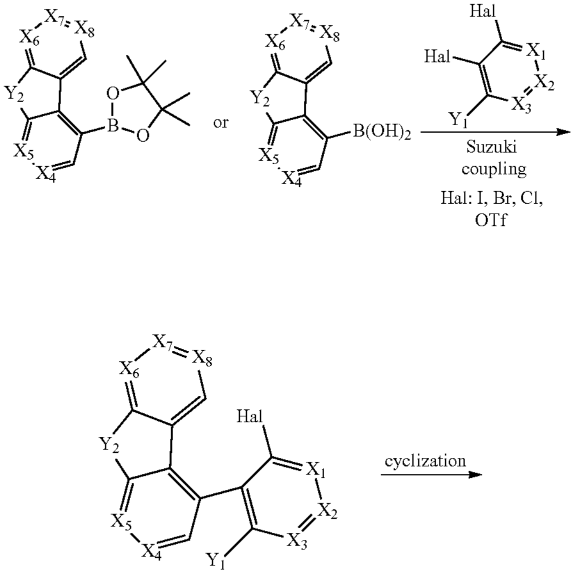

-continued
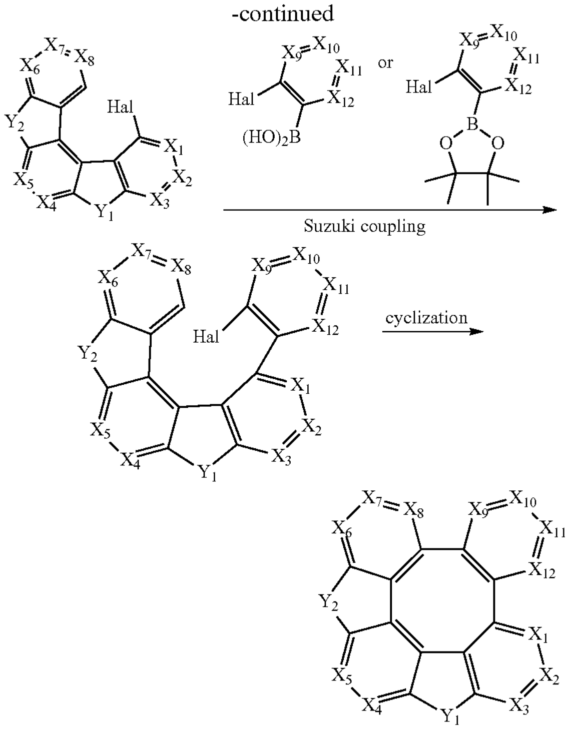
-continued
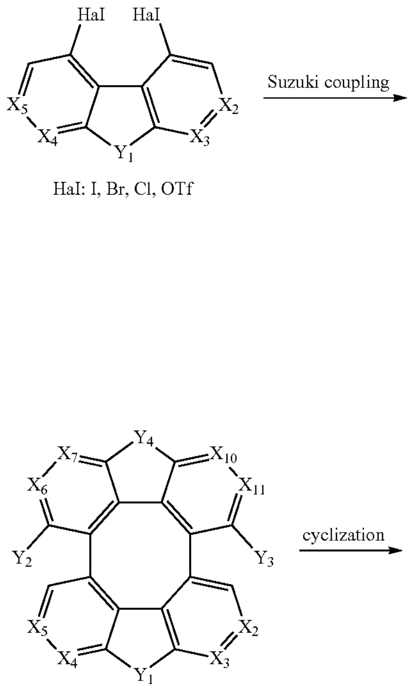
[Reaction Scheme 2]
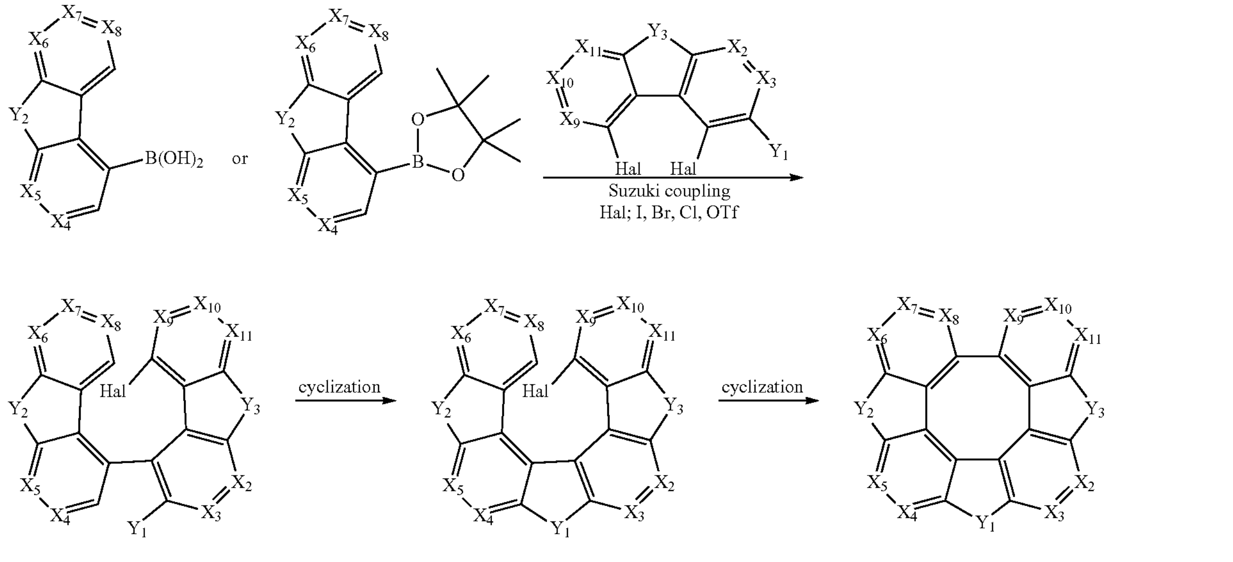
[Reaction Scheme 3]
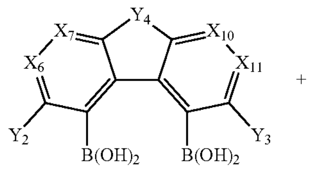
-continued
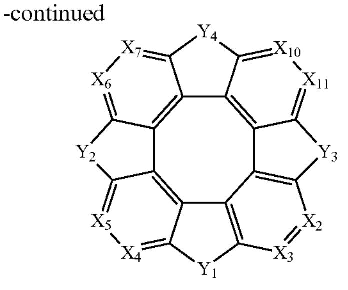

[Reaction Scheme 4]

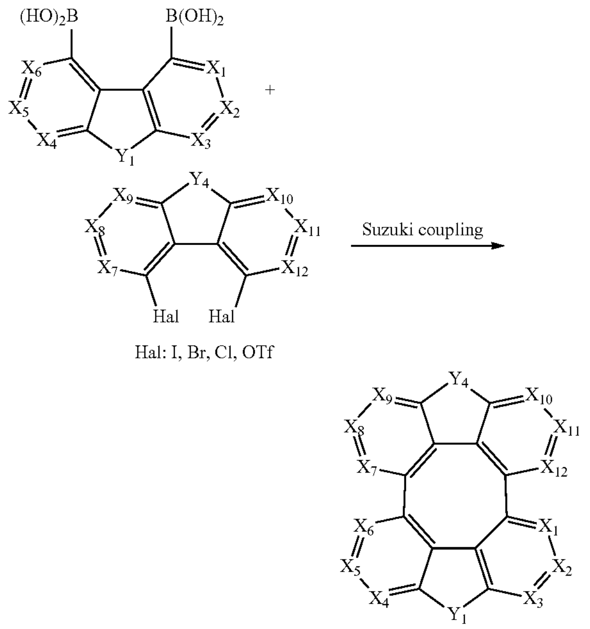

In reaction schemes 1 to 4, $Y_1$ to $Y_4$, and $X_1$ to $X_{12}$ are as defined in formulas 1-1 to 1-4. Although illustrative synthesis examples of the compound represented by formula 1 of the present disclosure are described above, one skilled in the art will be able to readily understand that all of them are based on a Buchwald-Hartwig cross-coupling reaction, an N-arylation reaction, an H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents which are defined in formula 1, but are not specified in the specific synthesis examples, are bonded.

The compound represented by formula 2 of the present disclosure may be produced by a synthetic method known to one skilled in the art, and for example, according to the methods disclosed in Korean Patent Application Laying-Open No. 2020-0000329 (published on Jan. 2, 2020), etc.

In addition, the non-deuterated analogues of the compound represented by formula 2 can be prepared by known coupling and substitution reactions. Also, the non-deuterated analogues may be prepared in a similar manner by using deuterated precursor materials, or more generally may be prepared by treating the non-deuterated compound with a deuterated solvent or D6-benzene in the presence of an H/D exchange catalyst such as a Lewis acid, e.g., aluminum trichloride or ethyl aluminum chloride, a trifluoromethanesulfonic acid, or a trifluoromethanesulfonic acid-D. In addition, the degree of deuteration can be controlled by changing the reaction conditions such as the reaction temperature. For example, the number of deuterium in formula 2 can be controlled by adjusting the reaction temperature and time, the equivalent of the acid, etc.

The organic electroluminescent device according to the present disclosure may comprise an anode, a cathode, and at least one organic layer between the anode and cathode in which the organic layer may comprise a plurality of organic electroluminescent materials, including the compound represented by formula 1 as the first organic electroluminescent material, and the compound represented by formula 2 as the second organic electroluminescent material. According to one embodiment of the present disclosure, the organic electroluminescent device according to the present disclosure may comprise an anode, a cathode, and at least one light-emitting layer between the anode and cathode in which the light-emitting layer may comprise the compound represented by formula 1 and the compound represented by formula 2.

The light-emitting layer includes a host and a dopant, in which the host includes a plurality of host materials and the compound represented by formula 1 may be included as the first host compound of the plurality of host materials, and the compound represented by formula 2 may be included as the second host compound of the plurality of host materials. The weight ratio of the first host compound and the second host compound is about 1:99 to about 99:1, preferably about 10:90 to about 90:10, more preferably about 30:70 to about 70:30, even more preferably about 40:60 to about 60:40, and most preferably about 50:50.

Herein, the light-emitting layer is a layer from which light is emitted, and may be a single layer or a multi-layer of which two or more layers are stacked. All of the first host material and the second host material may be included in one layer, or the first host material and the second host material may be included in respective different light-emitting layers. According to one embodiment of the present disclosure, the doping concentration of the dopant compound with respect to the host compound in the light-emitting layer may be less than 20 wt %.

The organic electroluminescent device of the present disclosure may further comprise at least one layer selected from a hole injection layer, a hole transport layer, a hole auxiliary layer, a light-emitting auxiliary layer, an electron transport layer, an electron injection layer, an interlayer, an electron buffer layer, a hole blocking layer, and an electron blocking layer. According to one embodiment of the present disclosure, the organic electroluminescent device of the present disclosure may further comprise an amine-based compound besides the plurality of host materials of the present disclosure as at least one of a hole injection material, a hole transport material, a hole auxiliary material, a light-emitting material, a light-emitting auxiliary material, and an electron blocking material. Further, according to one embodiment of the present disclosure, the organic electroluminescent device of the present disclosure may further comprise an azine-based compound besides the plurality of host materials of the present disclosure as at least one of an electron transport material, an electron injection material, an electron buffer material, and a hole blocking material.

The plurality of host materials according to the present disclosure may be used as light-emitting materials for a white organic light-emitting device. The white organic light-emitting device has been suggested to have various structures such as a parallel arrangement (side-by-side) method, a stacking method, or color conversion material (CCM) method, etc., according to the arrangement of R (red), G (green) or YG (yellowish green), B (blue) light-emitting units. In addition, the plurality of host materials according to one embodiment of the present disclosure may also be used in an organic electroluminescent device comprising a quantum dot (QD).

A hole injection layer, a hole transport layer, an electron blocking layer, or a combination thereof can be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. Further, the hole injection layer may be doped with a p-dopant. The electron blocking layer may be placed between the hole transport layer (or hole injection layer) and the light-emitting layer, and may block overflowing electrons from the light-emitting layer and confine the excitons in the light-emitting layer to prevent light leakage. The hole transport layer or the electron blocking layer may also be multilayers, wherein each of the multilayers may use a plurality of compounds.

An electron buffer layer, a hole blocking layer, an electron transport layer, an electron injection layer, or a combination thereof can be used between the light-emitting layer and the cathode. The electron buffer layer may be multilayers in order to control the electron injection and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds. In addition, the electron injection layer may be doped with an n-dopant.

The dopant comprised in the organic electroluminescent device of the present disclosure may be at least one phosphorescent or fluorescent dopant, and is preferably phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise a compound represented by the following formula 101, but is not limited thereto.

(101)

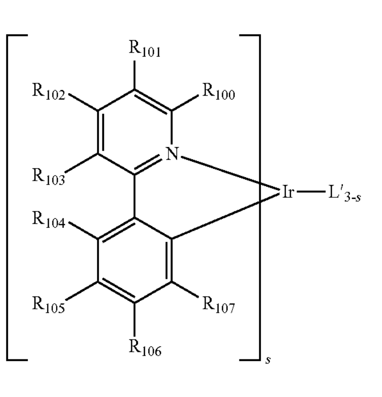

In formula 101, L' is selected from the following structures 1 to 3:

[Structure 1]

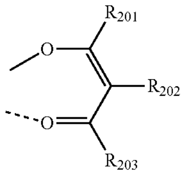

[Structure 2]

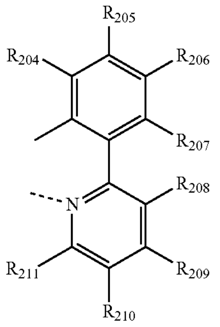

[Structure 3]

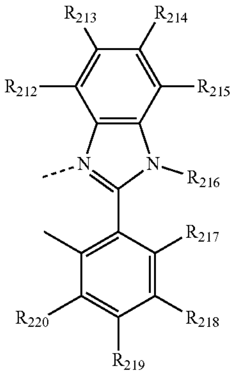

$R_{100}$ to $R_{103}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline, together with pyridine;

$R_{104}$ to $R_{107}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring(s), e.g., a substituted or unsubstituted, naphthalene, fluorene, dibenzothiophene, dibenzofuran, indenopyridine, benzofuropyridine, or benzothienopyridine, together with benzene;

$R_{201}$ to $R_{220}$, each independently, represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or may be linked to an adjacent substituent to form a ring(s); and
s represents an integer of 1 to 3.
The specific examples of the dopant compound are as follows, but are not limited thereto.
D-1
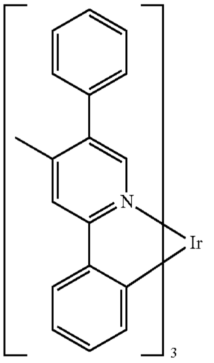
D-2
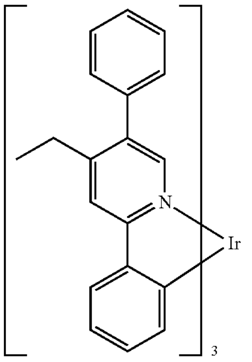
D-3
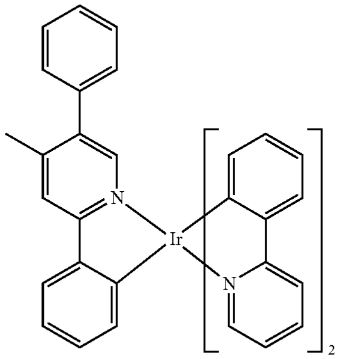
D-4
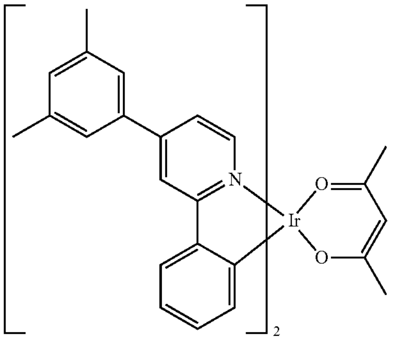
-continued
D-5
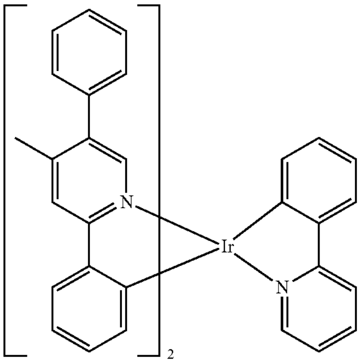
D-6
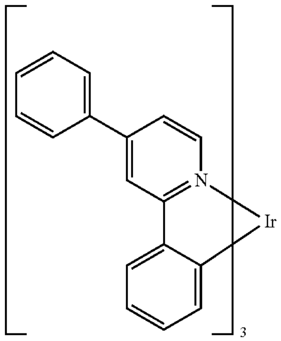
D-7
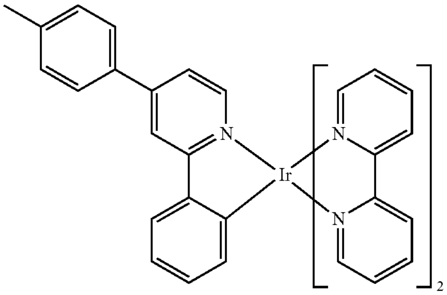
D-8
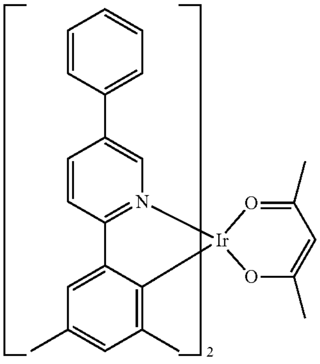

-continued
D-9
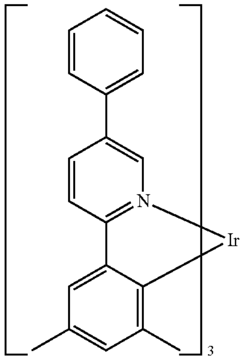
D-10
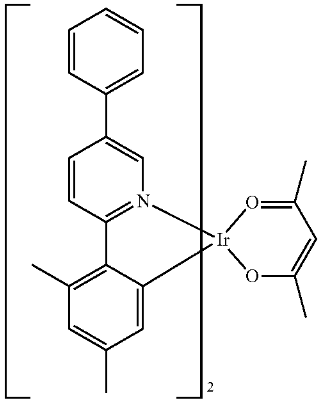
D-11
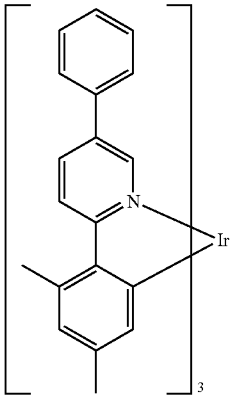
D-12
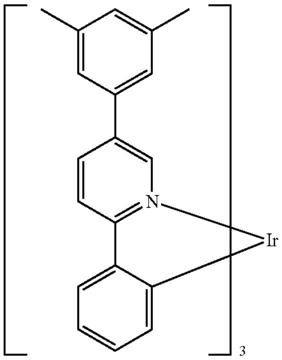
-continued
D-13
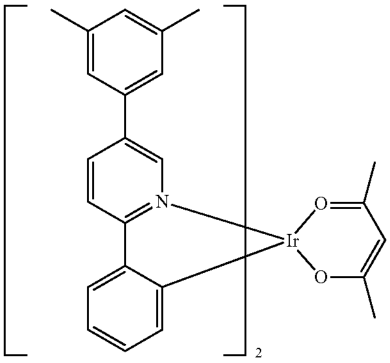
D-14
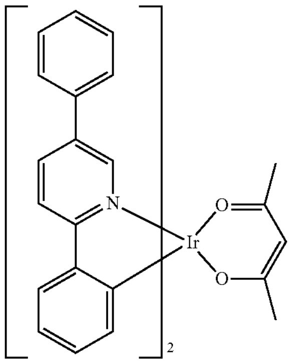
D-15
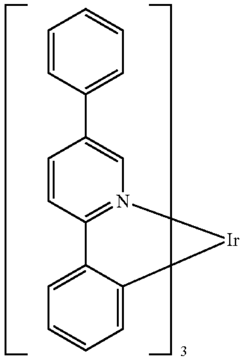
D-16
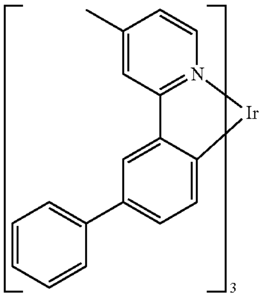

-continued
D-17
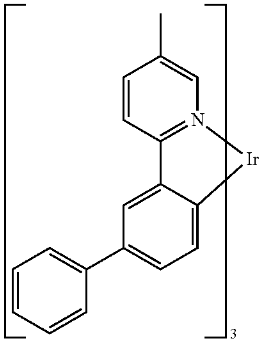
D-18
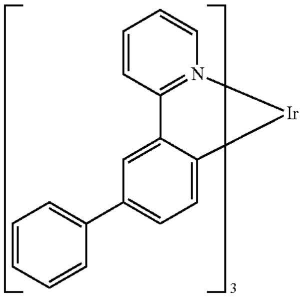
D-19
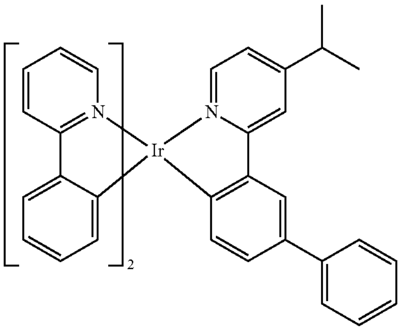
D-20
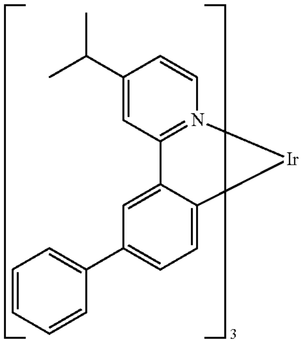
-continued
D-21
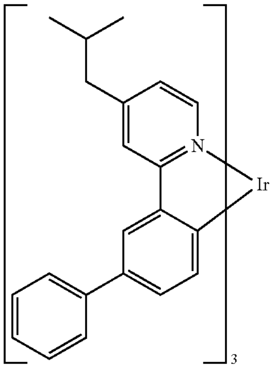
D-22
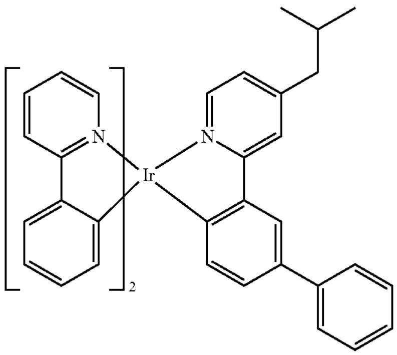
D-23
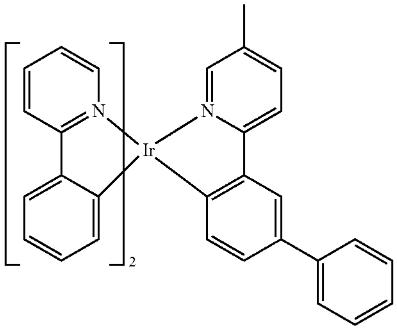
D-24
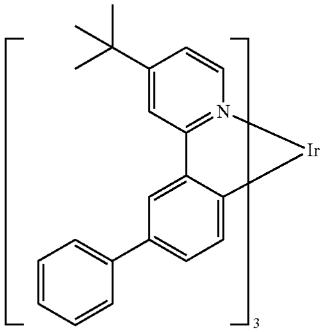

-continued
D-25
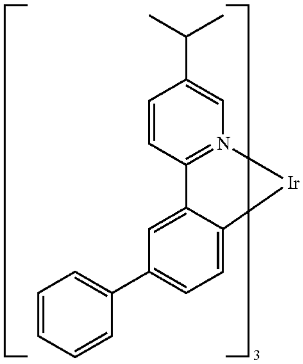
D-26
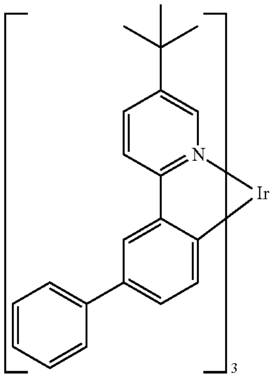
D-27
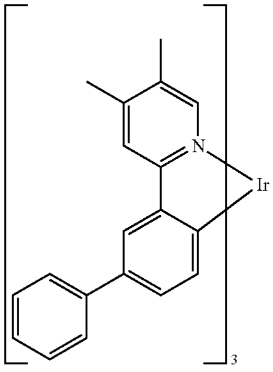
D-28
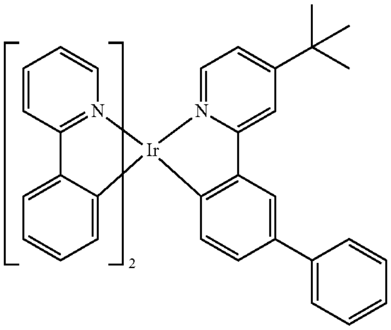
-continued
D-29
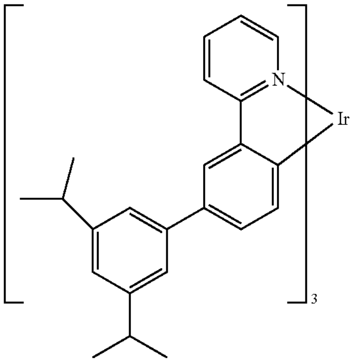
D-30
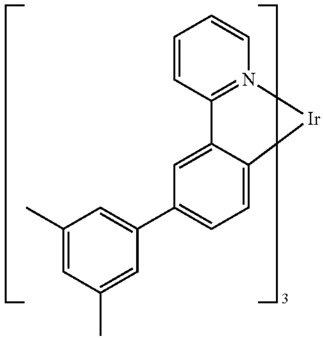
D-31
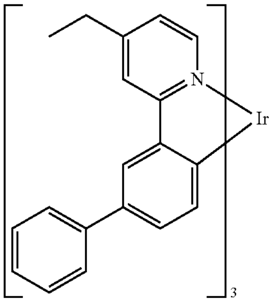
D-32
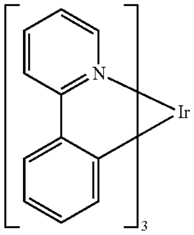
D-33
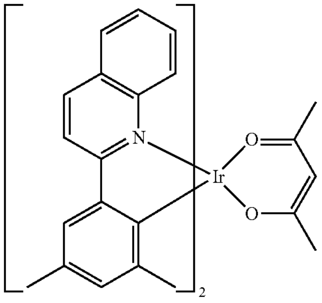

-continued
D-34
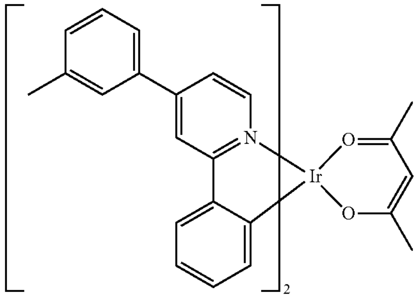
D-35
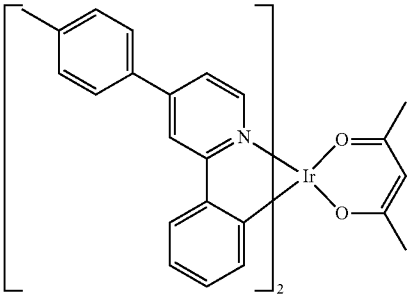
D-36
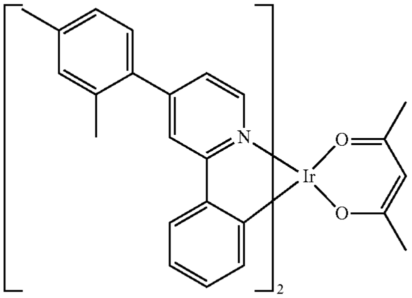
D-37
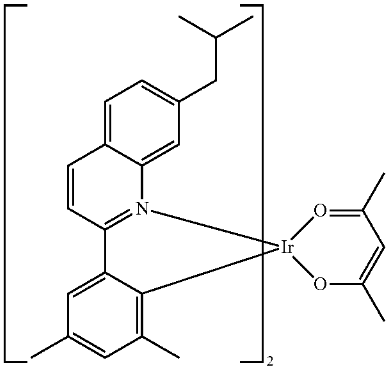
D-38
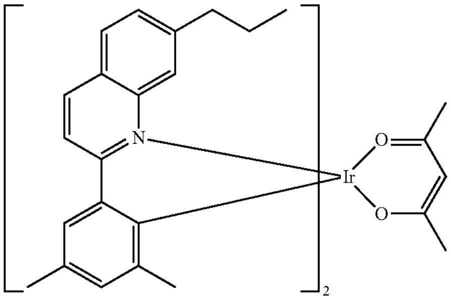
-continued
D-39
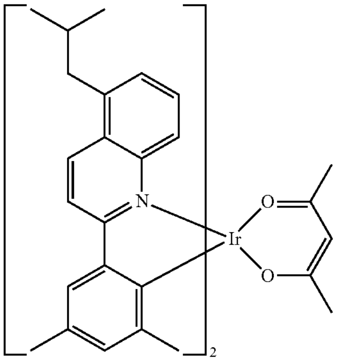
D-40
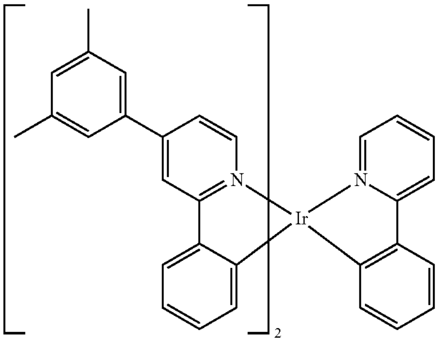
D-41
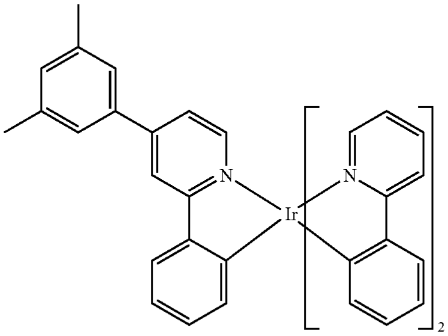
D-42
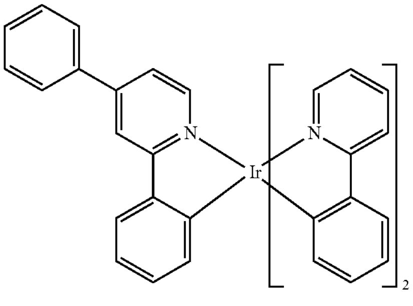

-continued
D-43
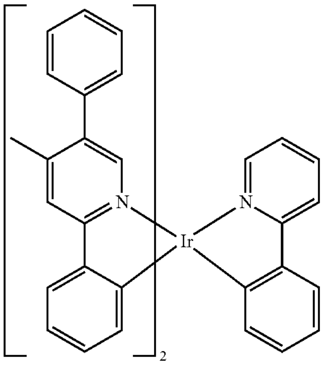
D-44
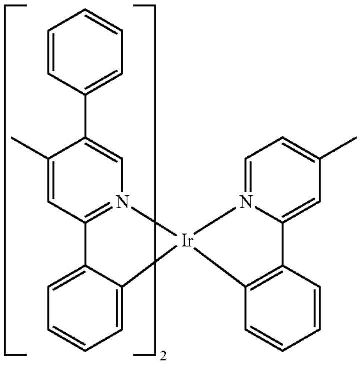
D-45
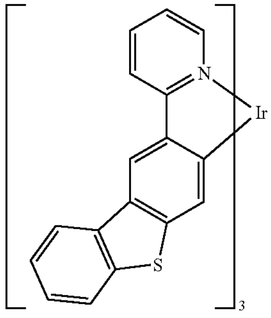
D-46
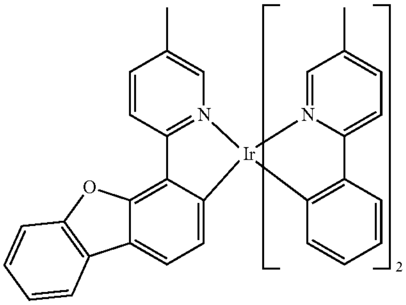
-continued
D-47
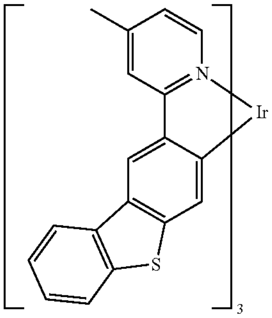
D-48
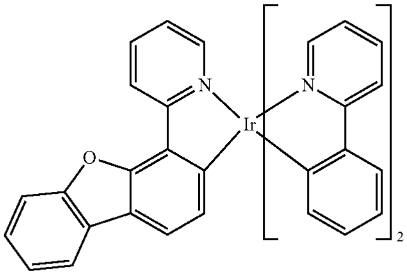
D-49
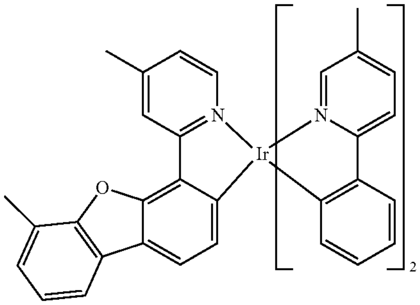
D-50
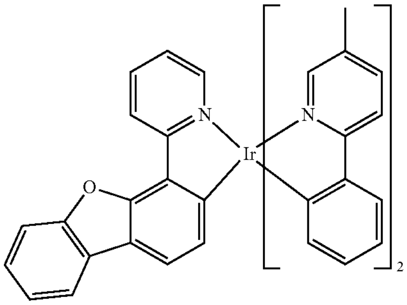
D-51
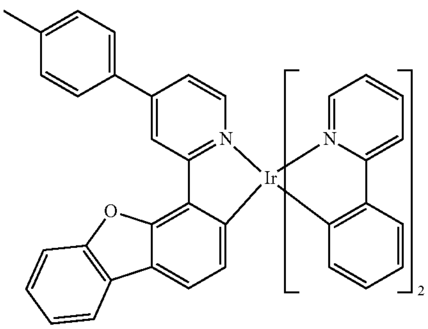

-continued
D-52
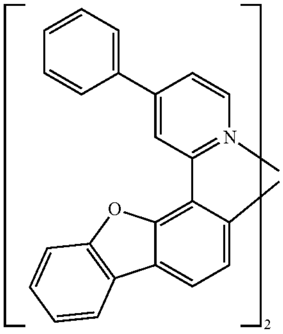
D-53
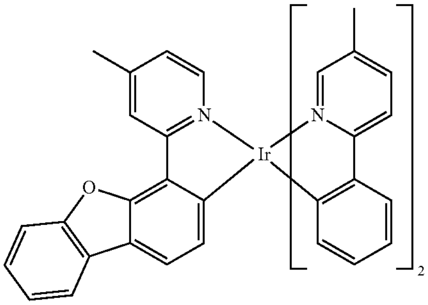
D-54
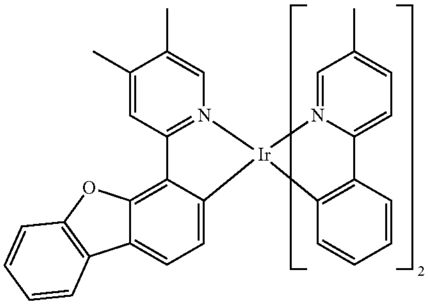
D-55
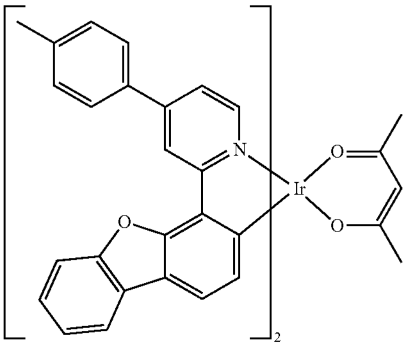
D-56
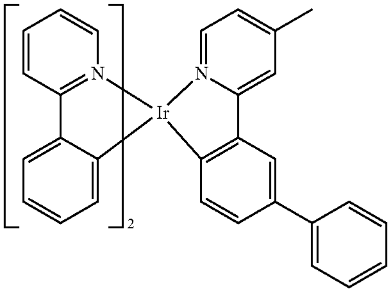
-continued
D-57
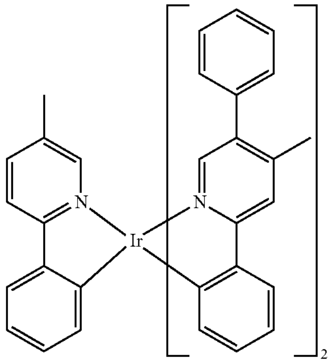
D-58
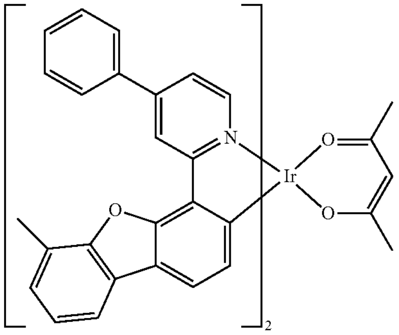
D-59
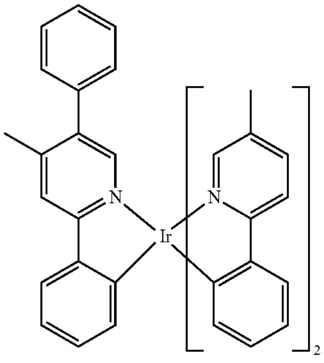
D-60
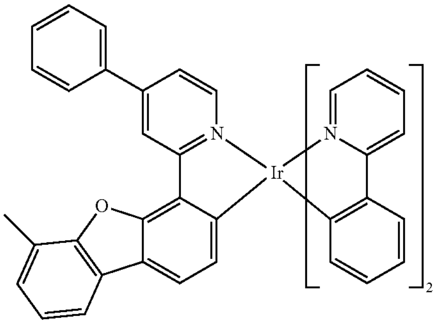

-continued
D-61
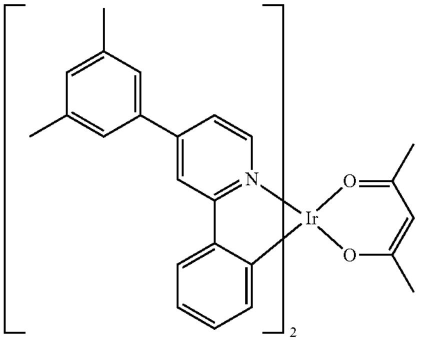
D-62
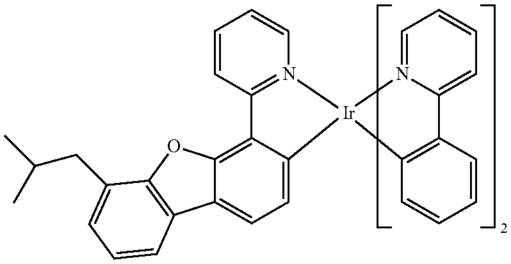
D-63
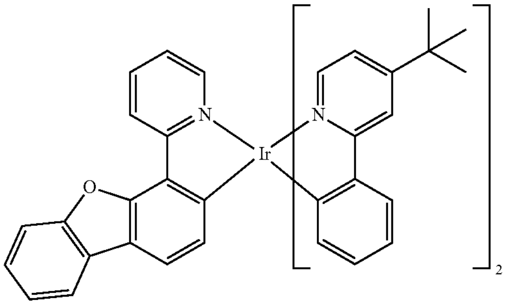
D-64
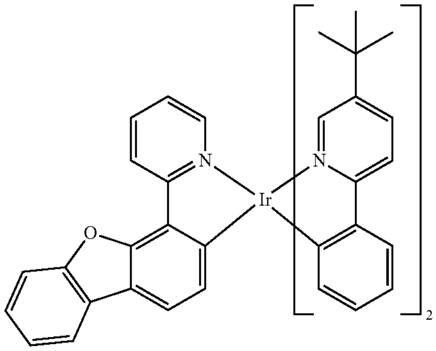
-continued
D-65
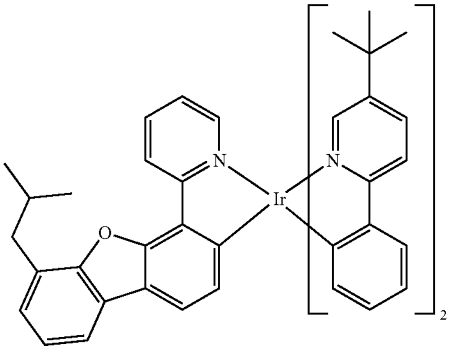
D-66
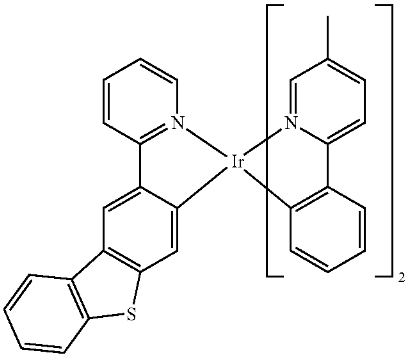
D-67
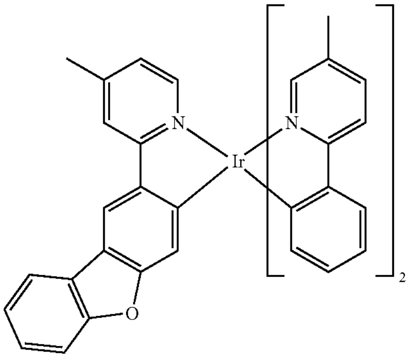
D-68
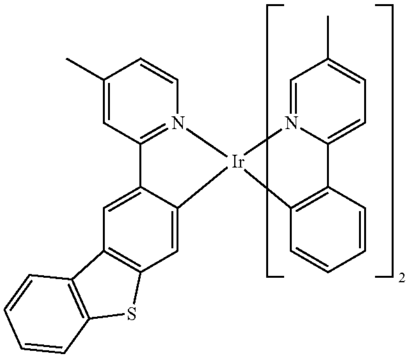

-continued
D-69
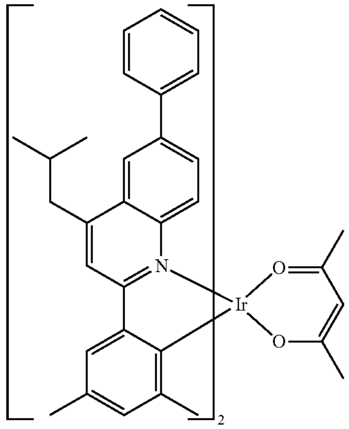
D-70
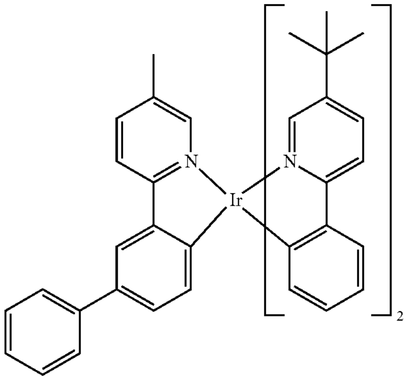
D-71
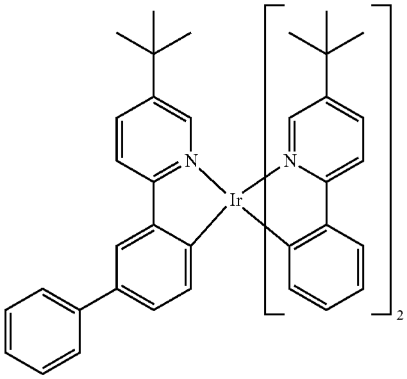
D-72
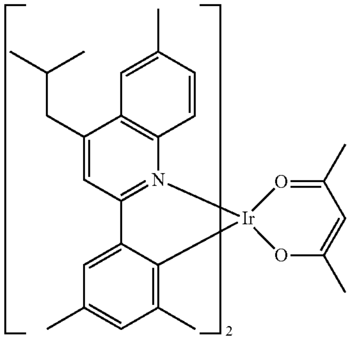
-continued
D-73
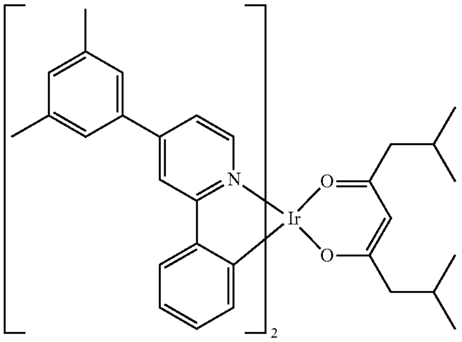
D-74
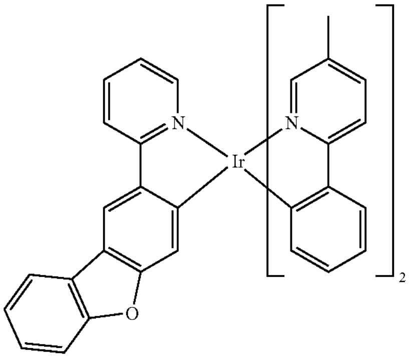
D-75
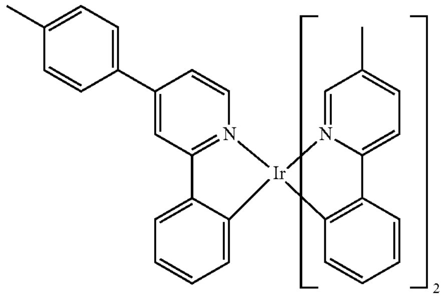
D-76
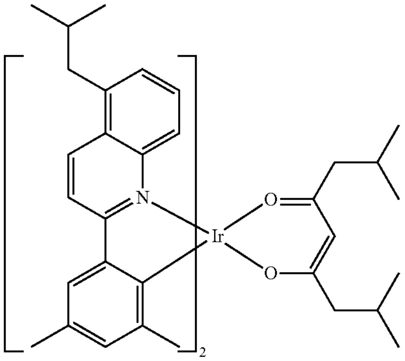

-continued
D-77
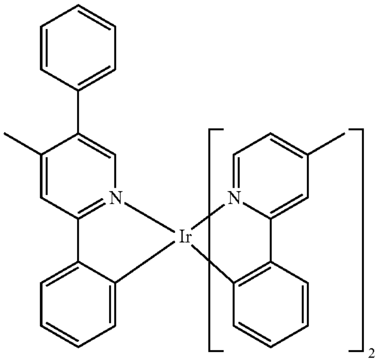
D-78
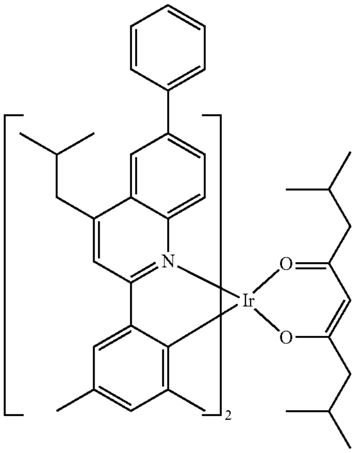
D-79
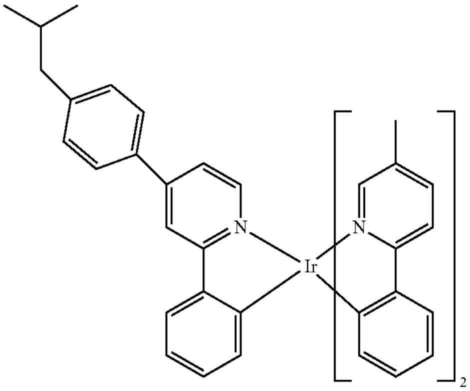
D-80
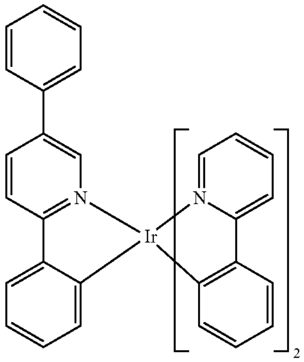
-continued
D-81
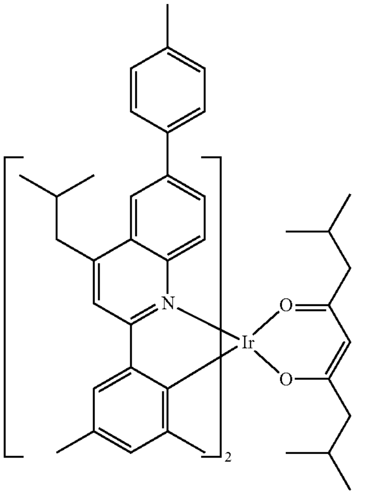
D-82
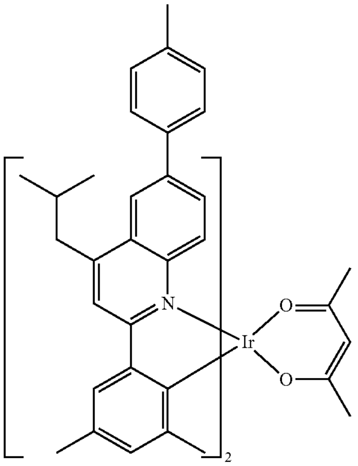
D-83
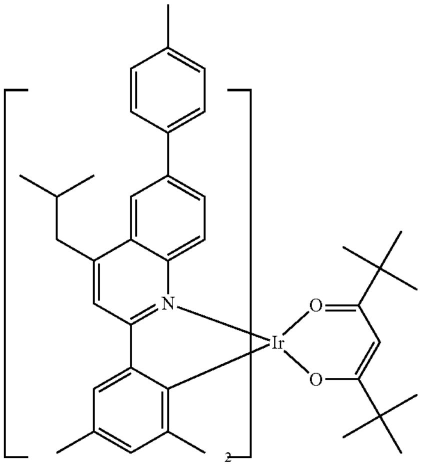

-continued
D-84
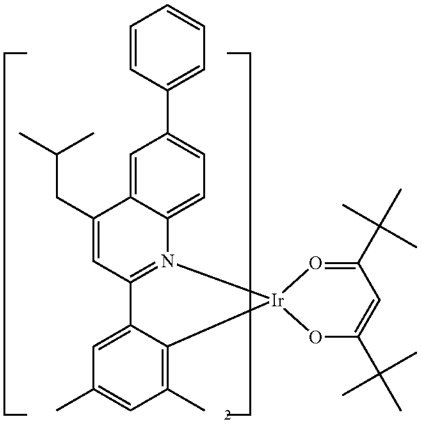
D-85
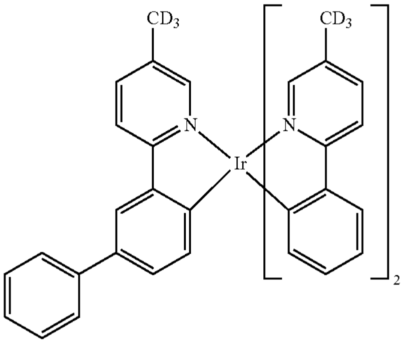
D-86
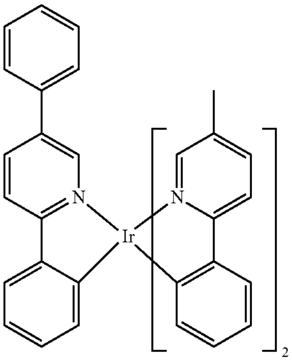
D-87
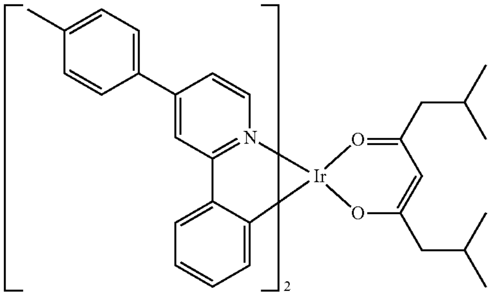
-continued
D-88
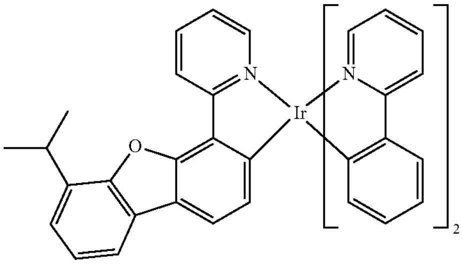
D-89
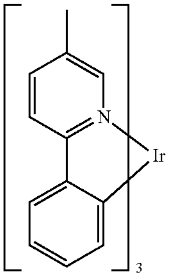
D-90
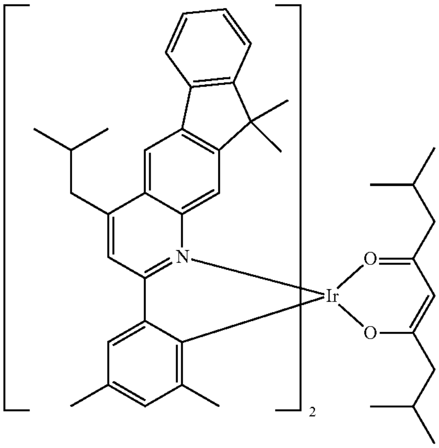
D-91
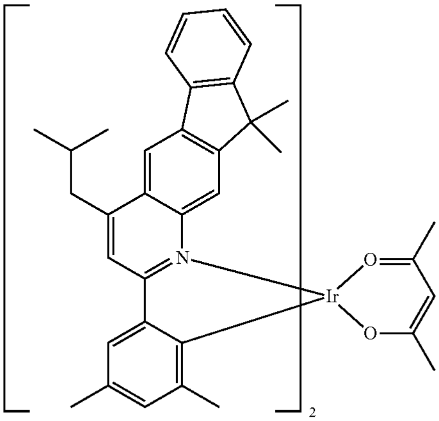

-continued
D-92
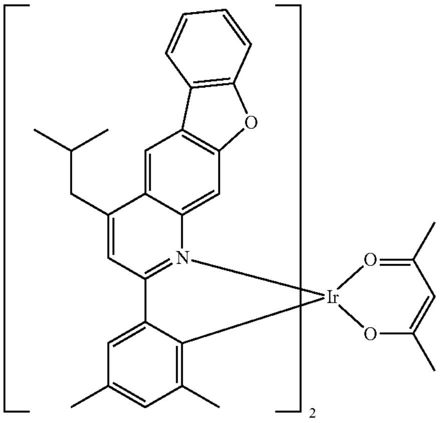
D-93
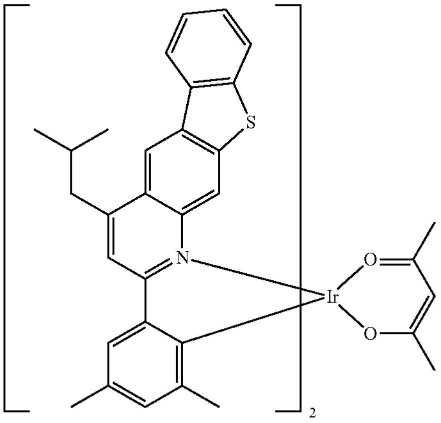
D-94
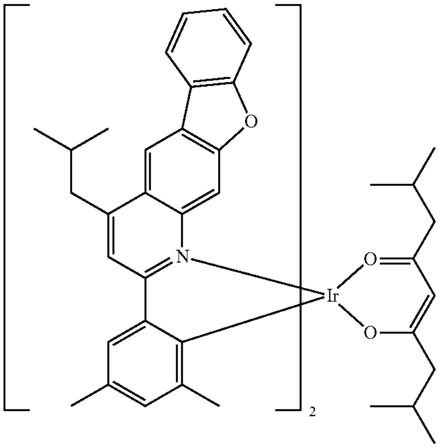
-continued
D-95
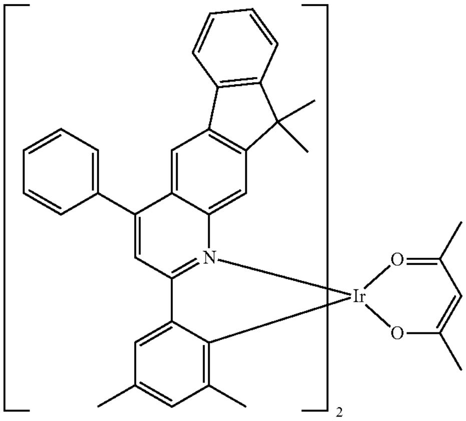
D-96
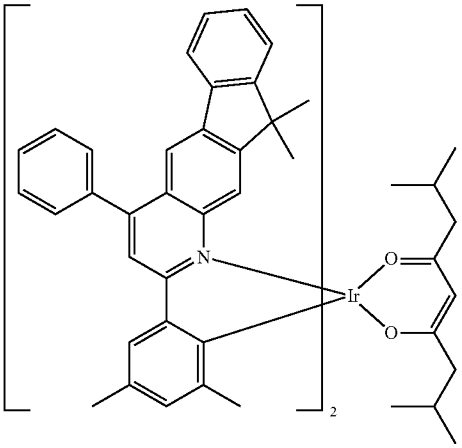
D-97
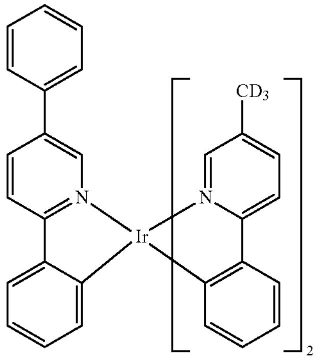
D-98
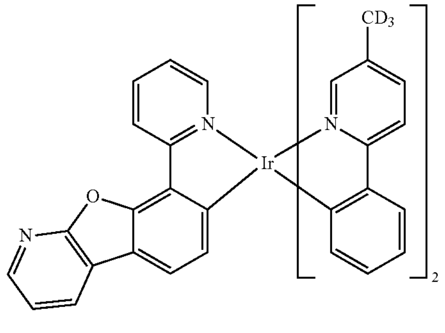

-continued
D-99
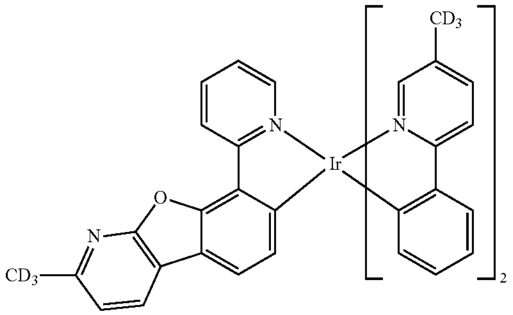
D-100
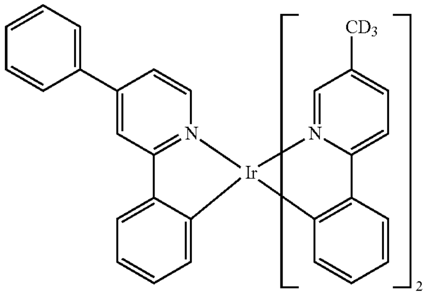
D-101
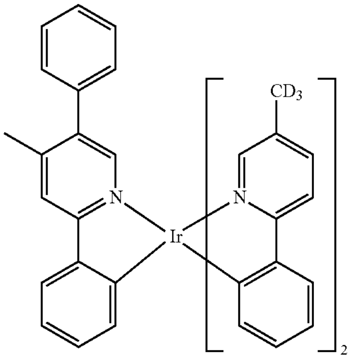
D-102
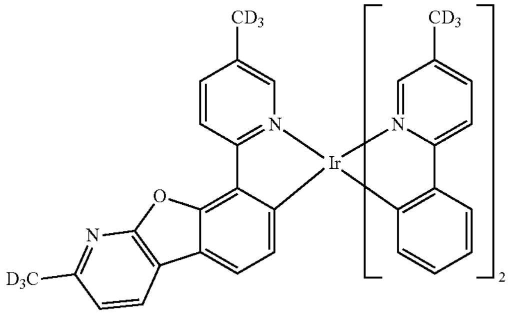
-continued
D-103
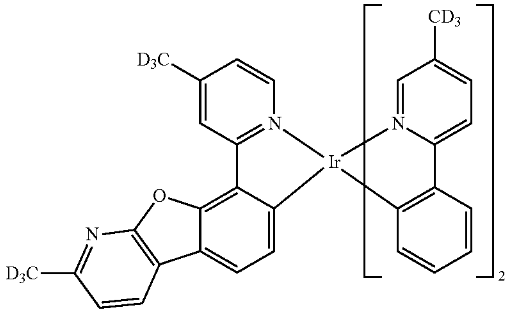
D-104
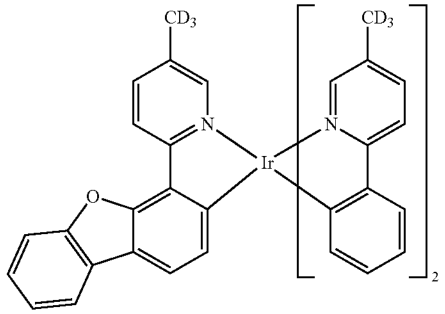
D-105
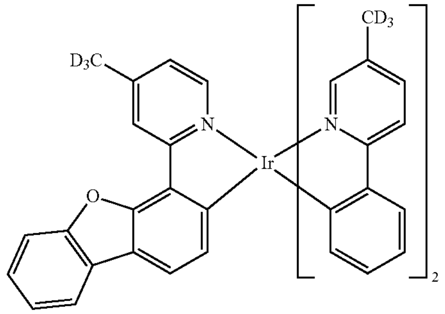
D-106
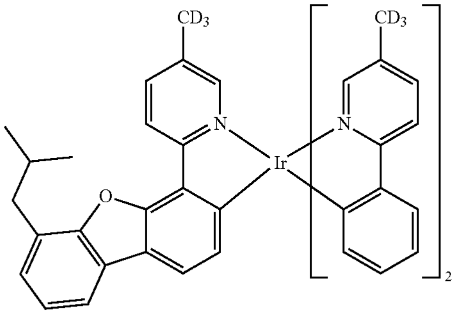

-continued
D-107
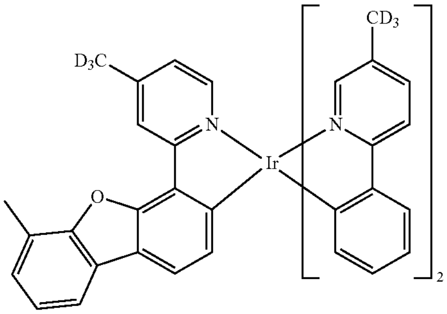
D-108
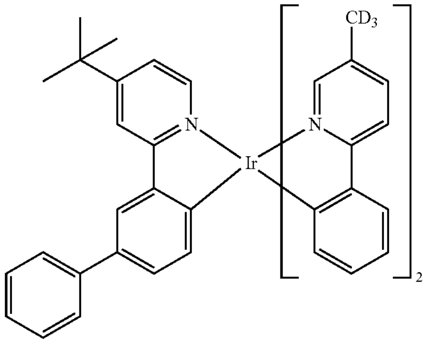
D-109
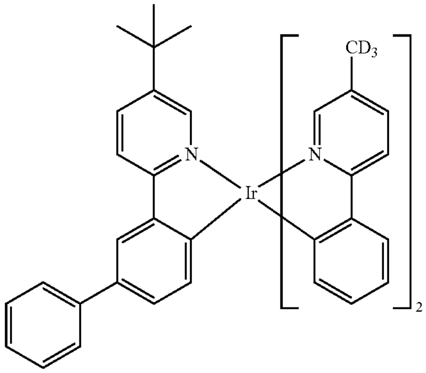
D-110
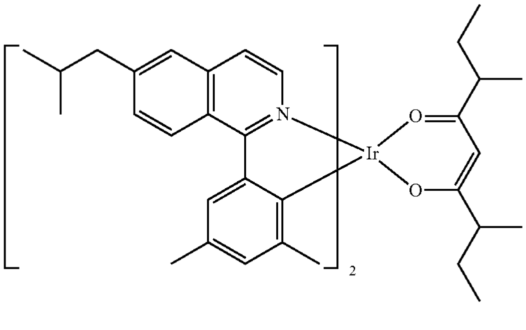
-continued
D-111
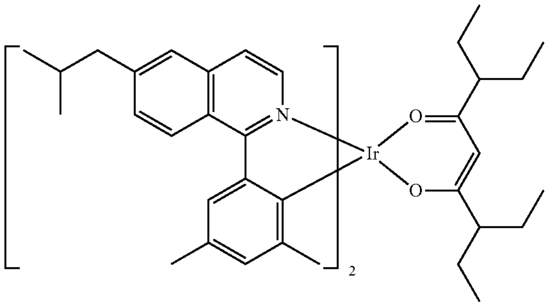
D-112
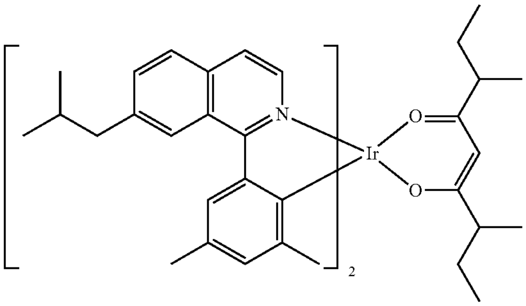
D-113
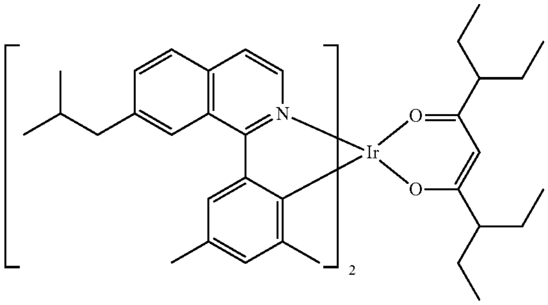
D-114
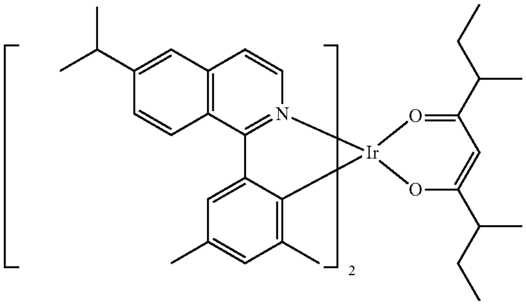
D-115
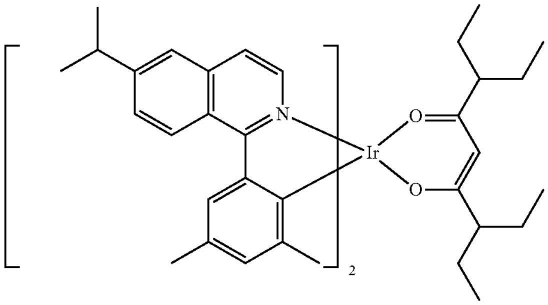

-continued
D-116
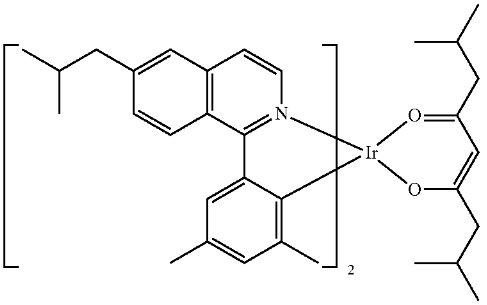
D-117
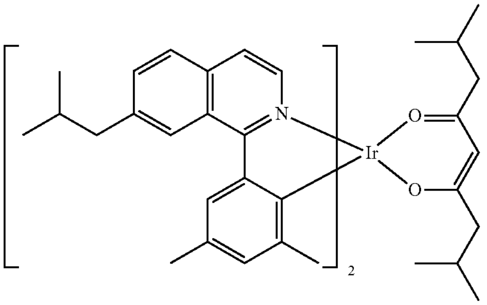
D-118
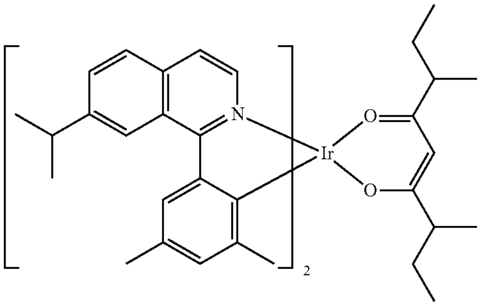
D-119
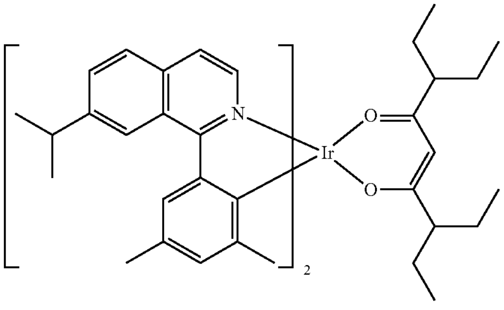
-continued
D-120
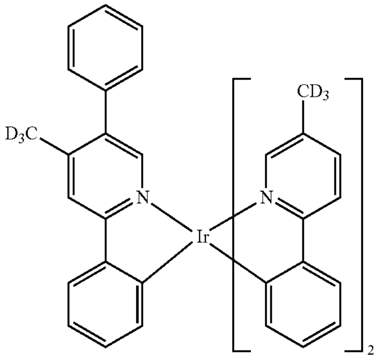
D-121
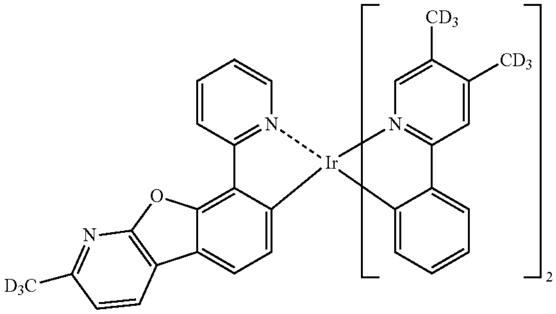
D-122
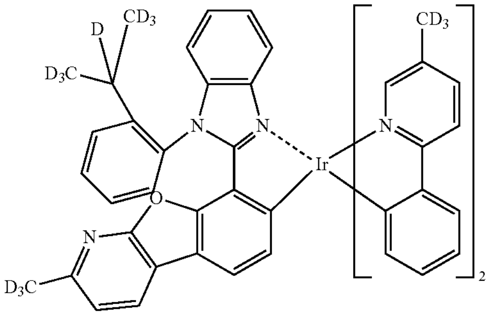
D-123
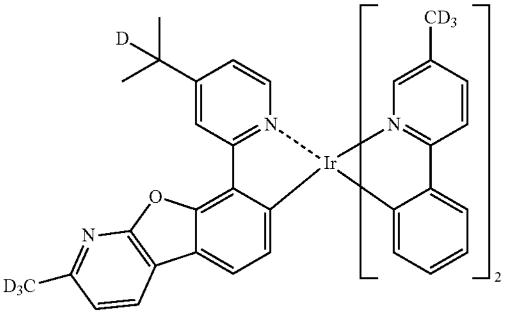

D-124
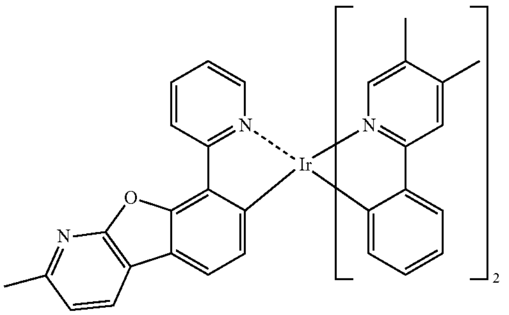
D-125
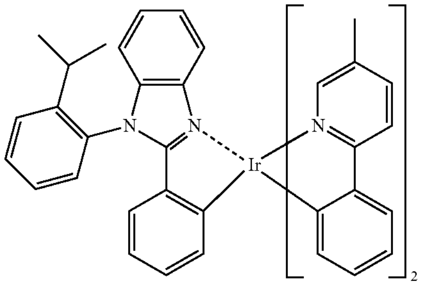
D-126
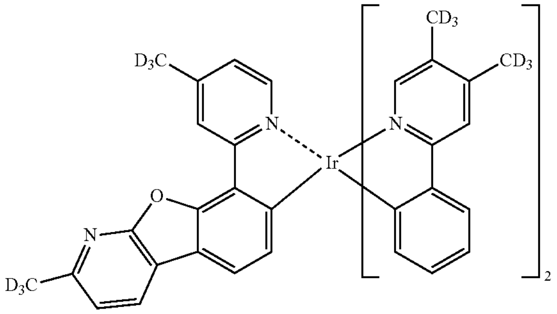
D-127
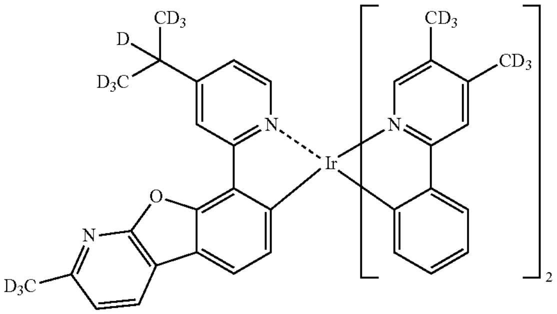
D-128
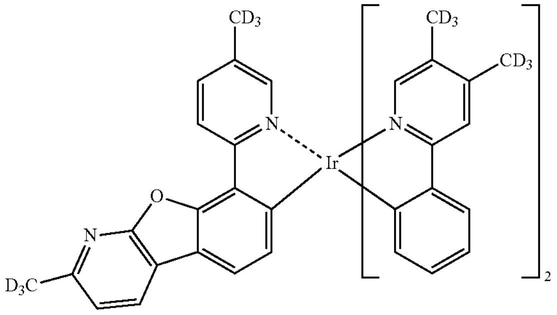
D-129
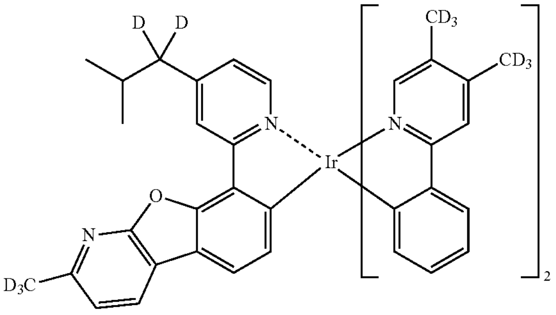
D-130
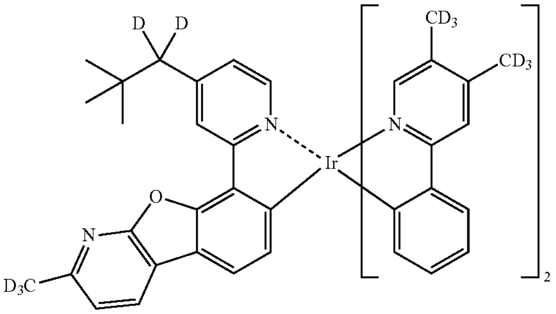
D-131
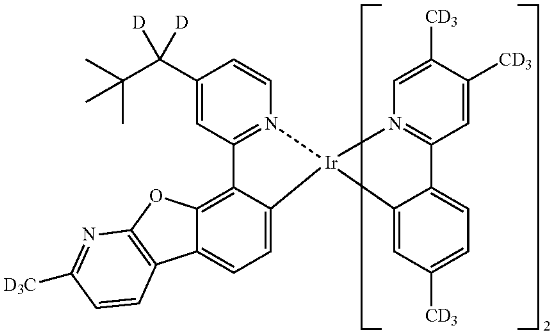
D-132
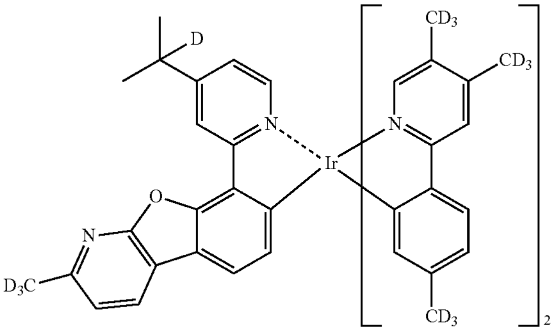

-continued
D-133
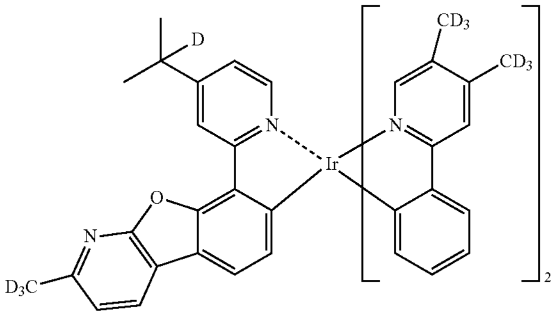
D-134
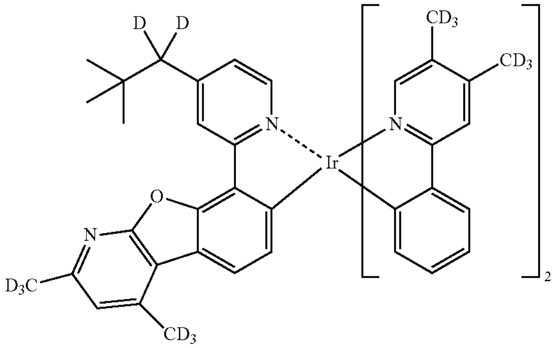
D-135
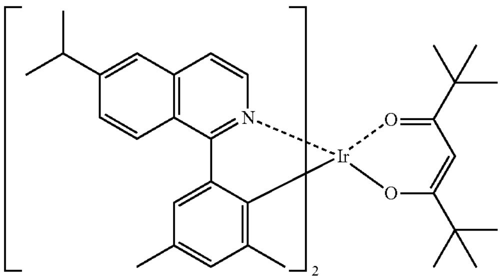
D-136
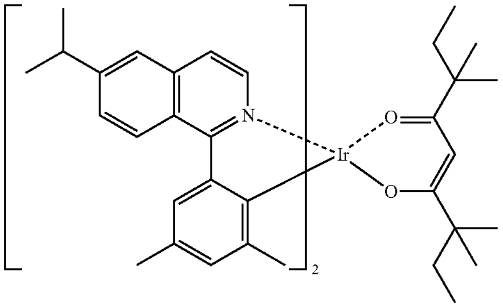
-continued
D-137
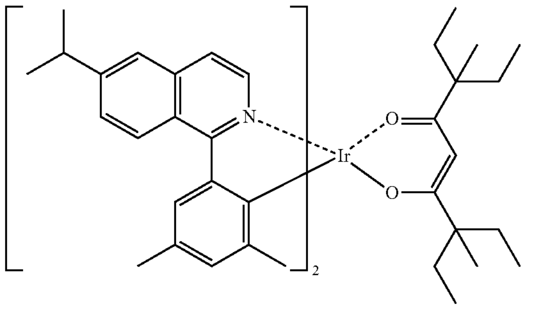
D-138
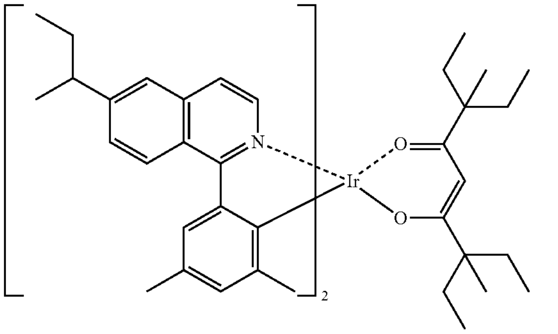
D-139
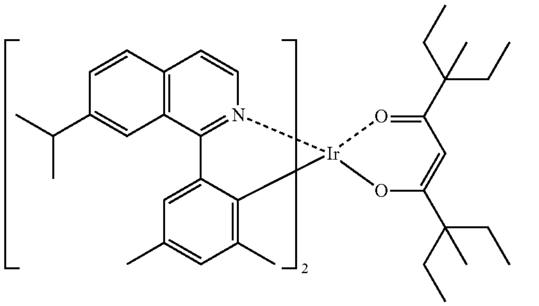
D-140
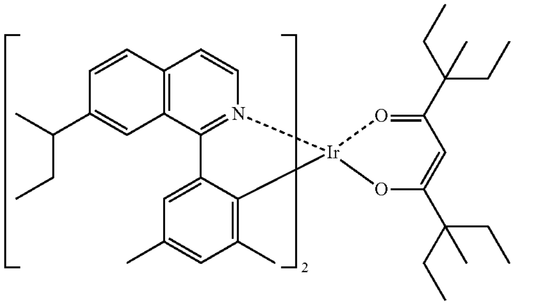

-continued
D-141
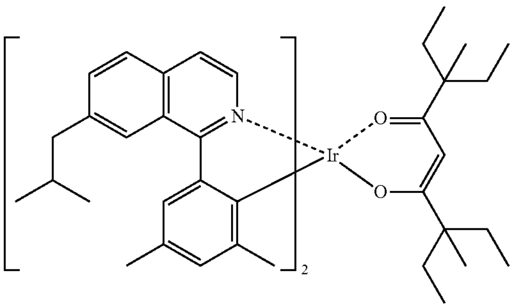
D-142
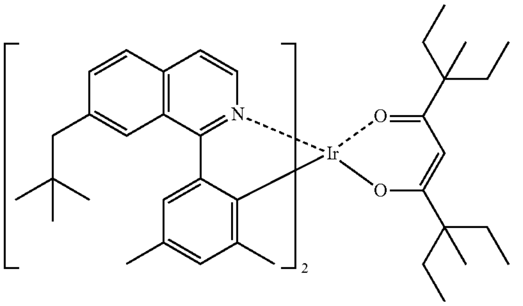
D-143
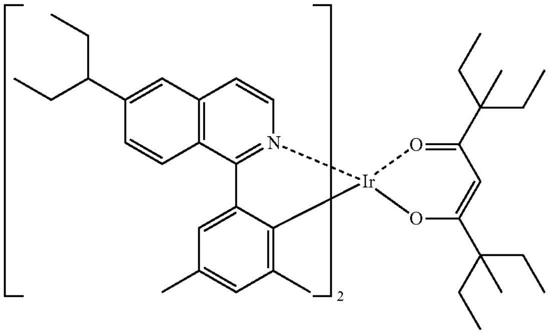
D-144
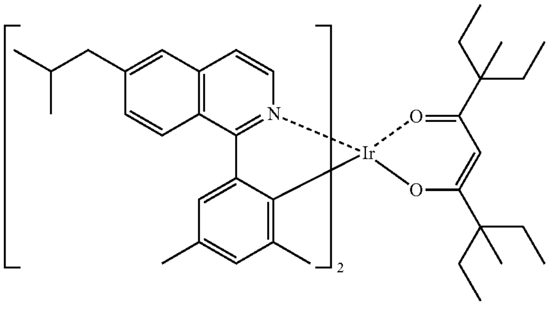
-continued
D-145
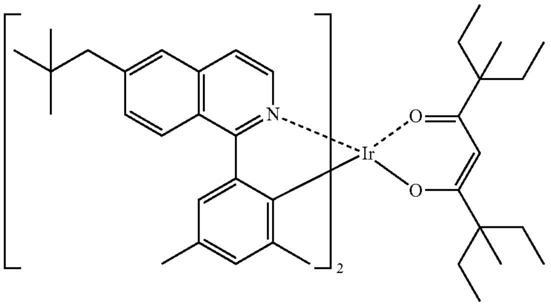
D-146
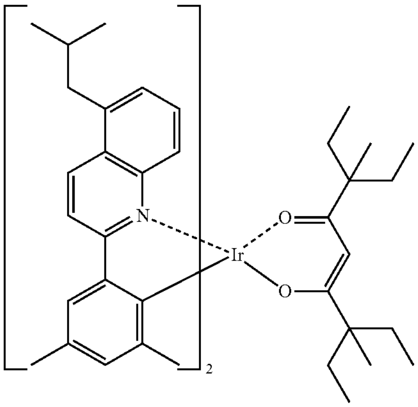
D-147
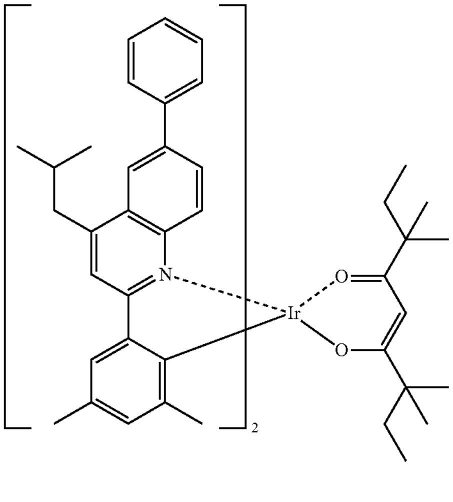

-continued

D-148

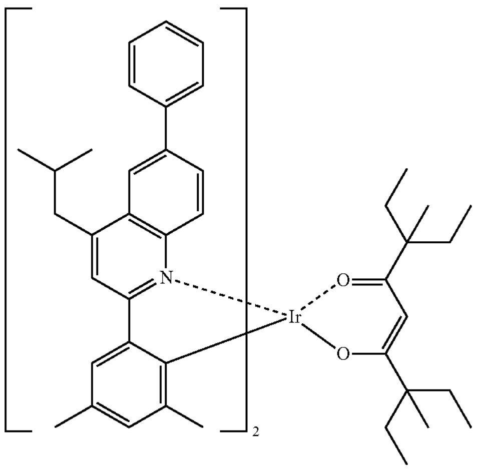

D-149

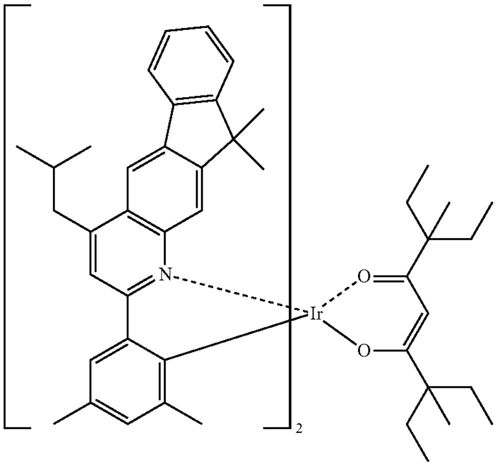

In order to form each layer of the organic electroluminescent device of the present disclosure, dry film-forming methods such as vacuum evaporation, sputtering, plasma, ion plating methods, etc., or wet film-forming methods such as ink jet printing, nozzle printing, slot coating, spin coating, dip coating, flow coating methods, etc., can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

The first and the second host compounds of the present disclosure may be film-formed by the above-listed methods, commonly by a co-evaporation process or a mixture-evaporation process. The co-evaporation is a mixed deposition method in which two or more materials are placed in a respective individual crucible source and a current is applied to both cells at the same time to evaporate the materials. The mixture-evaporation is a mixed deposition method in which two or more materials are mixed in one crucible source before evaporating them, and a current is applied to the cell to evaporate the materials. Further, if the first and the second host compounds are present in the same layer or different layers in an organic electroluminescent device, the two host compounds may individually form films.

For example, the second host compound may be deposited after depositing the first host compound.

The present disclosure may provide a display device by using the plurality of host materials including the compound represented by formula 1 and the compound represented by formula 2. That is, by using the plurality of host materials of the present disclosure, it is possible to manufacture a display system or a lighting system. Specifically, by using the plurality of host materials of the present disclosure, a display system, for example, for white organic light emitting devices, smart phones, tablets, notebooks, PCs, TVs, or cars; or a lighting system, for example an outdoor or indoor lighting system, can be produced.

Hereinafter, the preparation method of the compounds according to the present disclosure and the properties thereof, and the properties of an organic electroluminescent device comprising the plurality of host materials of the present disclosure will be explained in detail with reference to the representative compounds of the present disclosure. However, the present disclosure is not limited by the following examples.

Example 1: Preparation of Compound C-1

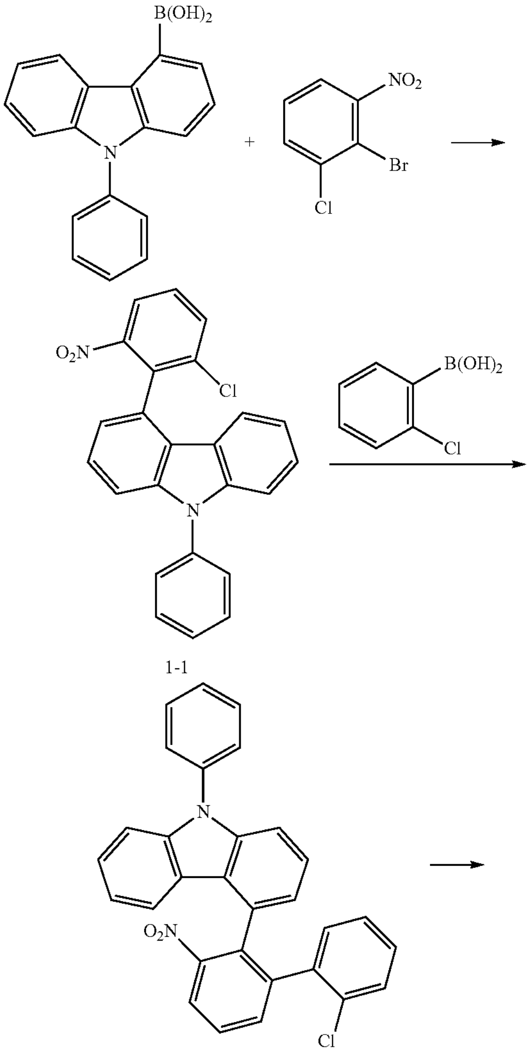

1-1

1-2

-continued

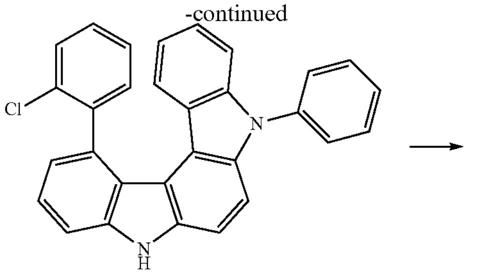

1-3

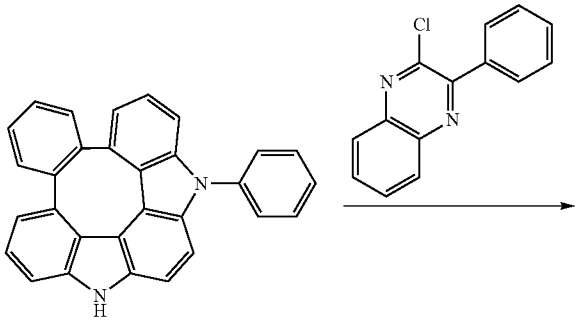

1-4

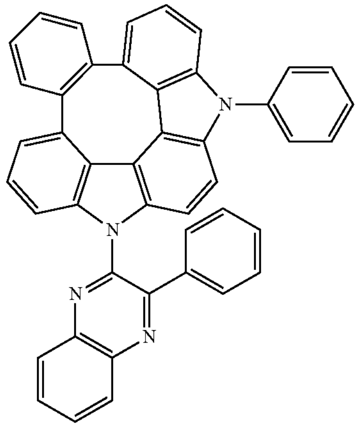

C-1

Synthesis of Compound 1-1

(9-phenyl-9H-carbazol-4-yl)boronic acid (96 g, 334.3 mmol), 2-bromo-1-chloro-3-nitrobenzene (71.8 g, 304 mmol), $Pd_2(dba)_3$ (15 g, 16.71 mmol), S-Phos (10.9 g, 26.76 mmol), and $K_3PO_4$ (315 g, 1.64 mol) were dissolved in 1500 mL of toluene in a flask, and the mixture was stirred at 130° C. for 4 hours. After completion of the reaction, an organic layer was extracted with ethyl acetate, and the residual moisture was removed using magnesium sulfate. The residue was dried, and separated by column chromatography to obtain compound 1-1 (67 g, yield: 56.6%).

Synthesis of Compound 1-2

Compound 1-1 (23.5 g, 58.9 mmol), (2-chlorophenyl) boronic acid (18.4 g, 117.8 mmol), $Pd_2(dba)_3$ (2.7 g, 2.95 mmol), S-Phos (2.4 g, 5.89 mmol), and $K_3PO_4$ (63 g, 294.5 mmol) were dissolved in 300 mL of toluene in a flask, and the mixture was stirred at 130° C. for 12 hours. After completion of the reaction, an organic layer was extracted with ethyl acetate, and the residual moisture was removed using magnesium sulfate. The residue was dried, and separated by column chromatography to obtain compound 1-2 (14 g, yield: 50%).

Synthesis of Compound 1-3

Compound 1-2 (13 g, 27.4 mmol), and triphenylphosphine (21.5 g, 82.1 mmol) were dissolved in 140 mL of o-DCB in a flask, and the mixture was stirred at 220° C. for 7 hours. After completion of the reaction, the reaction mixture was removed by distillation, and separated by column chromatography to obtain compound 1-3 (4 g, yield: 32%).

Synthesis of Compound 1-4

Compound 1-3 (10 g, 22.5 mmol), $Pd(OAc)_2$ (505 mg, 2.25 mmol), $Pcy_3$-$HBF_4$ (1.63 g, 4.5 mmol), and $Cs_2CO_3$ (22 g, 67.5 mmol) were dissolved in 113 mL of o-xylene in a flask, and the mixture was stirred at 160° C. for 4 hours. After completion of the reaction, an organic layer was extracted with ethyl acetate, and the residual moisture was removed using magnesium sulfate. The residue was dried, and separated by column chromatography to obtain compound 1-4 (1 g, yield: 11%).

Synthesis of Compound C-1

Compound 1-4 (4.5 g, 11.06 mmol), 2-chloro-3-phenylquinoxaline (4 g, 16.6 mmol), 4-dimethylaminopyridine (DMAP) (67 mg, 0.553 mmol), and $Cs_2CO_3$ (10.8 g, 331.8 mmol) were dissolved in 60 mL of dimethylsulfoxide (DMSO) in a flask, and the mixture was refluxed at 140° C. for 4 hours. After completion of the reaction, an organic layer was extracted with ethyl acetate, and the residual moisture was removed using magnesium sulfate. The residue was dried, and separated by column chromatography to obtain compound C-1 (2.5 g, yield: 37%).

| Compound | MW | M.P. |
|---|---|---|
| C-1 | 610.22 | 246° C. |

Example 2: Preparation of Compound C-29

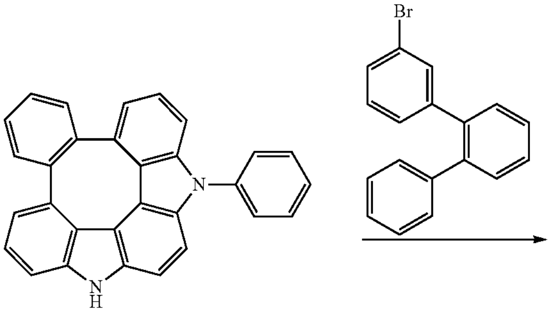

1-4

-continued

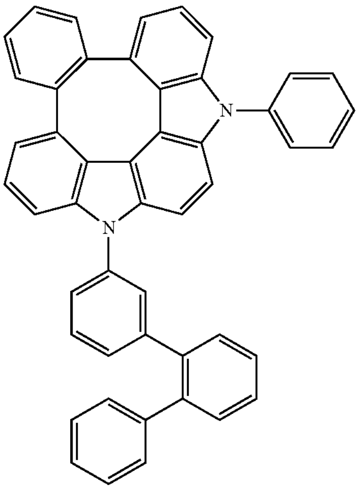

C-29

Compound 1-4 (4 g, 9.84 mmol), 3-bromo-1,1':2',1"-terphenyl (3.65 g, 11.8 mmol), $Pd_2(dba)_3$ (448 mg, 0.492 mmol), S-Phos (448 mg, 0.984 mmol), and NaOtBu (2.84 g, 29.52 mmol) were dissolved in 50 mL of o-xylene in a flask, and the mixture was stirred at 170° C. for 4 hours. After completion of the reaction, an organic layer was extracted with ethyl acetate, and the residual moisture was removed using magnesium sulfate. The residue was dried, and separated by column chromatography to obtain compound C-29 (1.5 g, yield: 24%).

| Compound | MW | M.P. |
|---|---|---|
| C-29 | 643.78 | 282° C. |

Example 3: Preparation of Compound C-196

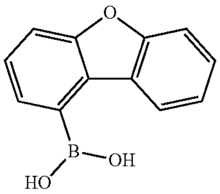

A

+

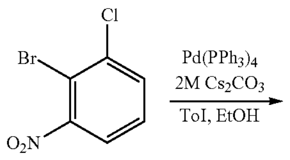

B

-continued

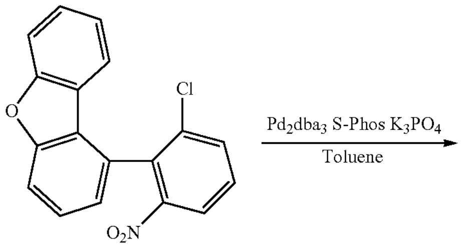

3-1

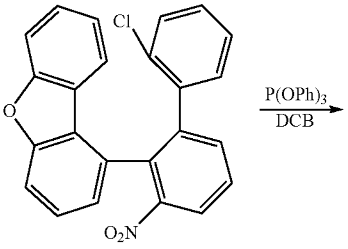

3-2

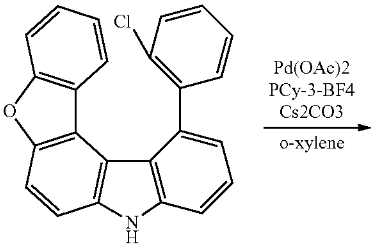

3-3

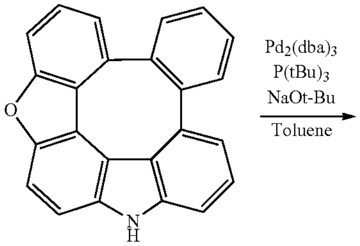

3-4

-continued

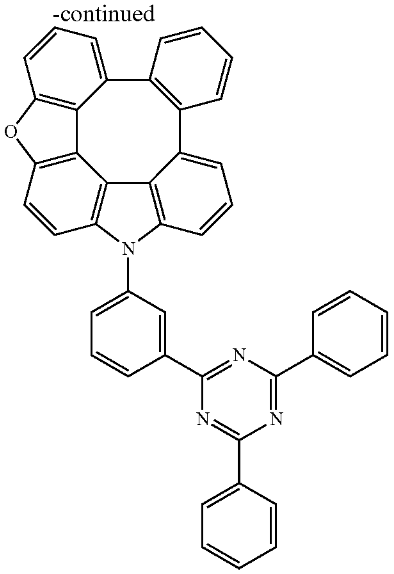

C-196

Synthesis of Compound 3-1

Compound A (60 g, 283 mmol), Compound B (100 g, 424 mmol), tetrakis(triphenylphosphine)palladium (16.3 g, 14.1 mmol), cesium carbonate (276 g, 849 mmol), 1400 mL of toluene, 350 mL of ethanol and 350 mL of distilled water were added into a reaction vessel, and the mixture was stirred at 130° C. for 12 hours. After completion of the reaction, the reaction mixture was cooled to room temperature, and extracted with ethyl acetate. The extracted organic layer was dried with magnesium sulfate, and the solvent was removed by rotary evaporator. Then, the residue was separated by column chromatography to obtain compound 3-1 (38 g, yield: 41%).

Synthesis of Compound 3-2

Compound 3-1 (38 g, 117 mmol), phenylboronic acid (35 g, 234 mmol), tris(dibenzylindeneacetone)dipalladium (5.3 g, 5.86 mmol), S-Phos (4.8 g, 11.7 mmol), tripotassium phosphate (62 g, 293 mmol), and 600 mL of toluene were added into a reaction vessel, and the mixture was stirred under reflux for 2 hours. After completion of the reaction, the reaction mixture was washed with distilled water, and extracted with ethyl acetate. The extracted organic layer was dried with magnesium sulfate, and the solvent was removed by rotary evaporator. Then, the residue was separated by column chromatography to obtain compound 3-2 (31 g, yield: 67%).

Synthesis of Compound 3-3

Compound 3-2 (21 g, 53.7 mmol), triphenylphosphite (70 mL, 268 mmol), and 180 mL of dichlorobenzene (DCB) were added into a reaction vessel, and the mixture was stirred at 200° C. for 12 hours. After completion of the reaction, the reaction mixture was distilled under reduced pressure to remove DCB, and washed with distilled water and extracted with ethyl acetate. The extracted organic layer was dried with magnesium sulfate, and the solvent was removed by rotary evaporator. Then, the residue was separated by column chromatography to obtain compound 3-3 (10 g, yield: 55%).

Synthesis of Compound 3-4

Compound 3-3 (6.6 g, 17.9 mmol), palladium (II) acetate (0.2 g, 0.89 mmol), $PCy_3$-$BF_4$ (1.3 g, 3.58 mmol), cesium carbonate (17 g, 53.7 mmol), and 90 mL of o-xylene were added into a reaction vessel, and the mixture was stirred under reflux at 160° C. for 4 hours. After completion of the reaction, the reaction mixture was washed with distilled water, and extracted with ethyl acetate. The extracted organic layer was dried with magnesium sulfate, and the solvent was removed by rotary evaporator. Then, the residue was separated by column chromatography to obtain compound 3-4 (1.8 g, yield: 32%).

Synthesis of Compound C-196

Compound 3-4 (1.8 g, 5.43 mmol), 2-(3-bromophenyl)-4,6-diphenyl-1,3,5-triazine (2.3 g, 5.97 mmol), tris(dibenzylindeneacetone)dipalladium (0.2 g, 0.27 mmol), tri-tert-butylphosphine (0.3 mL, 0.54 mmol), sodium ted-butoxide (1.3 g, 13.5 mmol), and 30 mL of toluene were added into a reaction vessel, and the mixture was stirred under reflux for 3 hours. After completion of the reaction, the reaction mixture was washed with distilled water, and extracted with ethyl acetate. The extracted organic layer was dried with magnesium sulfate, and the solvent was removed by rotary evaporator. Then, the residue was separated by column chromatography to obtain compound C-196 (3.3 g, yield: 95%).

| Compound | MW | UV | PL | M.P. |
|---|---|---|---|---|
| C-196 | 638.21 | 410 nm | 522 nm | 240° C. |

Example 4: Preparation of Compound C-36

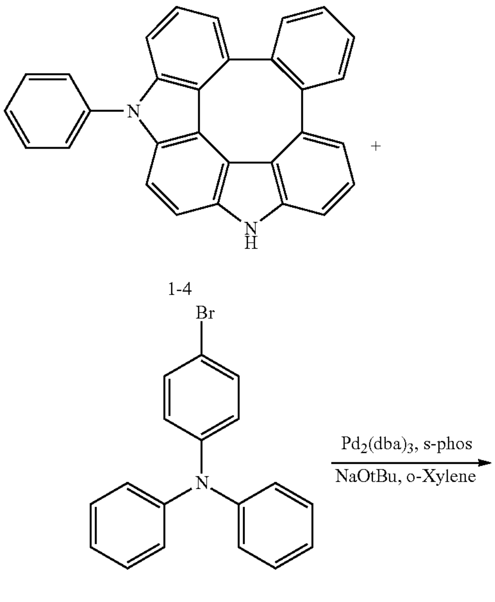

-continued

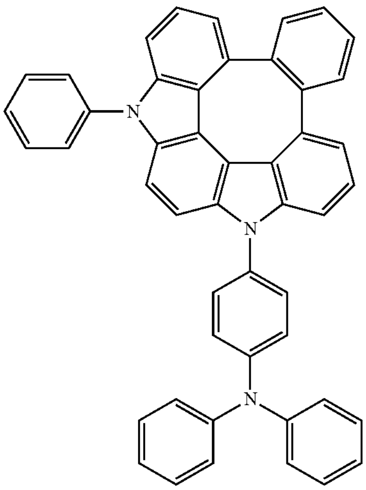

C-36

Compound 1-4 (4.0 g, 9.84 mmol), 4-bromo-N,N-diphenylaniline (3.2 g, 9.84 mmol), $Pd_2(dba)_3$ (0.45 g, 0.5 mmol), s-phos (0.4 g, 0.98 mmol), and NaOtBu (1.9 g, 19.7 mmol) were dissolved in 50 mL of o-xylene in a flask, and the mixture was stirred under reflux for 5 hours. After completion of the reaction, an organic layer was extracted with ethyl acetate, and separated by column chromatography to obtain compound C-36 (2.67 g, yield: 42%).

| Compound | MW | M.P. |
|---|---|---|
| C-36 | 649.78 | 312° C. |

Example 5: Preparation of Compound C-32

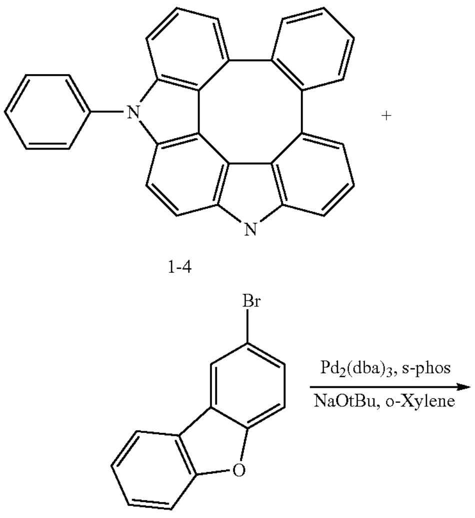

-continued

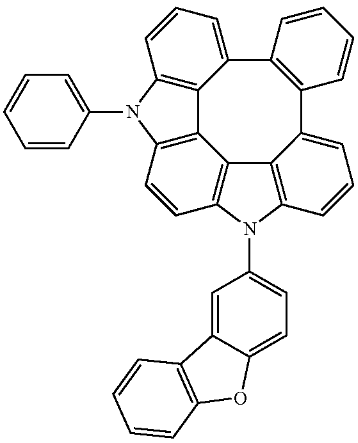

C-32

Compound 1-4 (4.0 g, 9.84 mmol), 2-bromodibenzo[b,d]furan (1.7 g, 9.84 mmol), $Pd_2(dba)_3$ (0.45 g, 0.5 mmol), s-phos (0.4 g, 0.98 mmol), and NaOtBu (1.9 g, 19.7 mmol) were dissolved in 50 mL of o-xylene in a flask, and the mixture was stirred under reflux for 5 hours. After completion of the reaction, an organic layer was extracted with ethyl acetate, and separated by column chromatography to obtain compound C-32 (1.68 g, yield: 30%).

| Compound | MW | M.P. |
|---|---|---|
| C-32 | 572.65 | 291° C. |

Example 6: Preparation of Compound C2-86

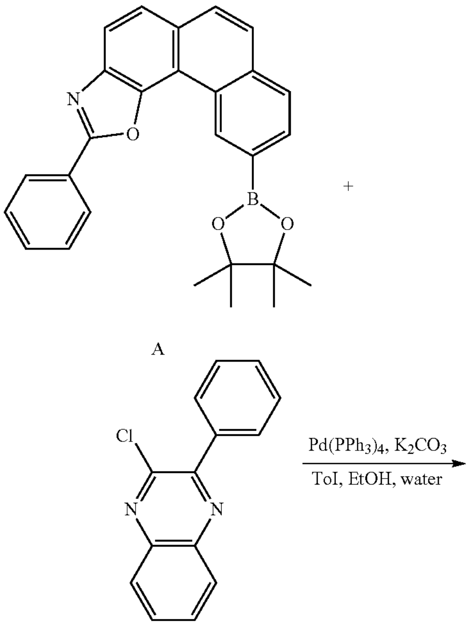

-continued

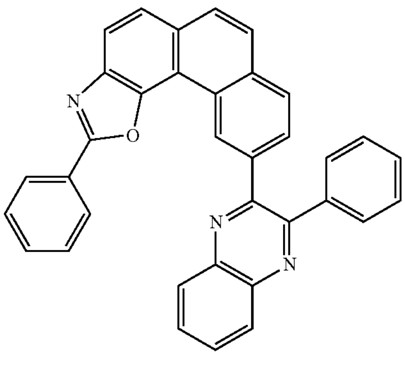

C2-86

Compound A (CAS: 2085325-18-2, 4.0 g, 9.5 mmol), 2-chloro-3-phenylquinoxaline (2.8 g, 11.4 mmol), tetrakis (triphenylphosphine)palladium ($Pd(PPh_3)_4$) (0.5 g, 0.5 mmol), potassium carbonate ($K_2CO_3$) (2.0 g, 19 mmol), 30 mL of toluene, 7 mL of EtOH, and 10 mL of water were added into a reaction vessel, and the mixture was stirred under reflux for one day. After completion of the reaction, the reaction mixture was cooled to room temperature, filtered by cellite with methylene chloride (MC), distilled under reduced pressure, and then separated by column chromatography with methylene chloride/hexane (MC/Hex) to obtain compound C2-86 (2.7 g, yield: 57%).

| Compound | MW | M.P. |
|---|---|---|
| C2-86 | 499.6 | 266° C. |

Example 7: Preparation of Compound C2-125

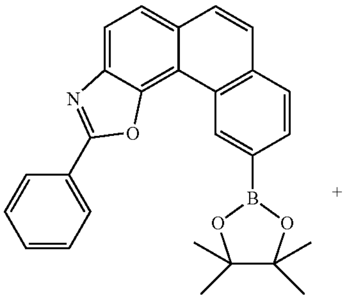

A

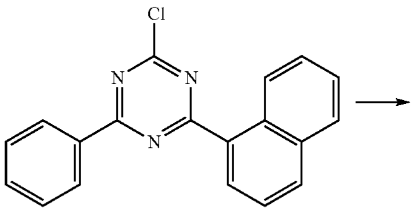

-continued

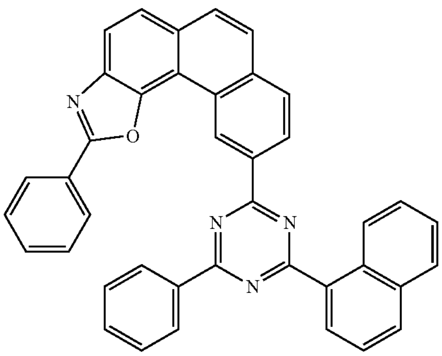

C2-125

Compound A (23.8 g, 56.6 mmol), 2-chloro-4-(naphthalen-1-yl)-6-phenyl-1,3,5-triazine (15.0 g, 47.2 mmol), $Pd(PPh_3)_4$ (2.72 g, 2.36 mmol), $K_2CO_3$ (16.3 g, 118 mmol), 240 mL of toluene, 60 mL of EtOH, and 60 mL of distilled water were added into a reaction vessel, and the mixture was stirred under reflux for 2 hours. After completion of the reaction, the reaction mixture was cooled to room temperature, and filtered by silica gel. Then, an organic layer was distilled under reduced pressure, and recrystallized with toluene to obtain compound C2-125 (13.8 g, yield: 51%).

| Compound | MW | M.P. |
|---|---|---|
| C2-125 | 576.6 | 231° C. |

Example 8: Preparation of Compound C2-116

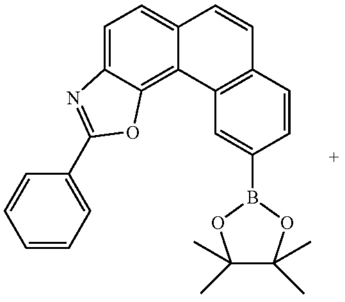

A

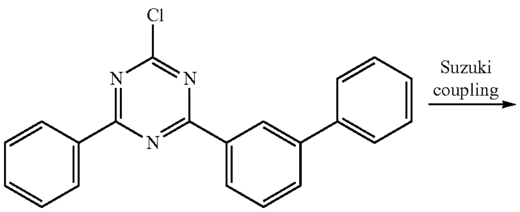

-continued

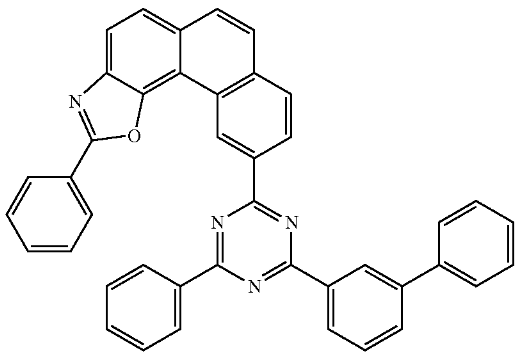

C2-116

Compound A (4.0 g, 9.5 mmol), 2-([1,1'-biphenyl]-3-yl)-4-chloro-6-phenyl-1,3,5-triazine (3.9 g, 11.4 mmol), $Pd(PPh_3)_4$ (0.5 g, 0.5 mmol), $K_2CO_3$ (2.6 g, 19 mmol), 30 mL of toluene, 7 mL of EtOH, and 10 mL of distilled water were added into a reaction vessel, and the mixture was stirred under reflux for 6 hours. After completion of the reaction, the reaction mixture was cooled to room temperature, and stirred at room temperature. The solid obtained by adding MeOH was filtered under reduced pressure, and separated by column chromatography with MC to obtain compound C2-116 (4.6 g, yield: 80%).

| Compound | MW | M.P. |
|---|---|---|
| C2-116 | 602.7 | 227° C. |

Example 9: Preparation of Compound C2-120

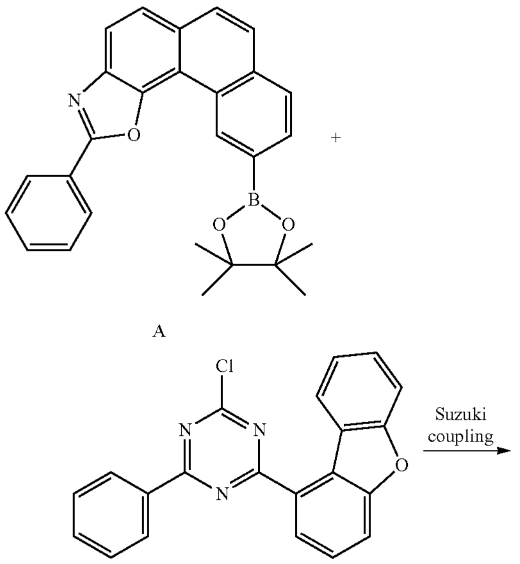

-continued

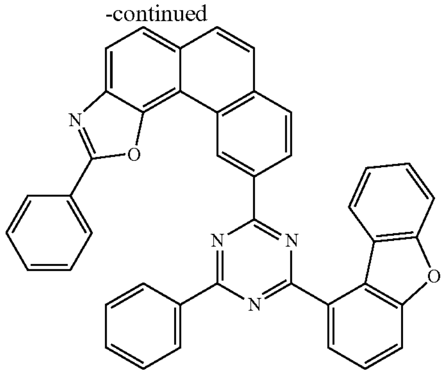

C2-120

Compound A (3.0 g, 7.1 mmol), 2-chloro-4-(dibenzo[b,d]furan-1-yl)-6-phenyl-1,3,5-triazine (3.4 g, 9.26 mmol), $Pd(PPh_3)_4$ (0.4 g, 0.36 mmol), $K_2CO_3$ (2.0 g, 14 mmol), 36 mL of toluene, 8 mL of EtOH, and 12 mL of distilled water were added into a reaction vessel, and the mixture was stirred under reflux for 6 hours. After completion of the reaction, the reaction mixture was cooled to room temperature, and stirred at room temperature. The solid obtained by adding MeOH was filtered under reduced pressure, and separated by column chromatography with MC to obtain compound C2-120 (3.3 g, yield: 75%).

| Compound | MW | M.P. |
|---|---|---|
| C2-120 | 616.7 | 282° C. |

Device Examples 1 to 3: Producing an OLED According to the Present Disclosure

OLEDs according to the present disclosure were produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 shown in Table 2 as a first hole injection compound was introduced into a cell of the vacuum vapor deposition apparatus, and compound HT-1 shown in Table 2 was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm on the ITO substrate. Next, compound HT-1 was deposited on the hole injection layer to form a first hole transport layer having a thickness of 80 nm. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows:

The first host compound and the second host compound shown in Table 1 below were introduced into two cells of the vacuum vapor depositing apparatus as hosts, and compound D-71 was introduced into another cell as a dopant. The two host materials were evaporated at a rate of 1:1 and the dopant material was simultaneously evaporated at a different rate, and the dopant was deposited in a doping amount of 3 wt % based on the total amount of the hosts and the dopant to form a light-emitting layer having a thickness of 40 nm on the second hole transport layer. Compound ETL-1 and compound EIL-1 were evaporated in a weight ratio of 50:50 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Comparative Examples 1 to 3: Producing an OLED Comprising a Comparative Compound as a Host OLEDs were produced in the same manner as in Device Example 1, except that the compound shown in Table 1 below was used alone as a first host or a second host.

The driving voltage, luminous efficiency, and light-emitting color at a luminance of 1,000 nit, and the time taken for luminance to decrease from 100% to 95% at a luminance of 5,000 nit (lifetime; T95) of the OLEDs produced in Device Examples 1 to 3, and Comparative Examples 1 to 3 are provided in Table 1 below.

TABLE 1

| | Fist Host | Second Host | Driving Voltage (V) | Luminous Efficiency (cd/A) | Light-Emitting Color | Life-time (T95, hr) |
|---|---|---|---|---|---|---|
| Comparative Example 1 | C-29 | — | 4.7 | 5.8 | Red | 9.3 |
| Comparative Example 2 | — | C2-120 | 3.5 | 30.8 | Red | 55 |
| Comparative Example 3 | — | C2-116 | 3.2 | 28.0 | Red | 33.9 |
| Device Example 1 | C-29 | C2-120 | 3.0 | 35.3 | Red | 551 |
| Device Example 2 | C-32 | C2-120 | 3.1 | 35.4 | Red | 563 |
| Device Example 3 | C-32 | C2-116 | 3.0 | 35.1 | Red | 322 |

From Table 1 above, it can be confirmed that the OLEDs comprising the plurality of host materials according to the present disclosure as host materials have improved driving voltage, luminous efficiency, and/or lifespan property, compared to the conventional OLED. Without wishing to be bound by theory, it is considered that by using the compound represented by formula 1 of the present disclosure in combination with the compound represented by formula 2 of the present disclosure, the HOMO (highest occupied molecular orbital) energy level increases compared to the case when using the conventional compound, which is a carbazole derivative, resulting in increase of the hole mobility. Thus, the hole injection from a hole transport layer becomes easier, and the balance between hole and electron and the formation of exciton may be improved, thereby improving the driving voltage, luminous efficiency and/or lifetime property of an OLED.

The compounds used in the Device Examples and the Comparative Examples are shown in Table 2 below.

TABLE 2

| | |
|---|---|
| Hole Injection Layer/ Hole Transport Layer | 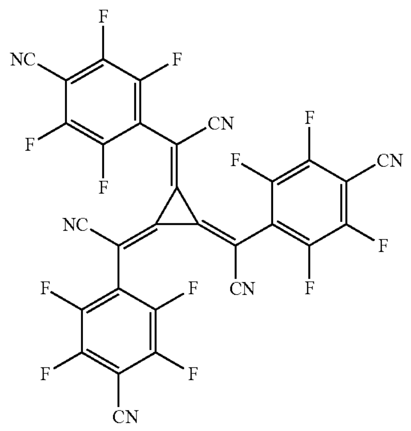 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F] HI-1 |

TABLE 2-continued
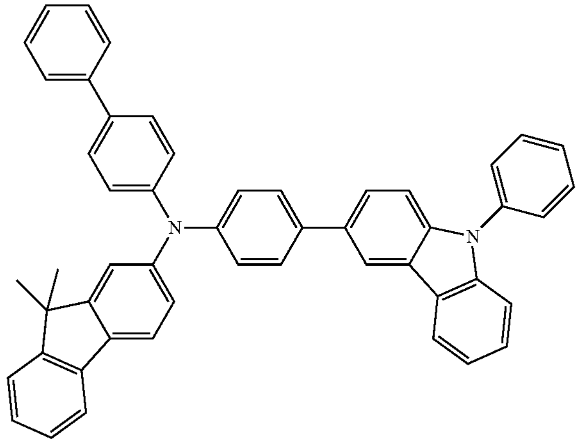 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT-1
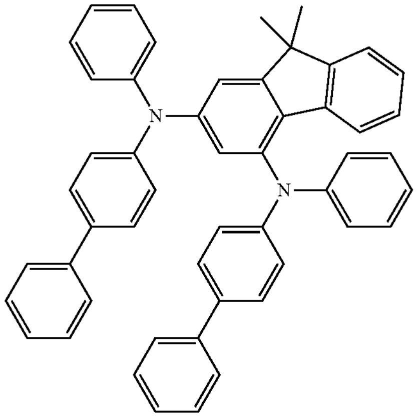 [SMILES: CC1(C)c2ccccc2-c2c(N(c3ccccc3)c3ccc(-c4ccccc4)cc3)cc(N(c3ccccc3)c3ccc(-c4ccccc4)cc3)cc21]
HT-2
Light-Emitting
Layer
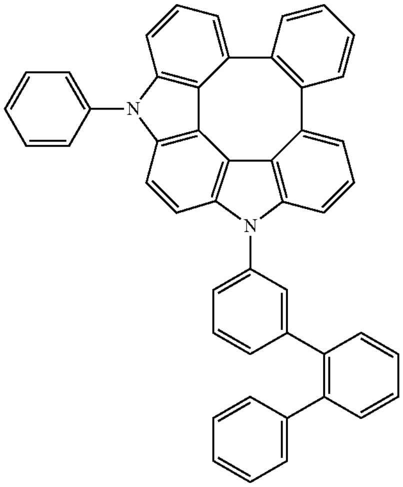 [SMILES: c1ccc(-c2ccccc2-c2cccc(-n3c4cccc5c6ccccc6c6cccc7c6c6c(c54)c3ccc6n7-c3ccccc3)c2)cc1]
C-29

TABLE 2-continued
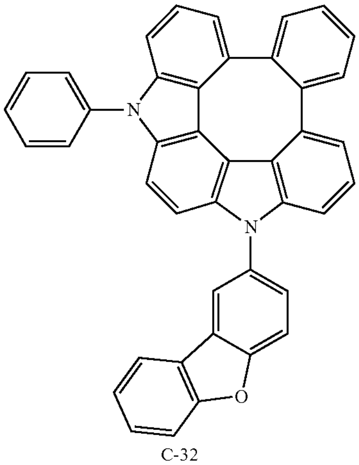
C-32
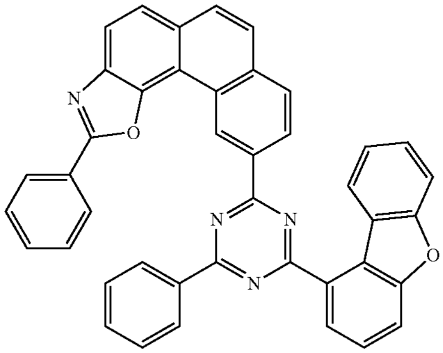 [SMILES: c1ccc(-c2nc(-c3ccc4ccc5ccc6nc(-c7ccccc7)oc6c5c4c3)nc(-c3cccc4oc5ccccc5c34)n2)cc1]
C2-120
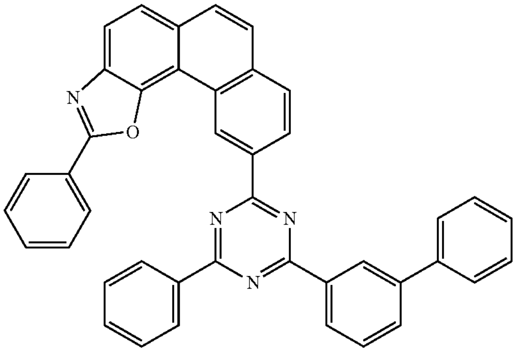 [SMILES: c1ccc(-c2cccc(-c3nc(-c4ccccc4)nc(-c4ccc5ccc6ccc7nc(-c8ccccc8)oc7c6c5c4)n3)c2)cc1]
C2-116
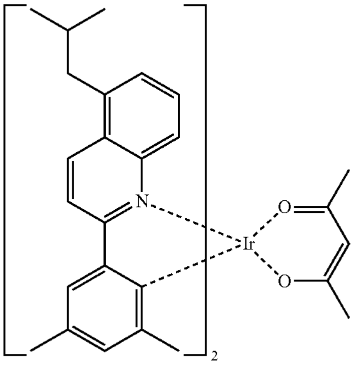
D-39

TABLE 2-continued

| | |
|---|---|
| Electron Transport Layer/ Electron Injection Layer | 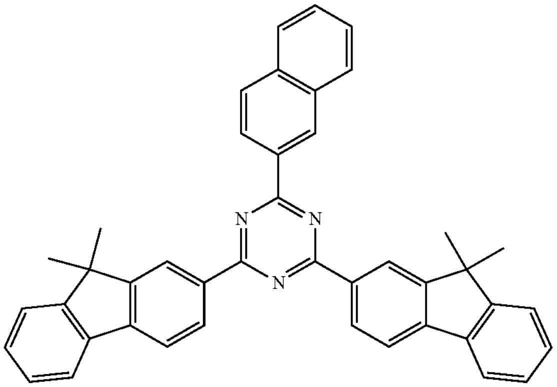 [SMILES: CC1(C)c2ccccc2-c2ccc(-c3nc(-c4ccc5c(c4)C(C)(C)c4ccccc4-5)nc(-c4ccc5ccccc5c4)n3)cc21] ETL-1 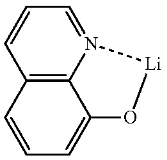 EIL-1 |

The invention claimed is:

1. A plurality of host materials comprising at least one first host compound and at least second host compound, wherein the first host compound is represented by the following formula 1-1, and the second host compound is represented by the following formula 2:

(1-1)

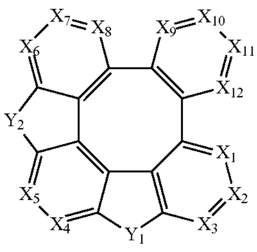

wherein $Y_1$ and $Y_2$, each independently, represents —N($L_1$-$(Ar_1)_n$)—, —O—, —S—, or —C($R_1$)($R_2$)—; with the proviso that $Y_1$ and $Y_2$ cannot simultaneously represent —O—;

$X_1$ to $X_{12}$, each independently, represent —N= or —C($R_a$)=; and $R_a$, each independently, represents hydrogen, a halogen, a cyano, a substituted or unsubstituted (C1-C30)alkyl, or a substituted or unsubstituted (C3-C30)cycloalkyl; or adjacent $R_a$'s may be linked to each other to form a ring(s), where if a plurality of $R_a$'s are present, each of $R_a$ may be the same or different;

$L_1$ represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene;

$Ar_1$ represents a substituted or unsubstituted (C6-C30) aryl, a substituted or unsubstituted (3- to 30-membered) heteroaryl, or —N($R_3$)($R_4$);

$R_1$ to $R_4$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, or a substituted or unsubstituted (C3-C30) cycloalkyl; or may be linked to an adjacent substituent to form a ring(s); and n represents an integer of 1 or 2, where if n is 2, each of $Ar_1$ may be the same or different;

(2)

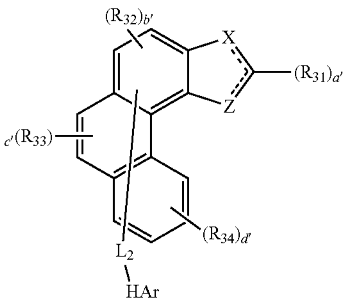

wherein

X represents —N=, —$NR_{35}$—, —O— or —S—;

Z represents —N=, —$NR_{36}$—, —O— or —S—, where if X represents —N=, Z represents —$NR_{36}$—, —O— or —S—, and if X represents —$NR_{35}$—, Z represents —N=, —O— or —S—;

HAr represents a substituted or unsubstituted (3- to 30-membered)heteroaryl;

$R_{31}$ represents a substituted or unsubstituted (C6-C30) aryl, or a substituted or unsubstituted (3- to 30-membered)heteroaryl;

$R_{32}$ to $R_{34}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or $-L_3-N(Ar_2)$ (Ars); or may be linked to an adjacent substituent to form a ring(s);

$R_{35}$ and $R_{36}$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or $-L_3-N(Ar_2)(Ar_3)$;

$L_2$ and $L_3$, each independently, represent a single bond, a substituted or unsubstituted (C6-C30)arylene, or a substituted or unsubstituted (3- to 30-membered)heteroarylene;

$Ar_2$ and $Ar_3$, each independently, represent hydrogen, a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl; and a' represents 1, b' and c', each independently, represent an integer of 1 or 2, and d' represents an integer of 1 to 4, where if each of b', c' and d' is an integer of 2 or more, each of $R_{32}$ to each of $R_{34}$ may be the same or different.

2. The plurality of host materials according to claim 1, wherein the substituents of the substituted alkyl, the substituted alkylene, the substituted alkenyl, the substituted aryl, the substituted arylene, the substituted heteroaryl, the substituted heteroarylene, the substituted cycloalkyl, the substituted cycloalkylene, the substituted alkoxy, the substituted trialkylsilyl, the substituted dialkylarylsilyl, the substituted alkyldiarylsilyl, the substituted triarylsilyl, the substituted fused ring of an aliphatic ring(s) and an aromatic ring(s), and the substituted ring, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 50-membered)heteroaryl unsubstituted or substituted with at least one of a (C1-C30)alkyl(s), a (C6-C30)aryl(s), and a di(C6-C30)arylamino(s); a (C6-C30)aryl unsubstituted or substituted with at least one of deuterium, a cyano(s), a (C1-C30)alkyl(s), a (3- to 50-membered)heteroaryl(s), a mono- or di-(C6-C30)arylamino(s), and a tri(C6-C30)arylsilyl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino; a mono- or di-(3- to 30-membered) heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30) alkoxycarbonyl; a (C6-C30)arylcarbonyl; a di(C6-C30) arylboronyl; a di(C1-C30)alkylboronyl; a (C1-C30)alkyl (C6-C30)arylboronyl; a (C6-C30)aryl(C1-C30)alkyl; and a (C1-C30)alkyl(C6-C30)aryl.

3. The plurality of host materials according to claim 1, wherein formula 1 is represented by at least one of the following formulas 1-1 to 1-4:

(1-1)

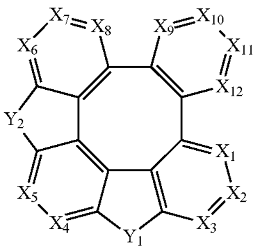

(1-2)

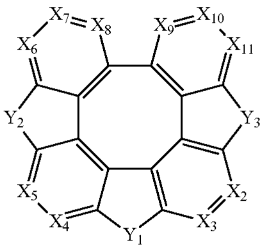

(1-3)

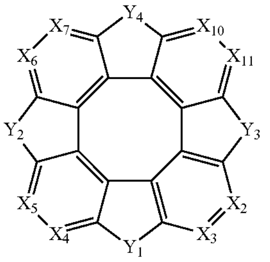

(1-4)

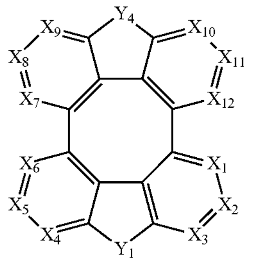

wherein $Y_1$, $Y_2$, $Y_3$, and $Y_4$, each independently, are the same as the definition of Y in claim 1, where if a plurality of $Ar_1$'s are present, each of $Ar_1$ may be the same or different;

$X_1$ to $X_{12}$, each independently, represent —N═ or —C($R_a$)═; and $R_a$, each independently, represents hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, or a substituted or unsubstituted (C3-C30) cycloalkyl; or adjacent $R_a$'s may be linked to each other to form a ring(s), where if a plurality of $R_a$'s are present, each of $R_a$ may be the same or different.

4. The plurality of host materials according to claim 1, wherein at least one of $Ar_1$(s) is at least one selected from those listed in the following group 1:

[Group 1]

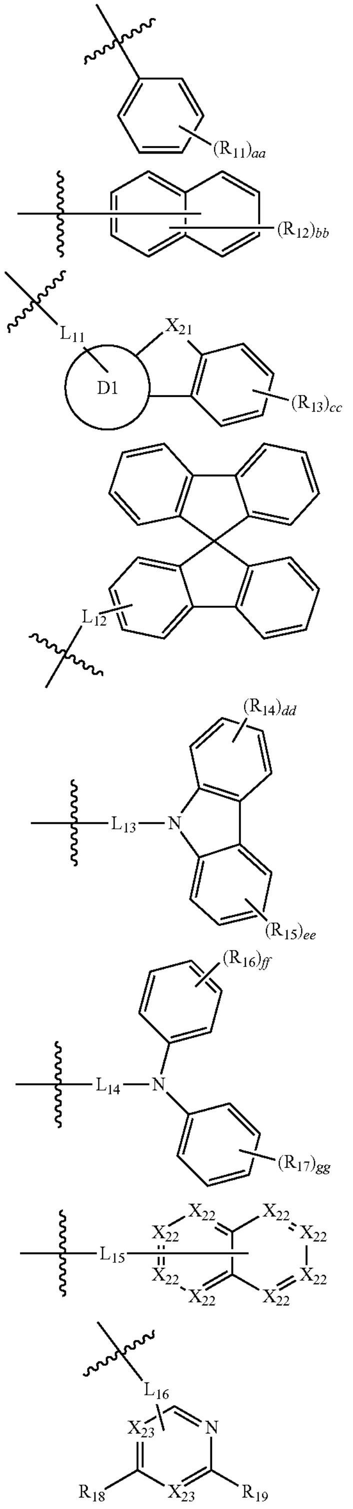

-continued

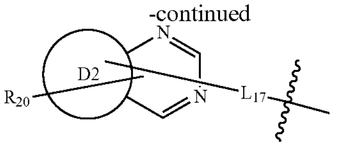

and

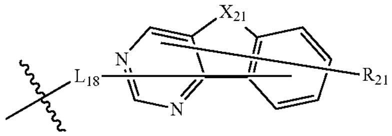

wherein

D1 and D2, each independently, represent a benzene ring or a naphthalene ring;

$X_{21}$ represents O, S, $NR_5$, or $C(R_6)(R_7)$;

$X_{22}$, each independently, represents $CR_8$ or N, with the proviso that at least one of $X_{22}$ represents N;

$X_{23}$, each independently, represents $CR_9$ or N;

$L_{11}$ to $L_{18}$, each independently, represent a single bond, a substituted or unsubstituted (C6-C30)arylene, or a substituted or unsubstituted (3- to 30-membered)heteroarylene;

$R_{11}$ to $R_{21}$ and $R_5$ to $R_9$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, or a substituted or unsubstituted (C3-C30)cycloalkyl, or may be linked to an adjacent substituent to form a ring(s); and aa, ff, and gg, each independently, represent an integer of 1 to 5, bb represents an integer of 1 to 7, and cc, dd, and ee, each independently, represent an integer of 1 to 4, where if each of aa to gg is an integer of 2 or more, each of $R_{11}$ to each of $R_{17}$ may be the same or different.

5. The plurality of host materials according to claim 1, wherein at least one of $Ar_1$(s) is at least one selected from those listed in the following groups 2 and 3:

[Group 2]

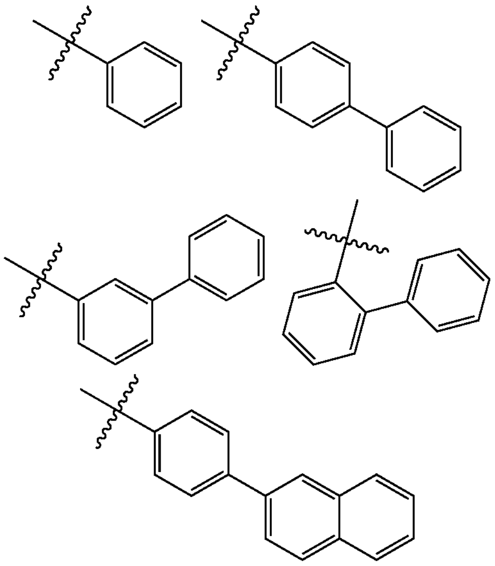

-continued
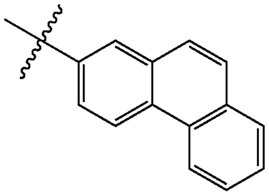
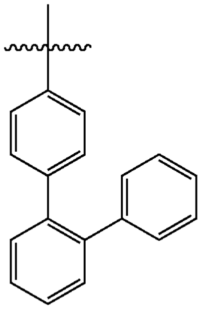
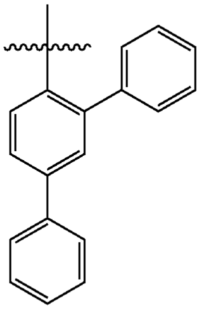
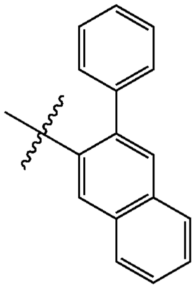
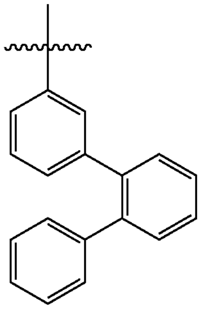
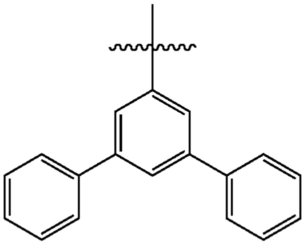
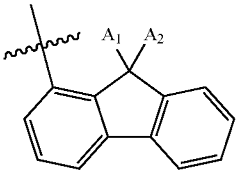
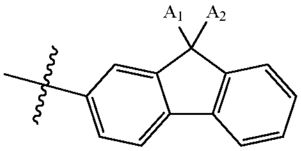
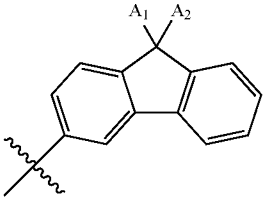
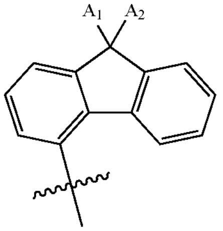
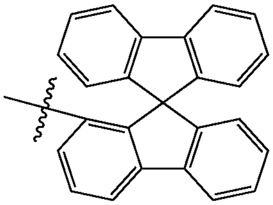
-continued
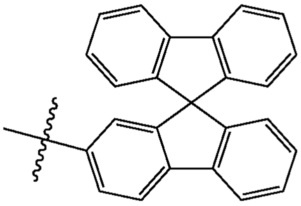
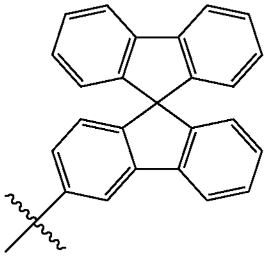
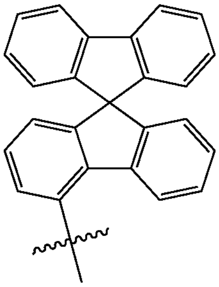
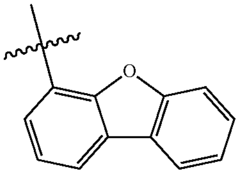
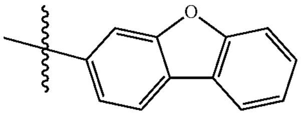
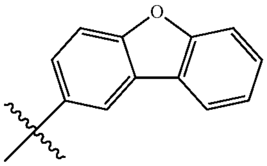
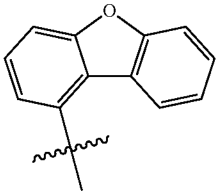
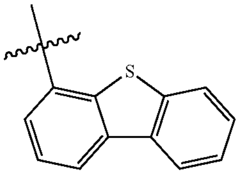
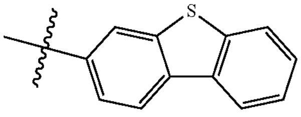
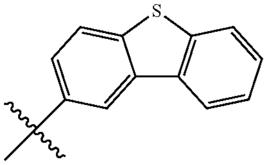
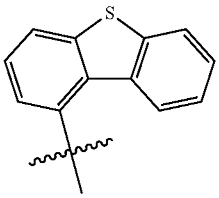
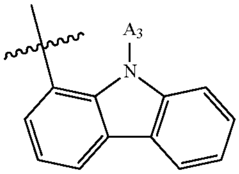
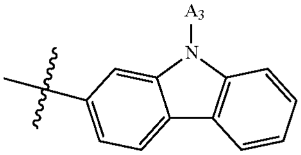
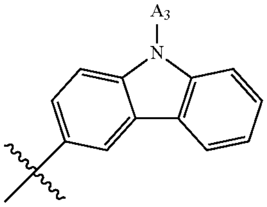

-continued
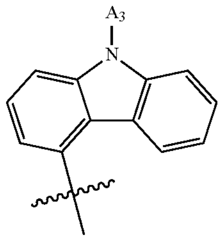
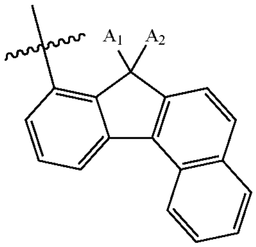
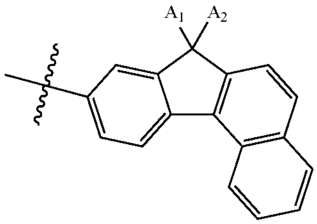
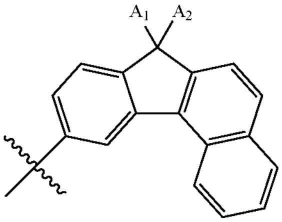
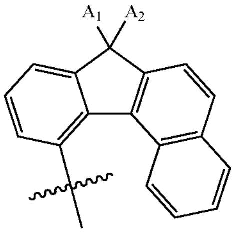
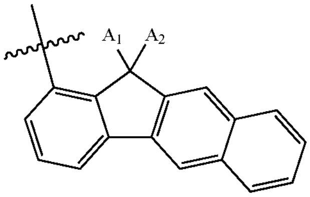
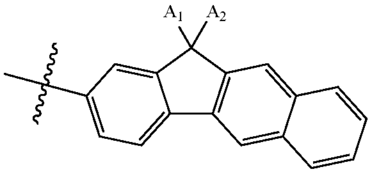
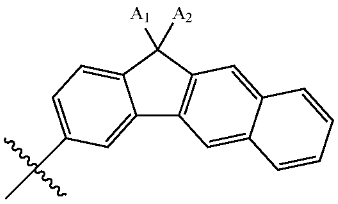
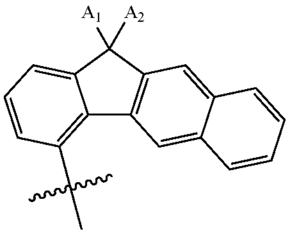
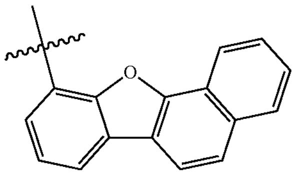
-continued
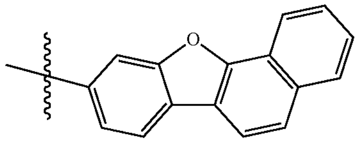
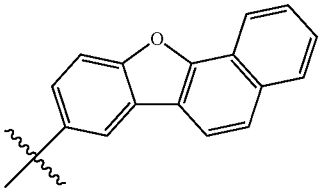
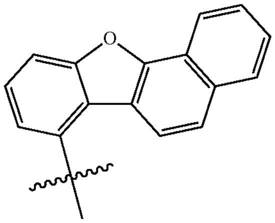
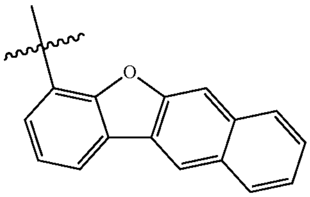
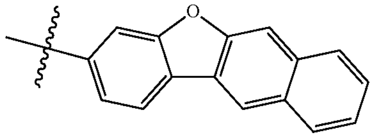
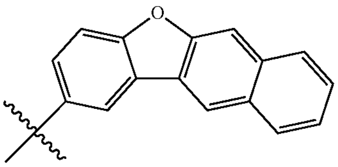
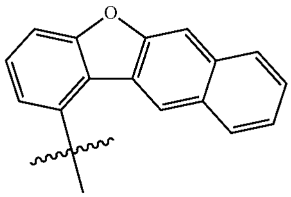
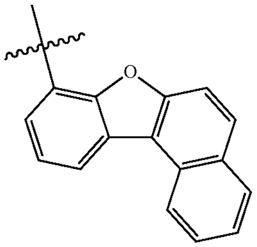
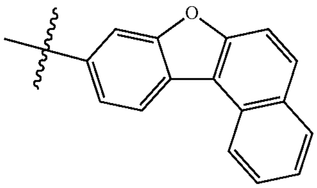

-continued
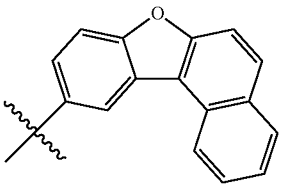
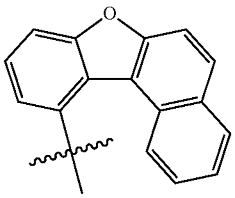
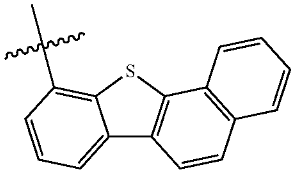
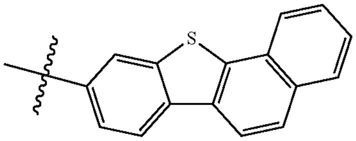
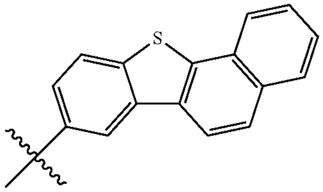
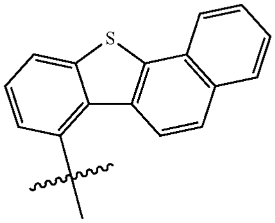
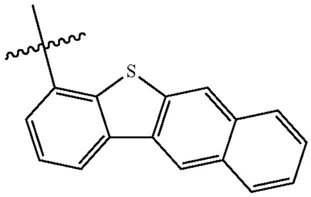
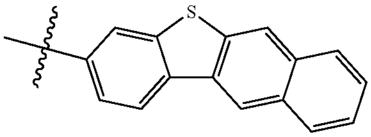
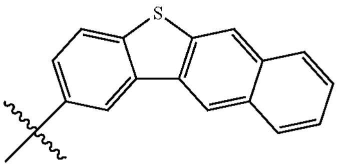
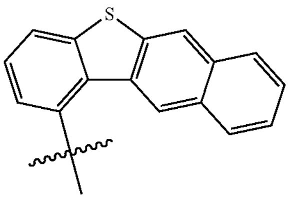
-continued
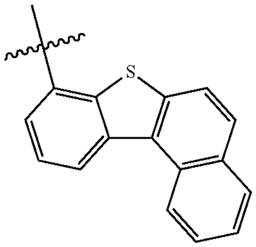
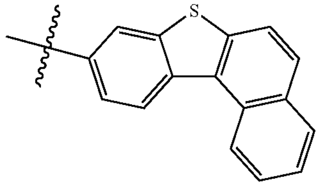
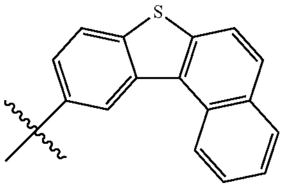
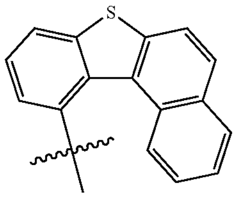
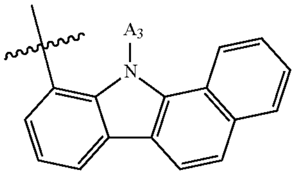
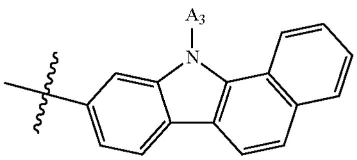
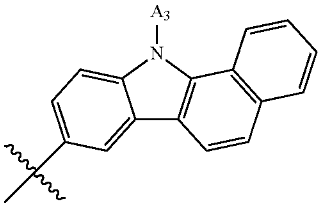
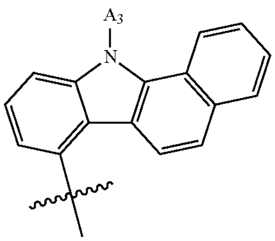
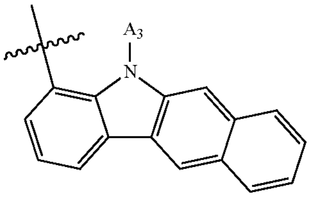

-continued
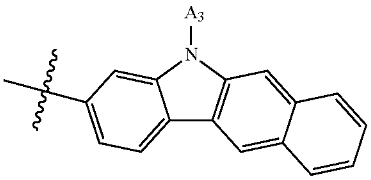
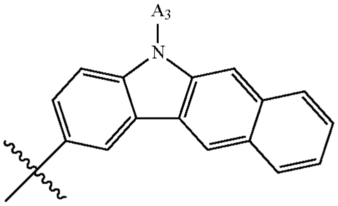
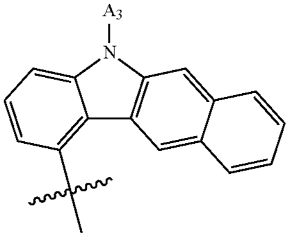
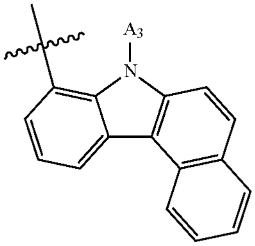
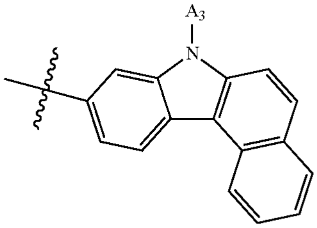
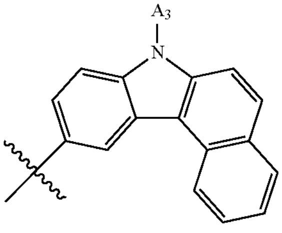
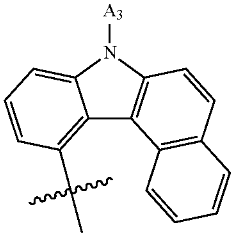
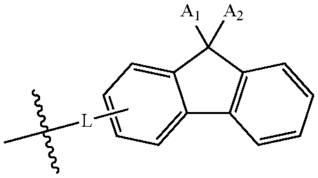
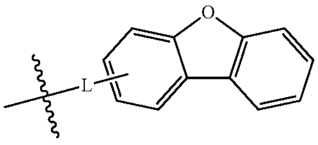
-continued
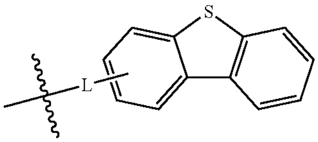
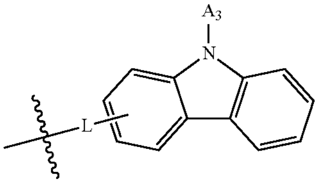
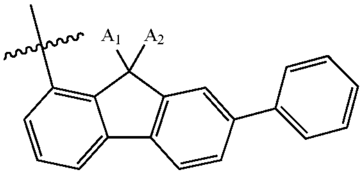
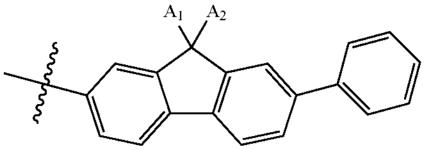
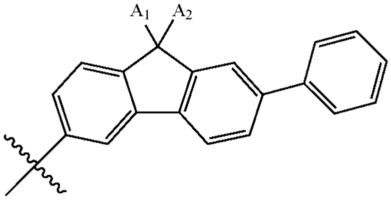
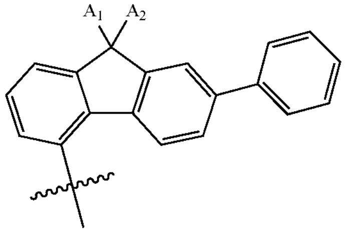
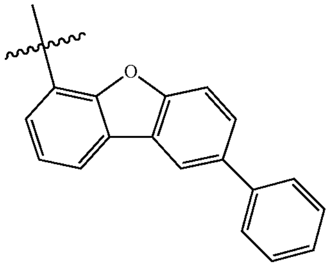
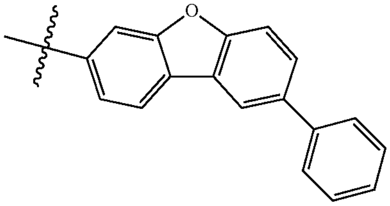
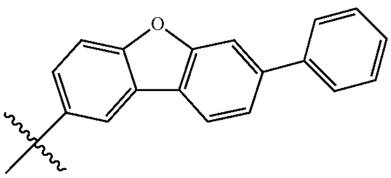

-continued
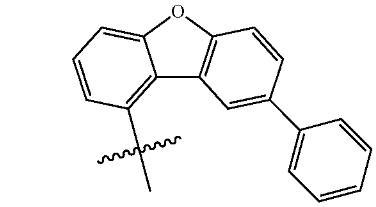
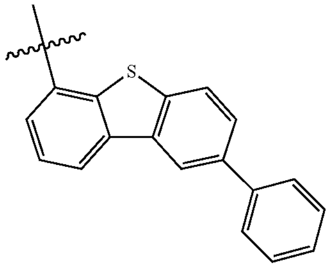
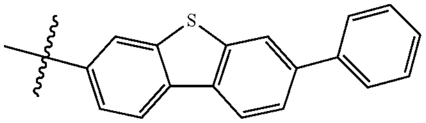
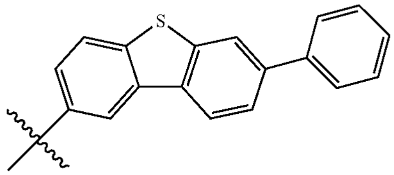
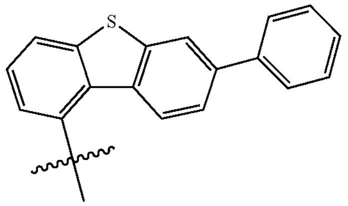
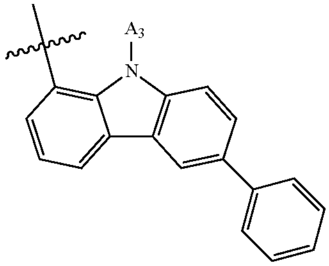
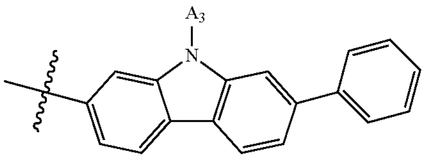
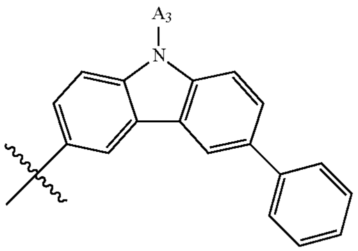
-continued
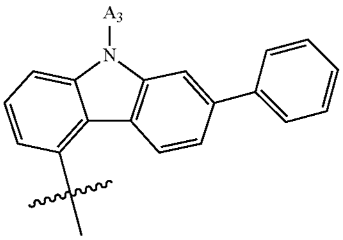
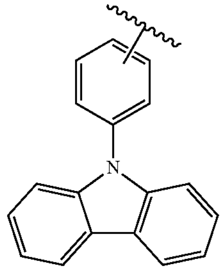
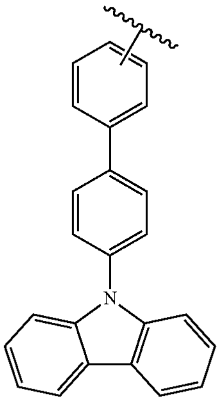
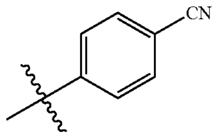
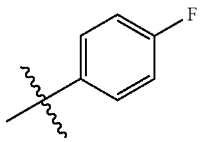
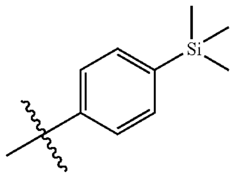
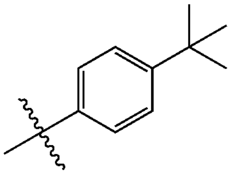
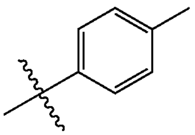
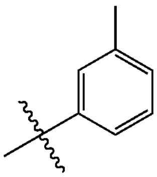
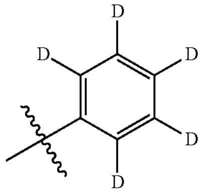
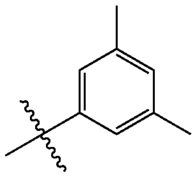
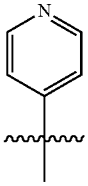
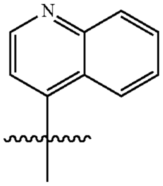

-continued
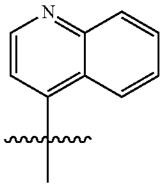
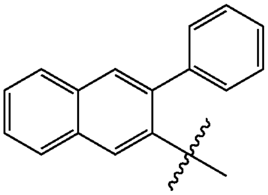
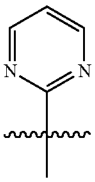
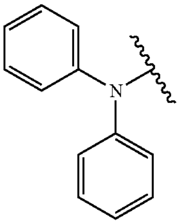
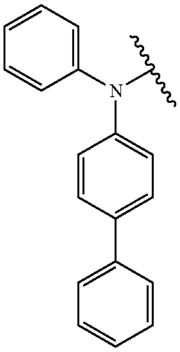
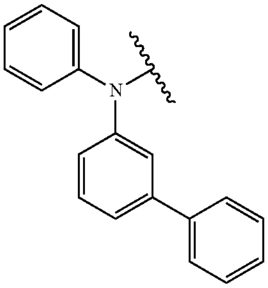
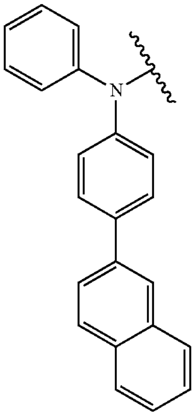
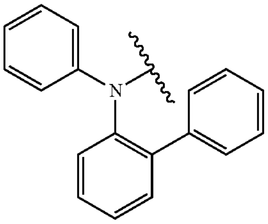
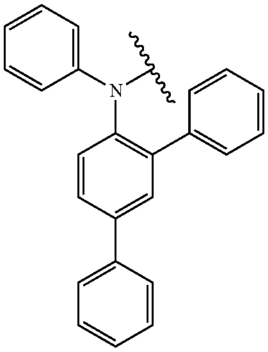
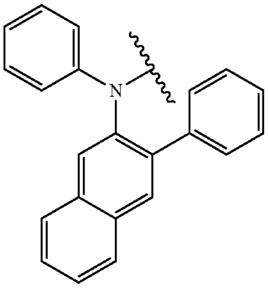
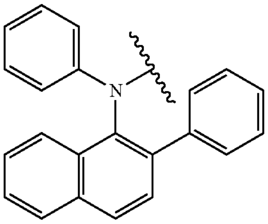
-continued
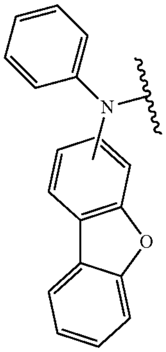
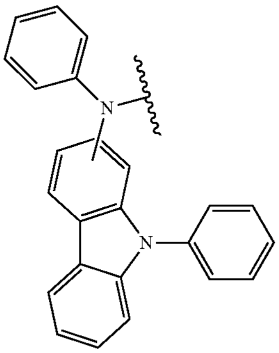
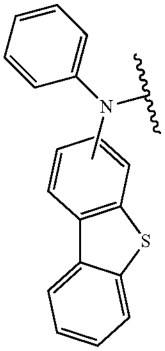
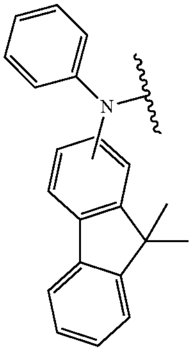
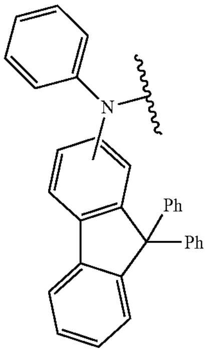
and
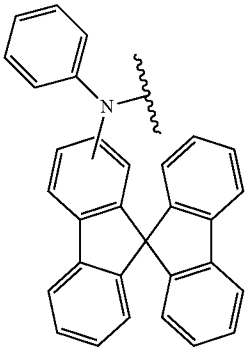
[Group 3]
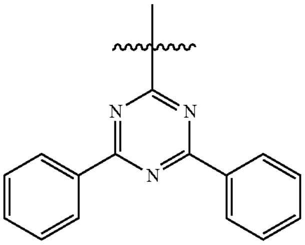
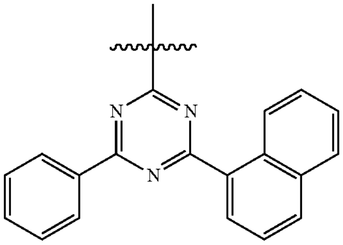

-continued
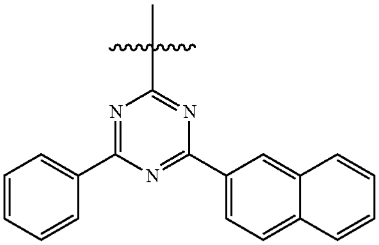
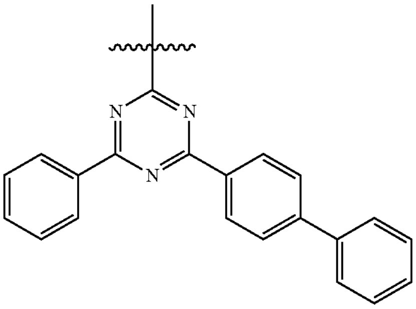
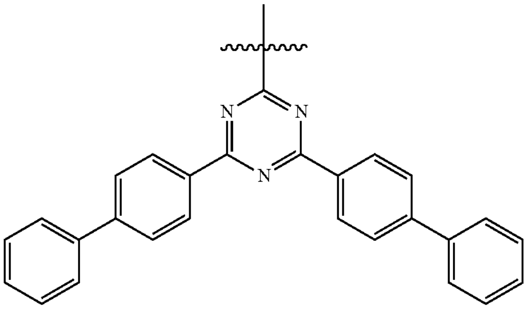
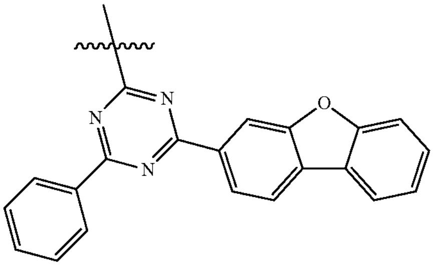
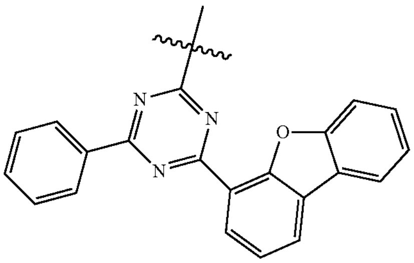
-continued
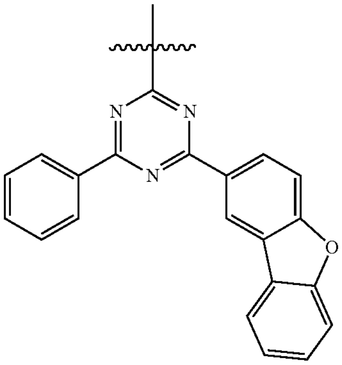
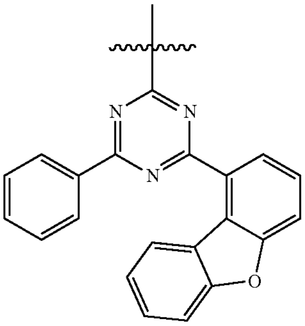
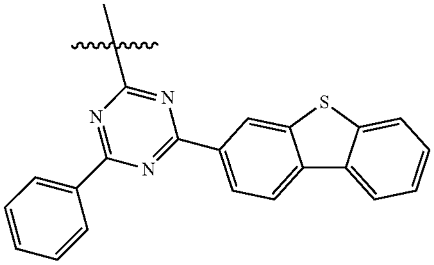
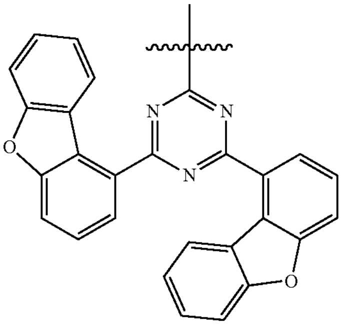
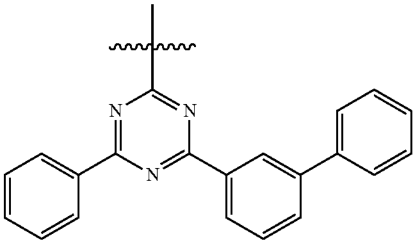

-continued
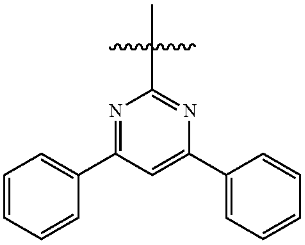
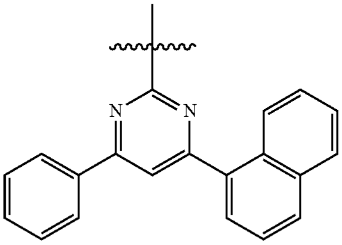
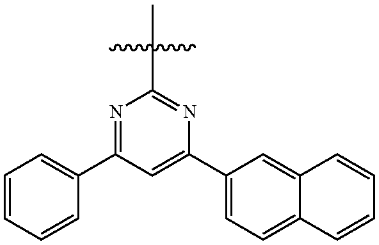
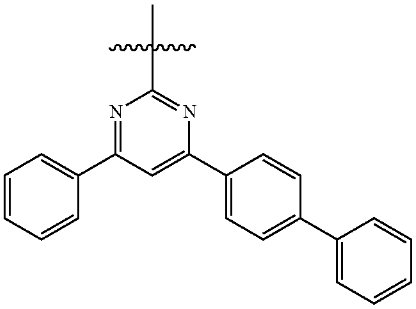
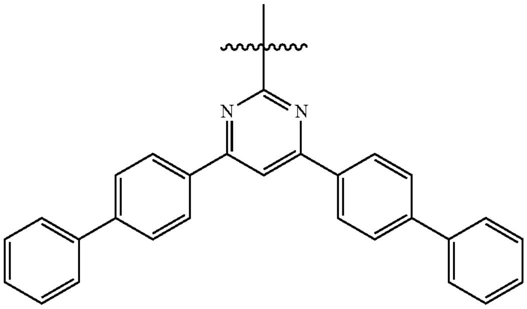
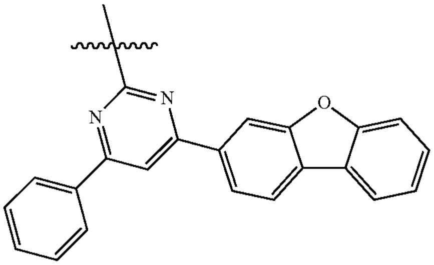
-continued
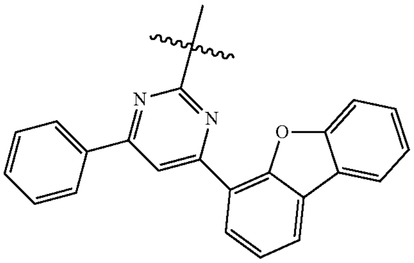
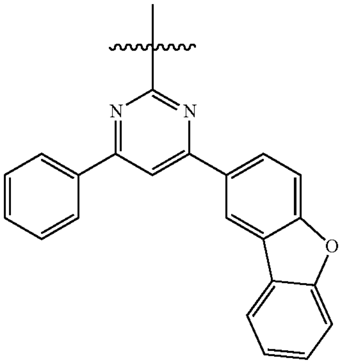
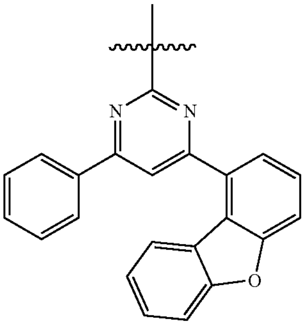
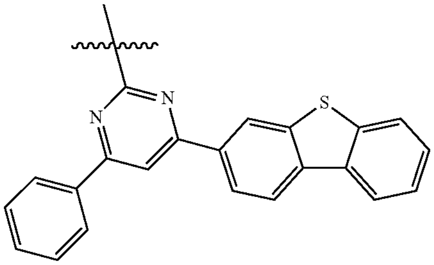
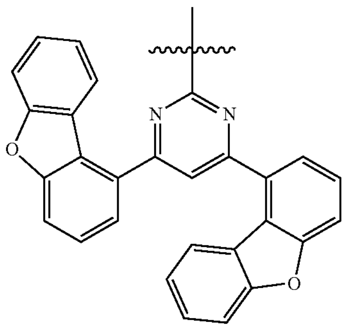

-continued
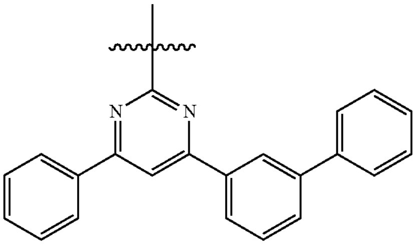
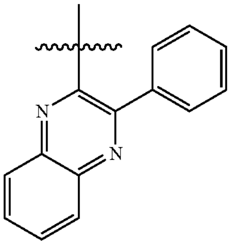
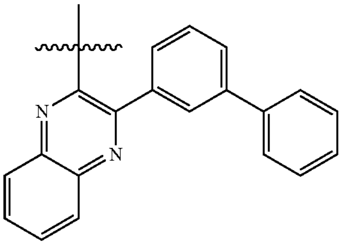
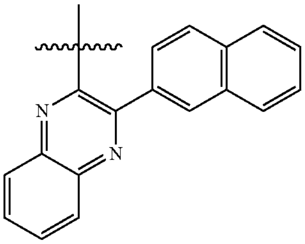
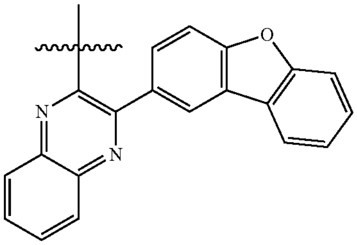
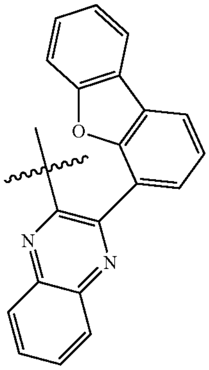
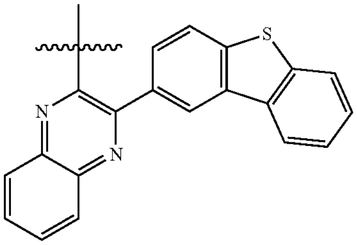
-continued
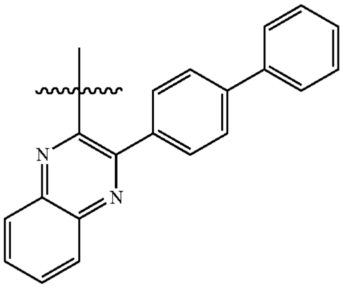
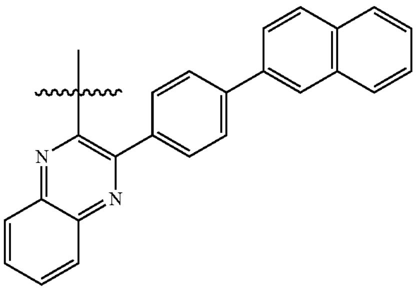
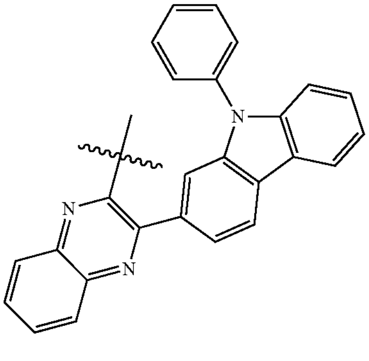
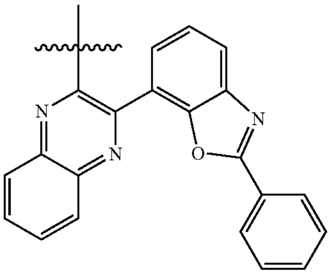
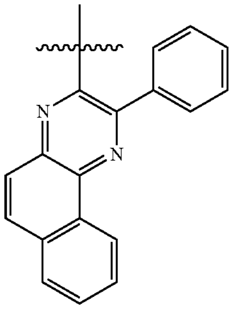
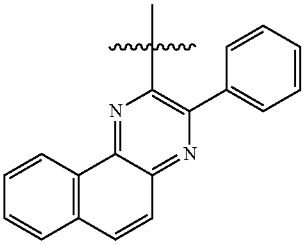

-continued
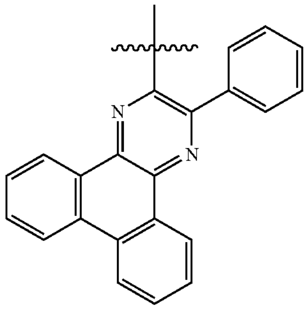
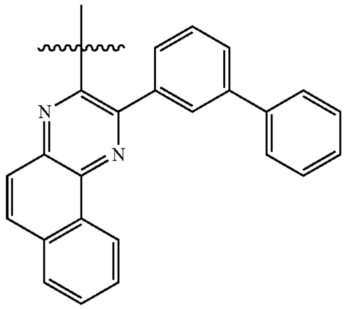
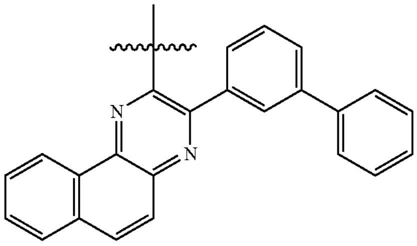
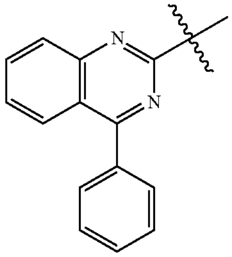
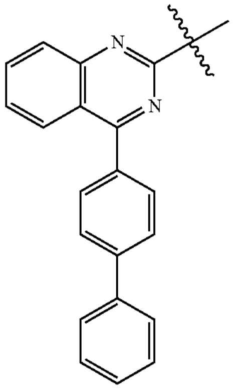
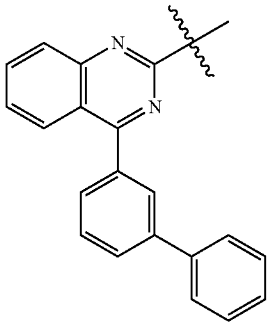
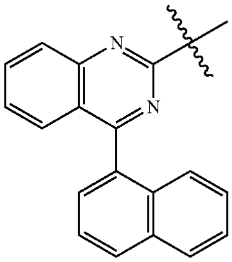
-continued
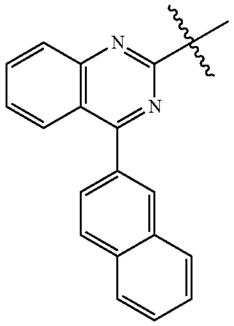
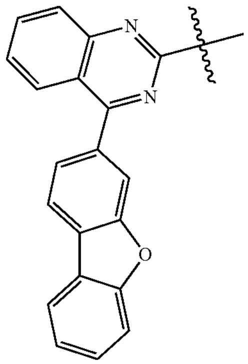
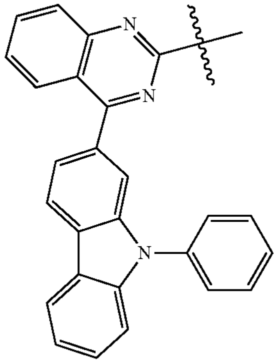
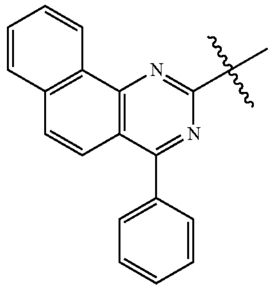
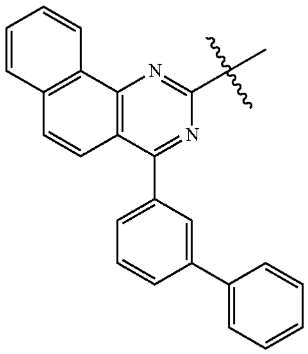
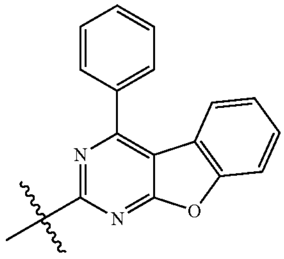
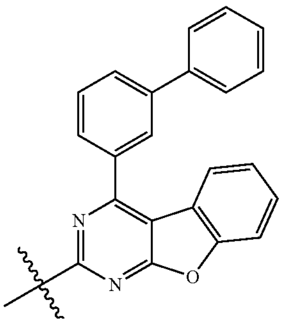

-continued

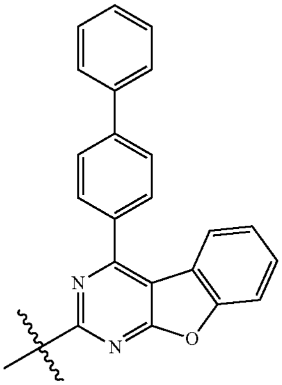

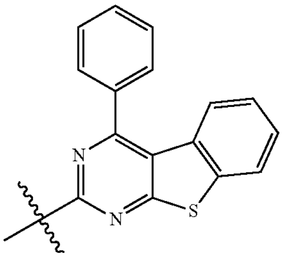

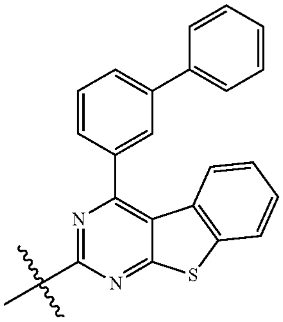

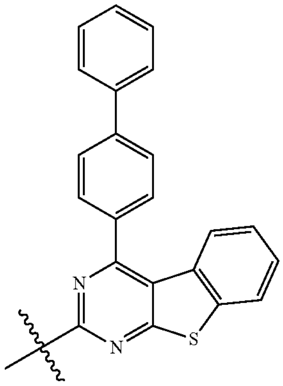

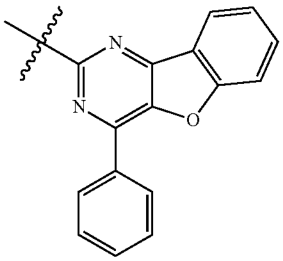

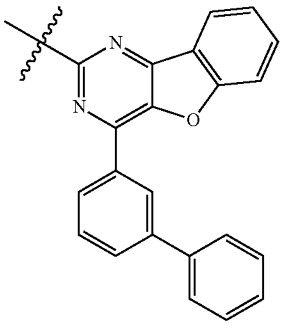

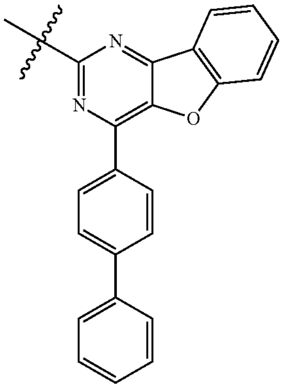

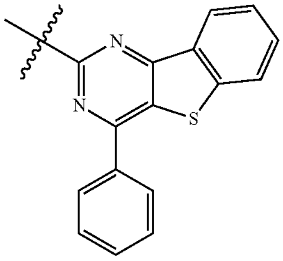

-continued

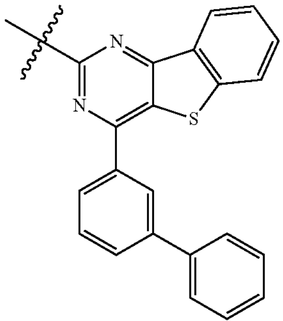

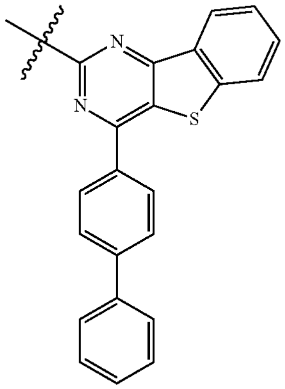

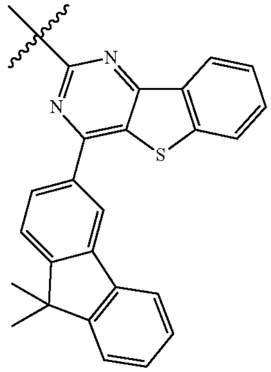

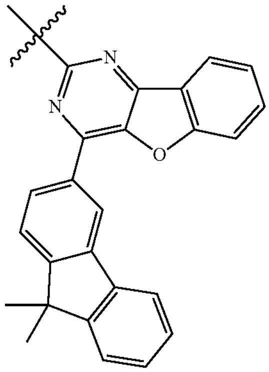

and

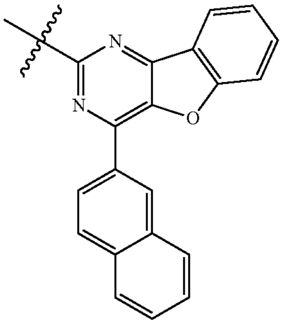

in group 2,

L represents a single bond, a substituted or unsubstituted (C1-C30)alkylene, a substituted or unsubstituted (C6-C30)arylene, a substituted or unsubstituted (3- to 30-membered)heteroarylene, or a substituted or unsubstituted (C3-C30)cycloalkylene; and $A_1$ to $A_3$, each independently, represent a substituted or unsubstituted (C1-C30)alkyl, or a substituted or unsubstituted (C6-C30)aryl.

6. The plurality of host materials according to claim 1, wherein in formula 1, $B_1$ to $B_7$, each independently, are not present, or represent a substituted or unsubstituted benzene ring, a substituted or unsubstituted naphthalene ring, a substituted or unsubstituted pyrrole ring, a substituted or unsubstituted furan ring, a substituted or unsubstituted thiophene ring, a substituted or unsubstituted cyclopentadiene ring, a substituted or unsubstituted fluorene ring, a substituted or unsubstituted pyridine ring, or a substituted or unsubstituted dibenzofuran ring, with the proviso that at least five of $B_1$ to $B_7$ are present, and adjacent rings of $B_1$ to $B_7$ are fused with each other.

7. The plurality of host materials according to claim 1, wherein formula 2 is represented by at least one selected from the following formulas 2-1 to 2-8:

(2-1)

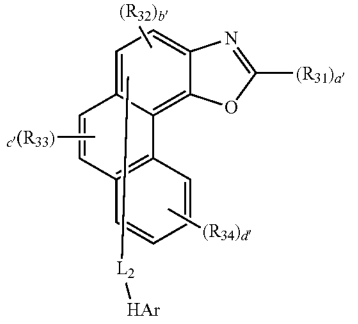

(2-2)

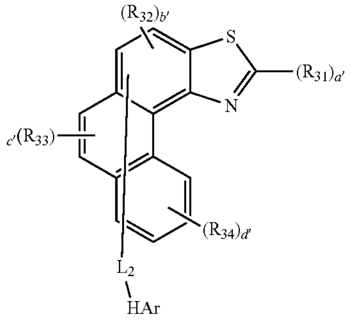

(2-3)

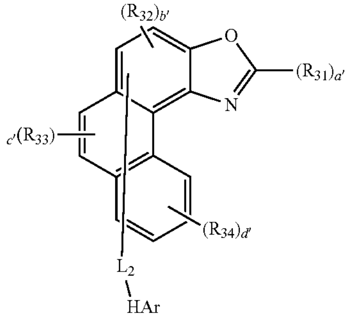

-continued (2-4)

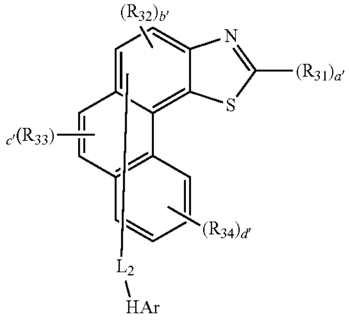

(2-5)

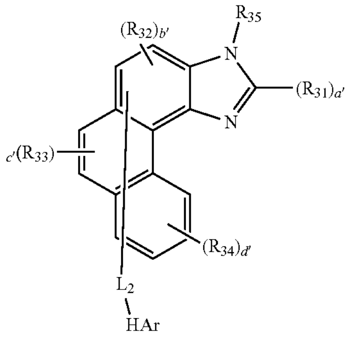

(2-6)

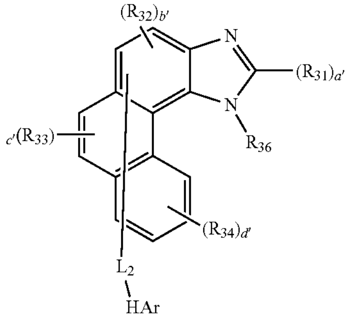

(2-7)

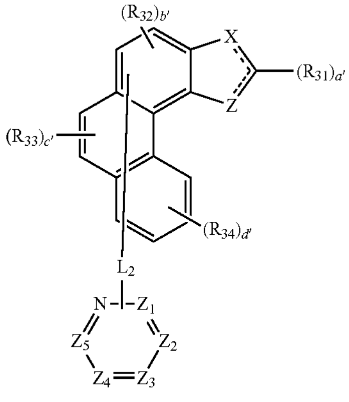

-continued (2-8)

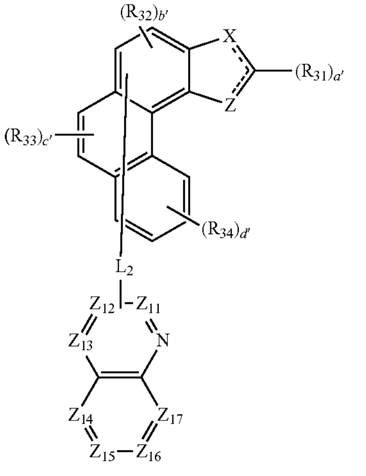

wherein

X, Z, HAr, $R_{31}$ to $R_{36}$, $L_2$ and a' to d' are as defined in claim 1;

$Z_1$ to $Z_5$ and $Z_{11}$ to $Z_{17}$, each independently, represent N or $CR_{37}$; and $R_{37}$, each independently, is the same as the definition of $R_{32}$.

8. The plurality of host materials according to claim 1, wherein in formula 2, HAr represents a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted triazanaphthyl, or a substituted or unsubstituted benzothienopyrimidinyl.

9. The plurality of host materials according to claim 1, wherein the compound represented by formula 1-1 is at least one selected from the following compounds:

C-1

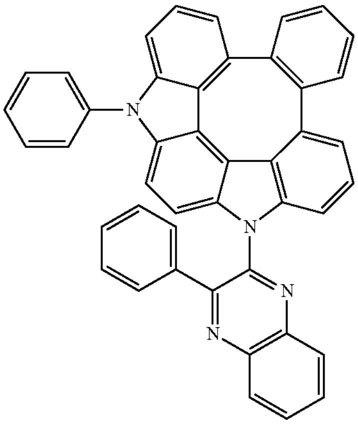

-continued

C-2

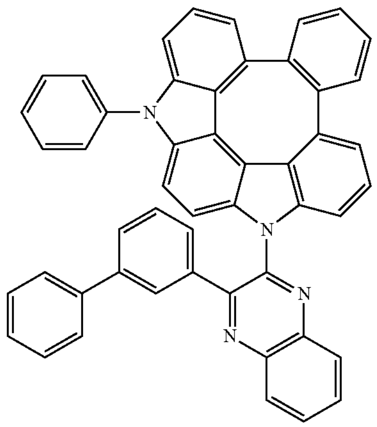

C-3

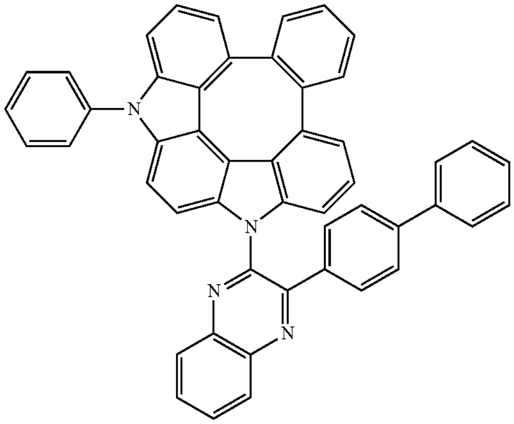

C-4

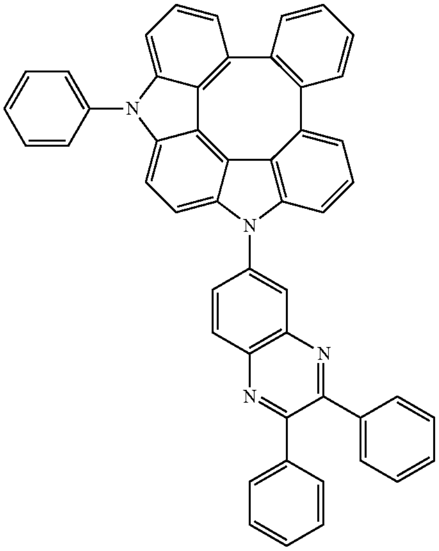

-continued
C-5
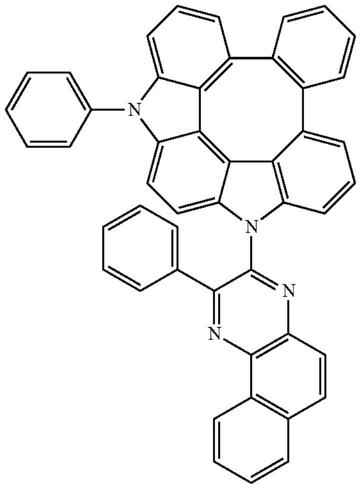
C-6
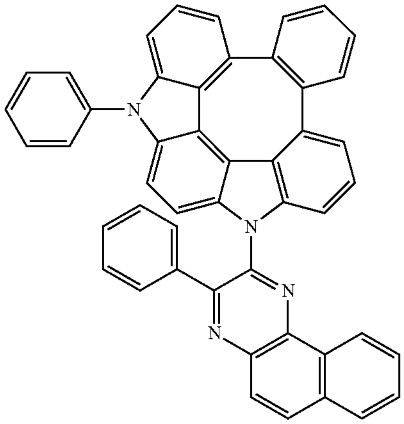
C-7
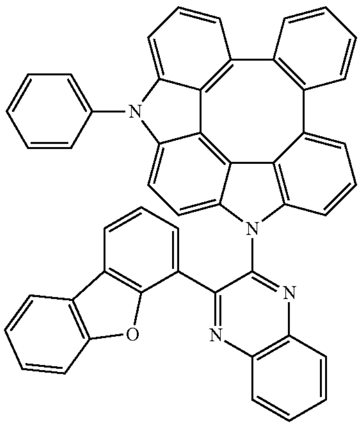
-continued
C-8
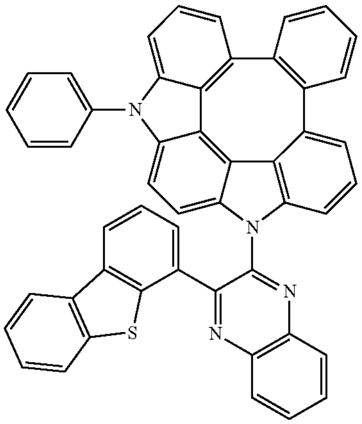
C-9
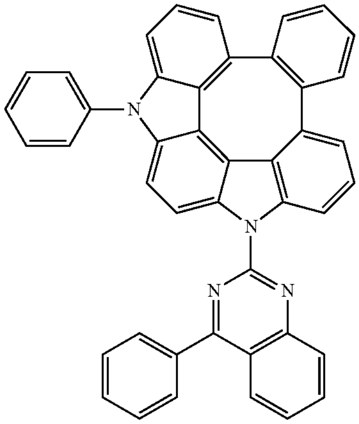
C-10
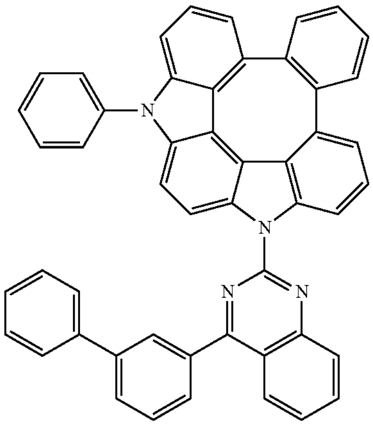

-continued
C-11
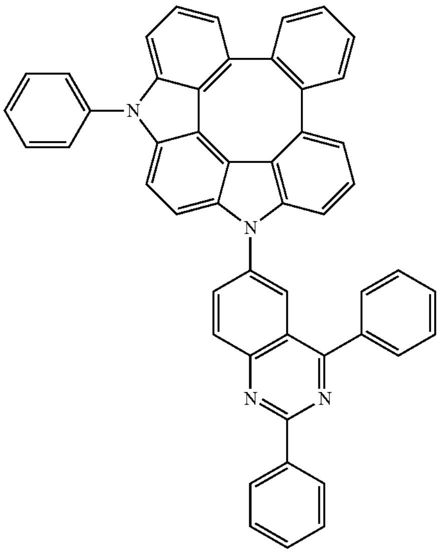
C-12
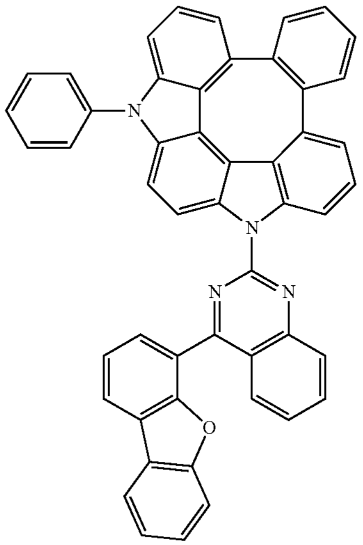
C-13
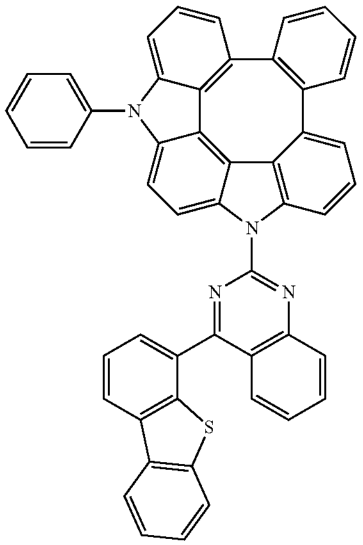
-continued
C-14
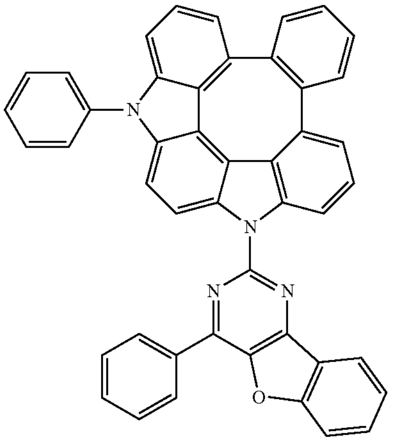
C-15
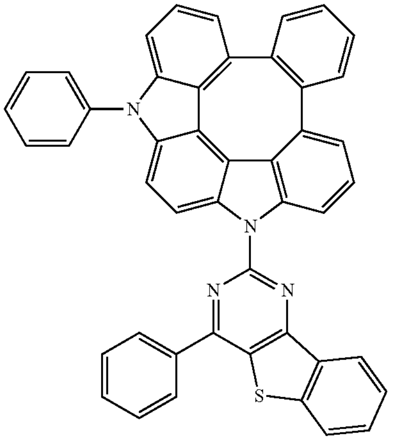
C-16
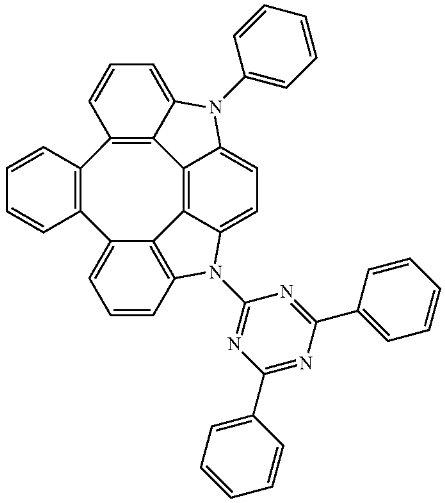

-continued
C-17
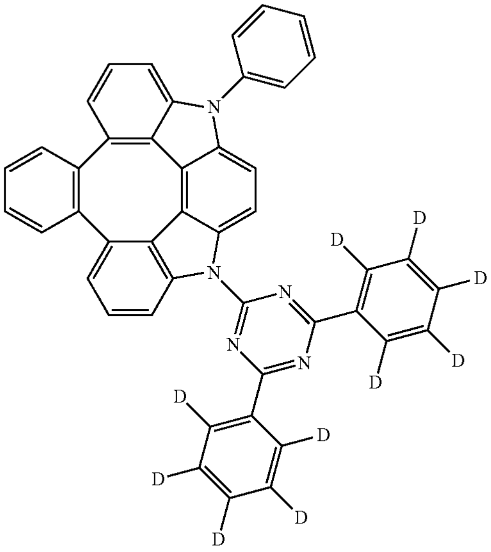
C-18
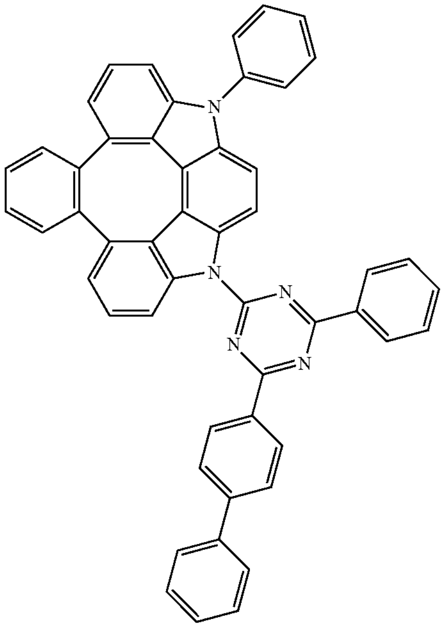
-continued
C-19
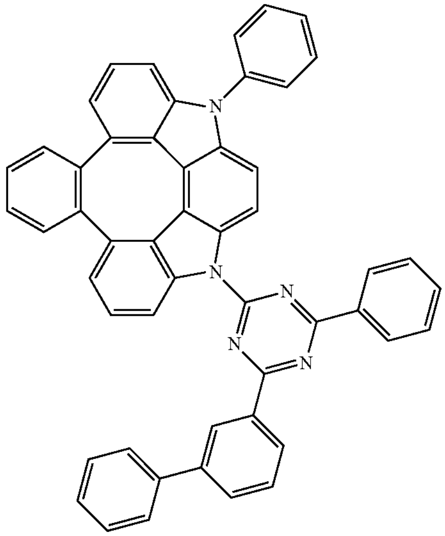
C-20
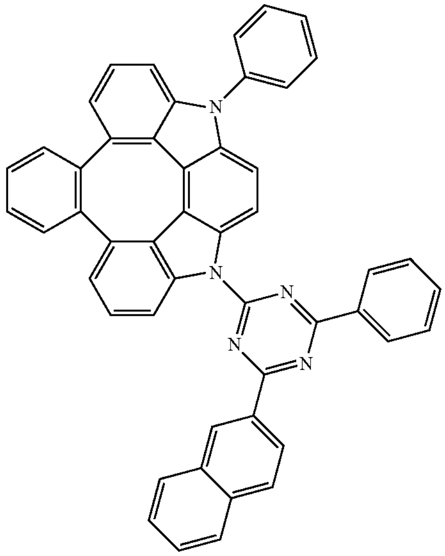

C-21
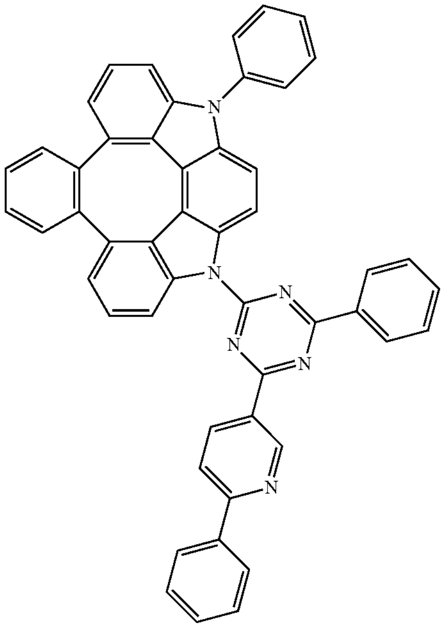
C-22
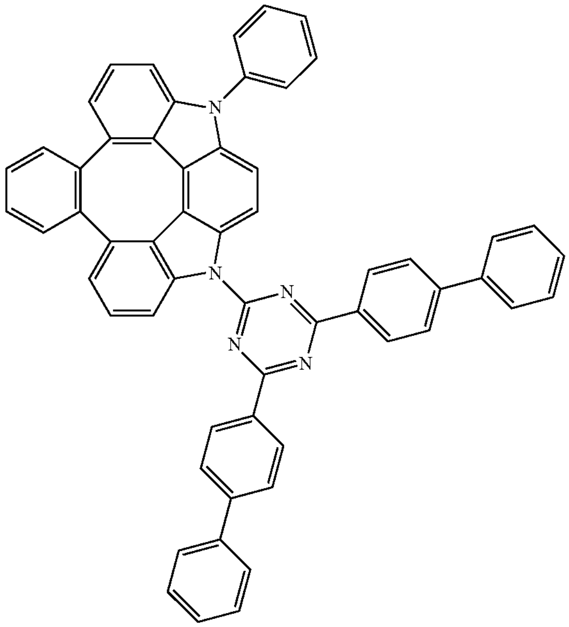
C-23
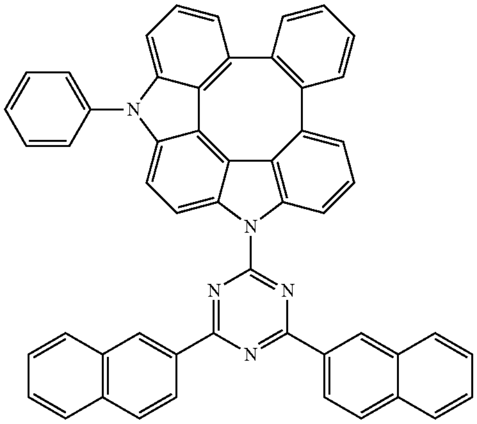
C-24
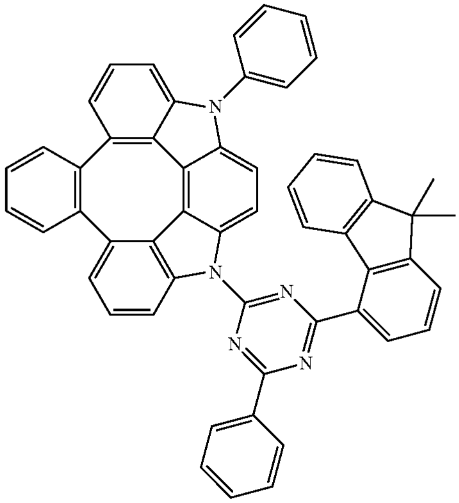
C-25
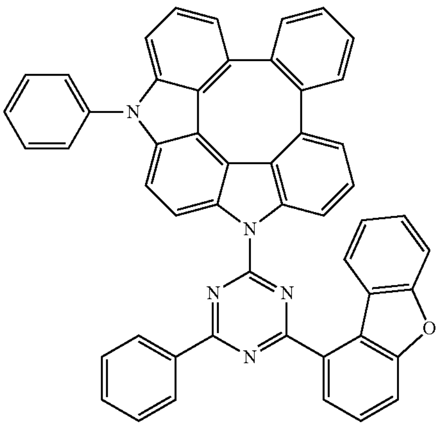

-continued
C-26
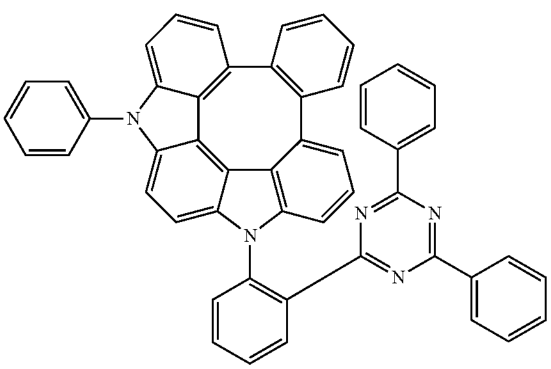
C-27
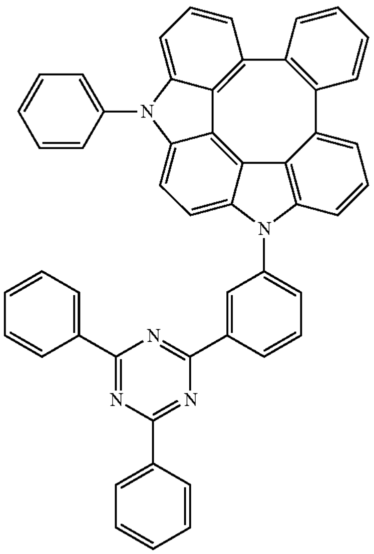
C-28
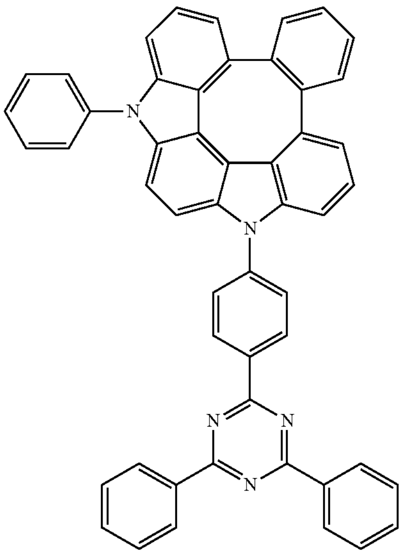
-continued
C-29
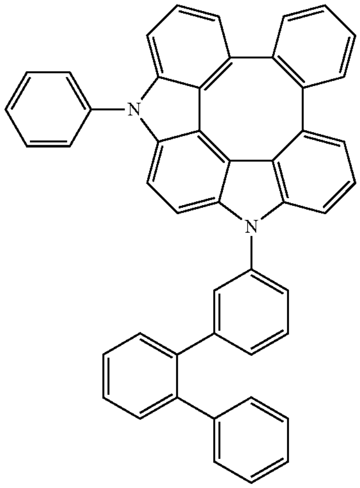
C-30
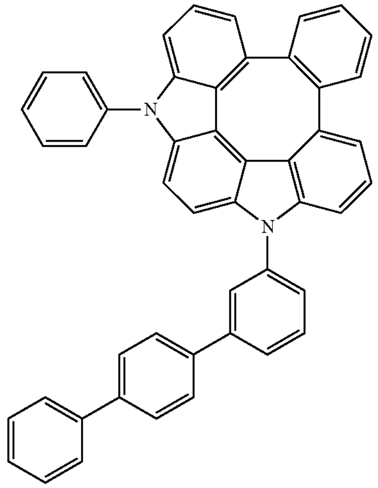
C-31
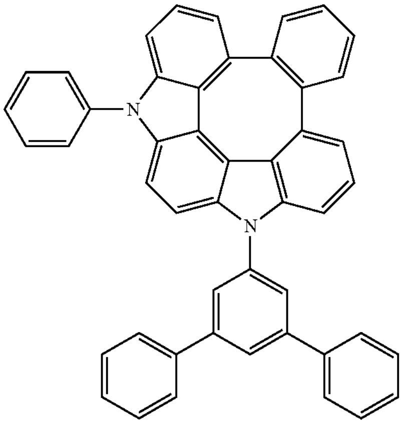

-continued
C-32
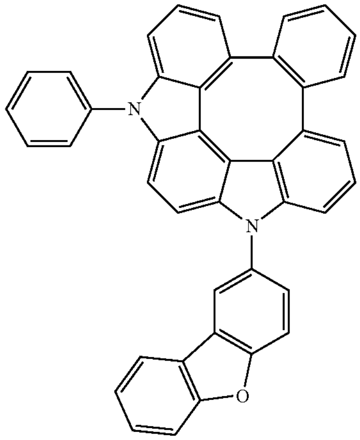
C-33
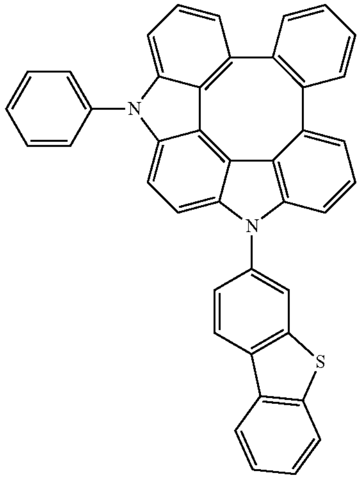
C-34
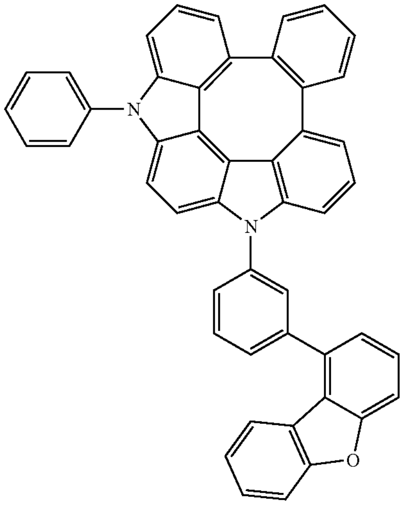
-continued
C-35
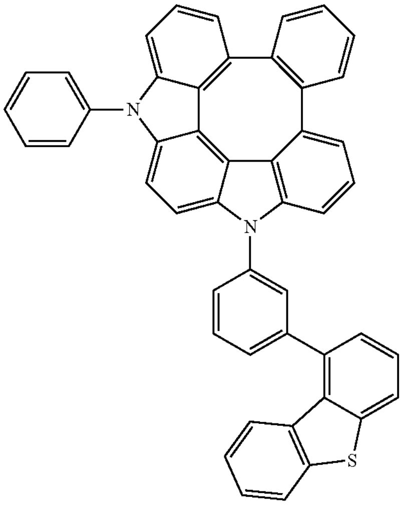
C-36
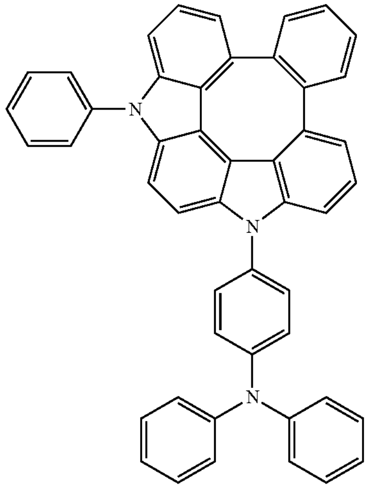
C-65
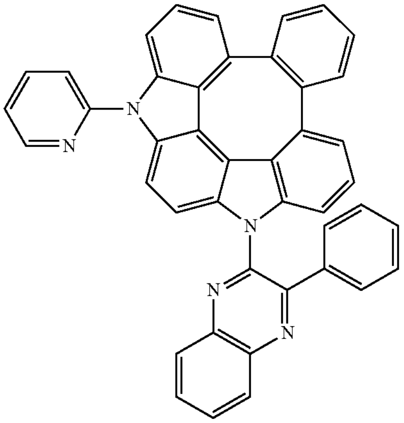

-continued
C-66
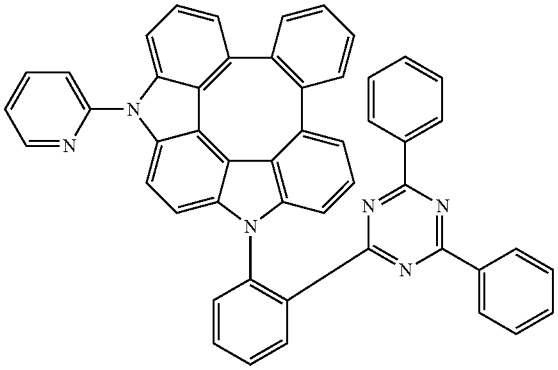
C-67
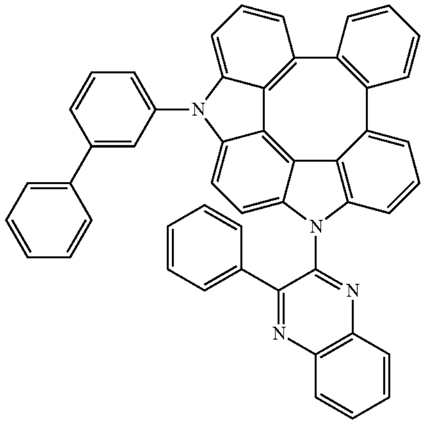
C-68
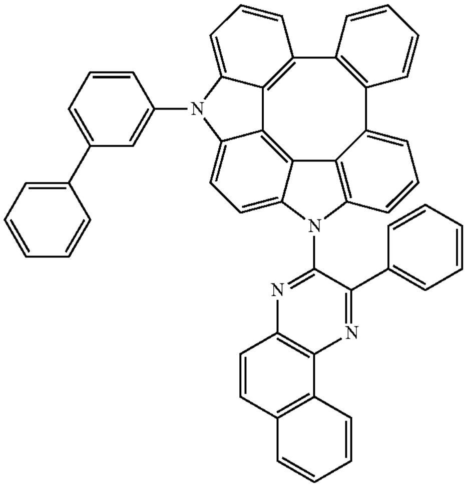
-continued
C-69
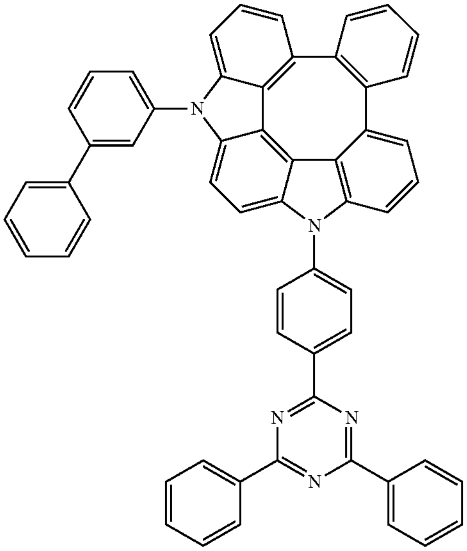
C-70
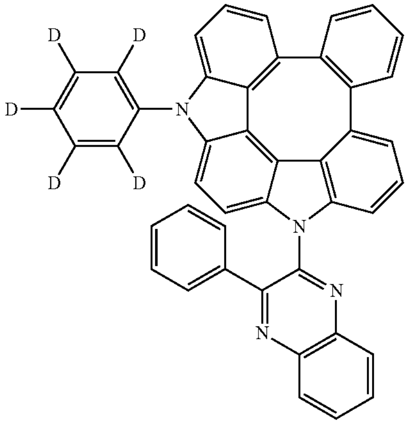
C-95
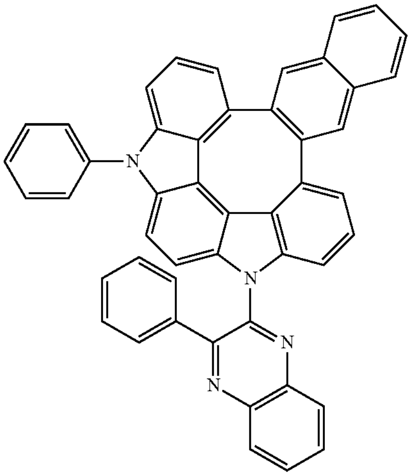

-continued
C-96
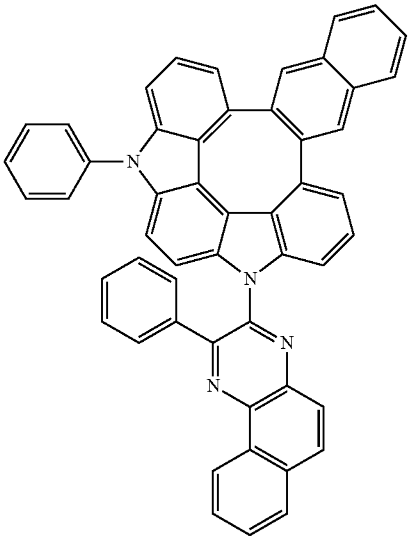
C-97
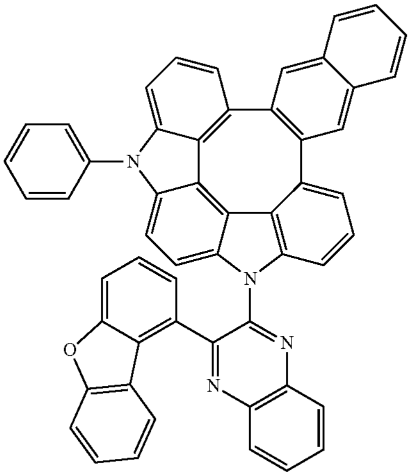
C-98
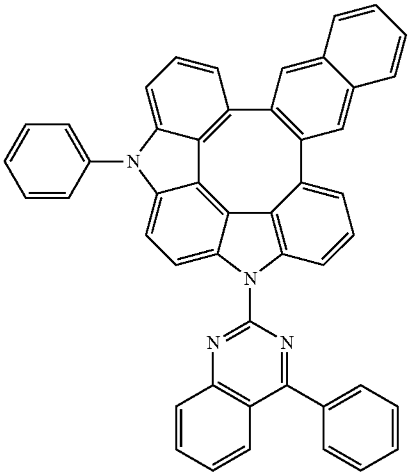
-continued
C-99
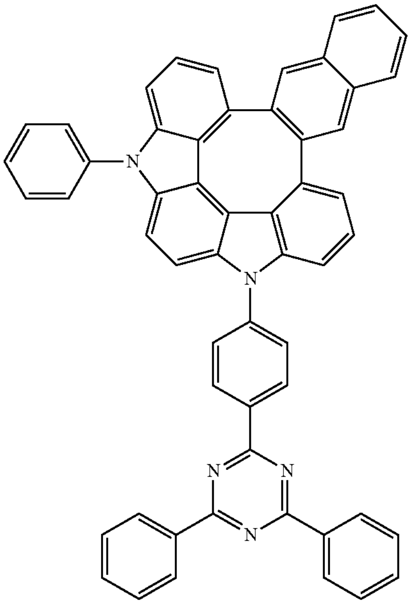
C-100
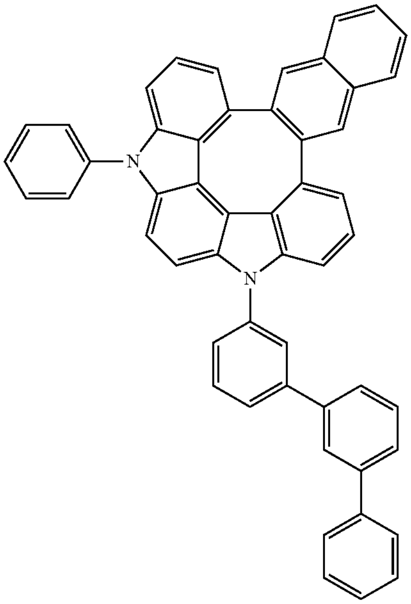

-continued
C-101
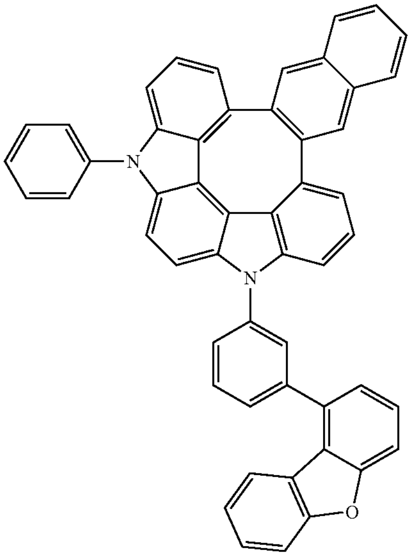
C-102
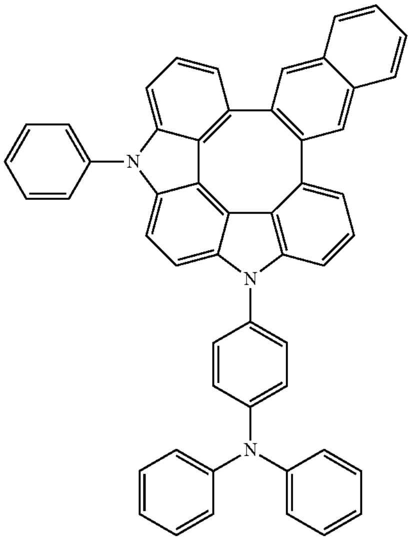
C-103
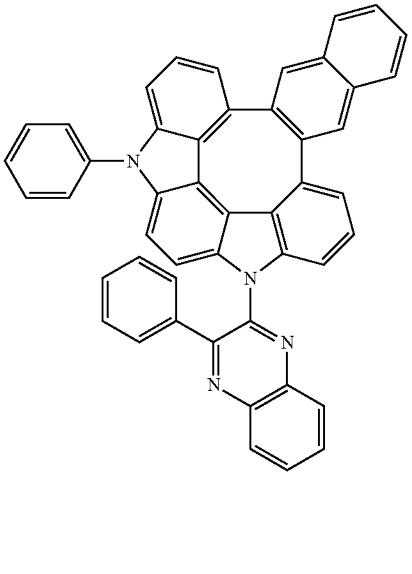
-continued
C-104
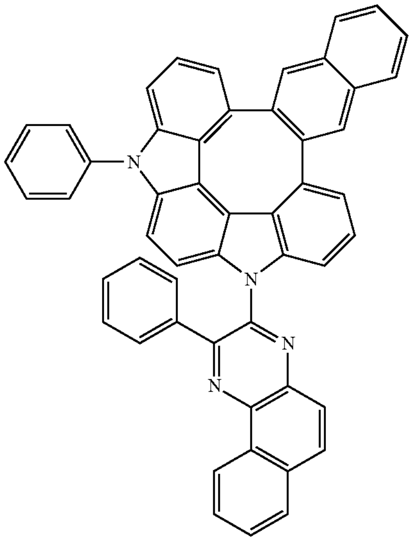
C-105
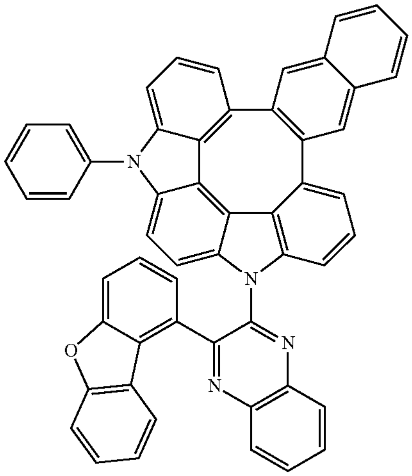
C-106
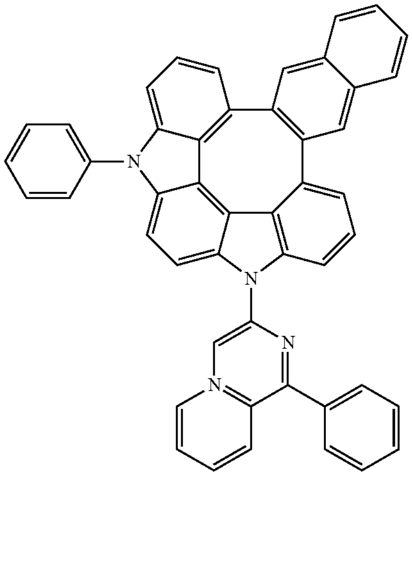

-continued
C-107
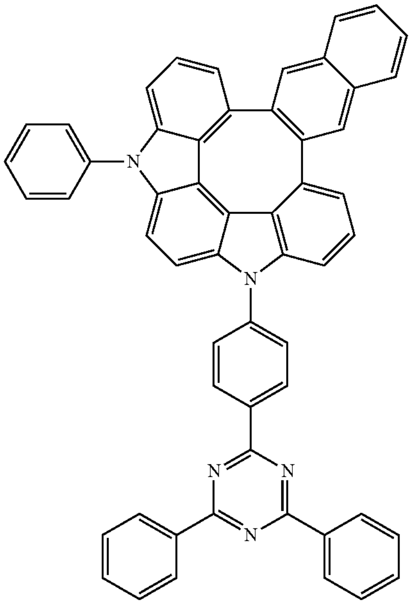
C-108
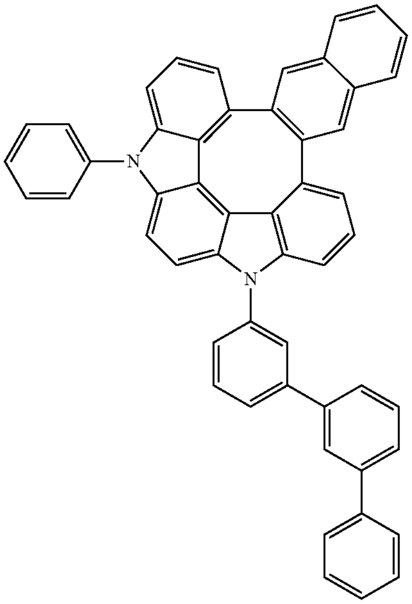
-continued
C-109
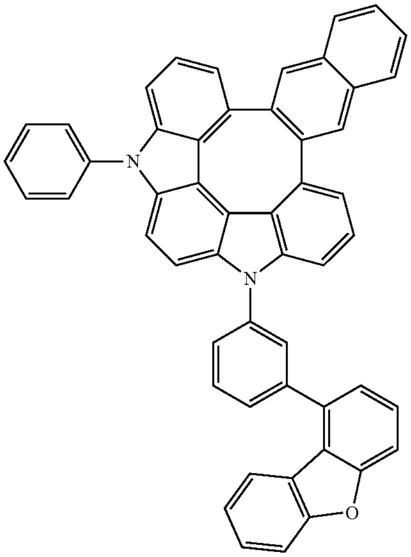
C-110
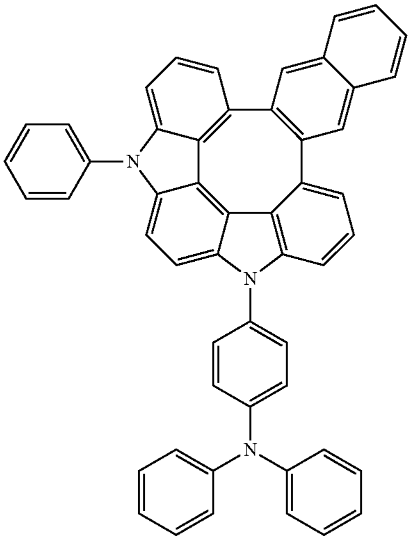
C-111
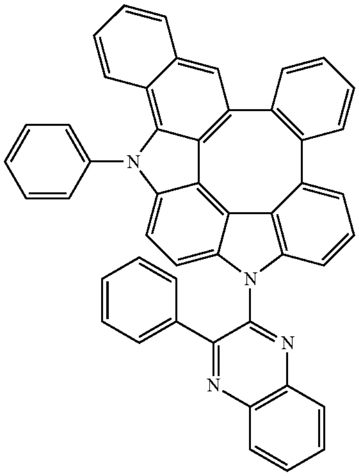

-continued
C-112
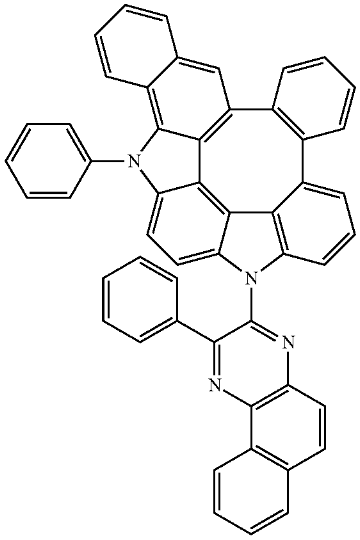
C-113
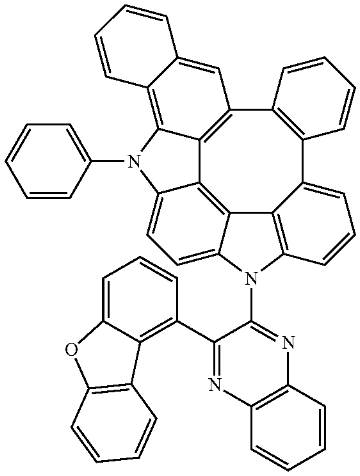
C-114
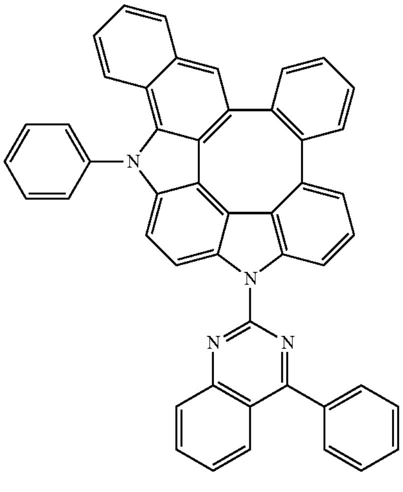
-continued
C-115
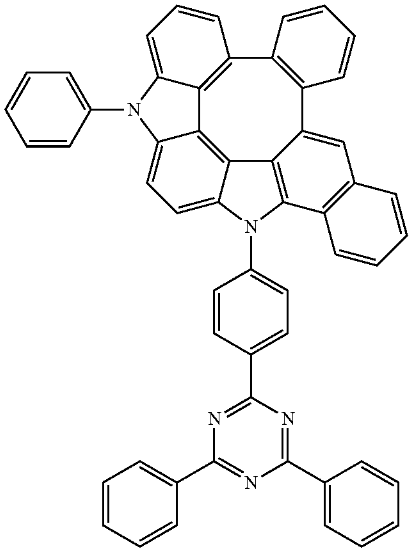
C-116
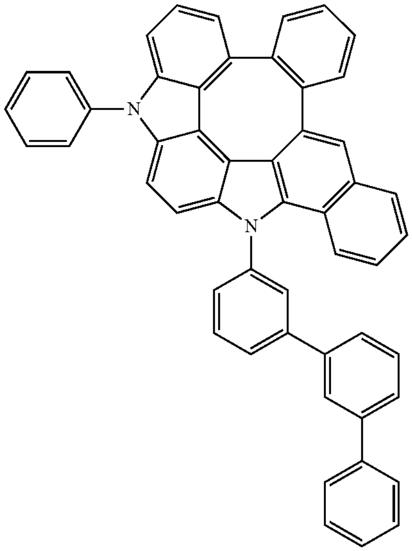
C-117
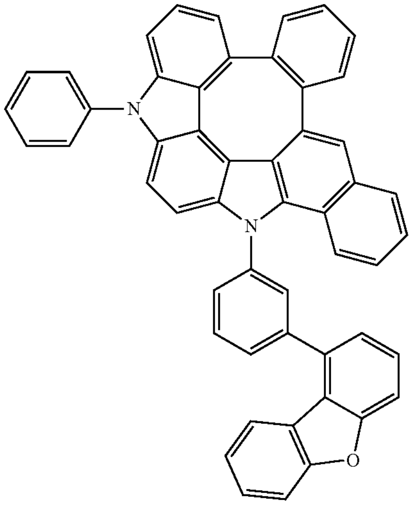

-continued
C-118
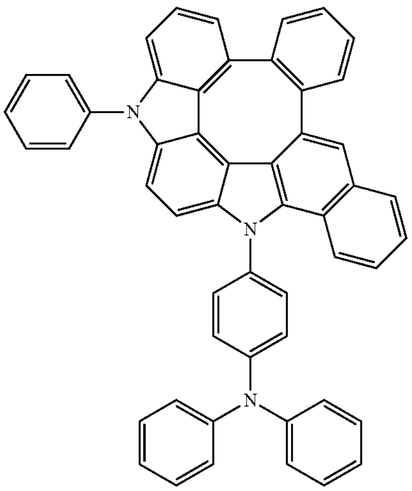
C-119
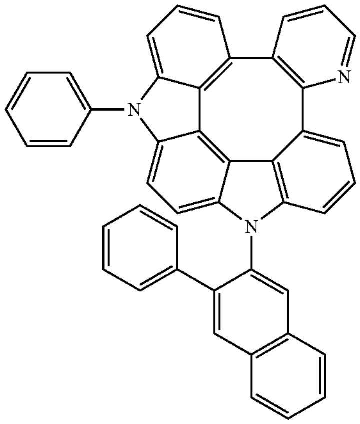
C-120
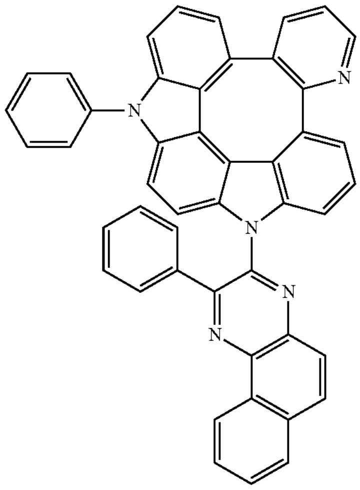
-continued
C-121
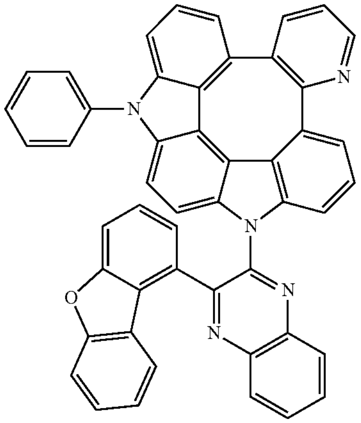
C-122
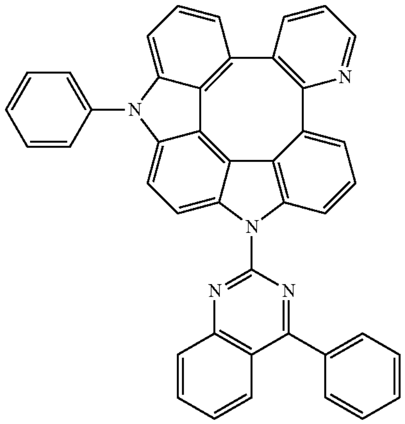
C-135
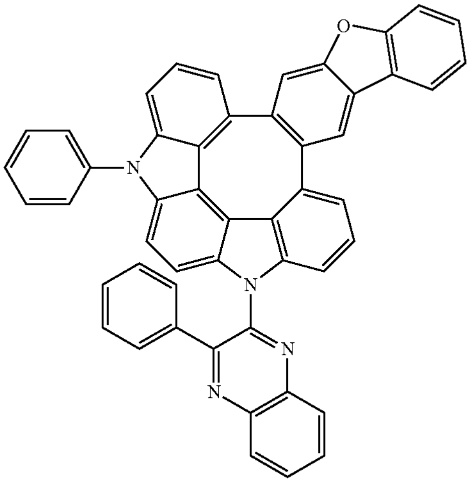

-continued
C-136
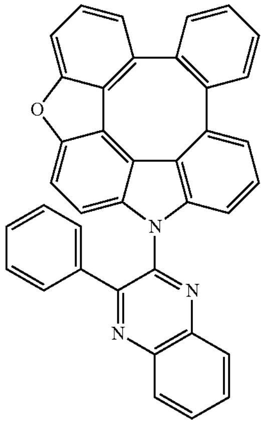
C-137
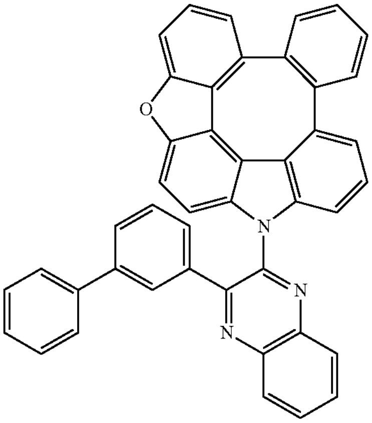
C-138
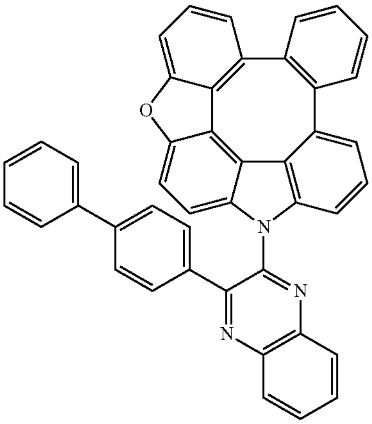
-continued
C-139
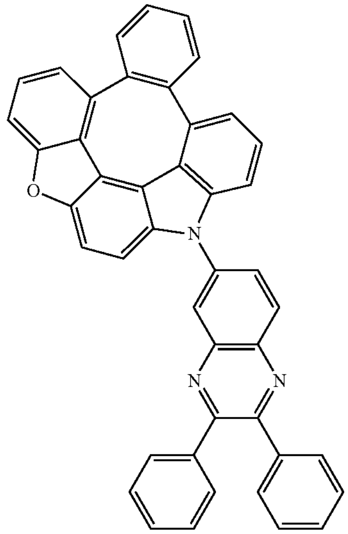
C-140
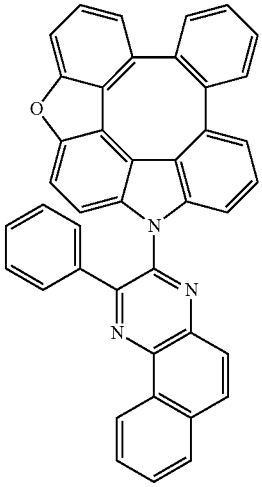
C-141
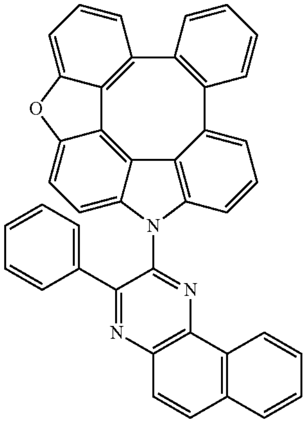

-continued
C-142
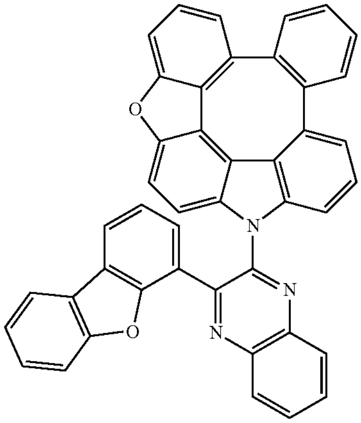
C-143
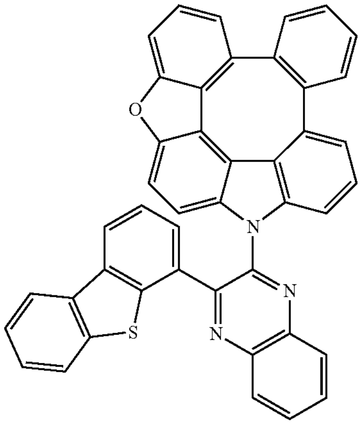
C-144
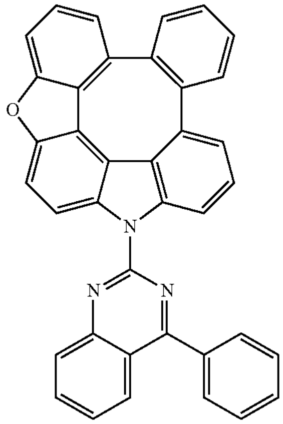
-continued
C-145
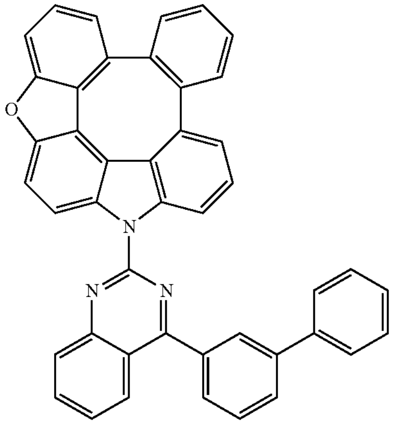
C-146
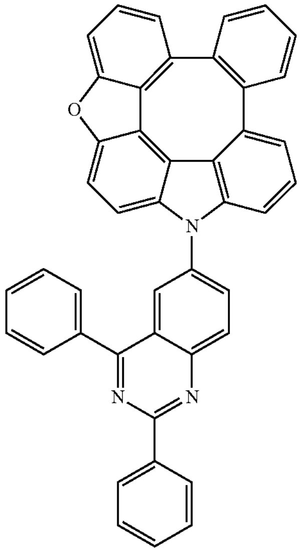
C-147
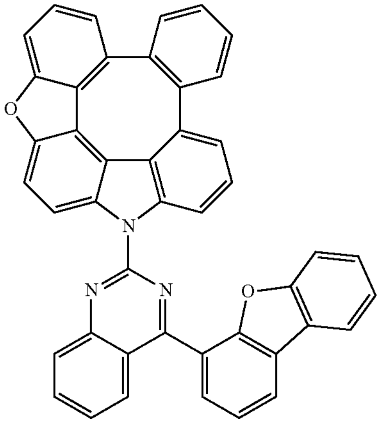

-continued
C-148
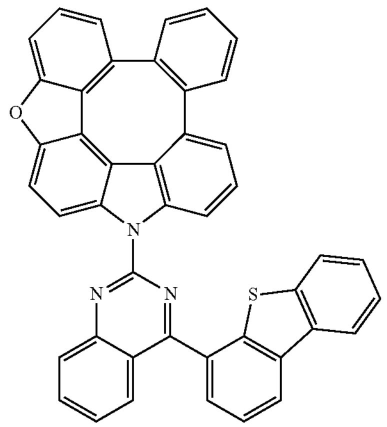
C-149
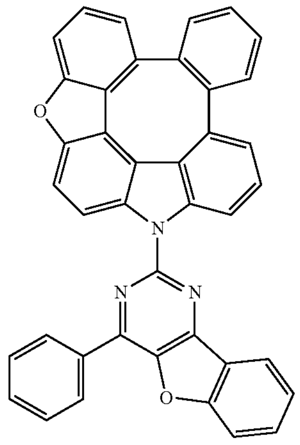
C-150
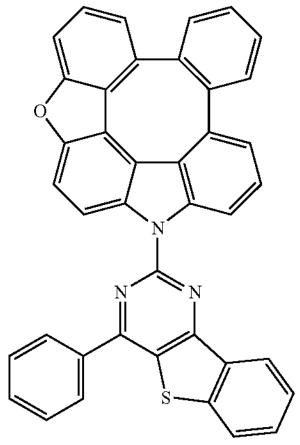
-continued
C-151
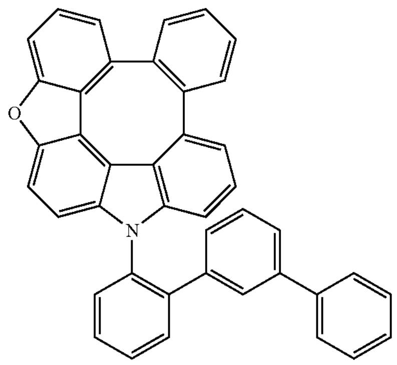
C-152
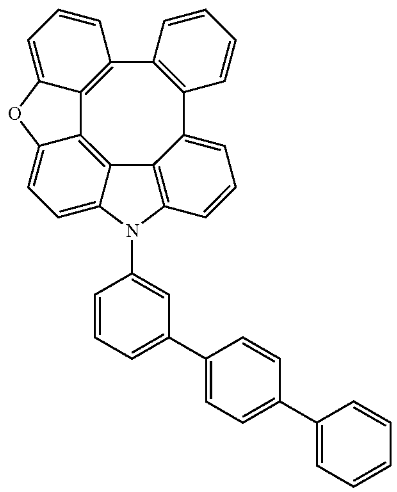
C-153
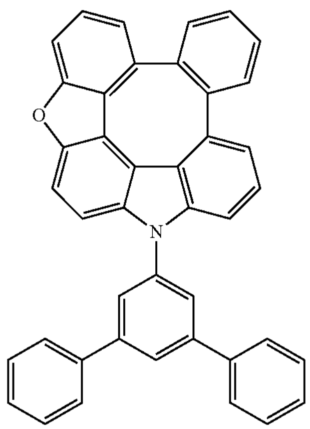

-continued
C-154
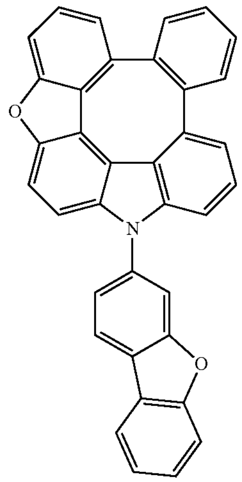
C-155
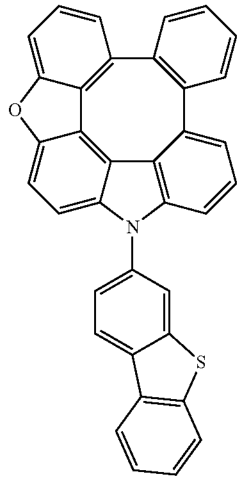
C-156
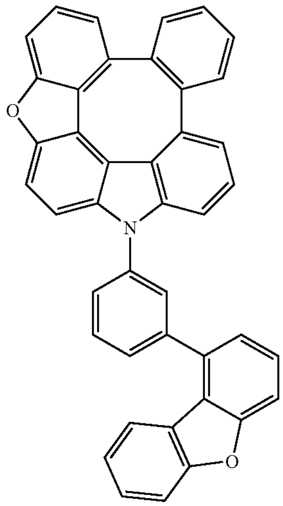
-continued
C-157
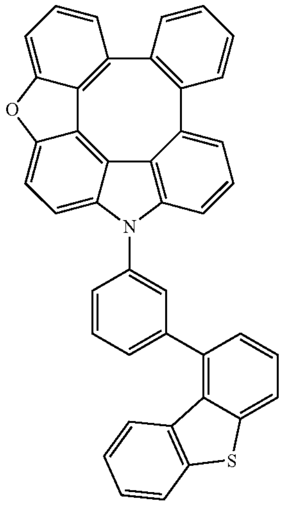
C-158
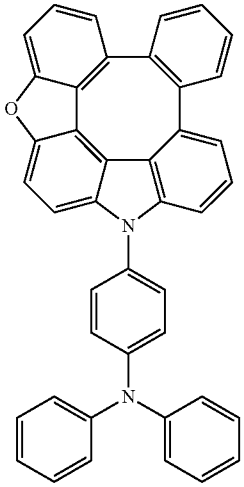
C-159
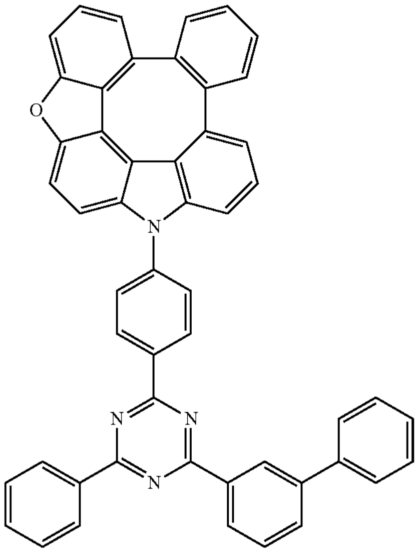

-continued
C-160
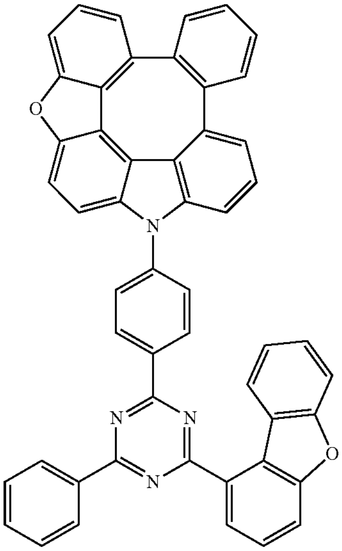
C-161
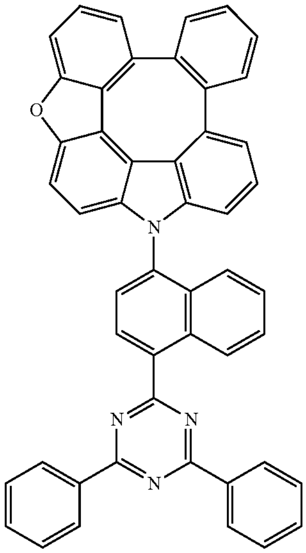
C-162
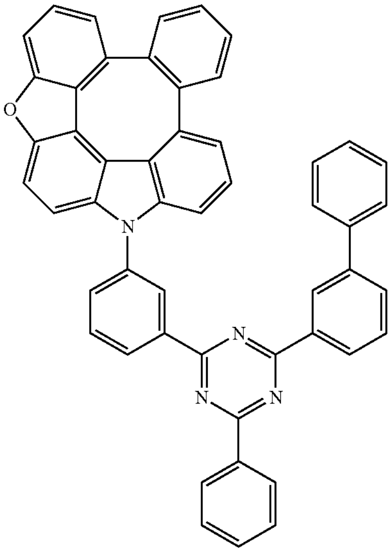
-continued
C-163
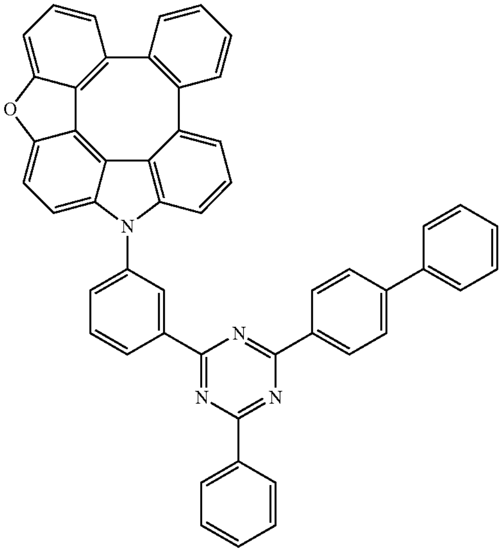
C-164
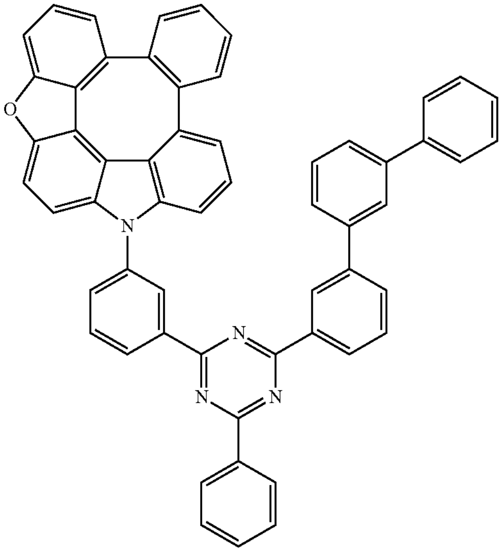

C-165
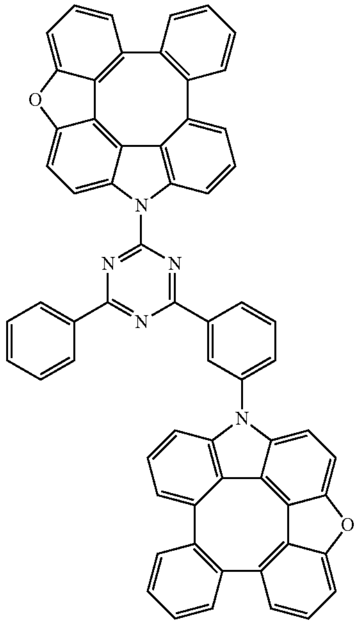
C-166
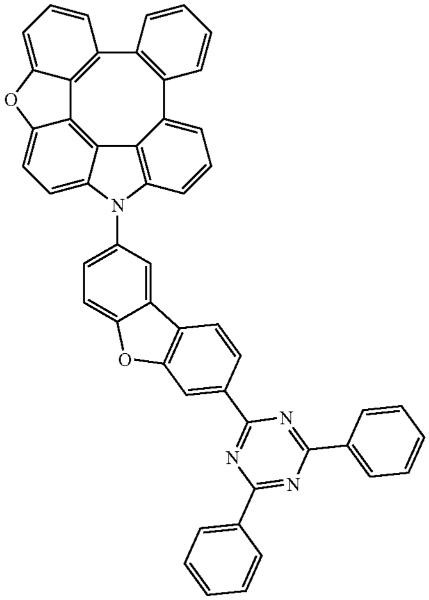
C-167
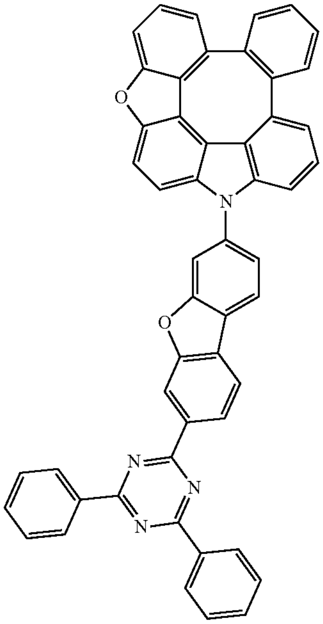
C-168
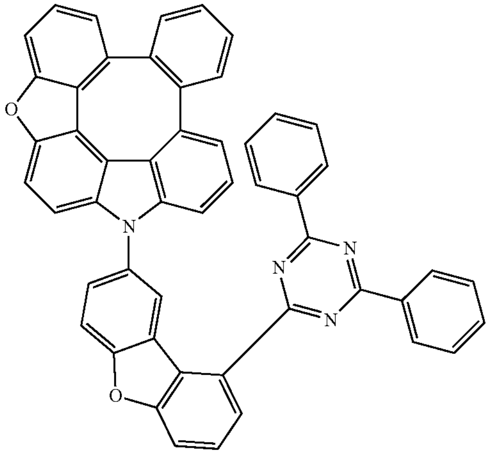
C-169
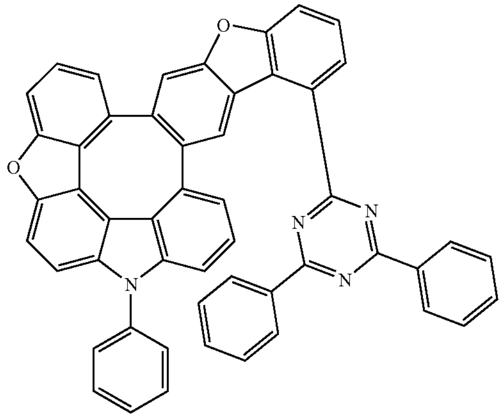

-continued
C-173
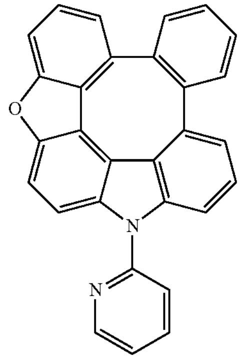
C-174
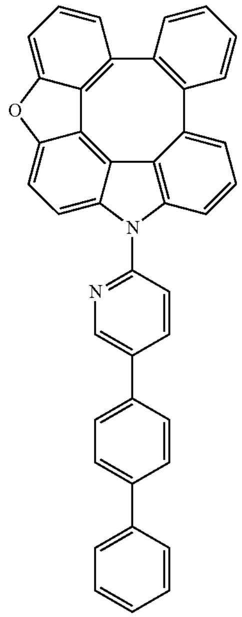
C-175
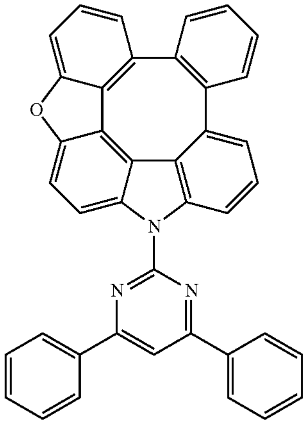
-continued
C-176
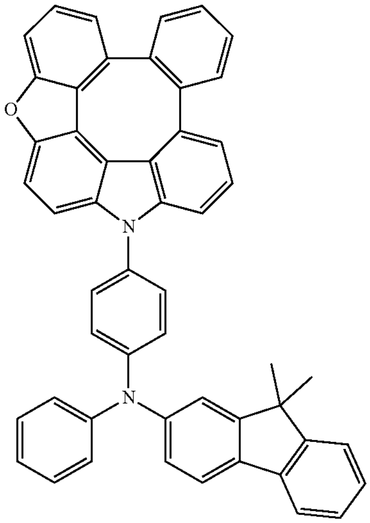
C-177
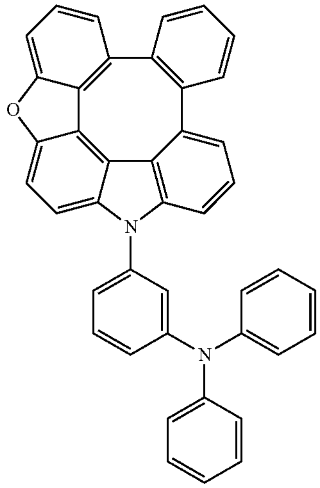
C-178
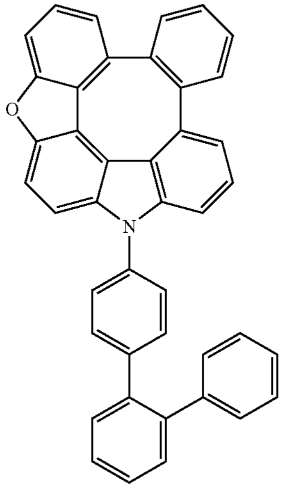

-continued
C-179
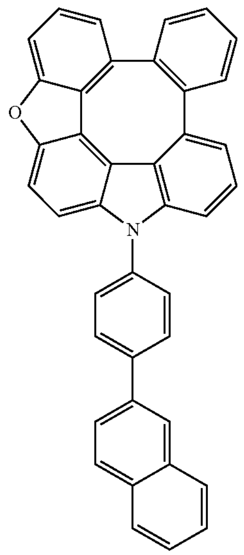
C-180
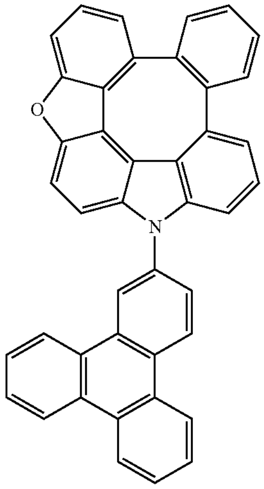
C-181
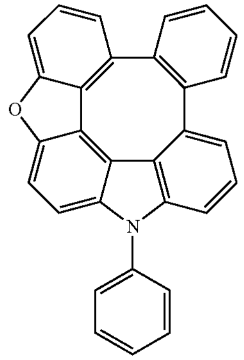
-continued
C-183
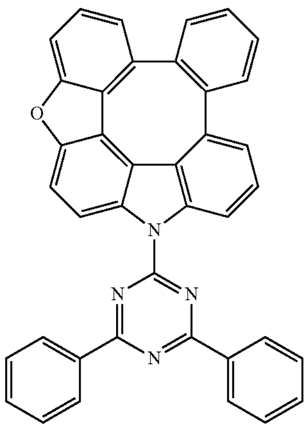
C-184
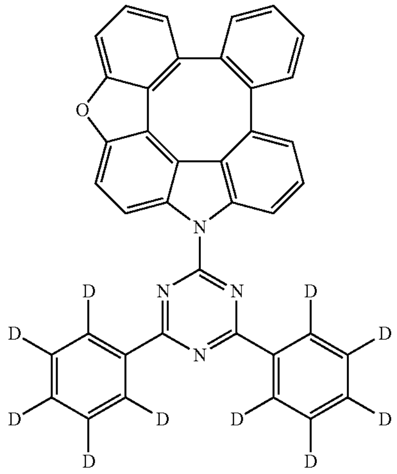
C-185
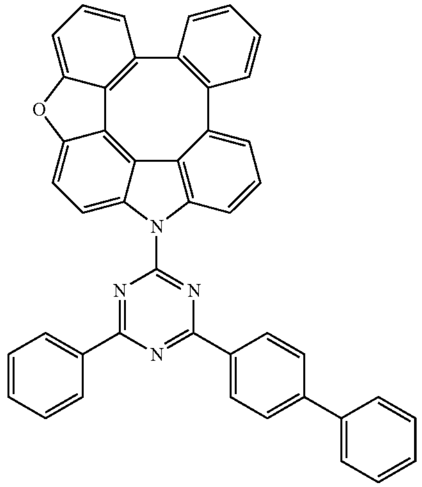

C-186
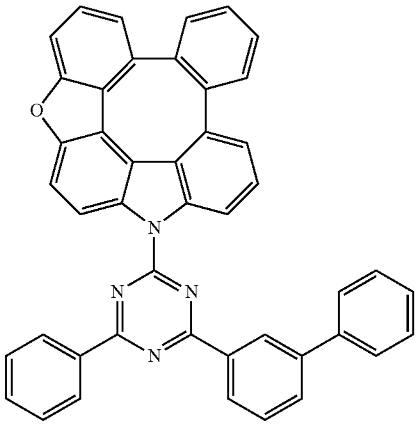
C-187
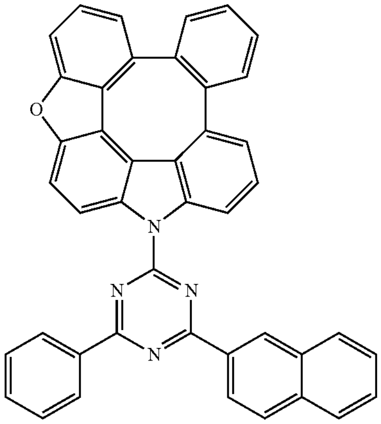
C-188
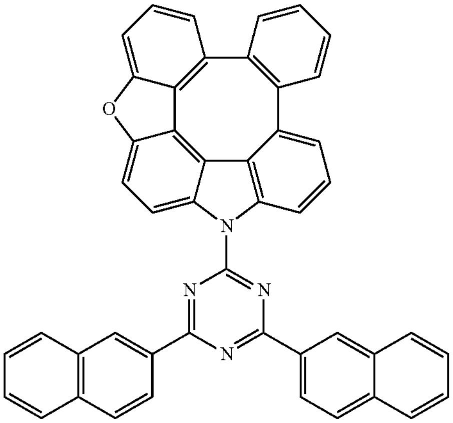
-continued
C-189
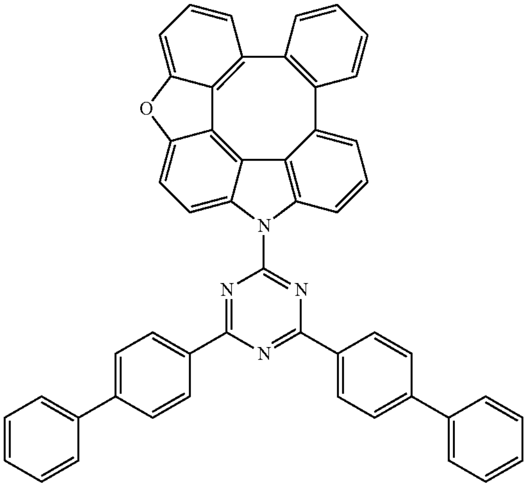
C-190
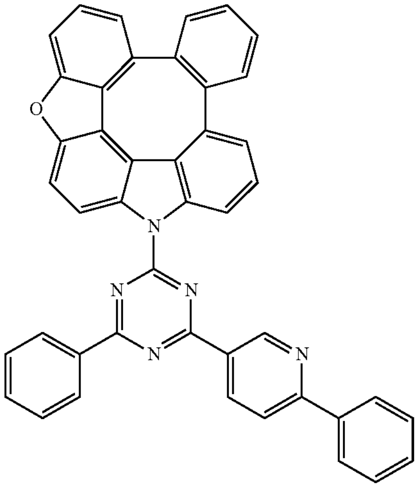
C-191
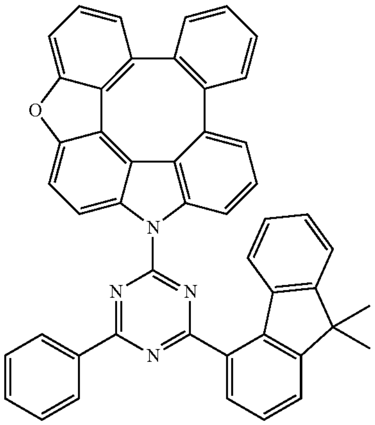

-continued
C-192
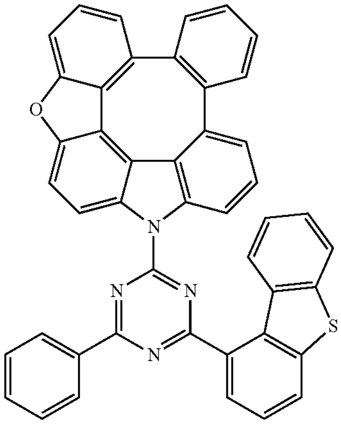
C-193
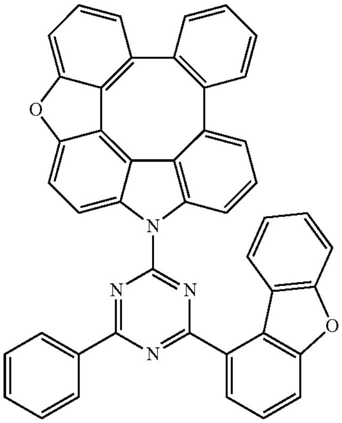
C-194
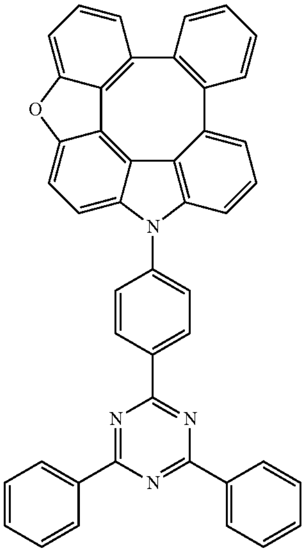
-continued
C-195
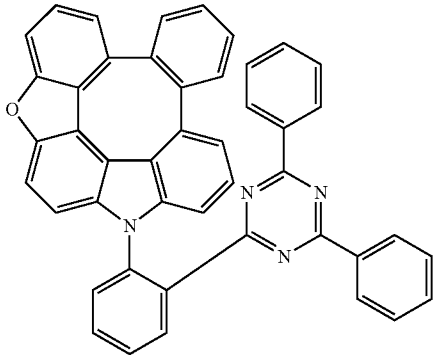
C-196
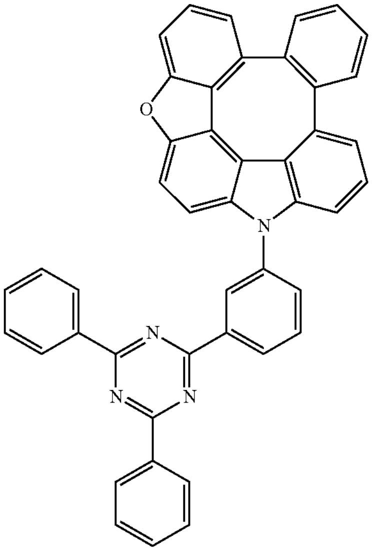
C-197
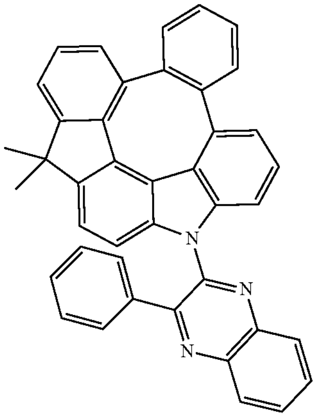

-continued
C-198
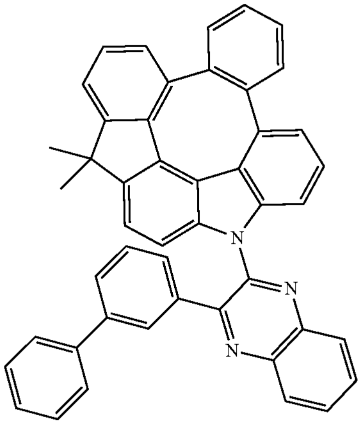
C-199
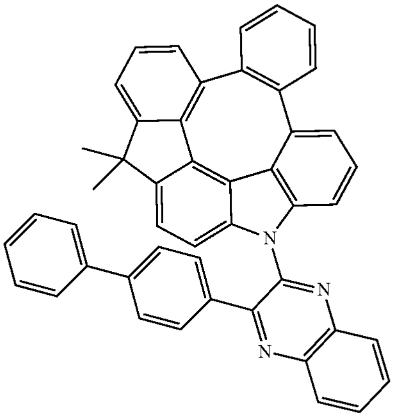
C-200
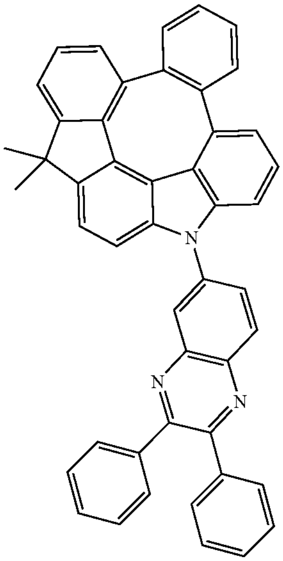
-continued
C-201
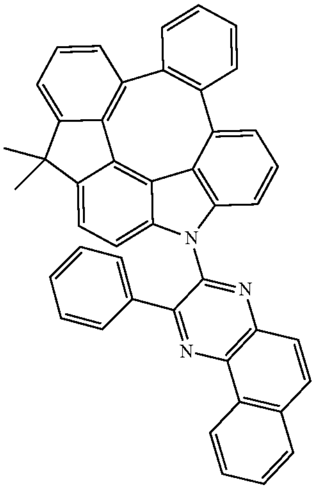
C-202
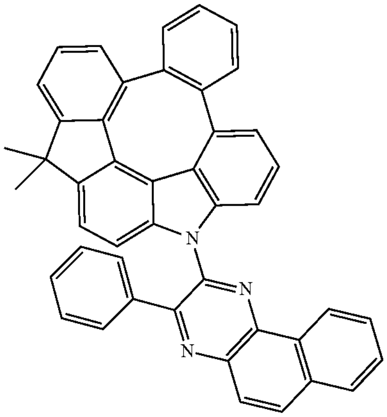
C-203
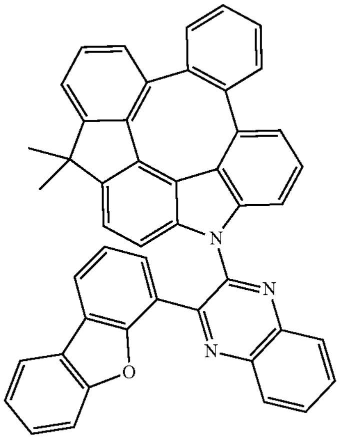

-continued
C-204
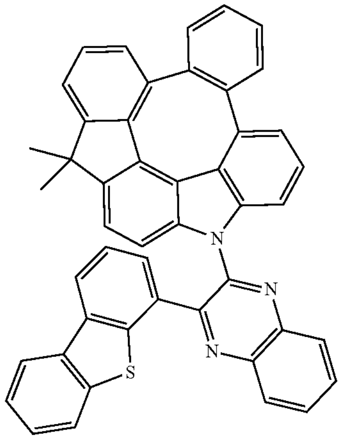
C-205
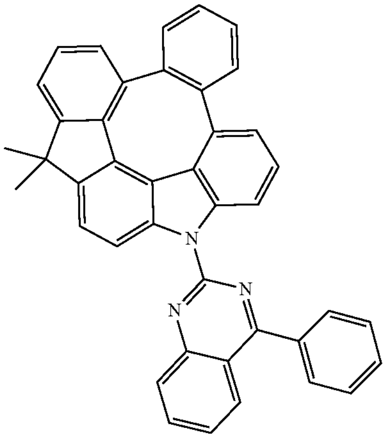
C-206
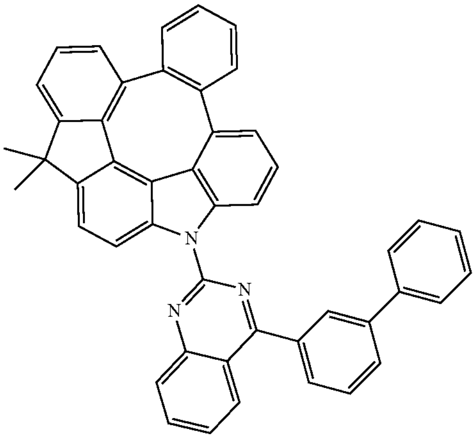
-continued
C-207
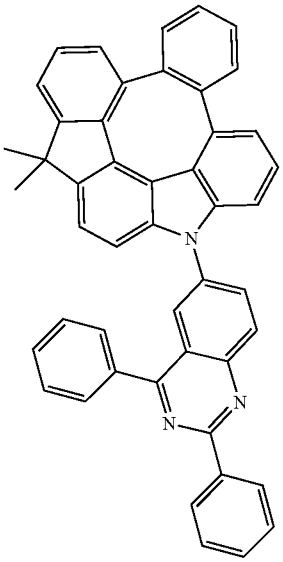
C-208
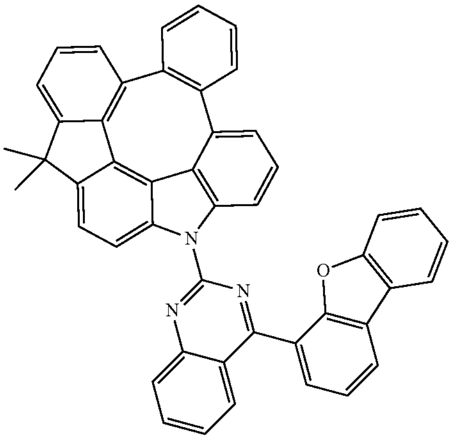
C-209
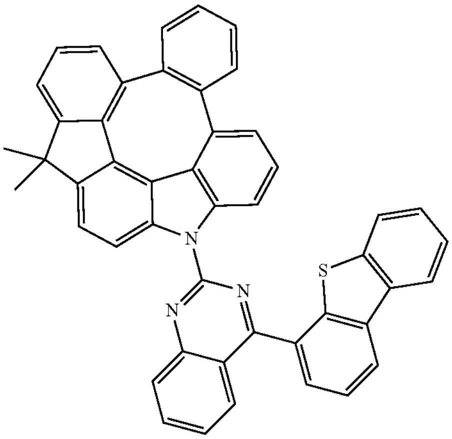

-continued
C-210
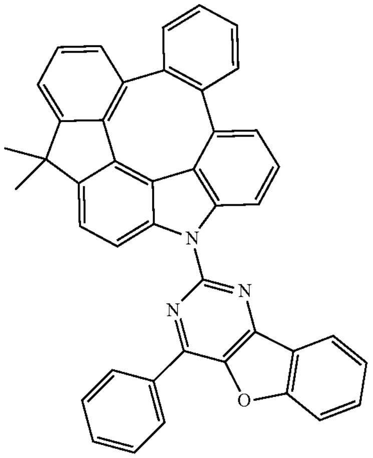
C-211
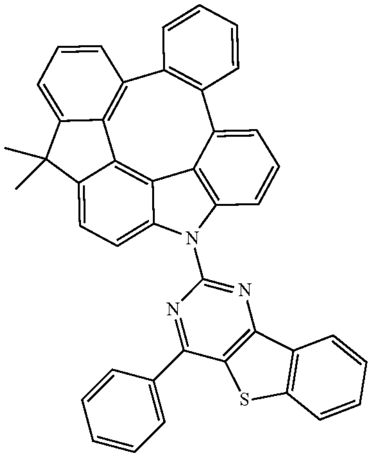
C-212
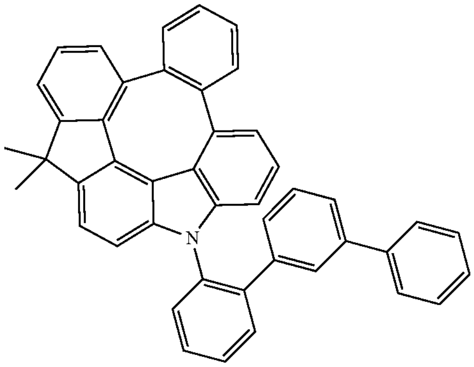
-continued
C-213
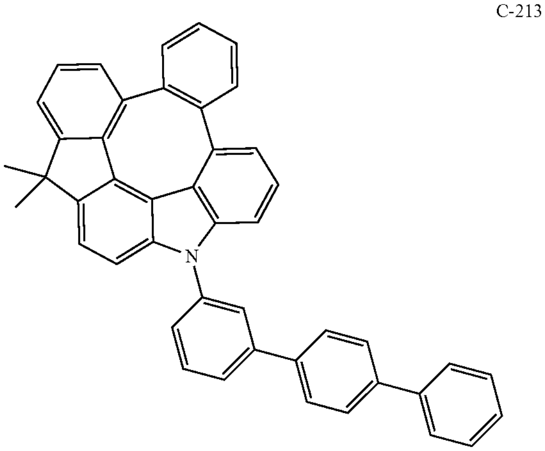
C-214
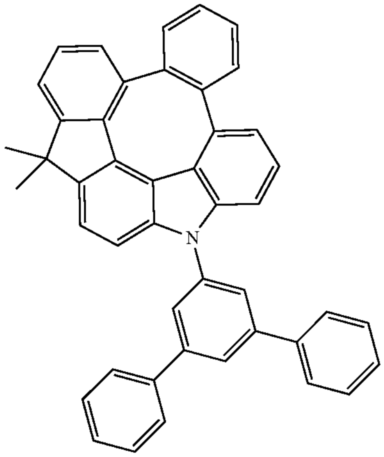
C-215
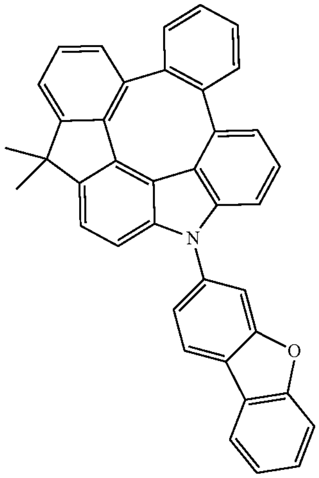

-continued
C-216
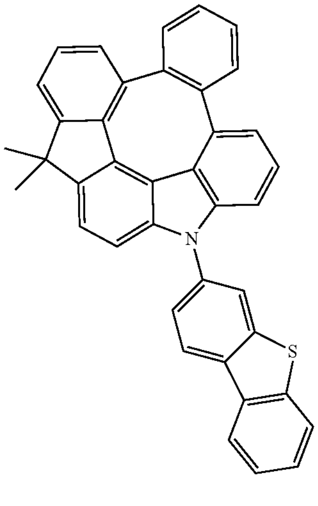
C-217
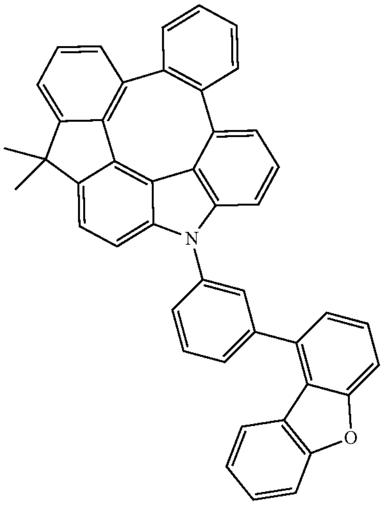
C-218
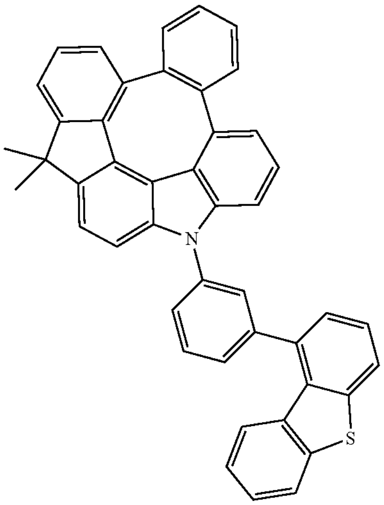
-continued
C-219
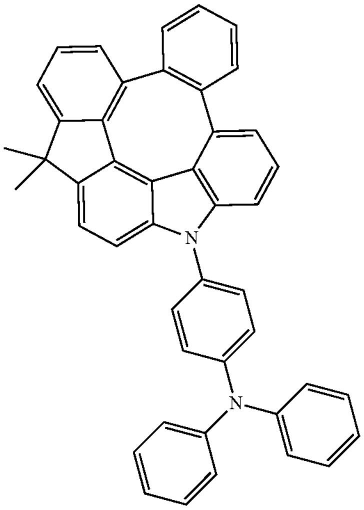
C-220
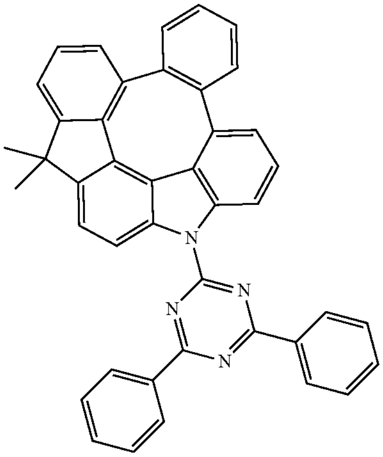
C-221
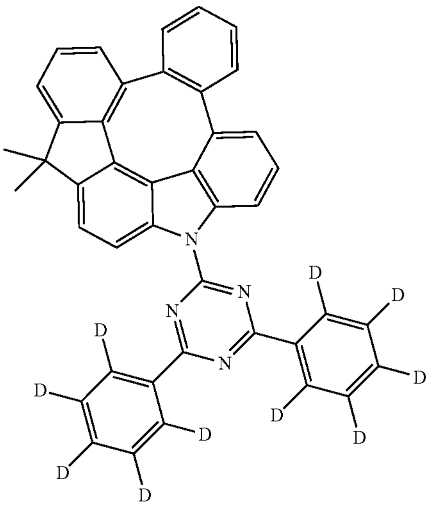

-continued
C-222
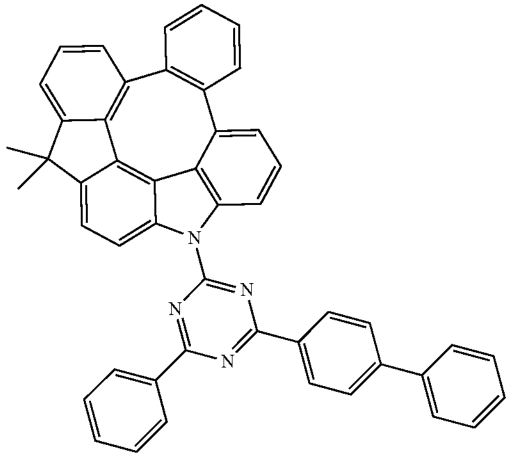
C-223
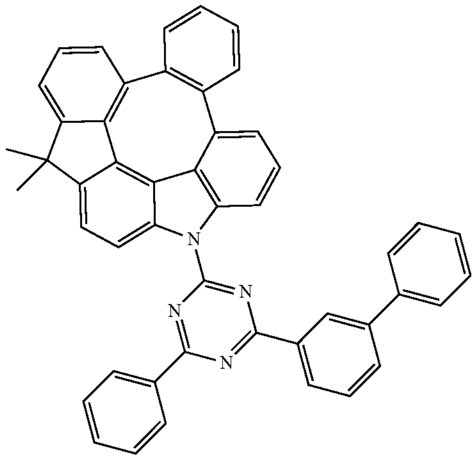
C-224
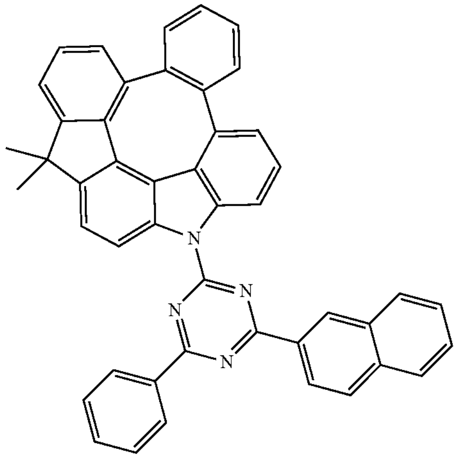
-continued
C-225
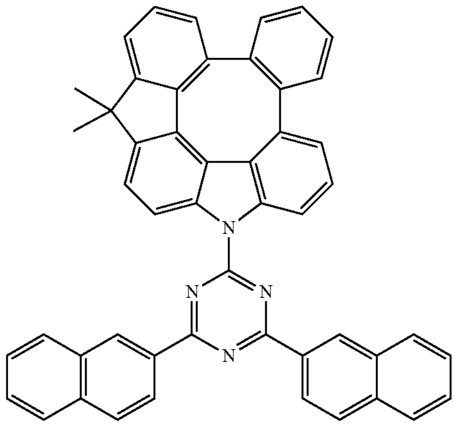
C-226
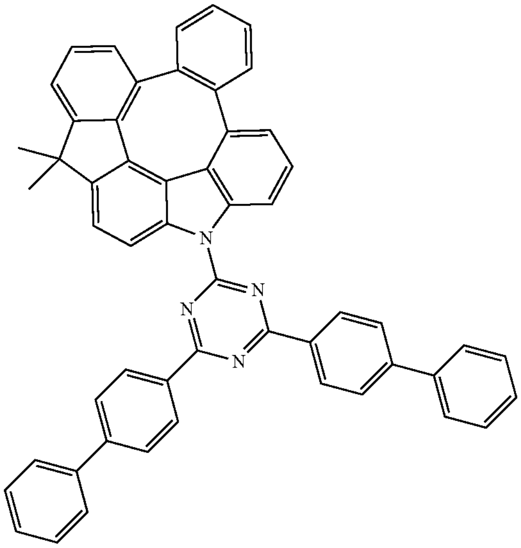
C-227
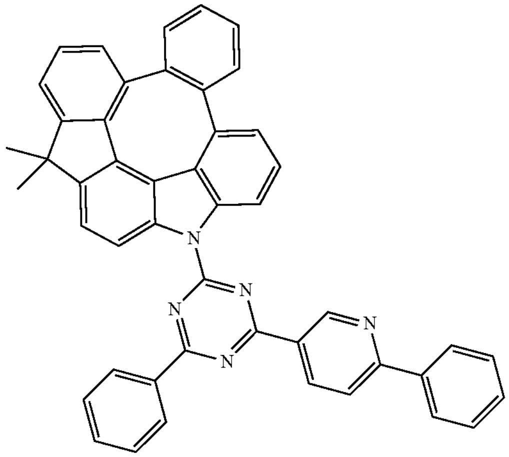

-continued
C-228
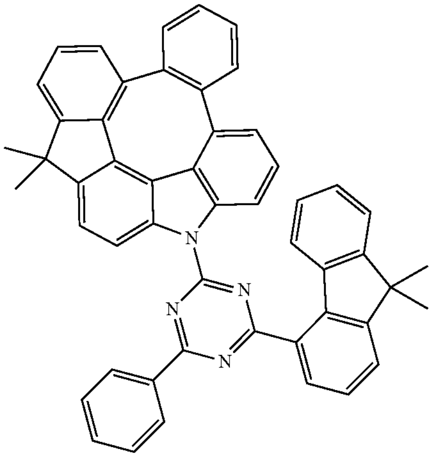
C-229
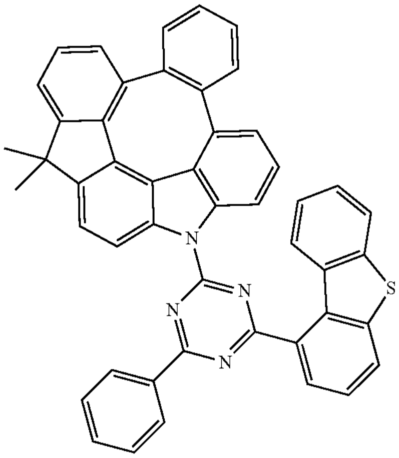
C-230
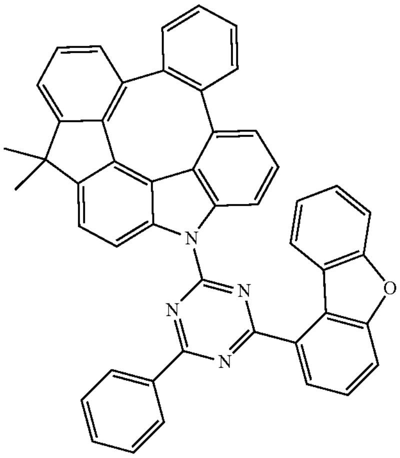
-continued
C-231
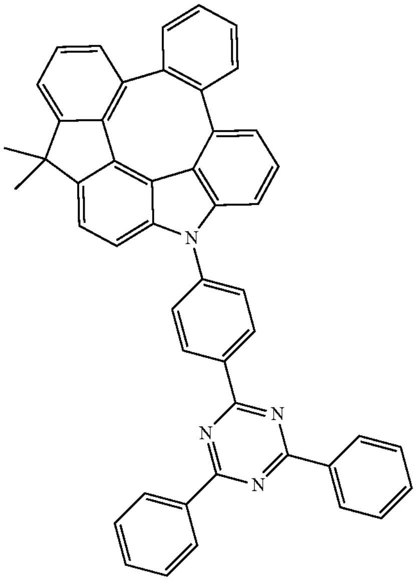
C-232
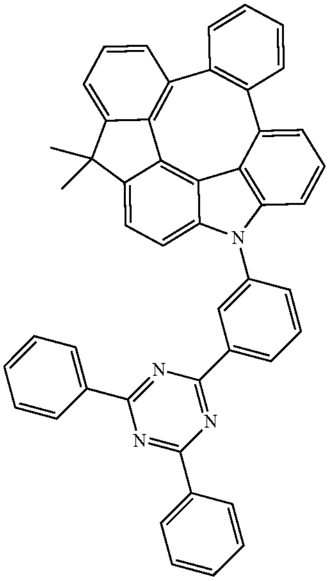
C-233
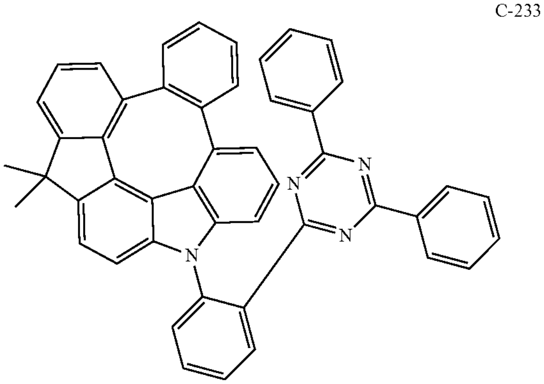

-continued
C-234
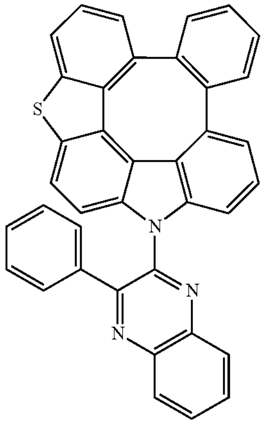
C-241
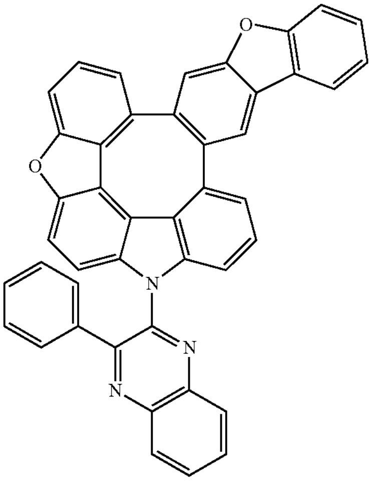
C-242
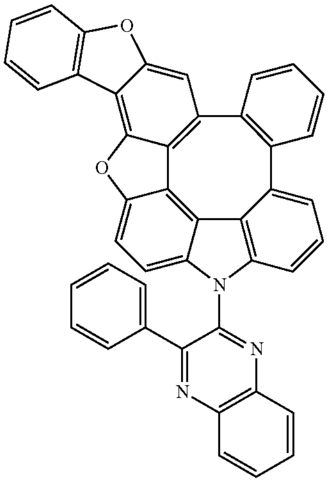
-continued
C-243
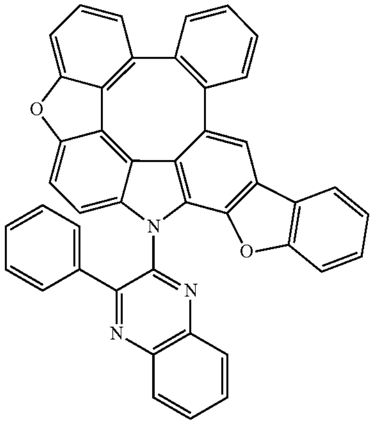
C-244
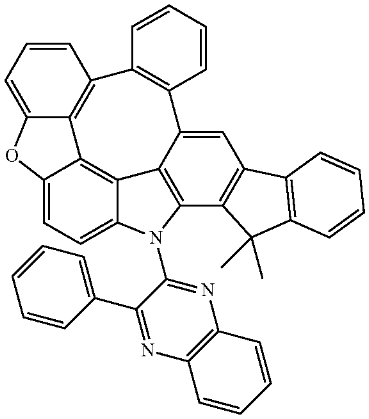
C-245
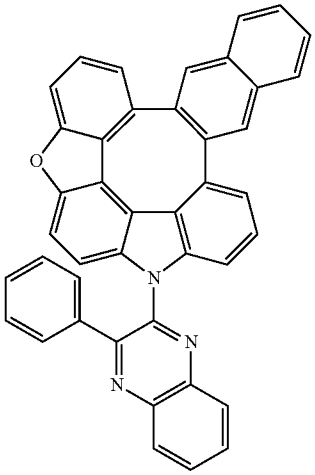

C-246
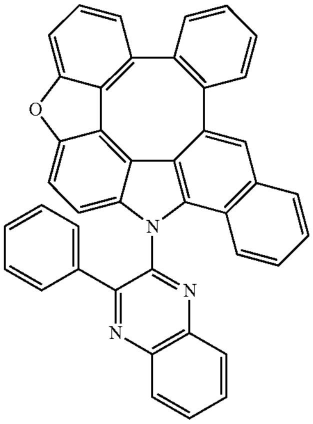
C-249
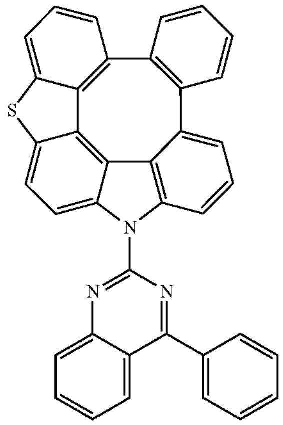
C-256
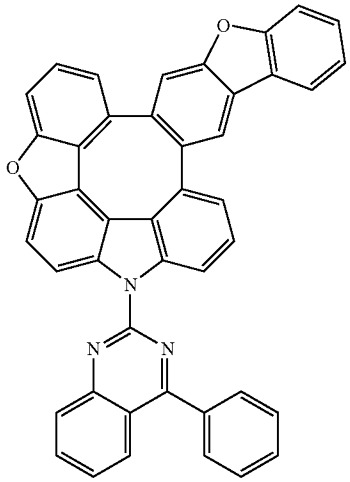
C-257
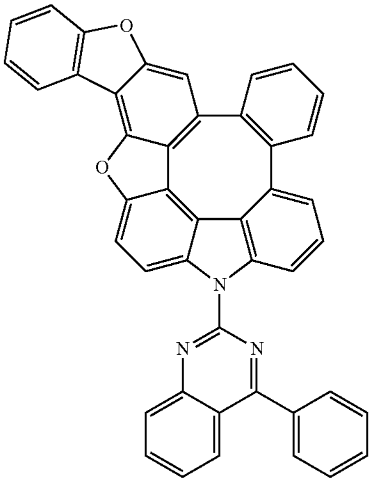
C-258
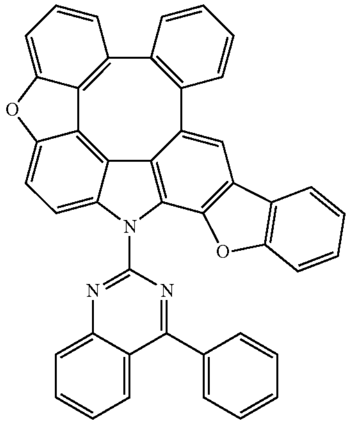
C-259
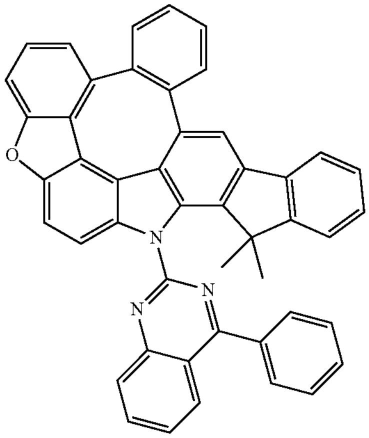

-continued
C-260
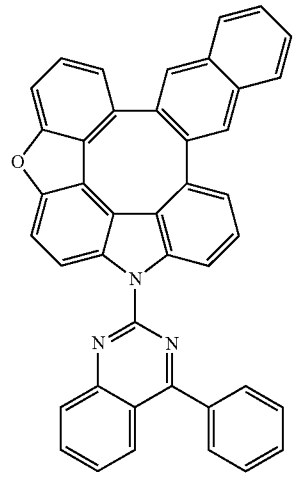
C-261
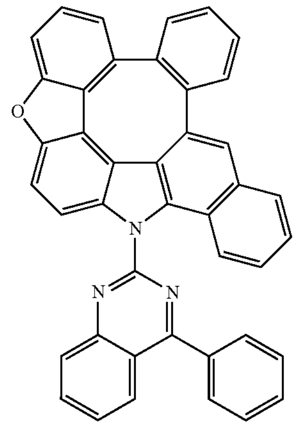
C-262
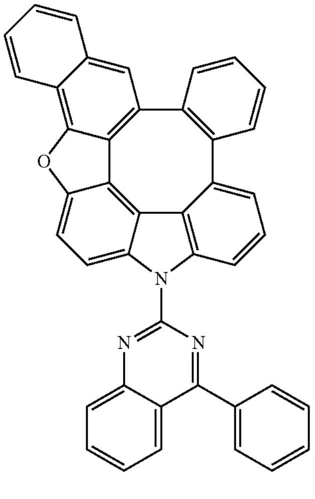
-continued
C-264
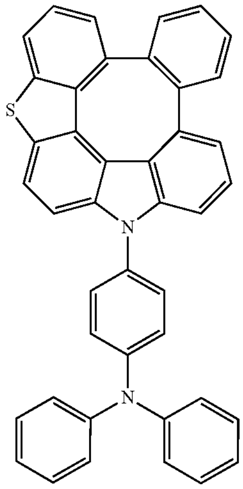
C-271
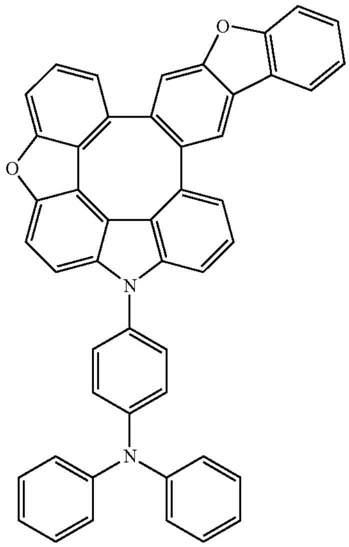
C-272
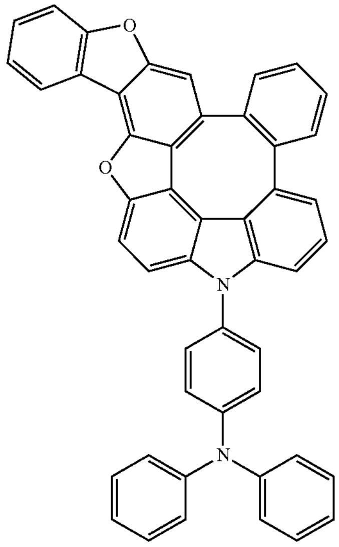

-continued
C-273
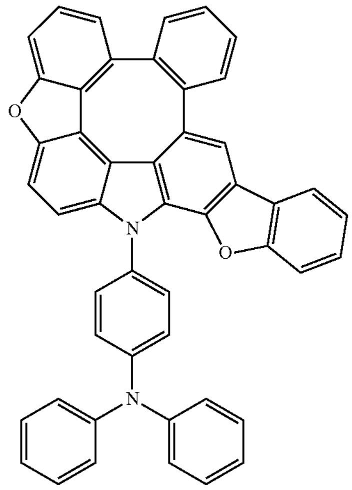
C-274
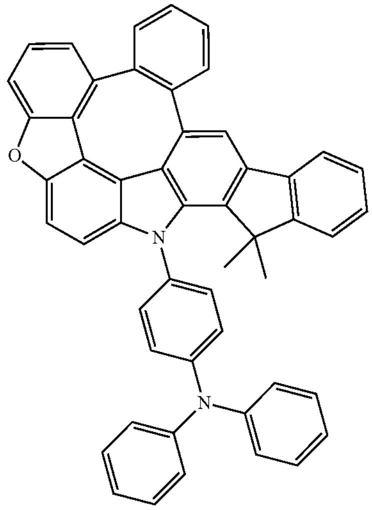
C-275
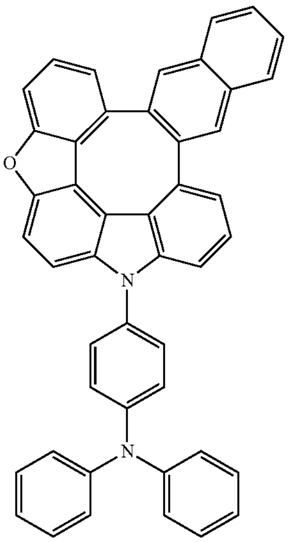
-continued
C-276
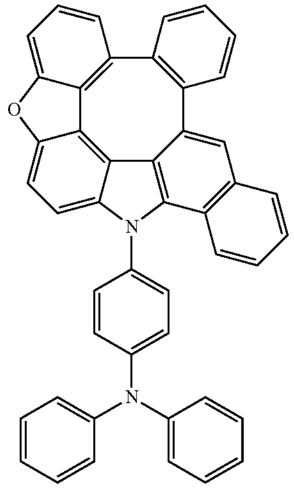
C-277
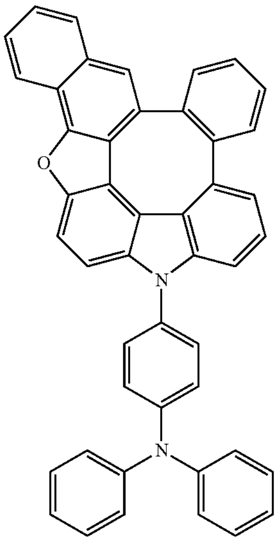
C-279
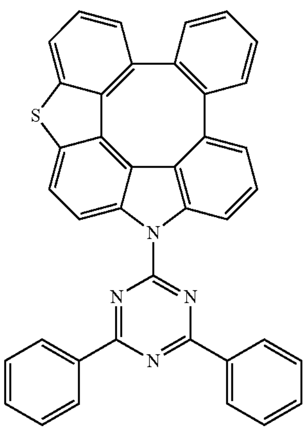

-continued
C-286
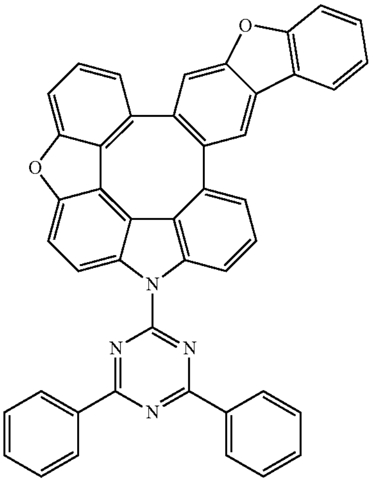
C-287
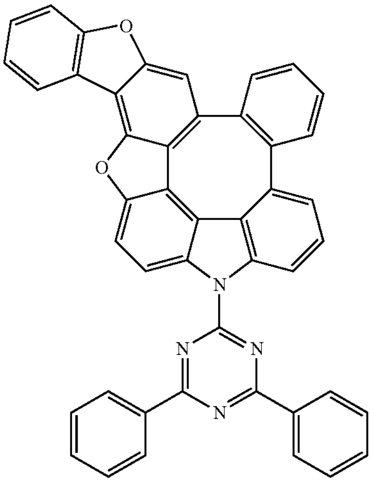
C-288
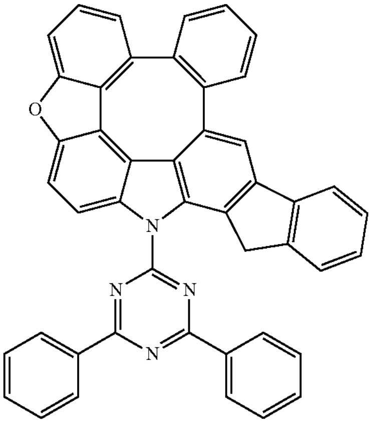
-continued
C-289
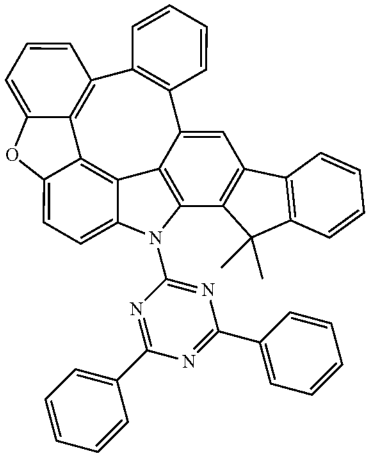
C-290
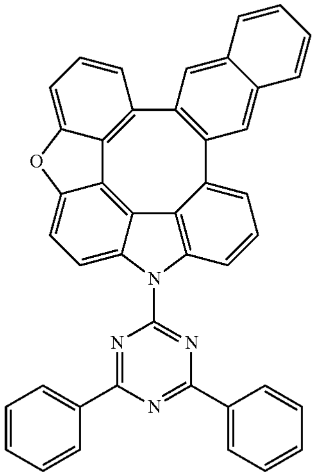
C-291
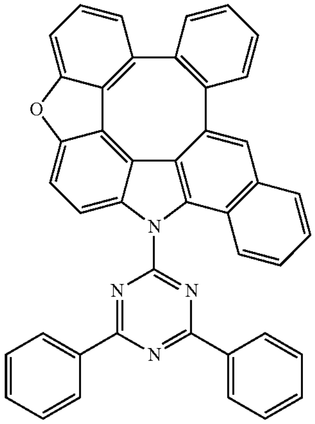

-continued
C-292
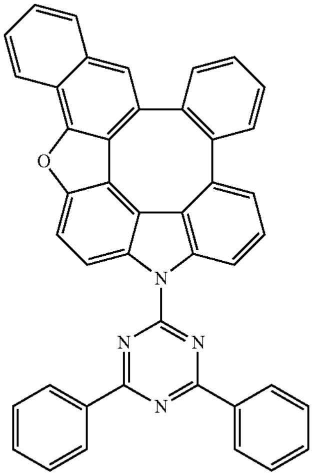
C-294
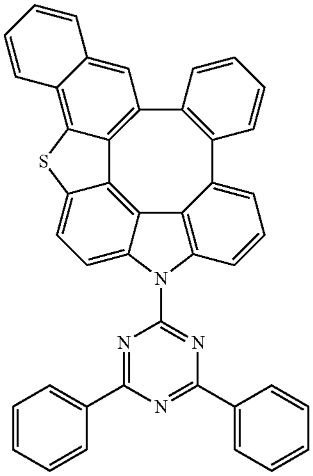
C-296
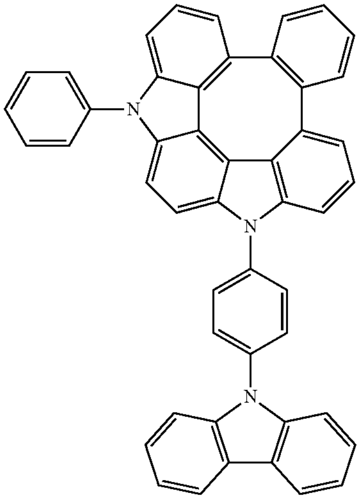
-continued
C-297
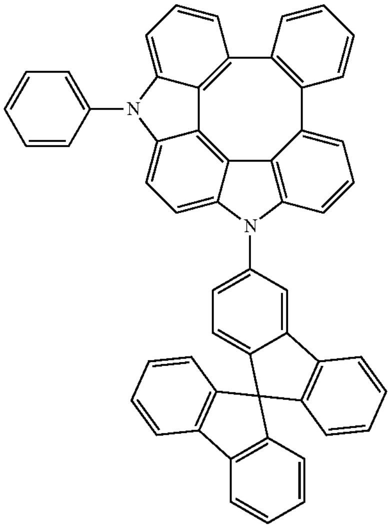
C-298
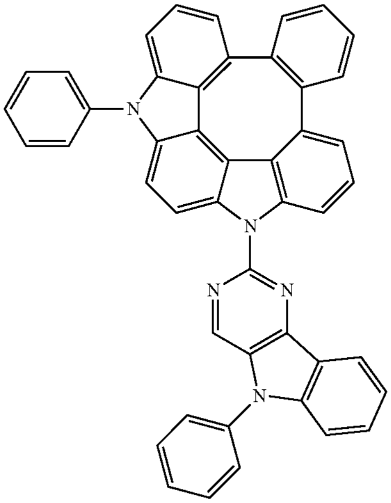
C-299
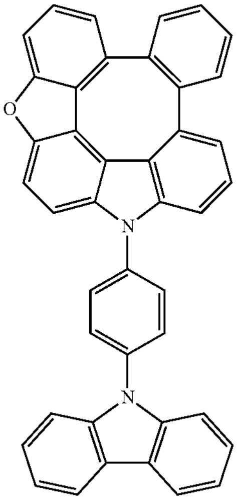
and -continued
C-300
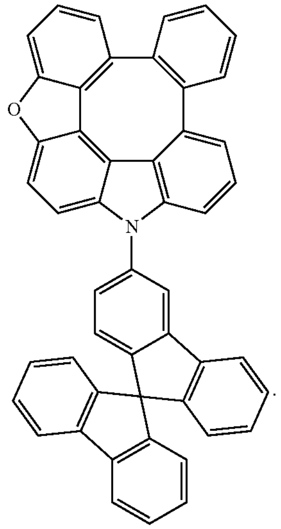
10. The plurality of host materials according to claim 1, wherein the compound represented by formula 2 is at least one selected from the following compounds:
C2-1
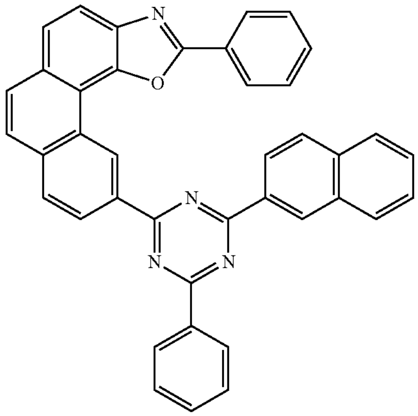
C2-2
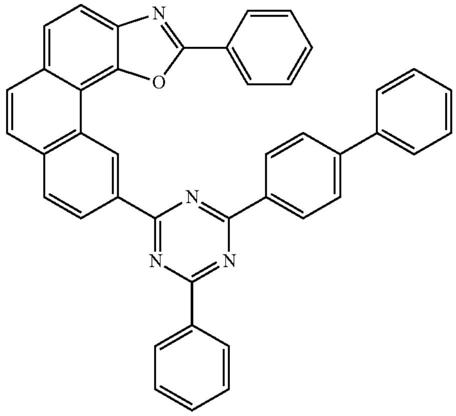
-continued
C2-3
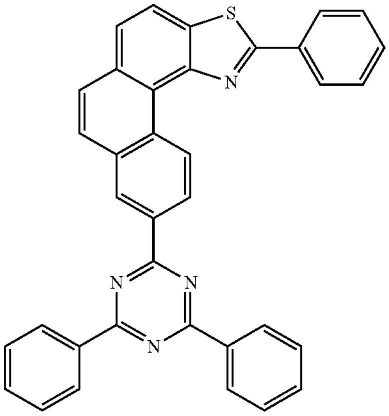
C2-4
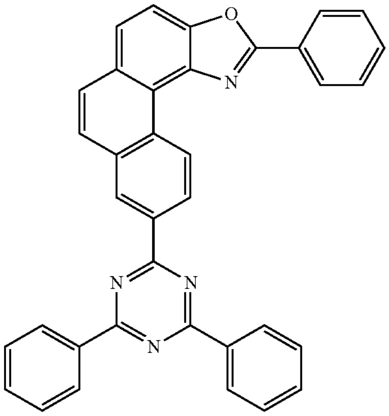
C2-5
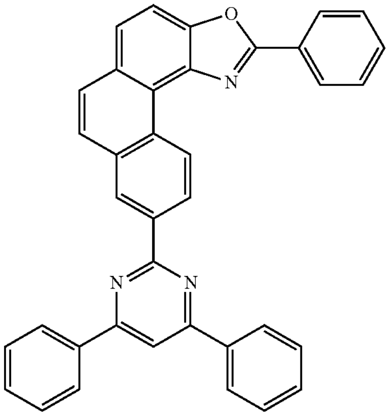

-continued
C2-6
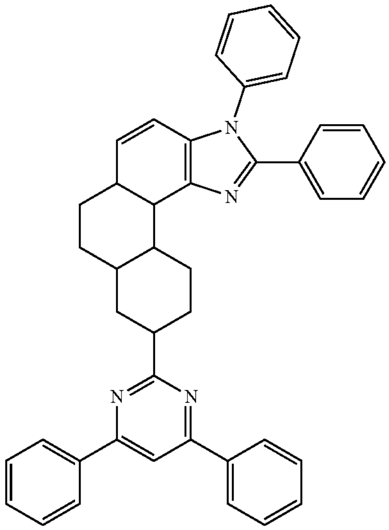
C2-7
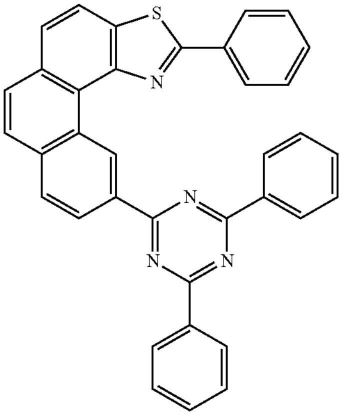
C2-8
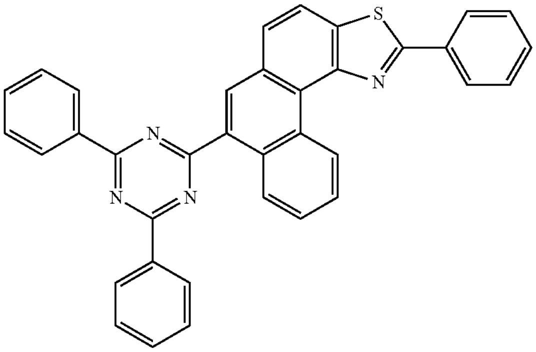
-continued
C2-9
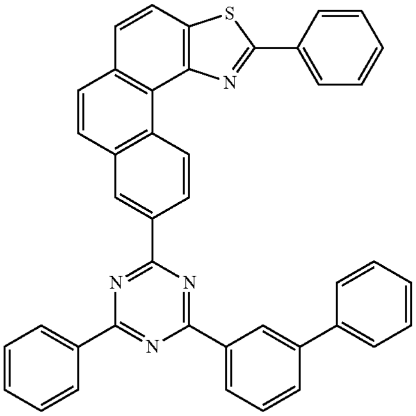
C2-10
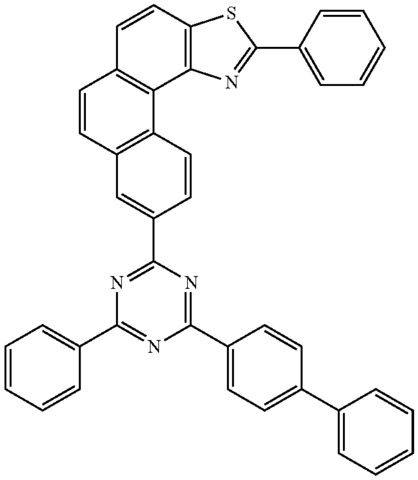
C2-11
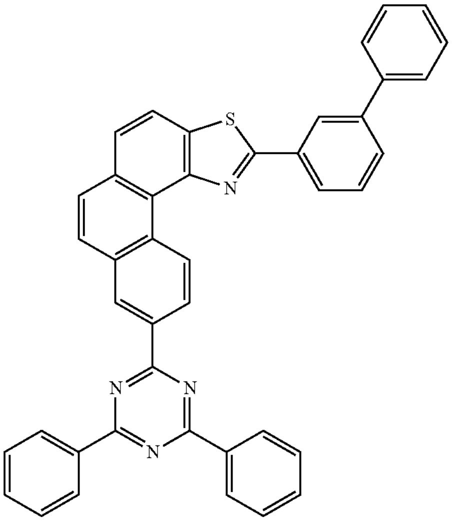

-continued
C2-12
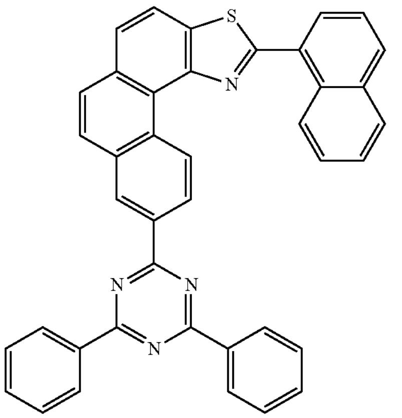
C2-13
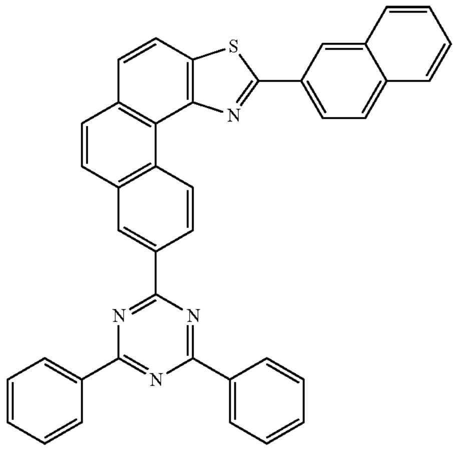
C2-14
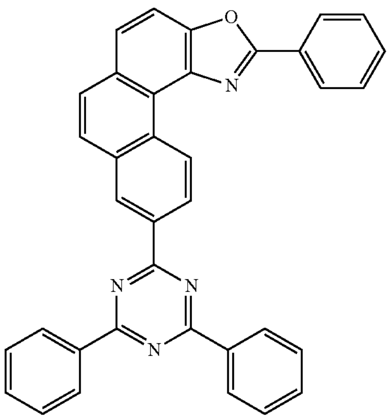
-continued
C2-15
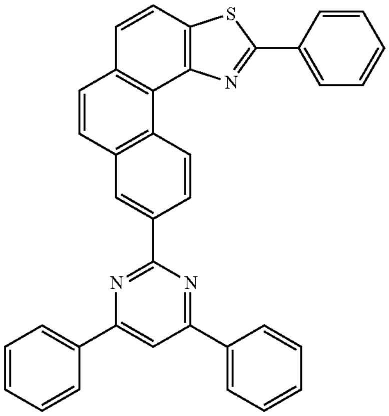
C2-16
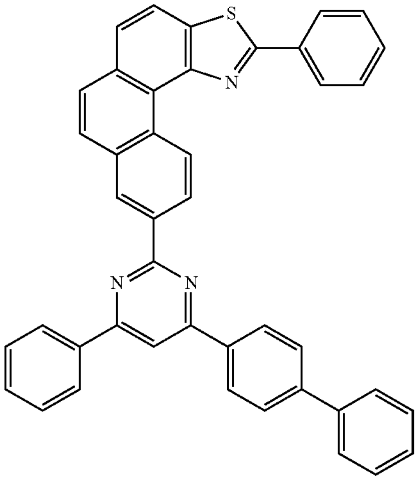
C2-17
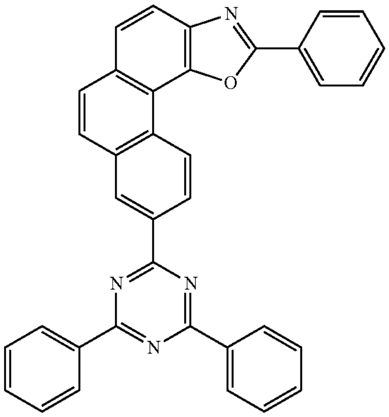

-continued
C2-18
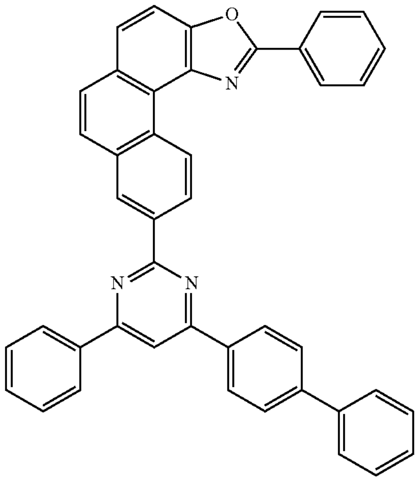
C2-19
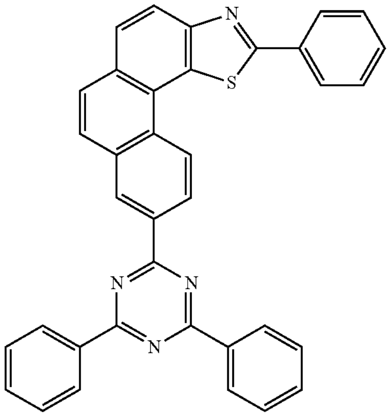
C2-20
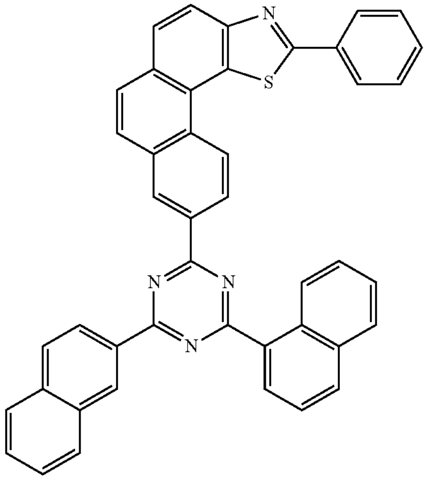
-continued
C2-21
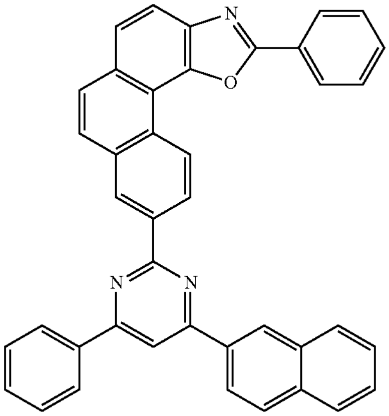
C2-22
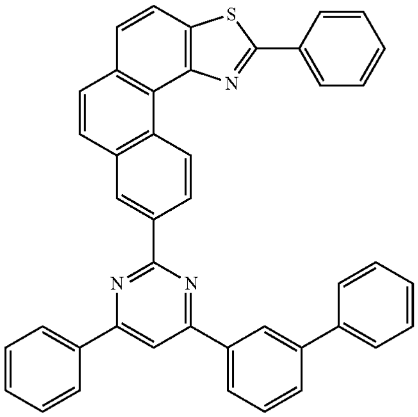
C2-23
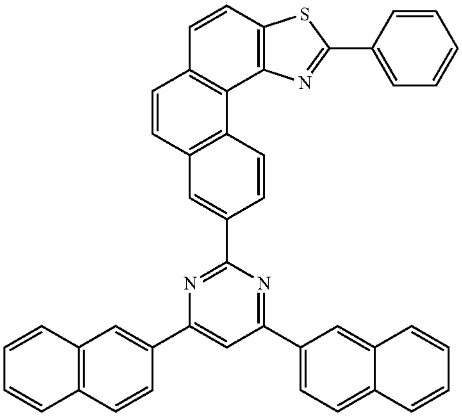

C2-24
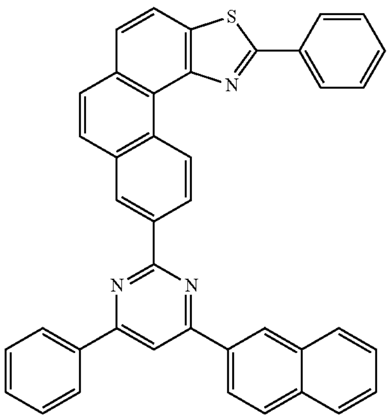
C2-25
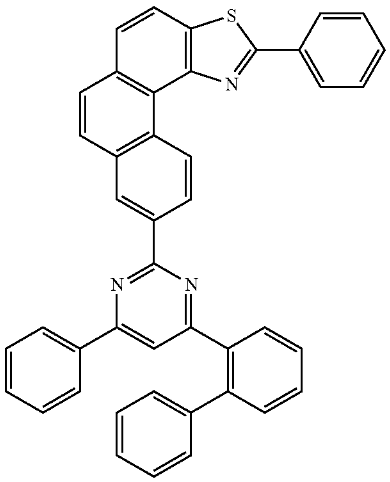
C2-26
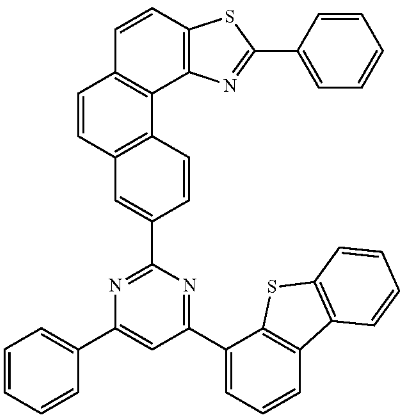
C2-27
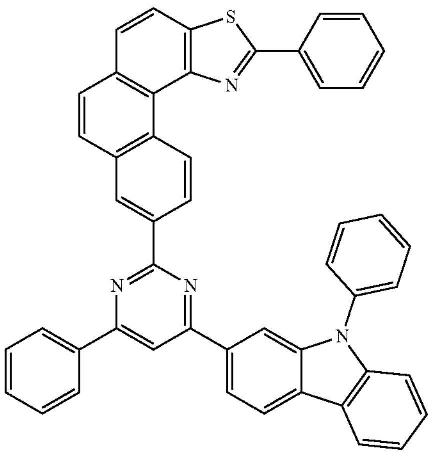
C2-28
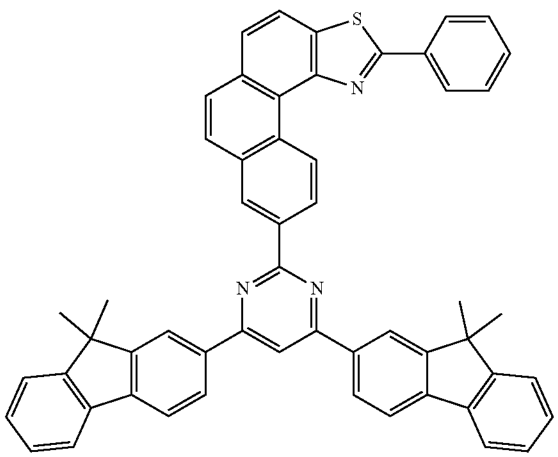
C2-29
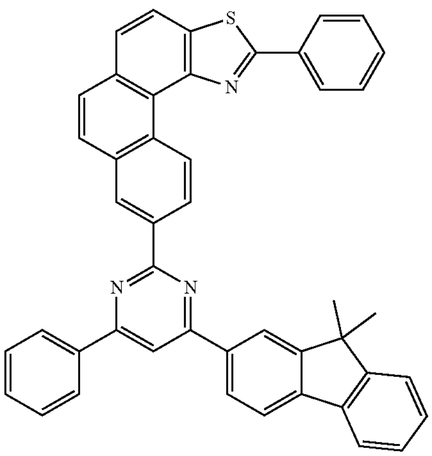

-continued
C2-30
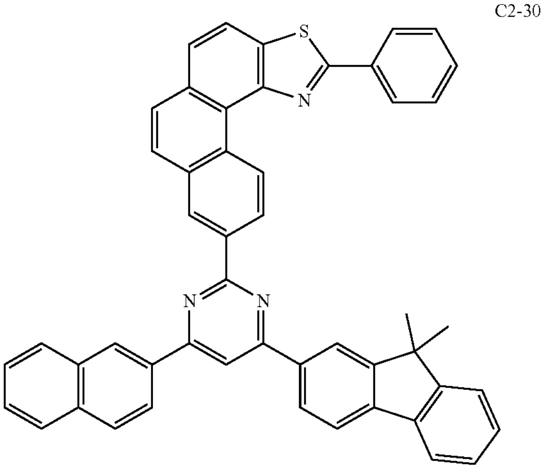
C2-31
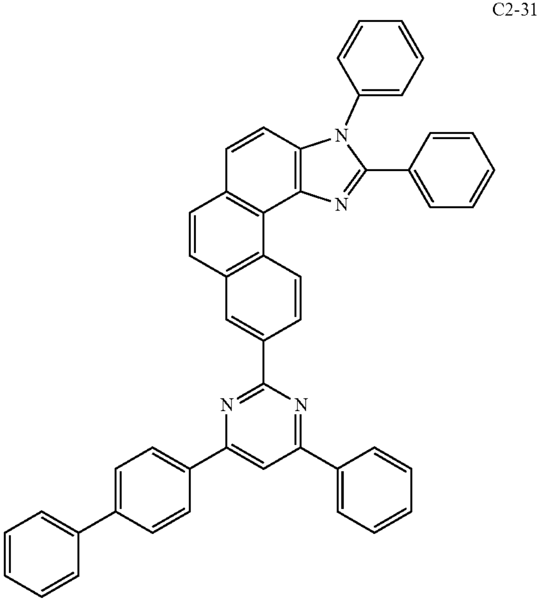
C2-32
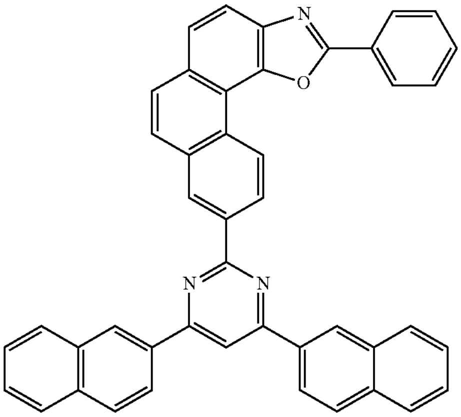
-continued
C2-33
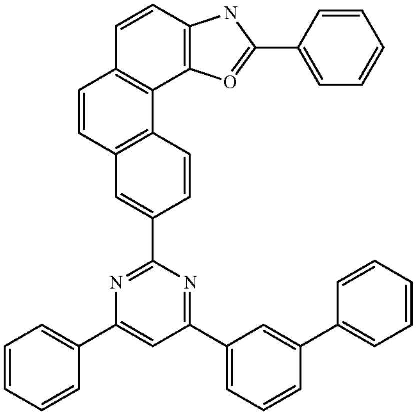
C2-34
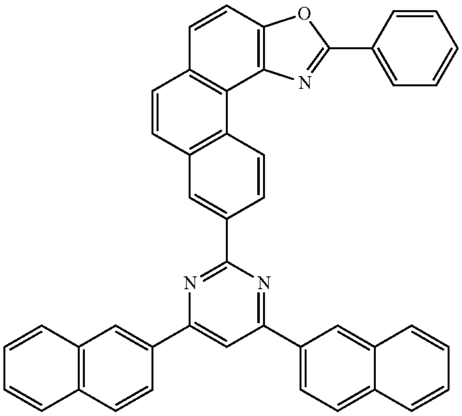
C2-35
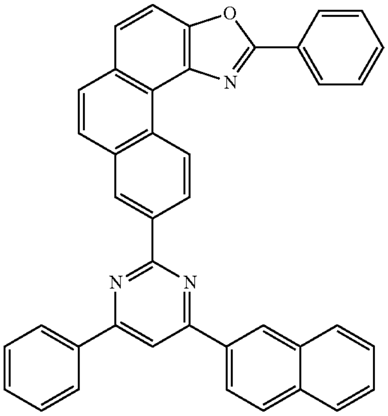

-continued
C2-36
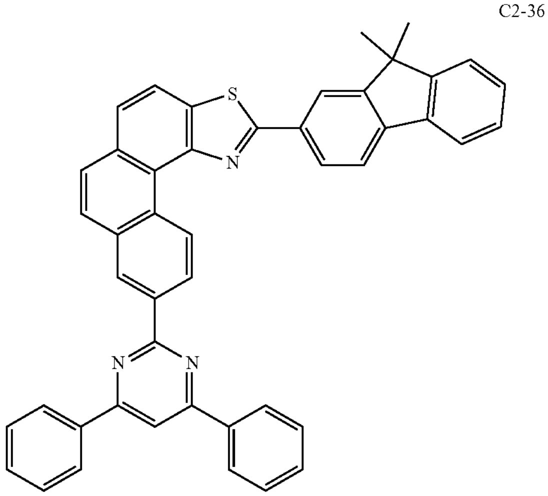
C2-37
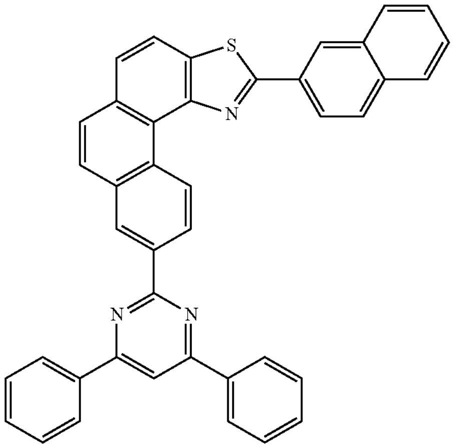
C2-38
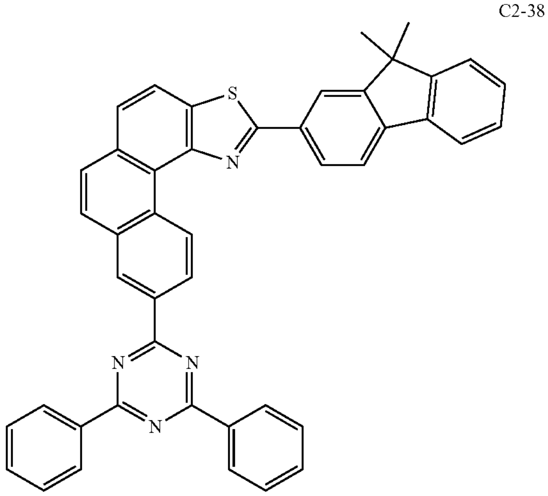
-continued
C2-39
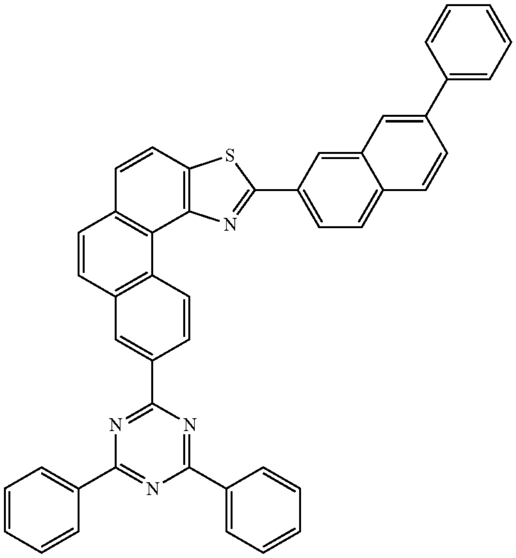
C2-40
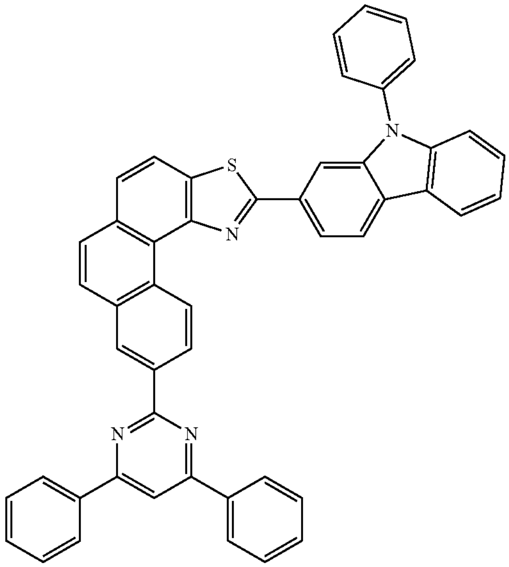
C2-41
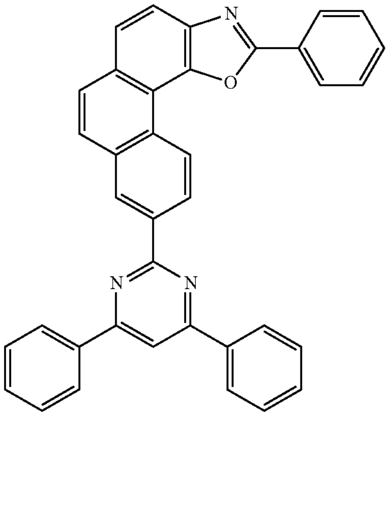

-continued
C2-42
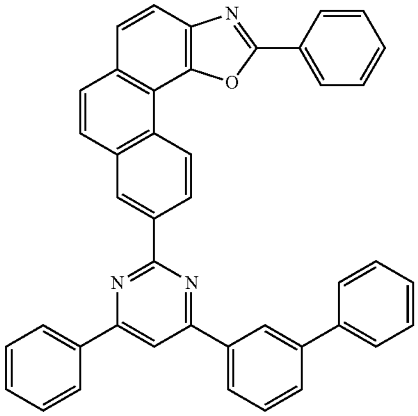
C2-43
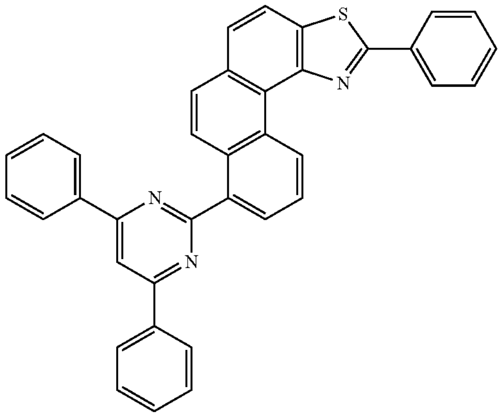
C2-44
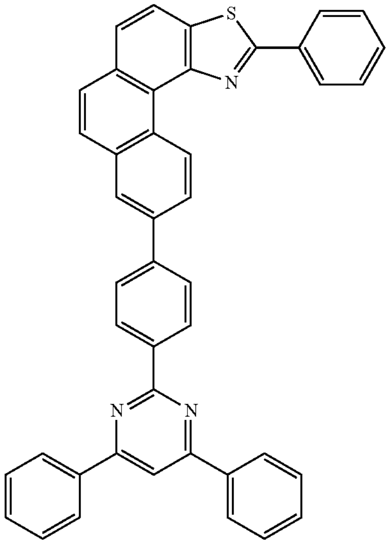
-continued
C2-45
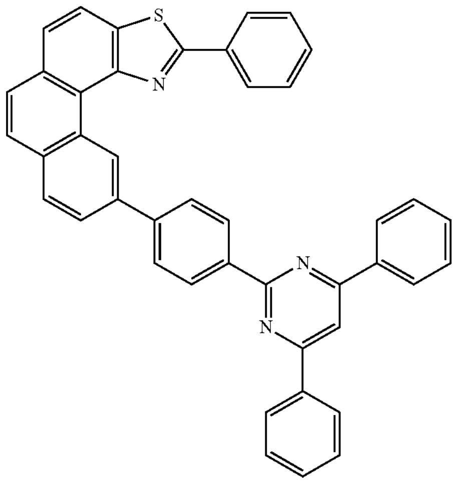
C2-46
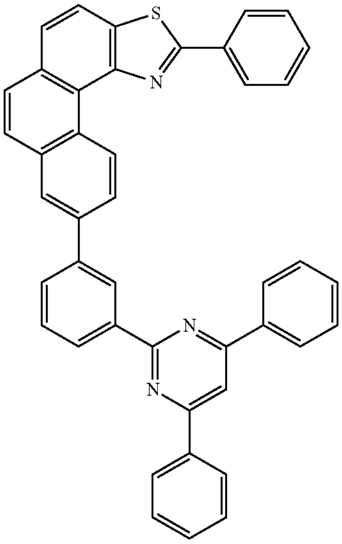
C2-47
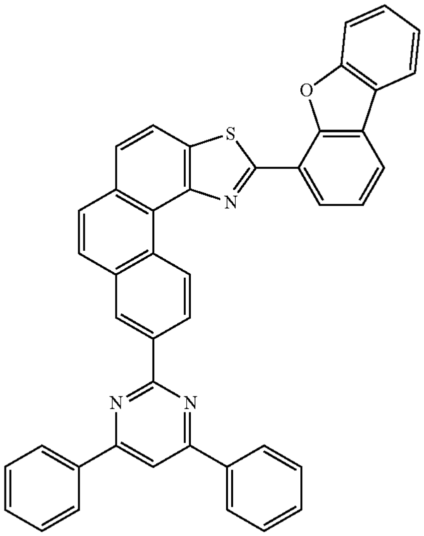

-continued
C2-48
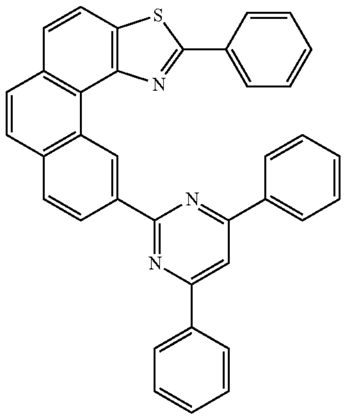
C2-49
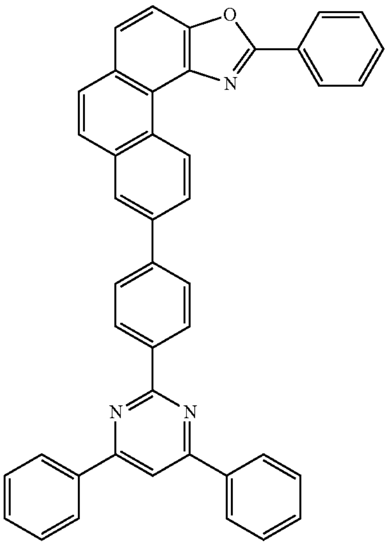
C2-50
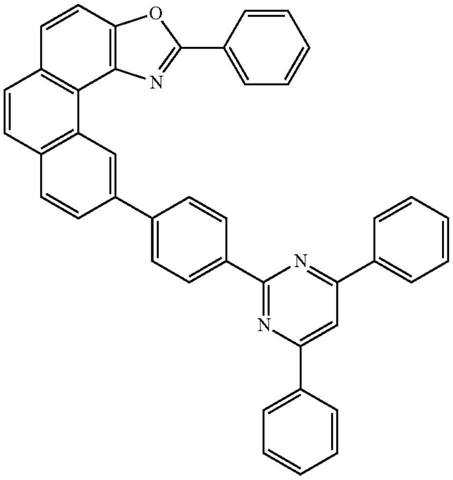
-continued
C2-51
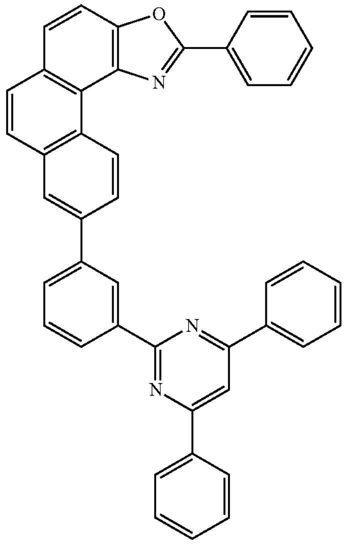
C2-52
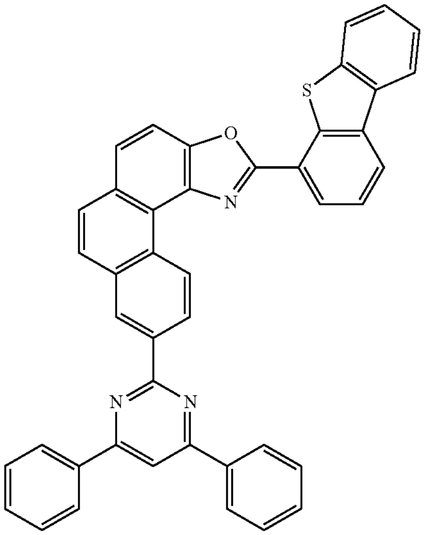
C2-53
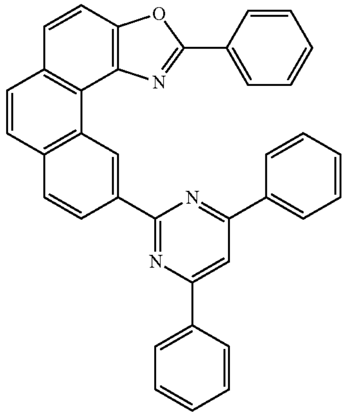

-continued
C2-54
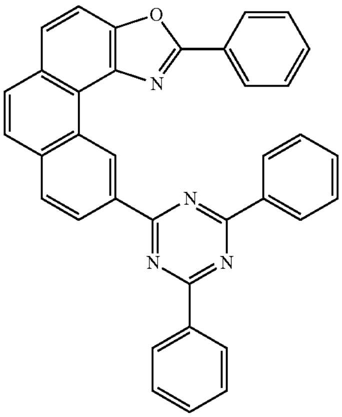
C2-55
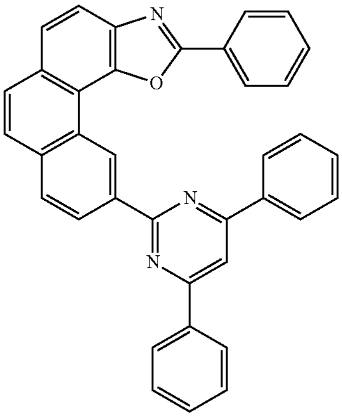
C2-56
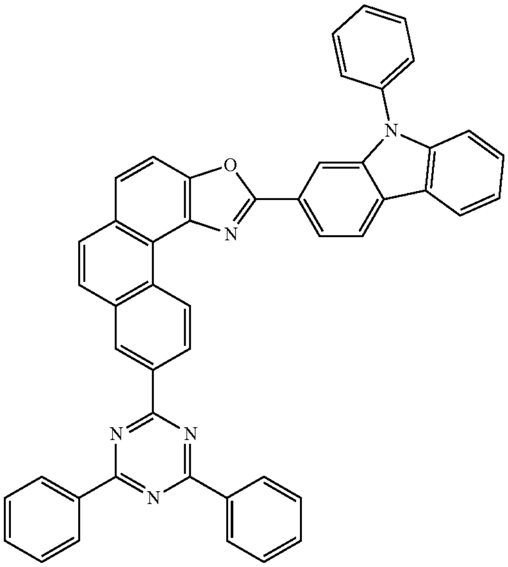
-continued
C2-57
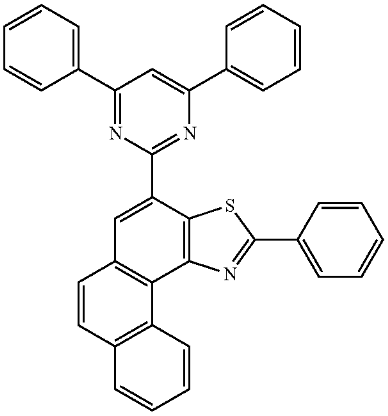
C2-58
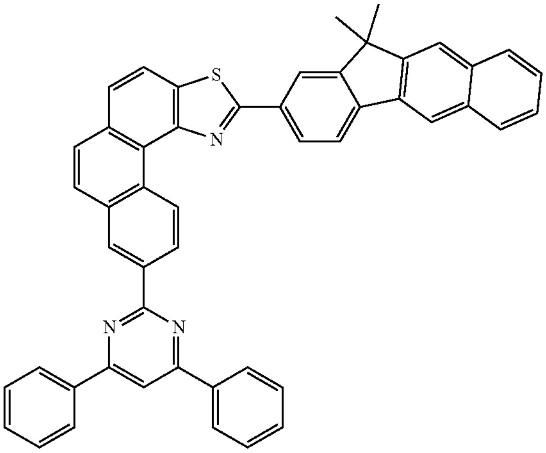
C2-59
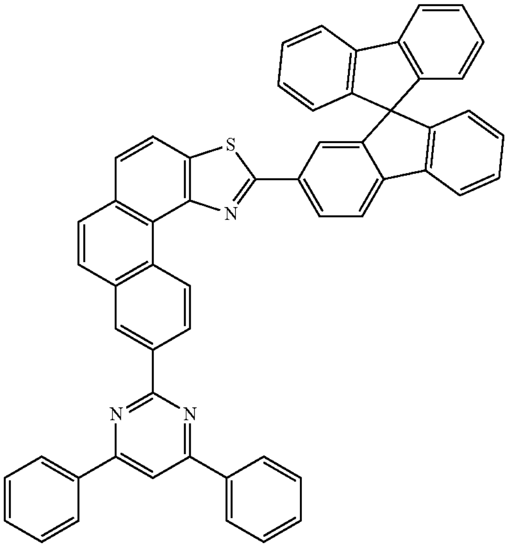

-continued
C2-60
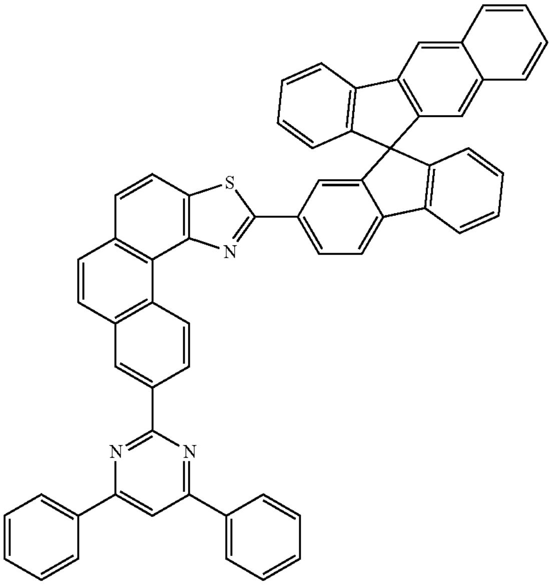
C2-61
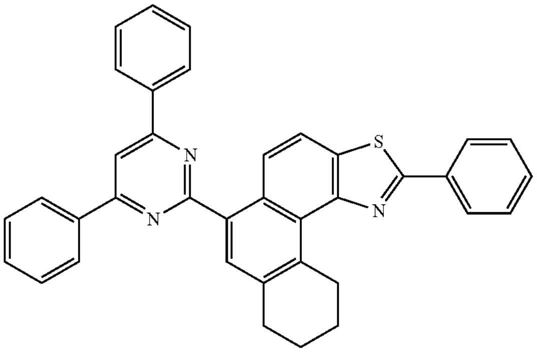
C2-62
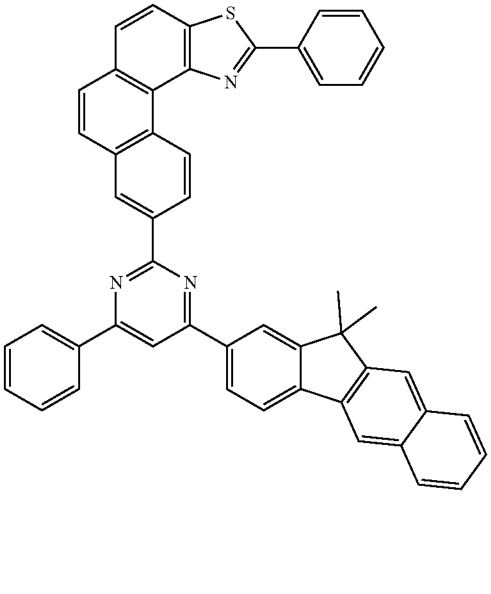
-continued
C2-63
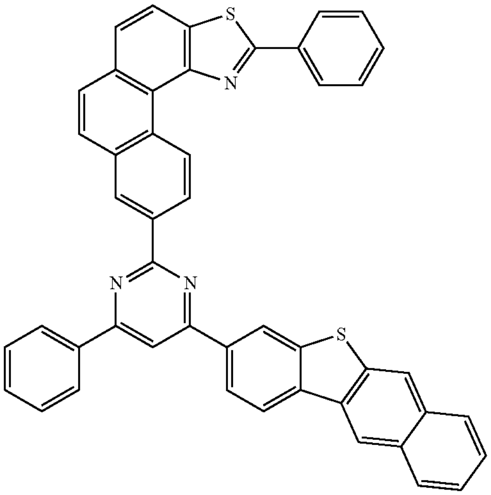
C2-64
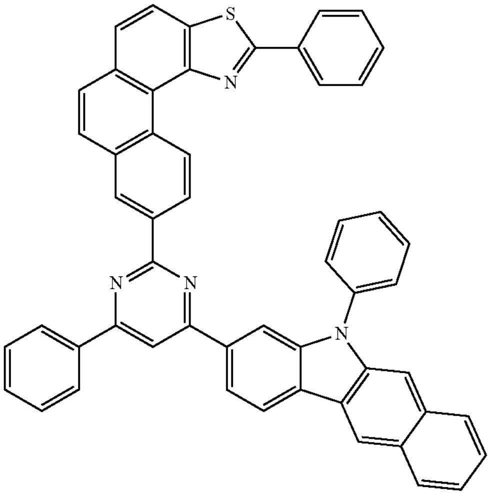
C2-65
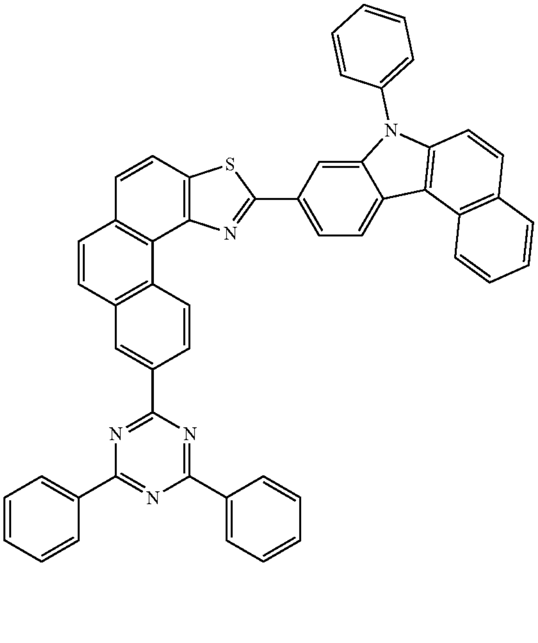

-continued
C2-66
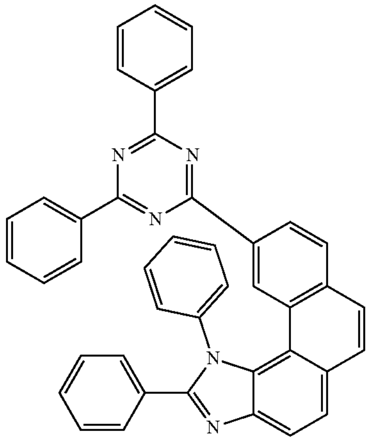
C2-67
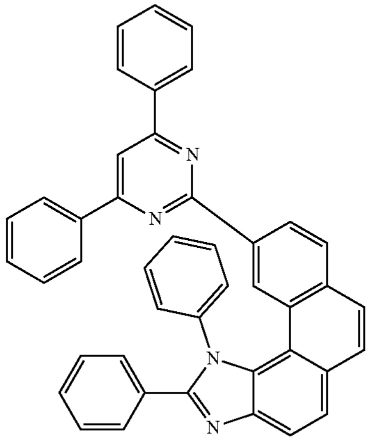
C2-68
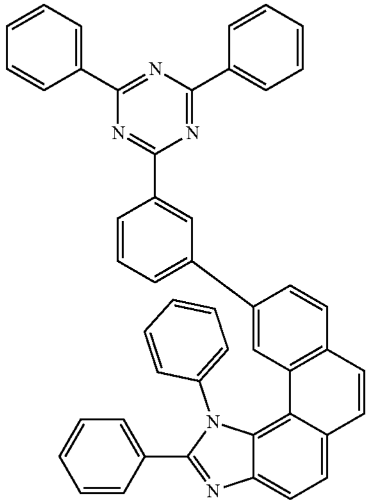
-continued
C2-69
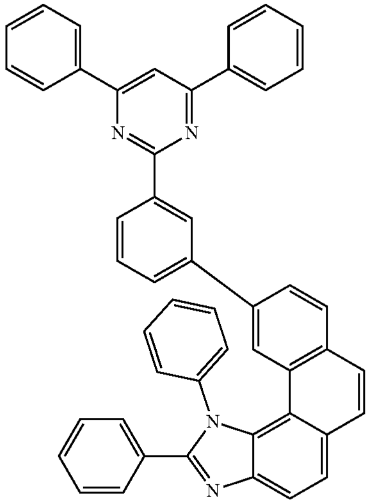
C2-70
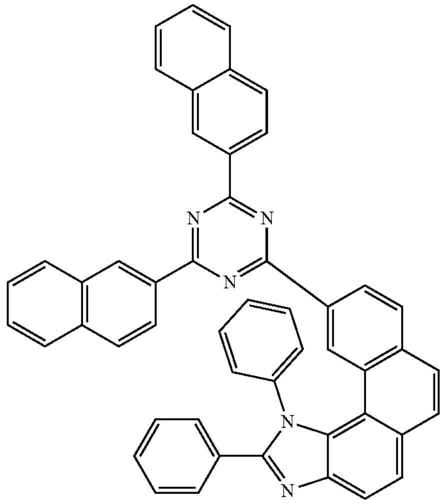
C2-71
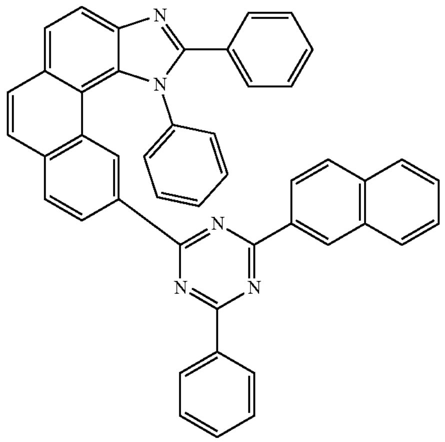

-continued
C2-72
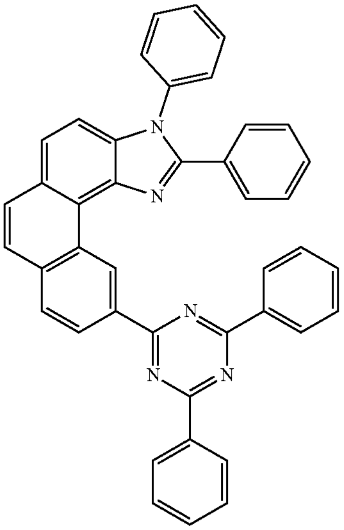
C2-73
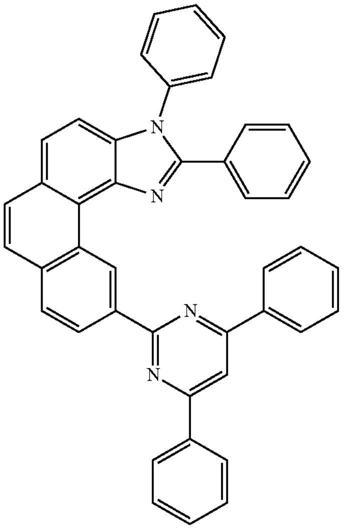
C2-74
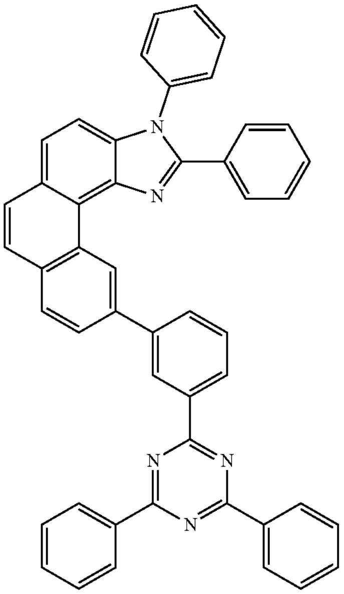
-continued
C2-75
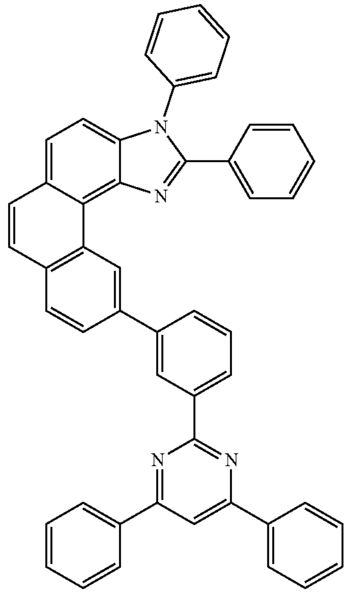
C2-76
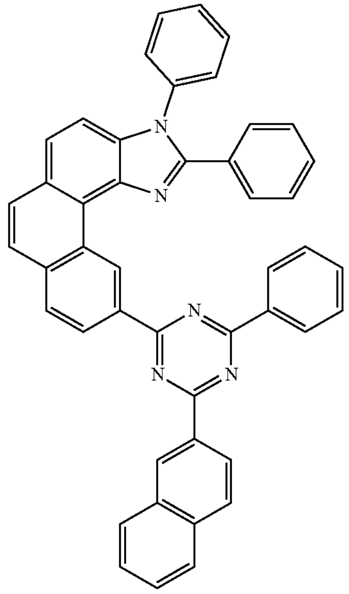

-continued
C2-77
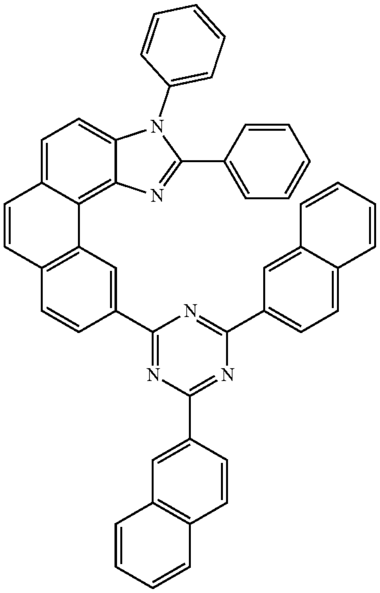
C2-78
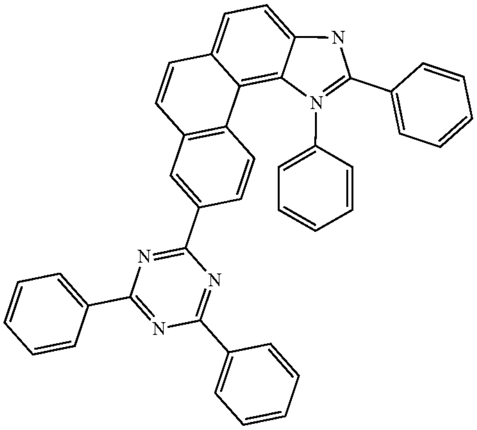
C2-79
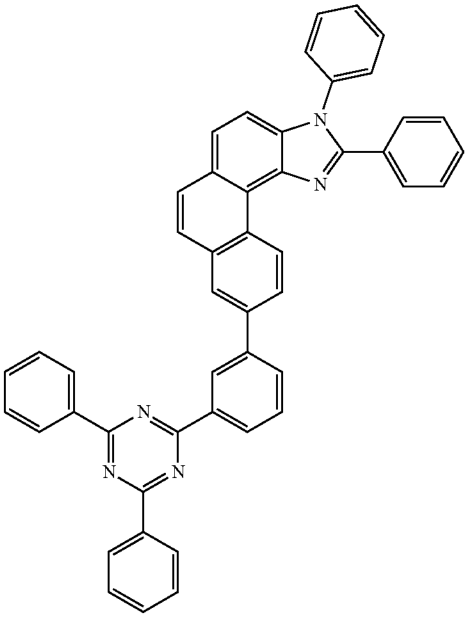
-continued
C2-80
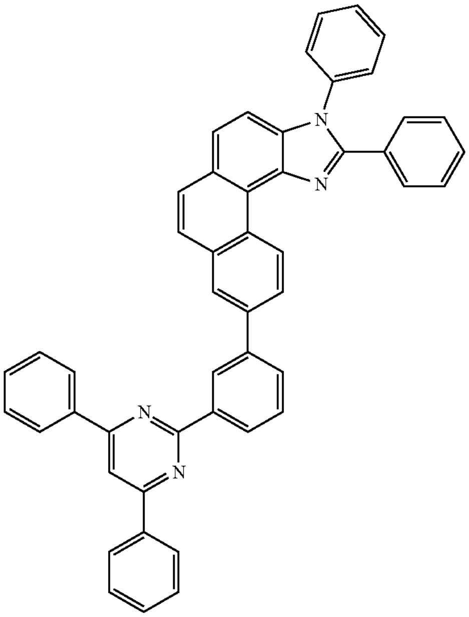
C2-81
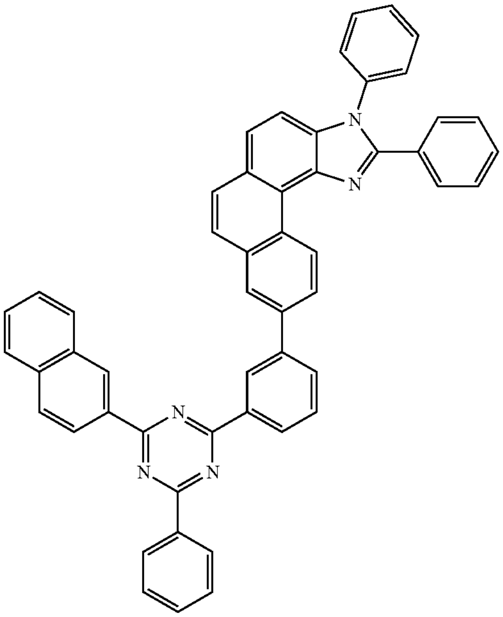

-continued
C2-82
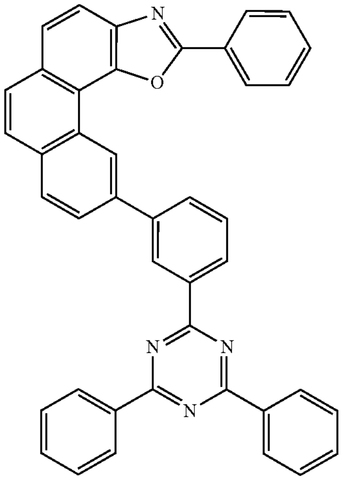
C2-83
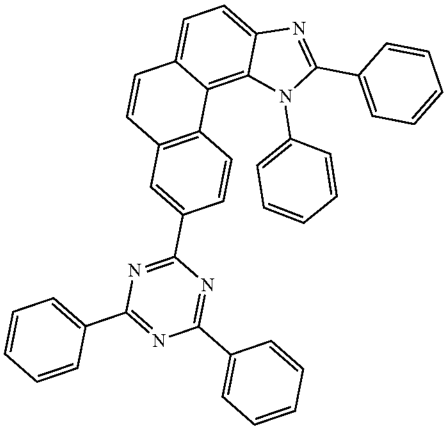
C2-84
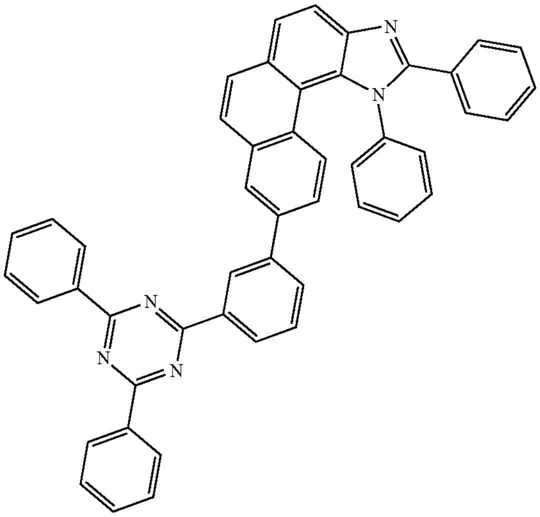
-continued
C2-85
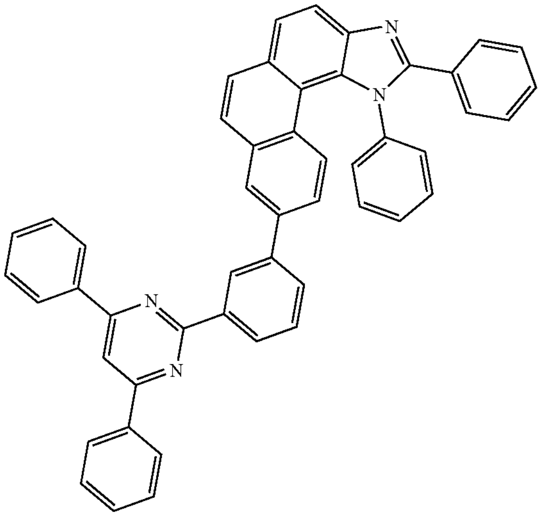
C2-86
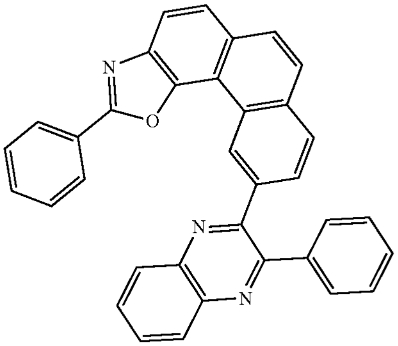
C2-87
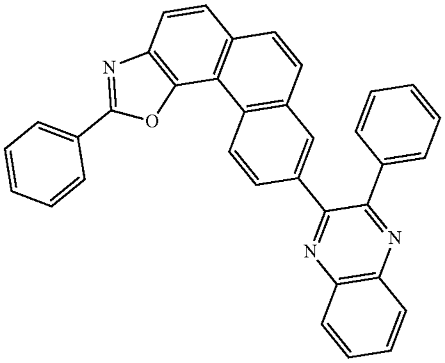

-continued
C2-88
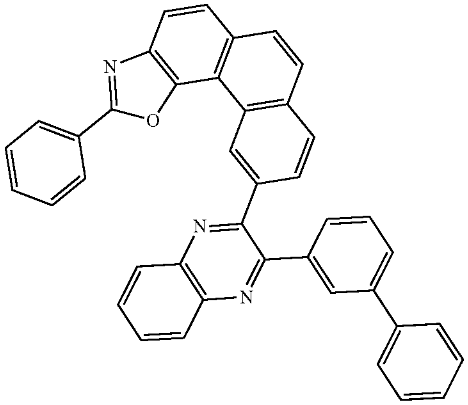
C2-89
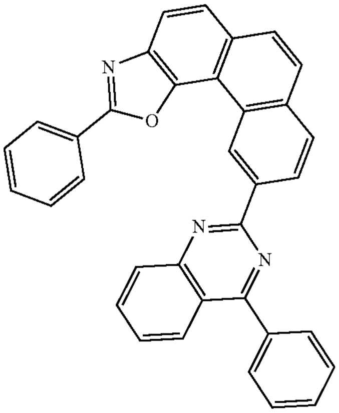
C2-90
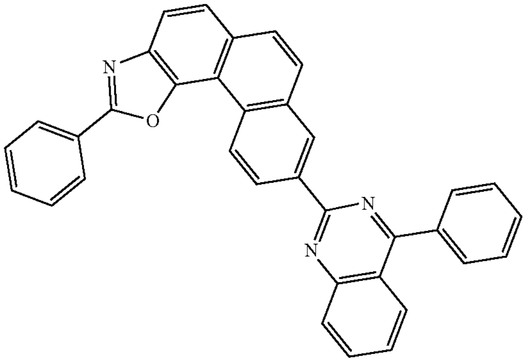
-continued
C2-91
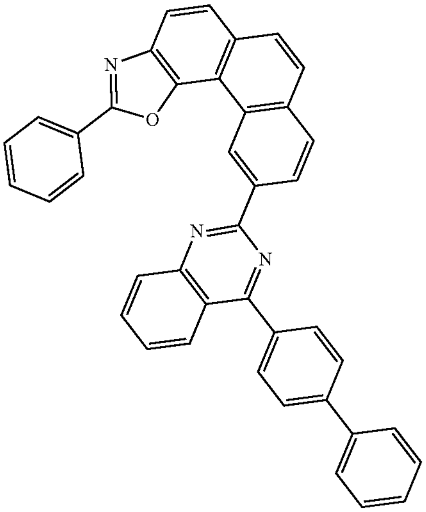
C2-92
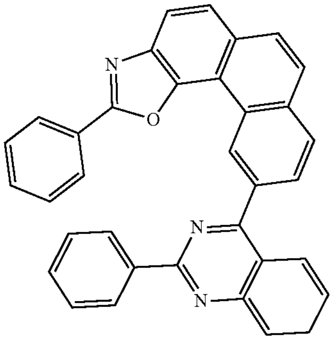
C2-93
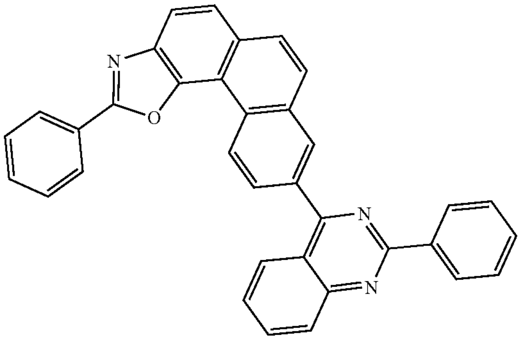
C2-94
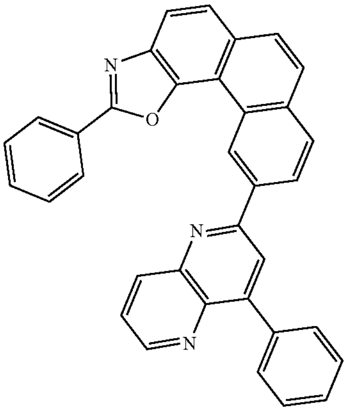

-continued
C2-95
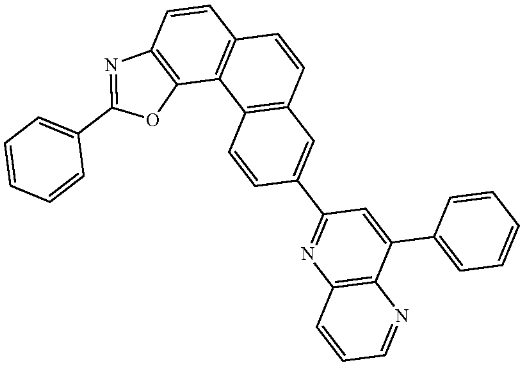
C2-96
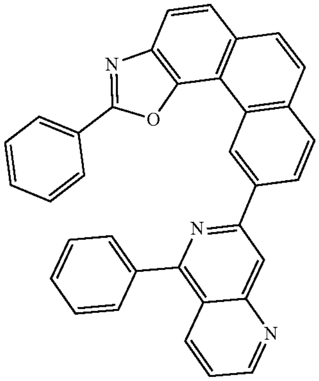
C2-97
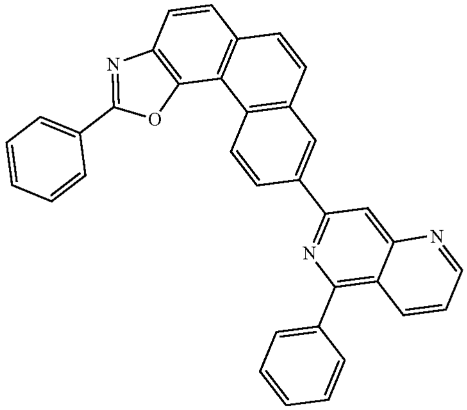
-continued
C2-98
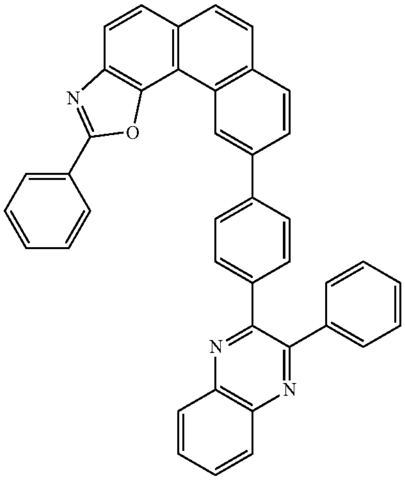
C2-99
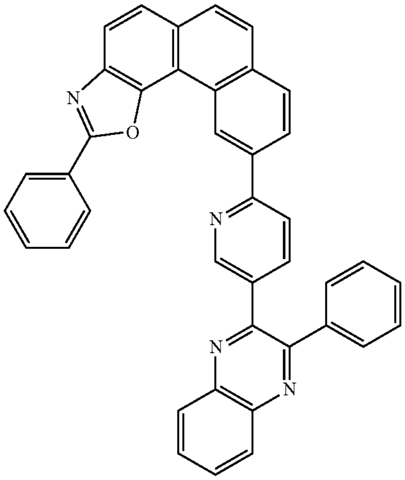
C2-100
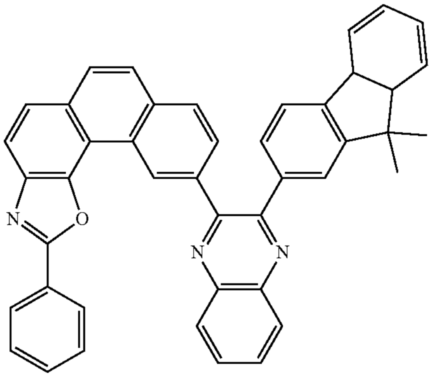

-continued
C2-101
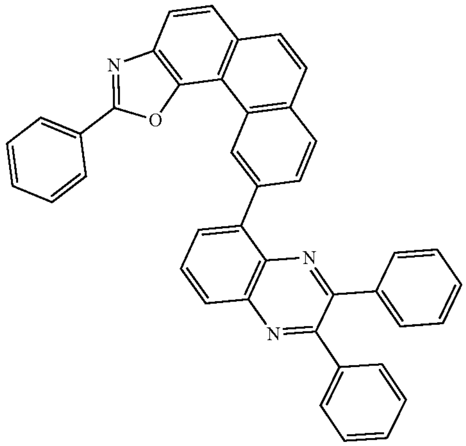
C2-102
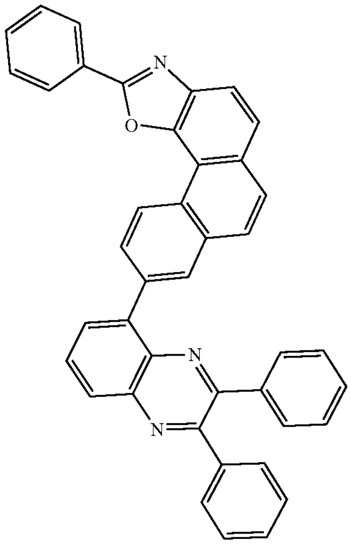
C2-103
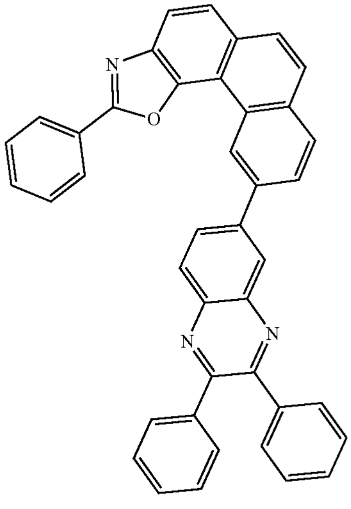
-continued
C2-104
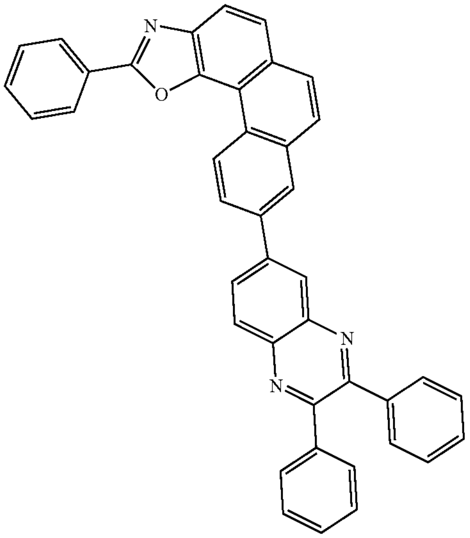
C2-105
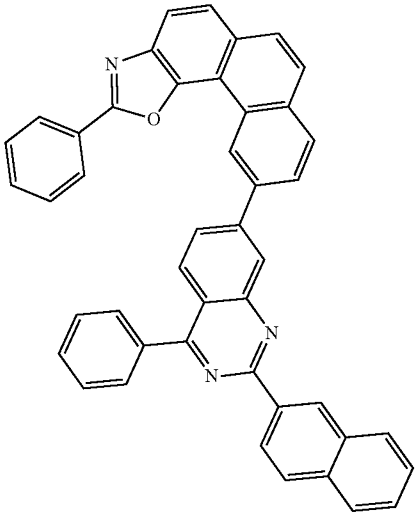
C2-106
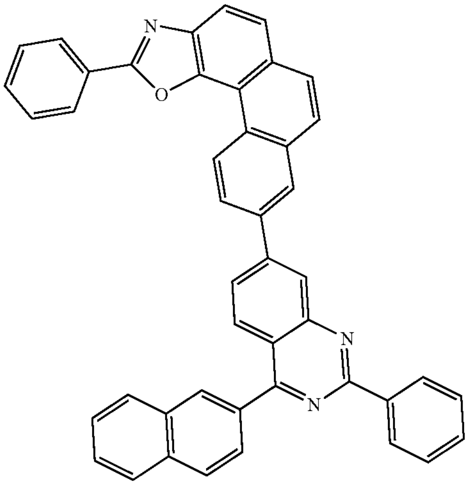

-continued
C2-107
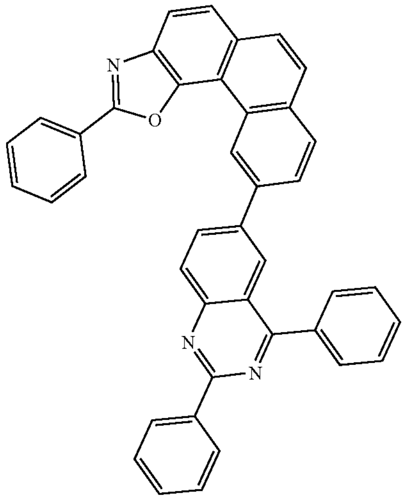
C2-108
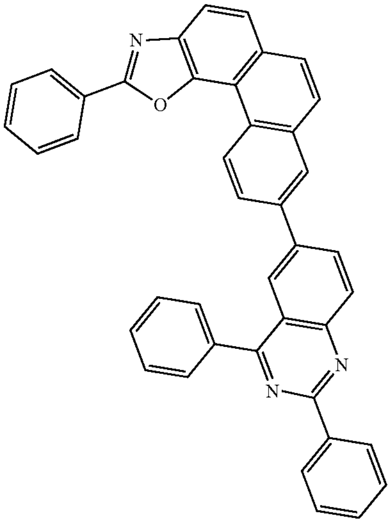
C2-109
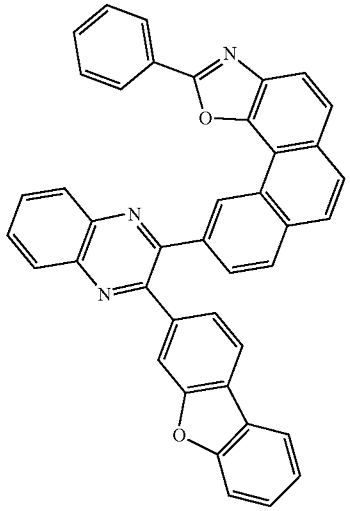
-continued
C2-110
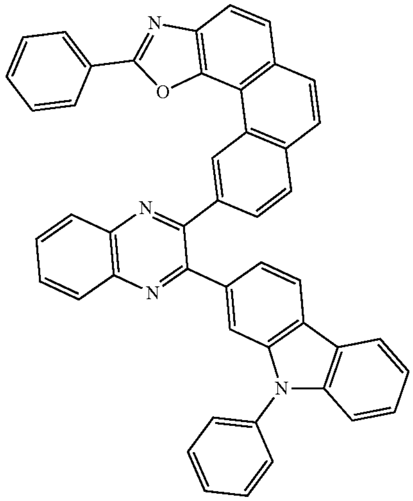
C2-111
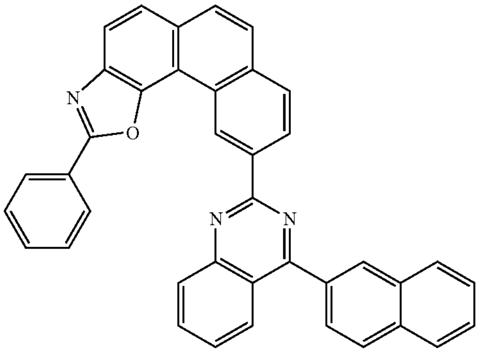
C2-112
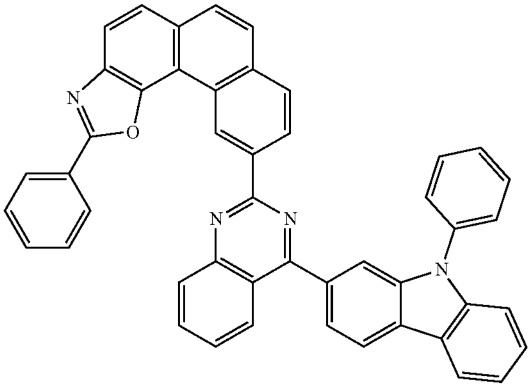
C2-113
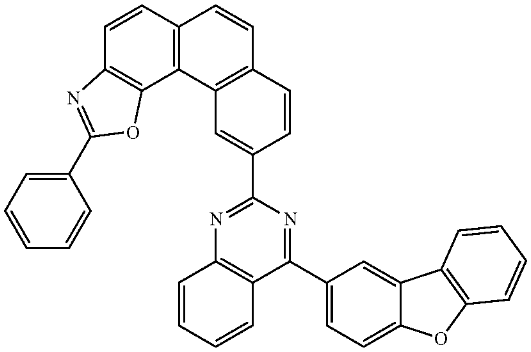

-continued
C2-114
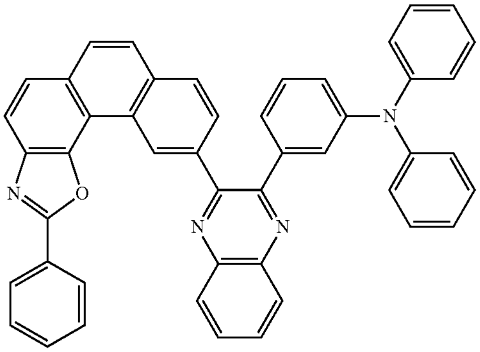
C2-115
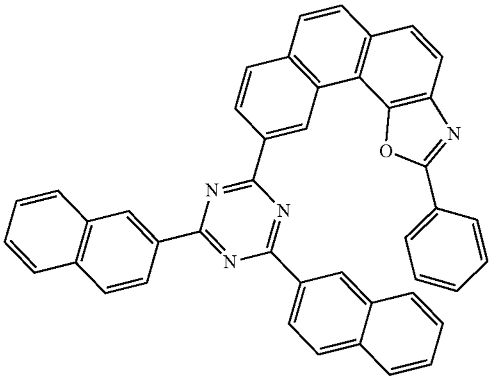
C2-116
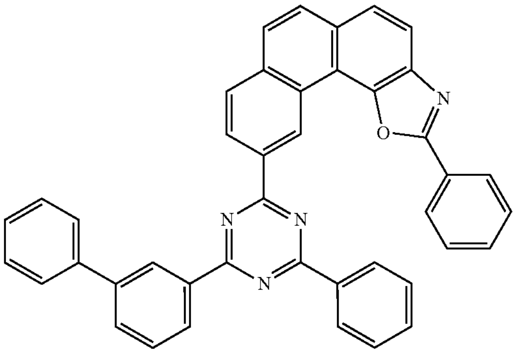
C2-117
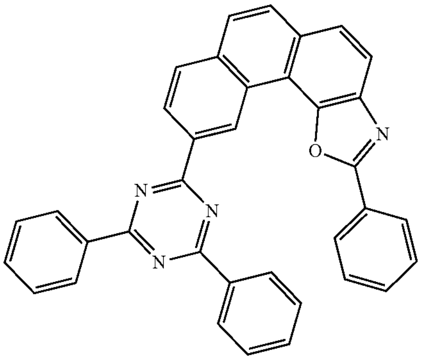
-continued
C2-118
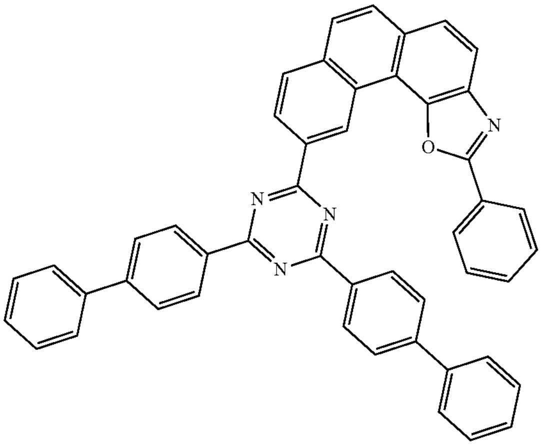
C2-119
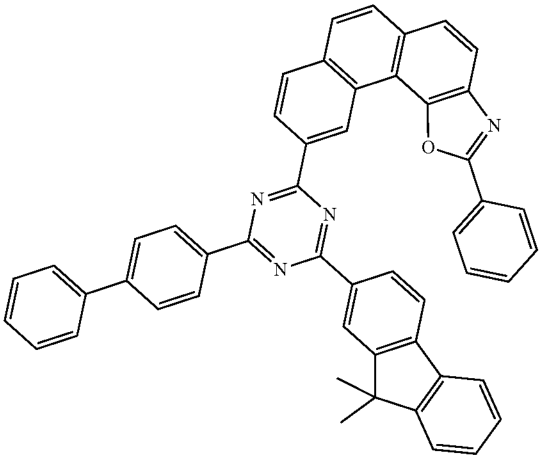
C2-120
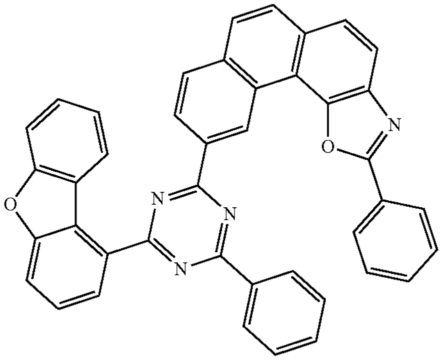

-continued
C2-121
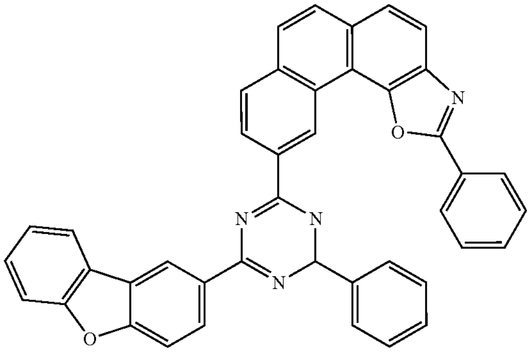
C2-122
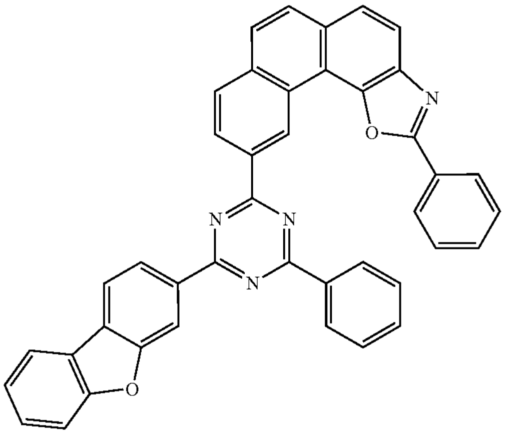
C2-123
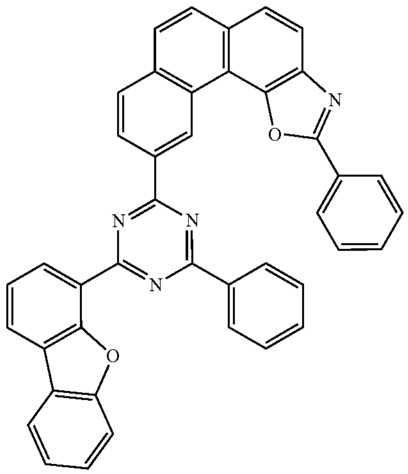
-continued
C2-124
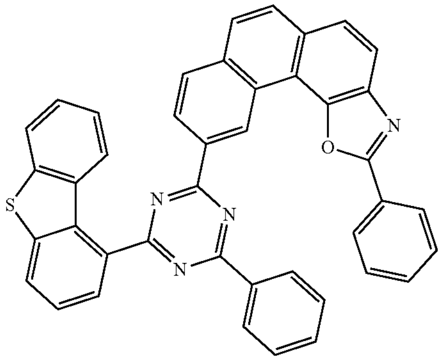
and
C2-125
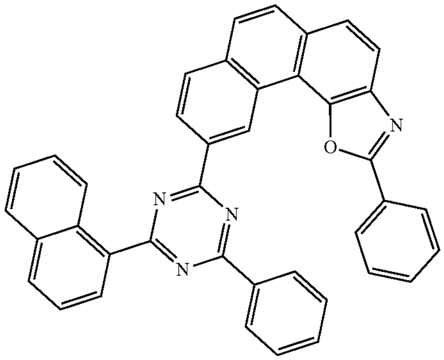
.
11. An organic electroluminescent device comprising an anode, a cathode, and at least one light-emitting layer between the anode and the cathode, wherein at least one of the light-emitting layers comprises the plurality of host materials according to claim 1.
* * * * *